(12) United States Patent
van der Walt et al.

(10) Patent No.: US 10,869,771 B2
(45) Date of Patent: Dec. 22, 2020

(54) SYSTEMS AND METHODS FOR JOINT REPLACEMENT

(71) Applicant: OrthAlign, Inc., Aliso Viejo, CA (US)

(72) Inventors: Nicholas van der Walt, Laguna Hills, CA (US); Charles Shapiro, Fountain Valley, CA (US); Richard Lane, Fort Wayne, IN (US); Matt Ryan, Aliso Viejo, CA (US)

(73) Assignee: OrthAlign, Inc., Aliso Viejo, CA (US)

( * ) Notice: Subject to any disclaimer, the term of this patent is extended or adjusted under 35 U.S.C. 154(b) by 39 days.

(21) Appl. No.: 16/267,737

(22) Filed: Feb. 5, 2019

(65) Prior Publication Data
US 2019/0328549 A1 Oct. 31, 2019

Related U.S. Application Data

(63) Continuation of application No. 15/716,971, filed on Sep. 27, 2017, now Pat. No. 10,238,510, which is a continuation of application No. 15/052,071, filed on Feb. 24, 2016, now Pat. No. 9,775,725, which is a continuation of application No. 13/398,712, filed on
(Continued)

(51) Int. Cl.
*A61F 2/46* (2006.01)
*A61B 17/56* (2006.01)
*A61B 5/11* (2006.01)
*A61B 17/17* (2006.01)
(Continued)

(52) U.S. Cl.
CPC .......... *A61F 2/4657* (2013.01); *A61B 5/1121* (2013.01); *A61B 17/1764* (2013.01); *A61B 17/56* (2013.01); *A61B 34/10* (2016.02); *A61B 34/20* (2016.02); *A61B 2034/108* (2016.02);
(Continued)

(58) Field of Classification Search
CPC .............................. A61F 2/4657; A61B 34/10
See application file for complete search history.

(56) References Cited

U.S. PATENT DOCUMENTS

| 3,174,080 | A | 3/1965 | Eldon |
| 3,670,324 | A | 6/1972 | Trevor, 3rd |

(Continued)

FOREIGN PATENT DOCUMENTS

| CA | 2241359 | 12/1999 |
| CA | 2 594 874 | 7/2006 |

(Continued)

OTHER PUBLICATIONS 510 (k) Summary for Total Knee Surgetics Navigation System, in 5 pages.
(Continued)

*Primary Examiner* — Christian A Sevilla
(74) *Attorney, Agent, or Firm* — Knobbe, Martens, Olson & Bear, LLP

(57) ABSTRACT

Systems and methods for joint replacement are provided. The systems and methods include a surgical orientation device, a reference sensor device, and at least one orthopedic fixture. The surgical orientation device, reference sensor device, and orthopedic fixtures can be used to locate the orientation of an axis in the body, to adjust an orientation of a cutting plane or planes along a bony surface, or otherwise to assist in an orthopedic procedure(s).

20 Claims, 81 Drawing Sheets

Related U.S. Application Data

Feb. 16, 2012, now Pat. No. 9,271,756, which is a continuation of application No. 13/115,065, filed on May 24, 2011, now Pat. No. 8,118,815, which is a continuation-in-part of application No. 12/509,388, filed on Jul. 24, 2009, now Pat. No. 8,998,910, and a continuation-in-part of application No. 13/011,815, filed on Jan. 21, 2011, now Pat. No. 9,339,226.

(60) Provisional application No. 61/297,215, filed on Jan. 21, 2010, provisional application No. 61/297,212, filed on Jan. 21, 2010, provisional application No. 61/369,390, filed on Jul. 30, 2010.

(51) Int. Cl.
*A61B 34/20* (2016.01)
*A61B 34/10* (2016.01)

(52) U.S. Cl.
CPC ............... *A61B 2034/2048* (2016.02); *A61B 2562/0219* (2013.01)

(56) References Cited

U.S. PATENT DOCUMENTS

| | | |
|---|---|---|
| 4,349,018 A | 9/1982 | Chambers |
| 4,421,112 A * | 12/1983 | Mains ............... A61B 17/152 606/75 |
| 4,436,099 A | 3/1984 | Raftopoulos |
| 4,459,985 A | 7/1984 | McKay et al. |
| 4,475,549 A | 10/1984 | Oh |
| 4,501,266 A | 2/1985 | McDaniel |
| 4,509,393 A | 4/1985 | Castiglione |
| 4,518,855 A | 5/1985 | Malak |
| 4,524,766 A | 6/1985 | Petersen |
| 4,529,348 A | 7/1985 | Johnson et al. |
| 4,567,885 A | 2/1986 | Androphy |
| 4,567,886 A | 2/1986 | Petersen |
| 4,621,630 A | 11/1986 | Kenna |
| 4,646,729 A | 3/1987 | Kenna |
| 4,716,894 A | 1/1988 | Lazzeri et al. |
| 4,718,078 A | 1/1988 | Bleidorn et al. |
| 4,738,253 A | 4/1988 | Buechel et al. |
| 4,759,350 A | 7/1988 | Dunn et al. |
| 4,823,807 A | 4/1989 | Russell et al. |
| 4,938,762 A | 7/1990 | Wehrli |
| 4,944,760 A | 7/1990 | Kenna |
| 4,945,799 A | 8/1990 | Knetzer |
| 4,952,213 A | 8/1990 | Bowman et al. |
| 5,002,547 A | 3/1991 | Poggie et al. |
| 5,053,037 A | 10/1991 | Lackey |
| 5,065,612 A | 11/1991 | Ooka et al. |
| 5,122,146 A | 6/1992 | Chapman et al. |
| 5,129,908 A | 7/1992 | Petersen |
| 5,141,512 A | 8/1992 | Farmer et al. |
| 5,171,244 A | 12/1992 | Caspari et al. |
| 5,213,112 A | 5/1993 | Niwa et al. |
| 5,249,581 A | 10/1993 | Horbal et al. |
| 5,251,127 A | 10/1993 | Raab |
| 5,279,309 A | 1/1994 | Taylor et al. |
| 5,296,855 A | 3/1994 | Matsuzaki et al. |
| 5,306,276 A | 4/1994 | Johnson et al. |
| 5,320,625 A | 6/1994 | Bertin |
| 5,324,293 A | 6/1994 | Rehmann |
| 5,325,029 A | 6/1994 | Janecke et al. |
| 5,329,933 A | 7/1994 | Graf |
| 5,342,367 A | 8/1994 | Ferrante et al. |
| 5,343,391 A | 8/1994 | Mushabac |
| 5,358,526 A | 10/1994 | Tornier |
| 5,376,093 A | 12/1994 | Newman |
| 5,395,377 A | 3/1995 | Petersen et al. |
| 5,417,694 A | 5/1995 | Marik et al. |
| 5,423,827 A | 6/1995 | Mumme |
| 5,431,653 A | 7/1995 | Callaway |
| 5,462,548 A | 10/1995 | Pappas et al. |
| 5,468,244 A | 11/1995 | Attfield et al. |
| 5,474,088 A | 12/1995 | Zaharkin et al. |
| 5,486,177 A | 1/1996 | Mumme et al. |
| 5,514,143 A | 5/1996 | Bonutti et al. |
| 5,529,070 A | 6/1996 | Augustine et al. |
| 5,540,696 A | 7/1996 | Booth, Jr. et al. |
| 5,540,697 A | 7/1996 | Rehmann et al. |
| 5,553,198 A | 9/1996 | Wang et al. |
| 5,576,727 A | 11/1996 | Rosenberg et al. |
| 5,584,837 A | 12/1996 | Peterson |
| 5,597,379 A | 1/1997 | Haines et al. |
| 5,611,353 A | 3/1997 | Dance et al. |
| 5,624,444 A | 4/1997 | Wixson et al. |
| 5,628,750 A | 5/1997 | Whitlock et al. |
| 5,645,077 A | 7/1997 | Foxlin |
| 5,653,764 A | 8/1997 | Murphy |
| 5,681,316 A | 10/1997 | DeOrio et al. |
| 5,683,398 A | 11/1997 | Carls et al. |
| 5,688,282 A | 11/1997 | Baron et al. |
| 5,720,752 A | 2/1998 | Elliot et al. |
| 5,724,264 A | 3/1998 | Rosenberg et al. |
| 5,748,767 A | 5/1998 | Raab |
| 5,769,861 A | 6/1998 | Vilsmeier |
| 5,776,137 A | 7/1998 | Katz |
| 5,788,700 A | 8/1998 | Morawa et al. |
| 5,824,085 A | 10/1998 | Sahay et al. |
| 5,840,047 A | 11/1998 | Stedham |
| 5,880,714 A | 3/1999 | Rosenberg et al. |
| 5,916,219 A | 6/1999 | Matsuno et al. |
| 5,919,149 A | 7/1999 | Allum |
| 5,935,086 A | 8/1999 | Beacon et al. |
| 5,976,156 A | 11/1999 | Taylor et al. |
| 6,027,507 A | 2/2000 | Anderson et al. |
| 6,036,696 A | 3/2000 | Lambrecht et al. |
| 6,056,756 A | 5/2000 | Eng et al. |
| 6,090,114 A | 7/2000 | Matsuno et al. |
| 6,094,019 A | 7/2000 | Saiki |
| 6,120,509 A | 9/2000 | Wheeler |
| 6,122,538 A | 9/2000 | Sliwa, Jr. et al. |
| 6,126,608 A | 10/2000 | Kemme et al. |
| 6,162,191 A | 12/2000 | Foxin |
| 6,167,292 A | 12/2000 | Badano et al. |
| 6,171,310 B1 | 1/2001 | Giordano |
| 6,195,615 B1 | 2/2001 | Lysen |
| 6,197,032 B1 | 3/2001 | Lawes et al. |
| 6,214,013 B1 | 4/2001 | Lambrech et al. |
| 6,214,014 B1 | 4/2001 | McGann |
| 6,216,029 B1 | 4/2001 | Paltieli |
| 6,246,898 B1 | 6/2001 | Vesely et al. |
| 6,258,095 B1 | 7/2001 | Lombardo et al. |
| 6,261,247 B1 | 7/2001 | Ishikawa et al. |
| 6,299,646 B1 | 10/2001 | Chambat et al. |
| 6,332,089 B1 | 12/2001 | Acker et al. |
| 6,348,058 B1 | 2/2002 | Melken et al. |
| 6,354,011 B1 | 3/2002 | Albrecht |
| 6,361,506 B1 | 3/2002 | Saenger et al. |
| 6,361,507 B1 | 3/2002 | Foxlin |
| 6,361,508 B1 | 3/2002 | Johnson et al. |
| 6,377,839 B1 | 4/2002 | Kalfas et al. |
| 6,381,485 B1 | 4/2002 | Hunter et al. |
| 6,383,149 B1 | 5/2002 | DeMayo |
| 6,395,005 B1 | 5/2002 | Lovell |
| 6,447,448 B1 | 9/2002 | Ishikawa et al. |
| 6,468,280 B1 | 10/2002 | Saenger et al. |
| 6,470,207 B1 | 10/2002 | Simon et al. |
| 6,471,637 B1 | 10/2002 | Green et al. |
| 6,473,635 B1 | 10/2002 | Rasche |
| 6,477,400 B1 | 11/2002 | Barrick |
| 6,477,421 B1 | 11/2002 | Andersen et al. |
| 6,478,799 B1 | 11/2002 | Williamson |
| 6,488,713 B1 | 12/2002 | Hershnerger |
| 6,499,488 B1 | 12/2002 | Hunter et al. |
| 6,514,259 B2 | 2/2003 | Picard et al. |
| 6,527,443 B1 | 3/2003 | Vilsmeier |
| 6,551,325 B2 | 4/2003 | Neubauer et al. |
| 6,585,666 B2 | 7/2003 | Suh et al. |
| 6,595,997 B2 | 7/2003 | Axelson, Jr. et al. |
| 6,595,999 B2 | 7/2003 | Marchione et al. |

(56) References Cited

U.S. PATENT DOCUMENTS

| | | |
|---|---|---|
| 6,607,487 B2 | 8/2003 | Chang et al. |
| 6,640,128 B2 | 10/2003 | Vilsmeier et al. |
| 6,648,896 B2 | 11/2003 | Overes et al. |
| 6,679,916 B1 | 1/2004 | Frankie et al. |
| 6,685,655 B2 | 2/2004 | DeMayo |
| 6,685,711 B2 | 2/2004 | Axelson et al. |
| 6,711,431 B2 | 3/2004 | Sarin et al. |
| 6,712,824 B2 | 3/2004 | Millard et al. |
| 6,715,213 B2 | 4/2004 | Richter |
| 6,725,080 B2 | 4/2004 | Melkent et al. |
| 6,725,173 B2 | 4/2004 | An |
| 6,743,235 B2 | 6/2004 | Rao |
| 6,770,078 B2 | 8/2004 | Bonutti |
| 6,786,877 B2 | 9/2004 | Foxlin |
| 6,802,864 B2 | 10/2004 | Tornier |
| 6,820,025 B2 | 11/2004 | Bachmann et al. |
| 6,827,723 B2 | 12/2004 | Carson |
| 6,917,827 B2 | 7/2005 | Kienzle, III |
| 6,923,817 B2 | 8/2005 | Carson et al. |
| 6,928,742 B2 | 8/2005 | Broers et al. |
| 6,947,783 B2 | 9/2005 | Immerz |
| 6,986,181 B2 | 1/2006 | Murphy et al. |
| 6,997,882 B1 | 2/2006 | Parker et al. |
| 7,007,699 B2 | 3/2006 | Martinelli et al. |
| 7,021,140 B2 | 4/2006 | Perkins |
| 7,027,477 B2 | 4/2006 | Sutter et al. |
| 7,037,310 B2 | 5/2006 | Murphy |
| 7,048,741 B2 | 5/2006 | Swanson |
| 7,089,148 B1 | 8/2006 | Bachmann et al. |
| 7,094,241 B2 | 8/2006 | Hodorek et al. |
| 7,104,998 B2 | 9/2006 | Yoon et al. |
| 7,105,028 B2 | 9/2006 | Murphy |
| 7,194,295 B2 | 3/2007 | Vilsmeier |
| 7,209,776 B2 | 4/2007 | Leitner |
| 7,219,033 B2 | 5/2007 | Kolen |
| 7,273,500 B2 | 9/2007 | Williamson |
| 7,331,932 B2 | 2/2008 | Leitner |
| 7,344,541 B2 | 3/2008 | Haines et al. |
| 7,392,076 B2 | 6/2008 | Moctezuma de la Barrera |
| 7,396,357 B2 | 7/2008 | Tornier et al. |
| 7,444,178 B2 | 10/2008 | Goldbach |
| 7,468,075 B2 | 12/2008 | Lang et al. |
| 7,468,077 B2 | 12/2008 | Rochetin |
| 7,497,029 B2 | 3/2009 | Plassky et al. |
| 7,520,880 B2 | 4/2009 | Claypool et al. |
| 7,547,307 B2 | 6/2009 | Carson et al. |
| 7,559,931 B2 * | 7/2009 | Stone .................... A61B 34/20 606/91 |
| 7,578,821 B2 | 8/2009 | Fisher et al. |
| 7,611,520 B2 | 11/2009 | Broers et al. |
| 7,611,522 B2 | 11/2009 | Gorek |
| 7,621,920 B2 | 11/2009 | Claypool et al. |
| 7,623,902 B2 | 11/2009 | Pacheco |
| 7,726,564 B2 | 6/2010 | Goldbach |
| 7,776,098 B2 | 8/2010 | Murphy |
| 7,831,292 B2 | 11/2010 | Quaid et al. |
| 7,834,847 B2 | 11/2010 | Boillot et al. |
| 7,846,092 B2 | 12/2010 | Murphy |
| 7,857,821 B2 | 12/2010 | Couture et al. |
| 7,885,705 B2 | 2/2011 | Murphy |
| 7,970,174 B2 | 6/2011 | Goldbach |
| 8,057,479 B2 | 11/2011 | Stone |
| 8,057,482 B2 | 11/2011 | Stone |
| 8,078,254 B2 | 12/2011 | Murphy |
| 8,118,815 B2 | 2/2012 | van der Walt |
| 8,241,296 B2 | 8/2012 | Wasielewski |
| 8,265,790 B2 | 9/2012 | Amiot et al. |
| 8,267,938 B2 | 9/2012 | Murphy |
| 8,277,455 B2 | 10/2012 | Couture et al. |
| 8,282,685 B2 | 10/2012 | Rochetin et al. |
| 8,355,773 B2 | 1/2013 | Leitner et al. |
| 8,412,308 B2 | 4/2013 | Goldbach |
| 8,421,854 B2 | 4/2013 | Zerkin |
| 8,446,473 B2 | 5/2013 | Goldbach |
| 8,512,346 B2 | 8/2013 | Couture |
| 8,551,108 B2 | 10/2013 | Pelletier et al. |
| 8,588,892 B2 | 11/2013 | Hladio et al. |
| 8,690,888 B2 | 4/2014 | Stein et al. |
| 8,718,820 B2 | 5/2014 | Amiot et al. |
| 8,734,432 B2 | 5/2014 | Tuma et al. |
| 8,764,758 B2 | 7/2014 | Echeverri |
| 8,888,786 B2 | 11/2014 | Stone |
| 8,911,447 B2 | 12/2014 | van der Walt et al. |
| 8,974,467 B2 | 3/2015 | Stone |
| 8,974,468 B2 | 3/2015 | Borja |
| 8,998,910 B2 | 4/2015 | Borja et al. |
| 9,044,218 B2 | 6/2015 | Young |
| 9,192,392 B2 | 11/2015 | van der Walt et al. |
| 9,262,802 B2 | 2/2016 | Aghazadeh |
| 9,271,756 B2 | 3/2016 | van der Walt et al. |
| 9,339,226 B2 | 5/2016 | van der Walt et al. |
| 9,375,178 B2 | 6/2016 | Aghazadeh |
| 9,456,769 B2 | 10/2016 | Stein et al. |
| 9,549,742 B2 | 1/2017 | Berend et al. |
| 9,572,586 B2 | 2/2017 | van der Walt et al. |
| 9,649,160 B2 | 5/2017 | van der Walt et al. |
| 9,775,725 B2 | 10/2017 | van der Walt et al. |
| 9,855,075 B2 | 1/2018 | van der Walt et al. |
| 9,931,059 B2 | 4/2018 | Borja |
| 10,206,714 B2 | 2/2019 | van der Walt et al. |
| 10,238,510 B2 | 3/2019 | van der Walt et al. |
| 10,321,852 B2 | 6/2019 | Borja |
| 10,363,149 B2 | 7/2019 | van der Walt et al. |
| 2002/0077540 A1 | 6/2002 | Kienzie, III |
| 2002/0103610 A1 | 8/2002 | Bachmann et al. |
| 2002/0107522 A1 | 8/2002 | Picard et al. |
| 2002/0133175 A1* | 9/2002 | Carson .................... A61B 90/36 606/130 |
| 2002/0198451 A1 | 12/2002 | Carson |
| 2003/0019294 A1 | 1/2003 | Richter |
| 2003/0069591 A1 | 4/2003 | Carson et al. |
| 2003/0093080 A1 | 5/2003 | Brown et al. |
| 2003/0105470 A1 | 6/2003 | White |
| 2003/0120282 A1 | 6/2003 | Scouten et al. |
| 2003/0163142 A1 | 8/2003 | Paltieli et al. |
| 2003/0181919 A1 | 9/2003 | Gorek |
| 2003/0184297 A1 | 10/2003 | Jakab |
| 2003/0199882 A1 | 10/2003 | Gorek |
| 2003/0204965 A1 | 11/2003 | Hennessey |
| 2003/0229356 A1 | 12/2003 | Dye |
| 2004/0006393 A1 | 1/2004 | Burkinshaw |
| 2004/0019382 A1 | 1/2004 | Amirouche et al. |
| 2004/0034313 A1 | 2/2004 | Leitner |
| 2004/0039396 A1 | 2/2004 | Couture et al. |
| 2004/0068260 A1 | 4/2004 | Cossette et al. |
| 2004/0087958 A1 | 5/2004 | Myers et al. |
| 2004/0087962 A1 | 5/2004 | Gorek |
| 2004/0097952 A1 | 5/2004 | Sarin et al. |
| 2004/0102792 A1 | 5/2004 | Sarin et al. |
| 2004/0106916 A1 | 6/2004 | Quaid et al. |
| 2004/0147926 A1 | 7/2004 | Iversen |
| 2004/0149036 A1 | 8/2004 | Foxlin et al. |
| 2004/0152970 A1 | 8/2004 | Hunter et al. |
| 2004/0153066 A1 | 8/2004 | Coon et al. |
| 2004/0153079 A1 | 8/2004 | Tsougarakis et al. |
| 2004/0181144 A1 | 9/2004 | Cinquin et al. |
| 2004/0201857 A1 | 10/2004 | Foxlin |
| 2004/0230197 A1 | 11/2004 | Tornier et al. |
| 2004/0243148 A1 | 12/2004 | Wasielewski |
| 2005/0021037 A1 | 1/2005 | McCombs et al. |
| 2005/0021044 A1 | 1/2005 | Stone et al. |
| 2005/0107799 A1 | 5/2005 | Graf et al. |
| 2005/0113846 A1 | 5/2005 | Carson |
| 2005/0149040 A1 | 7/2005 | Haines et al. |
| 2005/0197814 A1 | 9/2005 | Aram et al. |
| 2005/0209605 A1 | 9/2005 | Grimm et al. |
| 2005/0222574 A1 | 10/2005 | Giordano et al. |
| 2005/0234332 A1 | 10/2005 | Murphy |
| 2005/0251026 A1 | 11/2005 | Stone |
| 2005/0251148 A1 | 11/2005 | Friedrich |
| 2006/0009780 A1 | 1/2006 | Foley et al. |
| 2006/0015018 A1 | 1/2006 | Jutras et al. |
| 2006/0015120 A1 | 1/2006 | Richard et al. |
| 2006/0020177 A1 | 1/2006 | Seo et al. |

(56) References Cited

U.S. PATENT DOCUMENTS

| | | |
|---|---|---|
| 2006/0064105 A1 | 3/2006 | Raistrick et al. |
| 2006/0084977 A1 | 4/2006 | Lieberman |
| 2006/0089657 A1 | 4/2006 | Broers et al. |
| 2006/0094958 A1 | 5/2006 | Marquart et al. |
| 2006/0122491 A1 | 6/2006 | Murray et al. |
| 2006/0142656 A1 | 6/2006 | Malackowski et al. |
| 2006/0142657 A1 | 6/2006 | Quaid et al. |
| 2006/0161051 A1 | 7/2006 | Terrill-Grisoni et al. |
| 2006/0217733 A1 | 9/2006 | Plassky et al. |
| 2006/0217734 A1 | 9/2006 | Sanford et al. |
| 2006/0241639 A1 | 10/2006 | Kuczynski et al. |
| 2006/0270949 A1 | 11/2006 | Mathie et al. |
| 2006/0282023 A1 | 12/2006 | Leitner |
| 2007/0032748 A1 | 2/2007 | McNeil et al. |
| 2007/0043287 A1 | 2/2007 | Degraaf |
| 2007/0043375 A1 | 2/2007 | Anissian |
| 2007/0073296 A1 | 3/2007 | Panchbhavi |
| 2007/0100346 A1 | 5/2007 | Wyss et al. |
| 2007/0162142 A1 | 7/2007 | Stone |
| 2007/0179626 A1 | 8/2007 | de la Barrera et al. |
| 2007/0179628 A1 | 8/2007 | Rochetin |
| 2007/0219559 A1 | 9/2007 | Heavener et al. |
| 2007/0219561 A1 | 9/2007 | Lavallee et al. |
| 2007/0226986 A1 | 10/2007 | Park et al. |
| 2007/0249967 A1 | 10/2007 | Buly et al. |
| 2007/0270718 A1 | 11/2007 | Rochetin et al. |
| 2007/0270973 A1 | 11/2007 | Johnson et al. |
| 2007/0287911 A1 | 12/2007 | Haid et al. |
| 2008/0039868 A1 | 2/2008 | Tuemmler et al. |
| 2008/0058945 A1 | 3/2008 | Hajaj et al. |
| 2008/0071195 A1 | 3/2008 | Cuellar et al. |
| 2008/0103509 A1 | 5/2008 | Goldbach |
| 2008/0162074 A1 | 7/2008 | Schneider |
| 2008/0183179 A1 | 7/2008 | Siebel et al. |
| 2008/0195109 A1 | 8/2008 | Hunter et al. |
| 2008/0202200 A1 | 8/2008 | West |
| 2008/0211768 A1 | 9/2008 | Breen et al. |
| 2008/0243127 A1 | 10/2008 | Lang et al. |
| 2008/0249394 A1 | 10/2008 | Giori et al. |
| 2008/0262812 A1 | 10/2008 | Arata et al. |
| 2008/0275451 A1 | 11/2008 | McAllister et al. |
| 2008/0281328 A1 | 11/2008 | Lang et al. |
| 2008/0285805 A1 | 11/2008 | Luinge et al. |
| 2009/0000626 A1 | 1/2009 | Quaid et al. |
| 2009/0000627 A1 | 1/2009 | Quaid et al. |
| 2009/0012532 A1 | 1/2009 | Quaid et al. |
| 2009/0040224 A1 | 2/2009 | Igarashi et al. |
| 2009/0076507 A1 | 3/2009 | Claypool et al. |
| 2009/0076519 A1 | 3/2009 | Iversen |
| 2009/0088753 A1 | 4/2009 | Aram et al. |
| 2009/0138019 A1 | 5/2009 | Wasielewski |
| 2009/0171370 A1 | 7/2009 | Yoon et al. |
| 2009/0209884 A1 | 8/2009 | Van Vorhis et al. |
| 2009/0216247 A1 | 8/2009 | Collette |
| 2009/0216285 A1 | 8/2009 | Ek |
| 2009/0234360 A1 | 9/2009 | Alexander |
| 2009/0247863 A1 | 10/2009 | Proulx et al. |
| 2009/0248044 A1 | 10/2009 | Amiot et al. |
| 2009/0264737 A1 | 10/2009 | Haechler et al. |
| 2009/0270864 A1 | 10/2009 | Poncet |
| 2009/0270865 A1 | 10/2009 | Poncet et al. |
| 2009/0270868 A1 | 10/2009 | Park et al. |
| 2009/0270869 A1 | 10/2009 | Colquhoun et al. |
| 2009/0270874 A1 | 10/2009 | Santarella et al. |
| 2009/0270875 A1 | 10/2009 | Poncet |
| 2009/0270928 A1 | 10/2009 | Stone et al. |
| 2009/0276054 A1 | 11/2009 | Clifford et al. |
| 2009/0281545 A1 | 11/2009 | Stubbs |
| 2009/0289806 A1 | 11/2009 | Thornberry |
| 2009/0292227 A1 | 11/2009 | Scholten et al. |
| 2009/0299416 A1 | 12/2009 | Haenni et al. |
| 2009/0299483 A1 | 12/2009 | Amirouche et al. |
| 2009/0306679 A1 | 12/2009 | Murphy |
| 2009/0312973 A1 | 12/2009 | Hatlestad et al. |
| 2009/0318836 A1 | 12/2009 | Stone et al. |
| 2009/0318930 A1 | 12/2009 | Stone et al. |
| 2009/0318931 A1 | 12/2009 | Stone et al. |
| 2009/0324078 A1 | 12/2009 | Wu et al. |
| 2010/0016705 A1 | 1/2010 | Stone |
| 2010/0023018 A1 | 1/2010 | Theofilos |
| 2010/0063509 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0100011 A1 | 4/2010 | Roche |
| 2010/0100154 A1 | 4/2010 | Roche |
| 2010/0113980 A1 | 5/2010 | Herr et al. |
| 2010/0121334 A1 | 5/2010 | Couture et al. |
| 2010/0137871 A1 | 6/2010 | Borja |
| 2010/0153081 A1 | 6/2010 | Bellettre et al. |
| 2010/0179605 A1 | 7/2010 | Branch et al. |
| 2010/0182914 A1 | 7/2010 | DelRegno et al. |
| 2010/0192662 A1 | 8/2010 | Yanni |
| 2010/0198067 A1 | 8/2010 | Mahfouz et al. |
| 2010/0198275 A1 | 8/2010 | Chana et al. |
| 2010/0204551 A1 | 8/2010 | Roche |
| 2010/0204575 A1 | 8/2010 | Roche et al. |
| 2010/0204955 A1 | 8/2010 | Roche et al. |
| 2010/0211077 A1 | 8/2010 | Couture et al. |
| 2010/0239996 A1 | 9/2010 | Ertl |
| 2010/0249533 A1 | 9/2010 | Pierce et al. |
| 2010/0249534 A1 | 9/2010 | Pierce et al. |
| 2010/0249535 A1 | 9/2010 | Pierce et al. |
| 2010/0249659 A1 | 9/2010 | Sherman et al. |
| 2010/0249665 A1 | 9/2010 | Roche |
| 2010/0249787 A1 | 9/2010 | Roche |
| 2010/0249788 A1 | 9/2010 | Roche |
| 2010/0249790 A1 | 9/2010 | Roche |
| 2010/0249791 A1 | 9/2010 | Roche |
| 2010/0250276 A1 | 9/2010 | Pierce et al. |
| 2010/0250284 A1 | 9/2010 | Roche et al. |
| 2010/0250571 A1 | 9/2010 | Pierce et al. |
| 2010/0256504 A1 | 10/2010 | Moreau-Gaudry et al. |
| 2010/0261998 A1 | 10/2010 | Stiehl |
| 2010/0268067 A1 | 10/2010 | Razzaque et al. |
| 2010/0298661 A1 | 11/2010 | McCombie et al. |
| 2010/0324457 A1 | 12/2010 | Bean et al. |
| 2010/0326187 A1 | 12/2010 | Stein |
| 2010/0326194 A1 | 12/2010 | Stein et al. |
| 2010/0326210 A1 | 12/2010 | Stein et al. |
| 2010/0326211 A1 | 12/2010 | Stein |
| 2010/0327848 A1 | 12/2010 | Stein |
| 2010/0327880 A1 | 12/2010 | Stein |
| 2010/0328077 A1 | 12/2010 | Stein |
| 2010/0328098 A1 | 12/2010 | Stein et al. |
| 2010/0331633 A1 | 12/2010 | Stein |
| 2010/0331663 A1 | 12/2010 | Stein |
| 2010/0331679 A1 | 12/2010 | Stein |
| 2010/0331680 A1 | 12/2010 | Stein |
| 2010/0331681 A1 | 12/2010 | Stein et al. |
| 2010/0331682 A1 | 12/2010 | Stein et al. |
| 2010/0331683 A1 | 12/2010 | Stein et al. |
| 2010/0331685 A1 | 12/2010 | Stein et al. |
| 2010/0331687 A1 | 12/2010 | Stein et al. |
| 2010/0331704 A1 | 12/2010 | Stein et al. |
| 2010/0331718 A1 | 12/2010 | Stein |
| 2010/0331733 A1 | 12/2010 | Stein |
| 2010/0331734 A1 | 12/2010 | Stein |
| 2010/0331735 A1 | 12/2010 | Stein |
| 2010/0331736 A1 | 12/2010 | Stein |
| 2010/0331737 A1 | 12/2010 | Stein et al. |
| 2010/0331738 A1 | 12/2010 | Stein et al. |
| 2010/0331894 A1 | 12/2010 | Stein |
| 2010/0332152 A1 | 12/2010 | Stein |
| 2011/0028865 A1 | 2/2011 | Luinge et al. |
| 2011/0032184 A1 | 2/2011 | Roche et al. |
| 2011/0093081 A1 | 4/2011 | Chana et al. |
| 2011/0213275 A1 | 9/2011 | Boos et al. |
| 2011/0218458 A1 | 9/2011 | Valin et al. |
| 2011/0218546 A1 | 9/2011 | De La Fuente Klein et al. |
| 2011/0275957 A1 | 11/2011 | Bhandari |
| 2012/0029389 A1 | 2/2012 | Amiot et al. |
| 2012/0053488 A1 | 3/2012 | Boutin et al. |
| 2012/0053594 A1 | 3/2012 | Pelletier et al. |

(56) References Cited

U.S. PATENT DOCUMENTS

| | | |
|---|---|---|
| 2012/0093377 A1 | 4/2012 | Tsougarakis et al. |
| 2012/0157887 A1 | 6/2012 | Fanson et al. |
| 2012/0172712 A1 | 7/2012 | Bar-Tal |
| 2012/0203140 A1 | 8/2012 | Malchau et al. |
| 2013/0079678 A1 | 3/2013 | Stein et al. |
| 2013/0079679 A1 | 3/2013 | Roche et al. |
| 2013/0079680 A1 | 3/2013 | Stein et al. |
| 2013/0079790 A1 | 3/2013 | Stein et al. |
| 2013/0079791 A1 | 3/2013 | Stein et al. |
| 2013/0079793 A1 | 3/2013 | Stein et al. |
| 2013/0190887 A1 | 7/2013 | Fanson et al. |
| 2013/0274633 A1 | 10/2013 | Hladio et al. |
| 2014/0005673 A1 | 1/2014 | Pelletier et al. |
| 2014/0031672 A1 | 1/2014 | McCaulley et al. |
| 2014/0052149 A1 | 2/2014 | van der Walt et al. |
| 2014/0114179 A1 | 4/2014 | Muller et al. |
| 2014/0134586 A1 | 5/2014 | Stein et al. |
| 2014/0135658 A1 | 5/2014 | Hladio et al. |
| 2014/0135744 A1 | 5/2014 | Stein et al. |
| 2014/0135773 A1 | 5/2014 | Stein et al. |
| 2014/0136143 A1 | 5/2014 | Stein et al. |
| 2014/0182062 A1 | 7/2014 | Aghazadeh |
| 2014/0275940 A1 | 9/2014 | Hladio et al. |
| 2014/0276000 A1 | 9/2014 | Mullaney et al. |
| 2014/0276864 A1 | 9/2014 | Aghazadeh |
| 2014/0303631 A1 | 10/2014 | Thornberry |
| 2014/0330281 A1 | 11/2014 | Aghazadeh |
| 2014/0364858 A1 | 12/2014 | Li et al. |
| 2015/0018718 A1 | 1/2015 | Aghazadeh |
| 2015/0127009 A1 | 5/2015 | Berend et al. |
| 2015/0150569 A1 | 6/2015 | van der Walt et al. |
| 2015/0238204 A1 | 8/2015 | Stone |
| 2015/0272478 A1 | 10/2015 | Borja |
| 2016/0213383 A1 | 7/2016 | van der Walt et al. |
| 2016/0220318 A1 | 8/2016 | Falardeau et al. |
| 2016/0220385 A1 | 8/2016 | Falardeau et al. |
| 2016/0242934 A1 | 8/2016 | van der Walt et al. |
| 2017/0196571 A1 | 7/2017 | Berend et al. |
| 2017/0238946 A1 | 8/2017 | van der Walt et al. |
| 2017/0296203 A1 | 10/2017 | Stone |
| 2017/0296274 A1 | 10/2017 | van der Walt et al. |
| 2018/0153587 A1 | 6/2018 | van der Walt et al. |
| 2018/0168826 A1 | 6/2018 | van der Walt et al. |
| 2018/0193171 A1 | 7/2018 | van der Walt et al. |
| 2018/0206860 A1 | 7/2018 | van der Walt et al. |
| 2018/0296232 A1 | 10/2018 | Nielsen et al. |
| 2018/0296365 A1 | 10/2018 | Nielsen et al. |

FOREIGN PATENT DOCUMENTS

| | | |
|---|---|---|
| CA | 2 537 711 | 8/2007 |
| DE | 4 225 112 | 12/1993 |
| DE | 29704393 | 8/1997 |
| DE | 198 30 359 | 1/2000 |
| EP | 0 557 591 | 9/1993 |
| EP | 0 651 968 | 5/1995 |
| EP | 1 635 705 | 3/2006 |
| EP | 1 817 547 | 4/2012 |
| GB | 2 197 790 | 6/1988 |
| GB | 2 511 885 | 9/2014 |
| JP | 07-184929 | 7/1995 |
| JP | H08-240611 | 9/1996 |
| JP | 2006-314775 | 11/2006 |
| JP | 2006-528496 | 12/2006 |
| JP | 2007-503289 | 2/2007 |
| JP | 2007-534351 | 11/2007 |
| JP | 2008-521574 | 6/2008 |
| JP | 2008-537496 | 9/2008 |
| JP | 2009-511136 | 3/2009 |
| JP | 2011-502626 | 1/2011 |
| WO | WO 99/60939 | 12/1999 |
| WO | WO 2001/030247 | 5/2001 |
| WO | WO 02/000131 | 1/2002 |
| WO | WO 02/17798 | 3/2002 |
| WO | WO 2004/080323 | 9/2004 |
| WO | WO 2004/112610 | 12/2004 |
| WO | WO 2005/006993 | 1/2005 |
| WO | WO 2006/119387 | 11/2006 |
| WO | WO 2007/136784 | 11/2007 |
| WO | WO 2008/073999 | 6/2008 |
| WO | WO 2008/129414 | 10/2008 |
| WO | WO 2009/117833 | 10/2009 |
| WO | WO 2010/011978 | 1/2010 |
| WO | WO 2010/030809 | 3/2010 |
| WO | WO 2011/044273 | 4/2011 |
| WO | WO 2012/006172 | 1/2012 |
| WO | WO 2012/027815 | 3/2012 |
| WO | WO 2012/027816 | 3/2012 |
| WO | WO 2012/082164 | 6/2012 |
| WO | WO 2012/113054 | 8/2012 |
| WO | WO 2013/012561 | 1/2013 |
| WO | WO 2013/169674 | 11/2013 |
| WO | WO 2013/173700 | 11/2013 |
| WO | WO 2013/188960 | 12/2013 |
| WO | WO 2014/028227 | 2/2014 |
| WO | WO 2016/070288 | 5/2016 |
| WO | WO 2016/134168 | 8/2016 |
| WO | WO 2018/169980 | 9/2018 |
| WO | WO 2018/169995 | 9/2018 |

OTHER PUBLICATIONS 510 (k) Summary of Safety and Effectiveness for BrainLAB knee, in 5 pages.

Anderson MD., Kevin, et al., "Computer Assisted Navigation in Total Knee Arthroplasty", The Journal of Arthroplasty, 2005, vol. 20, No. 7, Suppl. 3, in 7 pages.

Ang, et al., An Active Hand-Held Instrument for Enhanced Microsurgical Accuracy, Medical Image Computing and Computer-Assisted Intervention, 2000, vol. 1935, pp. 878-887.

Arnold-Moore, et. al., Architecture of a Content Management Server for XML Document Applications, RMIT Multimedia Database Systems, Royal Melbourne Institute of Technology, Victoria Australia, in 12 pages.

ArthroCAD, Enhancing orthopedic outcomes through optimal alignment, 2012, Pages in 2 pages.

Bae et al., "Computer Assisted Navigation in Knee Arthroplasty", Clinics in Orthopedic Surgery, 2011, vol. 3, pp. 259-267.

Bargren, MD., et al,, Alignment in Total Knee Arthroplasty, Correlated Biomechanical and Clinical Observations, Clinical Orthopaedics and Related Research, Mar. 1, 1983, Issue 173, pp. 178-183, Philadelphia.

Bathis, H. et al., "Alignment in total knee arthroplasty", The Journal of Bone & Joint Surgery (BR), 2004, 86-B, pp. 682-687, British Editorial.

Bhandari, Design and Prototype of a Computer Assisted Surgical Navigation System for Total Knee Replacement Surgery, May 12, 2009, Pages in 294 pages.

Biomet Orthopedics, Inc, Vision Acetabular Surgical Techniques, website brochure, pp. 16 pages.

Biomet Orthopedics, Inc., Universal Ringlock® Acetabular Series, vol. website brochure, pp. 13 pages.

Brainlab, "Position Determination and Calibration in optical tracking systems", FLORENUS the technology merchants, in 2 pages.

Brainlab, "Tracking and imaging in Navigation", FLORENUS, in 2 pages.

Brennan, et al., Quantification of Inertial Sensor-Based 3D Joint Angle Measurement Accuracy Using and Instrumented Gimbal, Gait & Posture, May 23, 2011, vol. 34, pp. 320-323.

Chauhan, et al., Computer-Assisted Knee Arthroplasty Versus a Conventional Jig-Based Technique, The Journal of Bone & Joint Surgery, 2004, vol. 86-B, pp. 372-377.

Cutti, et al., Motion Analysis of the Upper-Limb Based on Inertial Sensors: Part 1—Protocol Description, Journal of Biomechanics, Jan. 1, 2007, vol. 40, pp. S250.

Decking, MD., et al., Leg Axis After Computer-Navigated Total Knee Arthroplasty, The Journal of Arthroplasty, 2005, vol. 20, Issue 3, pp. 282-288.

(56) References Cited

OTHER PUBLICATIONS

Depuy, Johnson & Johnson, Co. Summit Cemented Hip System, website brochure, pp. 21 pages.
De Momi, et al., "In-vitro experimental assessment of a new robust algorithm for hip joint centre estimation", Journal of Biomechanics, Feb. 26, 2009, vol. 42, pp. 989-995.
Digioia III, MD., et al., "Comparison of a Mechanical Acetabular Alignment Guide with Computer Placement of the Socket", The Journal of Arthroplasty, Apr. 2002, vol. 17, No. 3, in 6 pages.
Eric Foxlin, Chapter 7. Motion Tracking Requirements and Technologies, Handbook of Virtual Environment Technology, 2002, vol. Kay Stanney, Ed., Issue Lawrence Erlbaum Ass.
Favre, et al., 3D Evaluation of the Knee Joint Using Ambulatory System: Application to ACL-Deficient Knees, Journal of Biomechanics, Jan. 1, 2007, vol. 40, pp. S251.
Favre, et al., A New Ambulatory System for Comparative Evaluation of the Three-Dimensional Knee Kinematics, Applied to Anterior Cruciate Ligament Injuries, Knee Surgery, Sports Traumatology, Arthroscopy, Jan. 19, 2006, vol. 14, pp. 592-604.
Favre, et al., Ambulatory Measurement of 3D Knee Joint Angle, Journal of Biomechanics, Jan. 28, 2008, vol. 41, Issue 1029-1035.
Fixed Reference Surgical Technique, SIGMA High Performance Instruments, DePuy Orthopaedics, Inc., 2008, Warsaw, IN, in 52pages.
Ganapathi et al., "Limb Length and Femoral Offset Reconstruction During THA Using CT-Free Computer Navigation", The Journal of Bone and Joint Surgery, 2009, vol. 91-B, Supplement III, p. 399.
Goniometer, AllHeart.com, 2004, website: http://allheart.com/allheart, (1 page).
Haaker et al., "Computer-Assisted Navigation Increases Precision of Component Placement in Total Knee Arthroplasty", Clinical Orthopaedics and Related Research, Apr. 2005, vol. 433, pp. 152-159.
Hofstetter, Ph.D., et al., "Computer-Assisted Fluoroscopy-Based Reduction of Femoral Fractures and Antetorsion Correction", Computer Aided Surgery, 2000, vol. 5, pp. 311-325, Wiley-Liss, Inc.
Hsieh, Pang-Hsin, et al., "Image-guided periacetabular osteotomy: computer-assisted navigation compared with the conventional technique: A randomized study of 36 patients followed for 2 years", Acta Orthopaedica, Aug. 1, 2006, 77:4, pp. 591-597.
iASSIST Knee, Surgical Technique, Zimmer, Inc., 2012.
International Preliminary Report for Application No. PCT/US2004/018244, dated Dec. 13, 2005, in 11 pages.
International Search Report and Written Opinion issued in PCT Application No. PCT/US2013/039770, dated Sep. 25, 2013.
International Preliminary Report on Patentability issued in PCT Application No. PCT/US2013/039770, dated Nov. 11, 2014.
International Search Report and Written Opinion issued in PCT Application No. PCT/US2013/041556, dated Sep. 13, 2013.
International Preliminary Report on Patentability issued in PCT Application No. PCT/US2013/041556, dated Nov. 18, 2014.
International Search Report and Written Opinion issued in PCT Application No. PCT/US2013/053182, dated Nov. 11, 2013.
International Search Report for Application No. PCT/US2004/018244, dated Feb. 15, 2005, in 4 pages.
International Search Report for International Application No. PCT/US2009/051769 dated Nov. 19, 2009, in 11 pages.
International Search Report for International Application No. PCT/US2009/051769 dated Nov. 19, 2009, in 3 pages.
International Search Report for International Application No. PCT/US2011/022162, dated Jun. 16, 2011, in 4 pages.
International Search Report for International Application No. PCT/US2009/056553, dated Nov. 4, 2009, in 12 pages.
International Preliminary Report on Patentability issued in PCT Application No. PCT/US2013/053182, dated Feb. 17, 2015, in 10 pages.
International Search Report and Written Opinion issued in International Application No. PCT/US2016/018508, dated Jun. 22, 2016, in 19 pages.
Jenny, et al., Computer-Assisted Implantation of Total Knee Prosthesis: A Case-Control Comparative Study with Classical Instrumentation, Computer Aided Surgery, 2001, vol. 6, pp. 217-220.
Konyves et al., "The importance of leg length discrepancy after total hip arthroplasty", The Journal of Bone & Joint Surgery (BR), Feb. 2005, vol. 87-B, No. 2, pp. 155-157.
Leenders, MD., et al., "Reduction in Variability of Acetabular Cup Abduction Using Computer Assisted Surgery: A Prospective and Randomized Study", Computer Aided Surgery, 2002, vol. 7, pp. 99-106.
Leung, et al., Intraobserver Errors in Obtaining Visually Selected Anatomic Landmarks During Registration Process in Nonimage-based Navigation-assisted Total Knee Arthroplasty, The Journal of Arthroplasty, 2005, vol. 20, Issue 5, pp. 591-601.
Liebergall, Meir, et al., "Computerized Navigation for the Internal Fixation of Femoral Neck Fractures", The Journal of Bone & Joint Surgery Am, 2006, vol. 88, pp. 1748-1754.
Longo, et al., MIKA Surgical Technique, DJO Surgical, 2008, Austin Texas in 14 pages.
Luinge, Inertial Sensing of Human Movement, Twente University Press, Feb. 15, 1973, Pages in 88 pages.
MacKenzie, et al., A Two-Ball Mouse Affords Three Degrees of Freedom, Extended Abstracts of the CHI '97 Conference on Human Factors in Compounding Systems (as printed from the internet on Jun. 13, 2012 URL: http://www.yorku.ca/mack/CHI97a.htm), 1997, pp. 303-304.
Medical Research Ltd, Clinical Goniometer, http://www.mie-uk.com/Gonio, 1997, pp. 1 page.
Minimally Invasive TKA Genesis II Anterior Cut First, Surgical Technique, Smith & Nephew, Nov. 2003, Memphis TN, in 16 pages.
Noble et al., "Computer Simulation: How Can it Help the Surgeon Optimize Implant Position?", Clinical Orthopaedics and Related Research, Dec. 2003, vol. 417, pp. 242-252.
Parratte, Sebastien, et al., "Validation and Usefulness of a Computer-Assisted Cup-Positioning System in Total Hip Arthroplasty. A Prospective, Randomized, Controlled Study", The Journal of Bone & Joint Surgery Am, 2007, vol. 89, pp. 494-499.
Perseus Intelligent Cutting Guide, Orthokey, Product Guide, in 8 pages.
Perseus Intelligent Cutting Guide, Smart Instruments for Knee Arthroplasty, Orthokey, in 2 pages.
Ritter, M.D., et al., Postoperative Alignment of Total Knee Replacement, Its Effect on Survival, Clinical Orthopaedics and Related Research, Feb. 1, 1994, Issue 299, pp. 153-156, Philadelphia.
Rocon, et al., Application of Inertial Sensors and Rehabilitation Robotics, Rehabilitation Robotics 2007, Jun. 1, 2007, pp. 145-150.
Sacks-Davis et. al., Atlas: A nested Relational Database System for Text Applications, IEEE Transations on Knowledge and Data Engineering, v.7, n.3, Jun. 1995, pp. 454-470.
Schep, et al., "Computer assisted orthopaedic and trauma surgery State of the art and future perspectives", Injury Int. J. Care Injured 34, (website: www.elsevier.com/locate/injury), 2003 pp. 299-306.
Scott, M.S., et al., P.F.C. Sigma Knee System, Primary Surgical Technique Part 1 of 2, DePuy International Ltd., 2003, England, (up to p. 44), in 48 pages.
Scott, M.S., et al., P.F.C. Sigma Knee System, Primary Surgical Technique Part 2 of 2, DePuy International Ltd., 2003, England, Part A (up to p. 74), in 31 pages. (This reference was split in two due to size exceeding over 25MB).
Scott, M.S., et al., P.F.C. Sigma Knee System, Primary Surgical Technique Part 2 of 2, DePuy International Ltd., 2003, England, Part B (up to p. 104), in 31 pages. (This reference was split in two due to size exceeding over 25MB).
Sikorski et al., "Computer-Assisted Orthopaedic Surgery: Do We Need CAOS?", The Journal of Bone & Joint Surgery (BR), Apr. 2003, vol. 85-B, No. 3, pp. 319-323.
Slomczykowski, et al., "Novel Computer-Assisted Fluoroscopy System for Intraoperative Guidance: Feasibility Study for Distal Locking of Femoral Nails", Journal of Orthopaedic Trauma, 2001, vol. 15, No. 2, pp. 122-131, Lippincott Williams & Wilkins, Inc., Philadelphia.

(56) References Cited

OTHER PUBLICATIONS

Stulberg, et al., Computer-Assisted Total Knee Replacement Arthroplasty, Operative Techniques in Orthopaedics, Jan. 2000, vol. 10, Issue 1, pp. 25-39.
The Academy of Orthopaedic Surgeons, Academy News, http://www.aaos.org/wordhtml/2001news/b6-01.htm, Mar. 1, 2001, pp. 1 page.
Tilt Sensors: High Accuracy, Digital Series, Crossbow Technology, Inc., pp. 32-35.
Upadhyay et al., "Medical Malpractice in Hip and Knee Arthroplasty", The Journal of Arthroplasty, 2007, vol. 22, No. 6, Suppl. 2, pp. 2-7.
Visser, et al., 3D Analysis of Upper Body Movements in Bilateral Amputee Gait Using Inertial Sensors, Journal of Biomechanics, Jan. 1, 2007, vol. 40, Issue S509.
Wentzensen et al., "Image-based hip navigation", International Orthopaedics (SICOT), 2003, vol. 27 (Suppl. 1), pp. S43-S46.
Wolfstadt et al., "An intelligent instrument for improved leg length and hip offset accuracy in total hip arthroplasty", Abstract Only.
Written Opinion for International Application No. PCT/US2009/051769, dated Nov. 19, 2009, in 7 pages.
Written Opinion for International Application No. PCT/US2011/022162, dated Jun. 16, 2011, in 9 pages.
Written Opinion of the ISR for Application No. PCT/US2004/018244, dated Mar. 14, 2005, in 10 pages.
Wylde et al., "Prevalence and functional impact of patient-perceived leg length discrepancy after hip replacement", International Orthopaedics, 2009, vol. 33, pp. 905-909.
Wylde et al., "Patient-perceived leg length discrepancy after total hip replacement: prevalence and impact on functional outcome", International Orthopaedics, 2008, vol. 24, No. 2, pp. 210-216.
Zheng et al., "Technical Principles of Computer Assisted Orthopaedic Surgery", Suomen Ortopedia ja Traumatologia, Feb. 2008, vol. 31, pp. 135-147.
Zhou, et al., Use of Multiple Wearable Inertial Sensors in Upper Limb Motion Tracking, Medical Engineering & Physics, Jan. 1, 2008, vol. 30, pp. 123-133.
Zimmer NexGen Flexion Balancing Instruments, Surgical Technique, 2007, www.zimmer.com, in 44 pages.
Zorman, David, et al., "Computer-assisted total knee arthroplasty: comparative results in a preliminary series of 72 cases", ActaOrthop. Belg., 2005, 71, pp. 696-702.

\* cited by examiner

F3- Remove Distal Guide

F4 - Place in Extension

SYSTEMS AND METHODS FOR JOINT REPLACEMENT

CROSS-REFERENCE TO RELATED APPLICATIONS

This application is a continuation of U.S. patent application Ser. No. 15/716,971, filed Sep. 27, 2017, which is a continuation of U.S. patent application Ser. No. 15/052,071, filed Feb. 24, 2016, which is a continuation of U.S. patent application Ser. No. 13/398,712, filed Feb. 16, 2012, which is a continuation of U.S. patent application Ser. No. 13/115,065, filed May 24, 2011, the entire contents of each is incorporated in its entirety by reference herein. U.S. patent application Ser. No. 13/115,065 is a continuation-in-part of U.S. patent application Ser. No. 12/509,388, filed Jul. 24, 2009, the entire contents of which is incorporated in its entirety by reference herein, and is also a continuation-in-part of U.S. patent application Ser. No. 13/011,815, filed Jan. 21, 2011, which claims benefit under 35 U.S.C. § 119(e) to U.S. Provisional Patent Application No. 61/297,215, filed Jan. 21, 2010, U.S. Provisional Patent Application No. 61/297,212, filed Jan. 21, 2010, and U.S. Provisional Patent Application No. 61/369,390, filed Jul. 30, 2010, each of which is incorporated in its entirety by reference herein.

BACKGROUND OF THE INVENTIONS

Field of the Inventions

The present application is directed to systems and methods for joint replacement, in particular to systems and methods for knee joint replacement that utilize a surgical orientation device or devices.

Description of the Related Art

Joint replacement procedures, including knee joint replacement procedures, are commonly used to replace a patient's joint with a prosthetic joint component or components. Such procedures often use a system or systems of surgical tools and devices, including but not limited to cutting guides (e.g. cutting blocks) and surgical guides, to make surgical cuts along a portion or portions of the patient's bone(s).

Current systems and methods often use expensive, complex, bulky, and/or massive computer navigation systems which require a computer or computers, as well as three dimensional imaging, to track a spatial location and/or movement of a surgical instrument or landmark in the human body. These systems are used generally to assist a user to determine where in space a tool or landmark is located, and often require extensive training, cost, and room. Where such complex and costly systems are not used, simple methods are used, such as "eyeballing" the alignment of rods with anatomical features, including leg bones. These simple methods are not sufficiently accurate to reliably align and place prosthetic implant components and the bones to which such components are attached.

SUMMARY OF THE INVENTIONS

Accordingly, there is a lack of devices, systems and methods that can be used to accurately position components of prosthetic joints without overly complicating the procedures, crowding the medical personnel, and/or burdening the physician or health-care facility with the great cost of complex navigation systems.

Therefore, in accordance with at least one embodiment, a femoral jig assembly can comprise a distal guide assembly configured to be positioned adjacent to distal condyles of a femur, a microblock assembly releasably attachable to the distal guide assembly, the microblock assembly comprising a microblock member and a translating member configured to be moved relative the microblock member, and a cutting block assembly releasably attachable to the microblock assembly.

In accordance with another embodiment, a surgical orientation system can comprise a surgical orientation device comprising a first portable housing configured to be coupled with a knee bone by way of one or more orthopedic fixtures, a first sensor located within the first housing, the first sensor configured to monitor the orientation of the housing in a coordinate system and to generate a signal corresponding to the orientation of the surgical orientation device relative to the coordinate system, and a display module configured to display an indication of a change in one or more angle measurements relative to the coordinate system based at least in part on the signal, and a reference device comprising, a second portable housing configured to connect to a knee bone by way of one or more orthopedic fixtures, and a second sensor located within the second housing, the second sensor configured to monitor the orientation of the second housing relative to the coordinate system, the second sensor configured to generate orientation data corresponding to the monitored orientation of the reference device. The surgical orientation system can further comprise an orthopedic fixture configured to be connected to a knee bone and with the surgical orientation device and reference sensor such that the surgical orientation device and reference device are separately moveable relative to each other, wherein at least one of the surgical orientation device and reference device is further configured to determine the spatial location of the mechanical axis of the leg.

In accordance with another embodiment, an orthopedic system can comprise a portable surgical orientation device having an associated three-dimensional coordinate reference system and an interactive user interface configured to display one or more angle measurements corresponding to an offset from a flexion-extension angle or a varus-valgus angle of a mechanical axis of a femur, the surgical orientation device having a first sensor, a reference device having a second sensor, wherein each of the first and second sensors have at least one of a three-axis accelerometer and a three-axis gyroscope, at least one of the first and second sensors being configured to monitor an orientation of the surgical orientation device in the three-dimensional coordinate reference system and to generate orientation data corresponding to the monitored orientation of the surgical orientation device. The orthopedic system can further comprise a coupling device, an interface support member, and a femoral jig assembly comprising a microblock assembly and a cutting block assembly, the femoral jig assembly being releasably attachable to the orientation device via the coupling device, the second sensor via the interface support member, and distal condyles of a femur via the microblock assembly.

In accordance with another embodiment, an orthopedic system capable of monitoring orientation within a three-dimensional coordinate reference system can comprise a portable surgical orientation device having a user interface configured to indicate angular displacement of a mechanical axis of a femur in an anterior-posterior plane or in a medial-lateral plane, the surgical orientation device having a first sensor, and a reference device having a second sensor, wherein at least one of the first and second sensors comprises a three-axis accelerometer and a three-axis gyroscope, at least one of the first and second sensors being configured to monitor the orientation of the surgical orientation device in the three-dimensional coordinate reference system and to generate orientation data corresponding to the monitored orientation of the surgical orientation device. The orthopedic system can further comprise a fixture comprising a first member configured to couple with the surgical orientation device, a second member configured to couple with the reference device, and a base member configured to be secured to a portion of a distal femur, wherein at least one of the first member and the second member is movably coupled with the base member.

In accordance with another embodiment, an orthopedic system for monitoring orientation in a three-dimensional coordinate reference system can comprise a base member attachable to a proximal aspect of a tibia, at least one adjustment device connected to and moveable relative to the base member, and at least one probe for referencing a plurality of anatomical landmarks, the anatomical landmarks referencing a mechanical axis of the leg. The at least one adjustment device can be moveable in at least one degree of freedom to orient a cutting guide relative to a proximal feature of the tibia, such that the cutting guide is oriented at a selected angle relative to the mechanical axis. The orthopedic system can further comprise a first orientation device comprising an interactive user interface configured to display one or more angle measurements corresponding to an offset from a posterior slope angle or a varus-valgus angle of the mechanical axis the first orientation device having a first sensor, the first orientation device being coupled to or integrally formed with the at least one adjustment device, and a second orientation device having a second sensor, the second orientation device being coupled to or integrally formed with the base member, wherein each of the first and second sensors have at least one of a three-axis accelerometer and a three-axis gyroscope, at least one of the first and second sensors being configured to monitor orientation of the first orientation device in the three-dimensional coordinate reference system and to generate orientation data corresponding to the monitored orientation of the first orientation device.

In accordance with another embodiment, an implant alignment device can comprise an orthopedic fixture having a base configured to couple with a distal portion of a femur or a proximal portion of a tibia, a moveable portion configured to move relative to the base, and a guide member configured to couple with the moveable portion, a reference device coupled to or integrally formed with the base or moveable portion of the orthopedic fixture, the reference device configured to sense changes in orientation of a long axis of the femur or tibia relative to a fixed reference frame, and a surgical orientation device coupled to or integrally formed with the base or moveable portion of the orthopedic fixture to enable positioning of the guide member in a prescribed orientation relative to the proximal tibia or distal femur.

In accordance with another embodiment, an orientation system can comprise an orthopedic positioning jig comprising a first member and a second member that is movable in two degrees of freedom relative to the first member and that is constrained in one degree of freedom, a first orientation device configured as a tilt meter coupled with the first member and a second orientation device configured as a tilt meter coupled with the second member, the first and second orientation devices operably coupled to indicate angular orientation of a natural or surgically created anatomical feature.

In accordance with another embodiment, a method for performing total knee arthroplasty on a knee joint of a patient can comprise preparing a distal portion of a femur for receiving a knee implant, comprising placing the knee joint in flexion and exposing the distal end of the femur, coupling a first orthopedic fixture to a distal portion of the femur, the first orthopedic fixture comprising a surgical orientation device, the surgical orientation device comprising an orientation sensor and an interactive user interface configured to display an indication of a change in one or more angle measurements corresponding to a flexion-extension angle or a varus-valgus angle of a mechanical axis of the femur, the first orthopedic fixture further comprising a reference device, the reference device comprising a reference sensor. The method can further comprise monitoring the orientation of the reference sensor while swinging the leg to obtain information regarding the location of the mechanical axis of the leg, adjusting a varus/valgus and flexion/extension angle of a portion of the first orthopedic fixture by monitoring the first surgical orientation device and moving the reference device relative to the surgical orientation device, attaching a cutting block to the first orthopedic fixture, the cutting block being oriented relative the adjusted varus/valgus and flexion/extension angle, and resecting the distal end of the femur.

In accordance with another embodiment, a method for performing total knee arthroplasty on a knee joint of a patient can comprise attaching a base member of an orthopedic fixture to a proximal aspect of a tibia such that movement of the tibia produces corresponding movement of the base member, the orthopedic fixture comprising at least one member moveable relative the base member, the moveable member comprising a probe for referencing a plurality of anatomical landmarks, attaching a portable surgical orientation device to the moveable member, the portable surgical orientation device comprising an interactive user interface, the surgical orientation device having a first sensor, attaching a reference device to the base member, the reference device having a second sensor, moving the moveable member and probe to contact anatomical locations on the leg, directing the surgical orientation device to determine the spatial location or orientation of the mechanical axis based on the anatomical locations, and moving the moveable member such that a cutting guide is oriented at a selected angle relative to the mechanical axis.

In accordance with another embodiment, a method for resolving angular orientation can comprise coupling with a bone an orthopedic positioning jig comprising a first member and a second member that is movable in two degrees of freedom and constrained in one degree of freedom, the orthopedic fixture having a cutting guide and a first orientation device configured as a tilt meter coupled with the first member and a second orientation device configured as a tilt meter coupled with the second member, and moving the first member relative to the second member to indicate angular orientation of the cutting guide relative to an axis of interest.

In accordance with another embodiment, a method of preparing for orthopedic surgery can comprise determining the orientation of a mechanical axis of a bone or joint, coupling an orthopedic orientation assembly with an extremity of a patient, the orientation assembly having a positioning device, a reference device and a surgical orientation device coupled with the positioning device, and maintaining an alignment between the reference sensor and the surgical orientation device while moving the surgical orientation device to collect data indicative of orientation.

In accordance with another embodiment, a method of determining an anatomical feature during a knee procedure can comprise coupling an orientation system with a distal aspect of a femur, the orientation system comprising a housing, an orientation sensor disposed within the housing, and a user interface operably coupled with the orientation sensor, interacting with the user interface to begin an analysis of potential sources of error in the orientation system after coupling the orientation system to the distal femoral aspect, and moving the orientation system to collect data indicative of the anatomical feature relevant to the knee procedure.

DETAILED DESCRIPTION OF THE PREFERRED EMBODIMENT

Although certain preferred embodiments and examples are disclosed below, it will be understood by those skilled in the art that the inventive subject matter extends beyond the specifically disclosed embodiments to other alternative embodiments and/or uses of the invention, and to obvious modifications and equivalents thereof. Thus it is intended that the scope of the inventions herein disclosed should not be limited by the particular disclosed embodiments described herein. Thus, for example, in any method or process disclosed herein, the acts or operations making up the method/process may be performed in any suitable sequence, and are not necessarily limited to any particular disclosed sequence. For purposes of contrasting various embodiments with the prior art, certain aspects and advantages of these embodiments are described where appropriate herein. Of course, it is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

In addition, in this description, a "module" includes, but is not limited to, software or hardware components which perform certain tasks. Thus, a module may include object-oriented software components, class components, procedures, subroutines, data structures, segments of program code, drivers, firmware, microcode, circuitry, data, tables, arrays, etc. Those with ordinary skill in the art will also recognize that a module can be implemented using a wide variety of different software and hardware techniques.

The following sections describe in detail systems and methods for a total knee joint replacement procedure. The knee joint often requires replacement in the form of prosthetic components due to strain, stress, wear, deformation, misalignment, and/or other conditions in the joint. Prosthetic knee joint components are designed to replace a distal portion or portions of a femur and/or a proximal portion or portions of a tibia.

Figure 1:
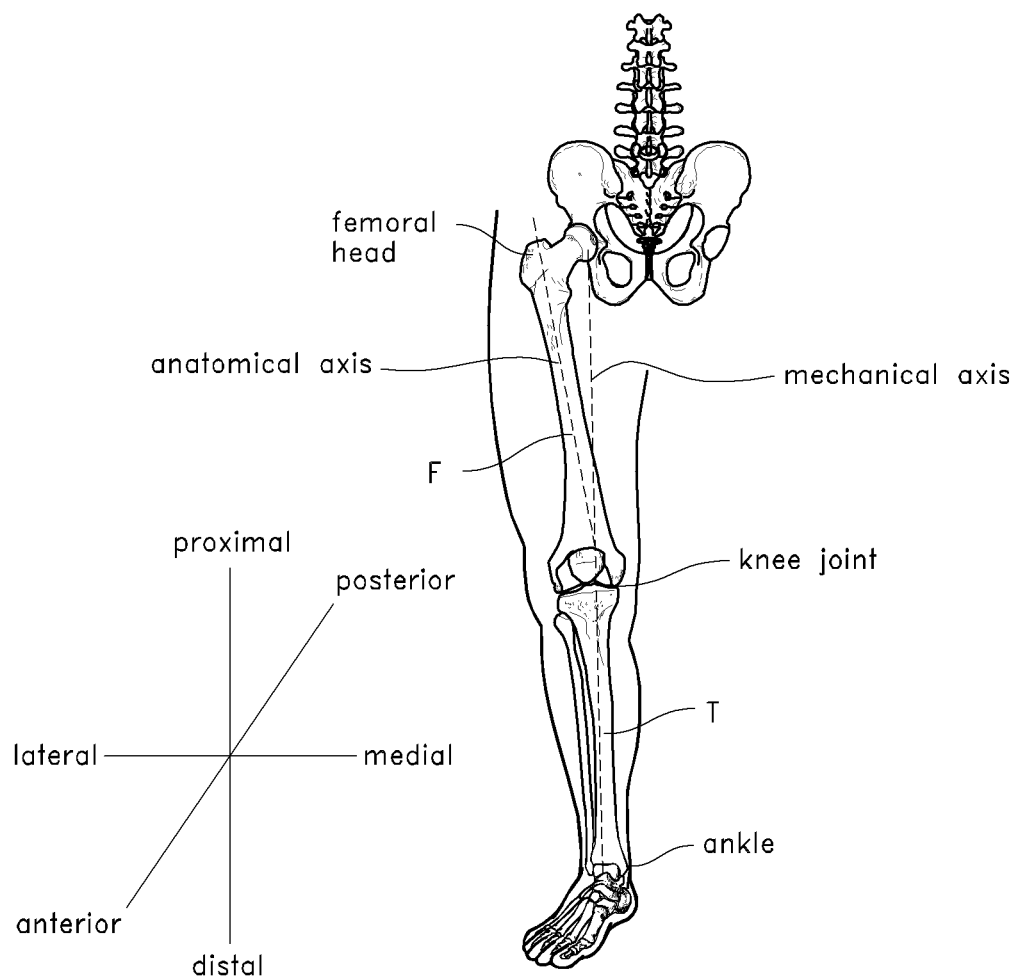
FIG. 1 shows a representation of a human leg, identifying the femoral head, knee joint, femur, tibia, and ankle.

FIG. 1 illustrates a femur F and tibia T, with the distal portion of the femur F and proximal portion of the tibia T forming the knee joint. To provide the reader with the proper orientation of the instruments and to assist in more fully understanding the construction of the instruments, a small chart is included on FIG. 1 and FIG. 33. The charts indicate the general directions—anterior, posterior, medial, and lateral, as well as proximal and distal. These terms relate to the orientation of the knee bones, such as the femur and tibia and will be used in the descriptions of the various instruments consistent with their known medical usage. Additionally, the terms varus/valgus and posterior/anterior are used herein to describe directional movement. Varus/valgus is a broad term as used herein, and includes, without limitation, rotational movement in a medial and/or lateral direction relative to the knee joint shown in FIG. 1 (e.g. right and left in the page). Posterior/anterior is a broad term as used herein, and includes, without limitation, rotational movement in a posterior and/or anterior direction (e.g. in a flexion/extension direction, or into and out of the page) relative to the knee joint shown in FIG. 1.

Prior to replacing the knee joint with prosthetic components, surgical cuts commonly called resections are generally made with a cutting tool or tools along a portion or portions of both the proximal tibia and distal femur. These cuts are made to prepare the tibia and femur for the prosthetic components. After the cuts are made, the prosthetic components can be attached and/or secured to the tibia and femur.

The desired orientation and/or position of these cuts, and of the prosthetic components, can be determined pre-operatively and based, for example, on a mechanical axis running through an individual patient's leg. Once the desired locations of these cuts are determined pre-operatively, the surgeon can use the systems and methods described herein to make the cuts accurately. While the systems and methods are described in the context of a knee joint replacement procedure, the systems and/or their components and methods can similarly be used in other types of medical procedures, including but not limited to shoulder and hip replacement procedures.

I. Overview of Systems and Methods

Figure 2A:
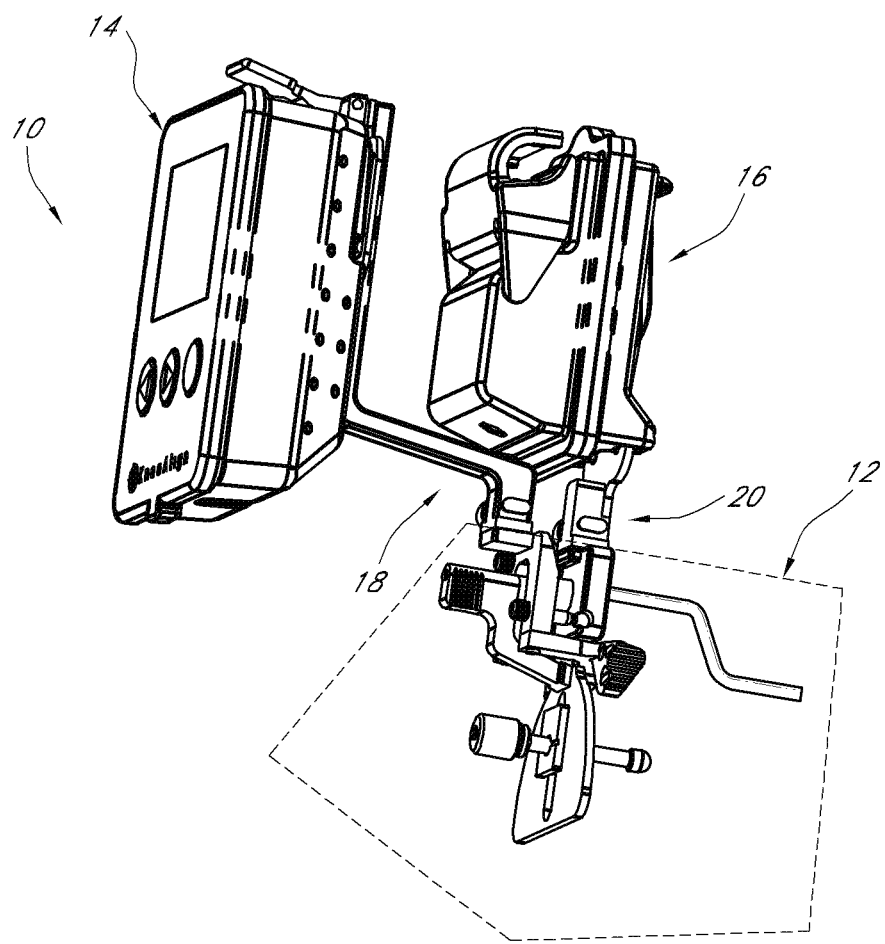
FIG. 2A shows an assembled view of a femoral preparation system that according to one embodiment of the present invention, including an anterior probe.
Figure 2B:
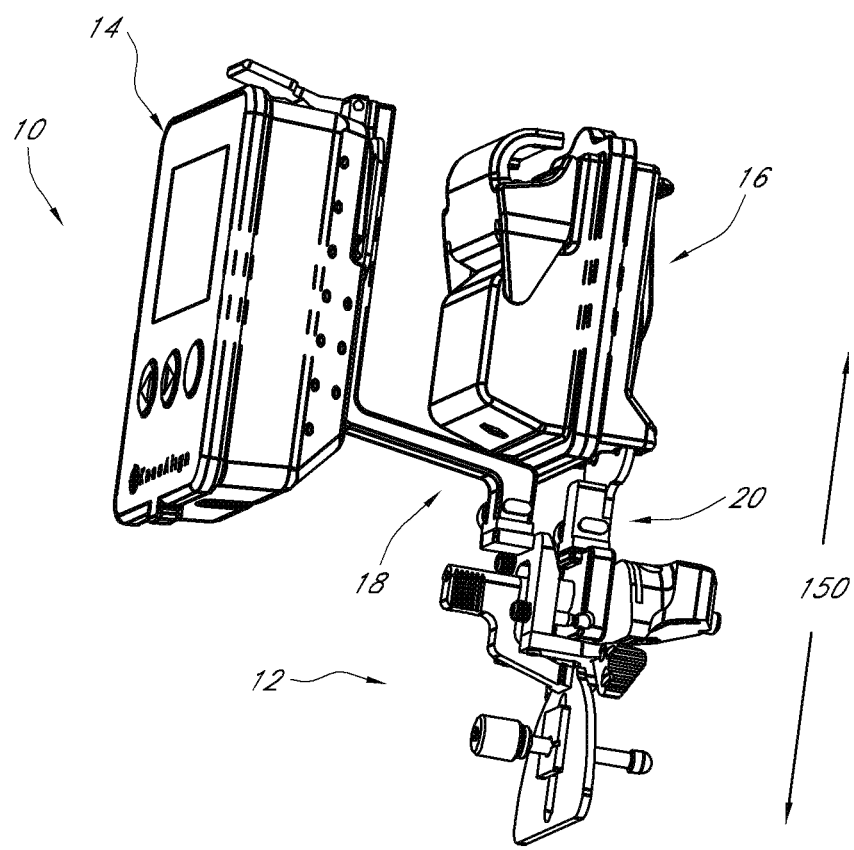
FIG. 2B shows an assembled view of the femoral preparation system shown in FIG. 2A, including a cutting block instead of the anterior probe.
Figure 33:
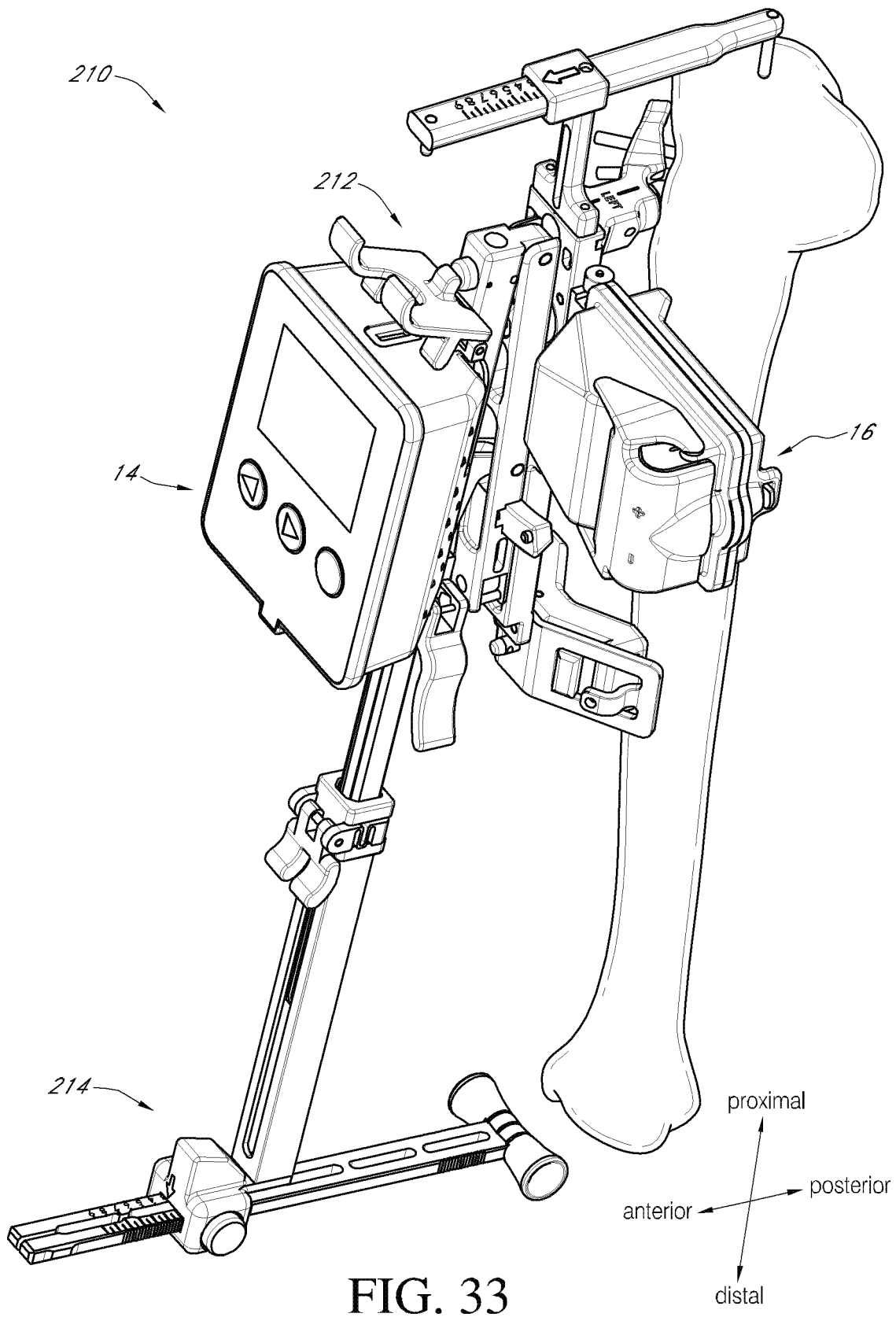
FIG. 33 is an assembled view of a tibial preparation system according to one embodiment.

FIGS. 2A, 2B, and 33 show various systems which can be used in orthopedic procedures, including but not limited to knee joint replacement procedures. The systems can include a femoral preparation system 10, and a tibial preparation system 210. As described below, each of these systems can be embodied in a number of variations with different advantages.

II. Femoral Preparation Systems

With reference to FIGS. 2A and 2B, the femoral preparation system 10 can be used to modify a natural femur with a distal femoral resection, enabling a prosthetic component to be securely mounted upon the distal end of the femur. The femoral preparation system 10 can comprise, for example, a femoral jig assembly 12, a surgical orientation device 14, a reference device 16, a first coupling device 18, and a second coupling device 20.

A. Surgical Orientation Devices & Systems

The surgical orientation device 14 can be used to measure and record the location of anatomical landmarks used in a total knee procedure, such as the location of the mechanical axis of a leg (and femur). "Surgical orientation device" is a broad term and is to be given its ordinary and customary meaning to a person of ordinary skill in the art (i.e. it is not to be limited to a special or customized meaning) and includes, without limitation, any device that can be used to provide orientation information or perform orientation calculations for use in a surgical or other procedure. The mechanical axis of a leg, as defined herein, generally refers to an axial line extending from the center of rotation of a proximal head of a femur (e.g. the center of the femoral head) through, ideally, the approximate center of the knee, to a center, or mid-point, of the ankle (see, for example, FIG. 1). The mechanical axis of the femur is the same axial line extending from the center of rotation of the proximal head of the femur through the center of the distal end of the femur (the center of distal end of the femur is commonly described as the center of the intercondylar notch). Generally, an ideal mechanical axis in a patient allows load to pass from the center of the hip, through the center of the knee, and to the center of the ankle. The surgical orientation device 14, in conjunction with the reference device 16 described herein, can be used to locate the spatial orientation of the mechanical axis. In certain techniques described herein, the surgical orientation device 14 and the reference device 16 can be used to locate one, two, or more planes intersecting the mechanical axis. The surgical orientation device 14 and the reference device 16 can also be used for verifying an alignment of an orthopedic fixture or fixtures, or a cutting plane or planes, during an orthopedic procedure. The surgical orientation device 14, and the reference device 16, as described herein, can each be used alone or in conjunction with other devices, components, and/or systems.

Figure 3:
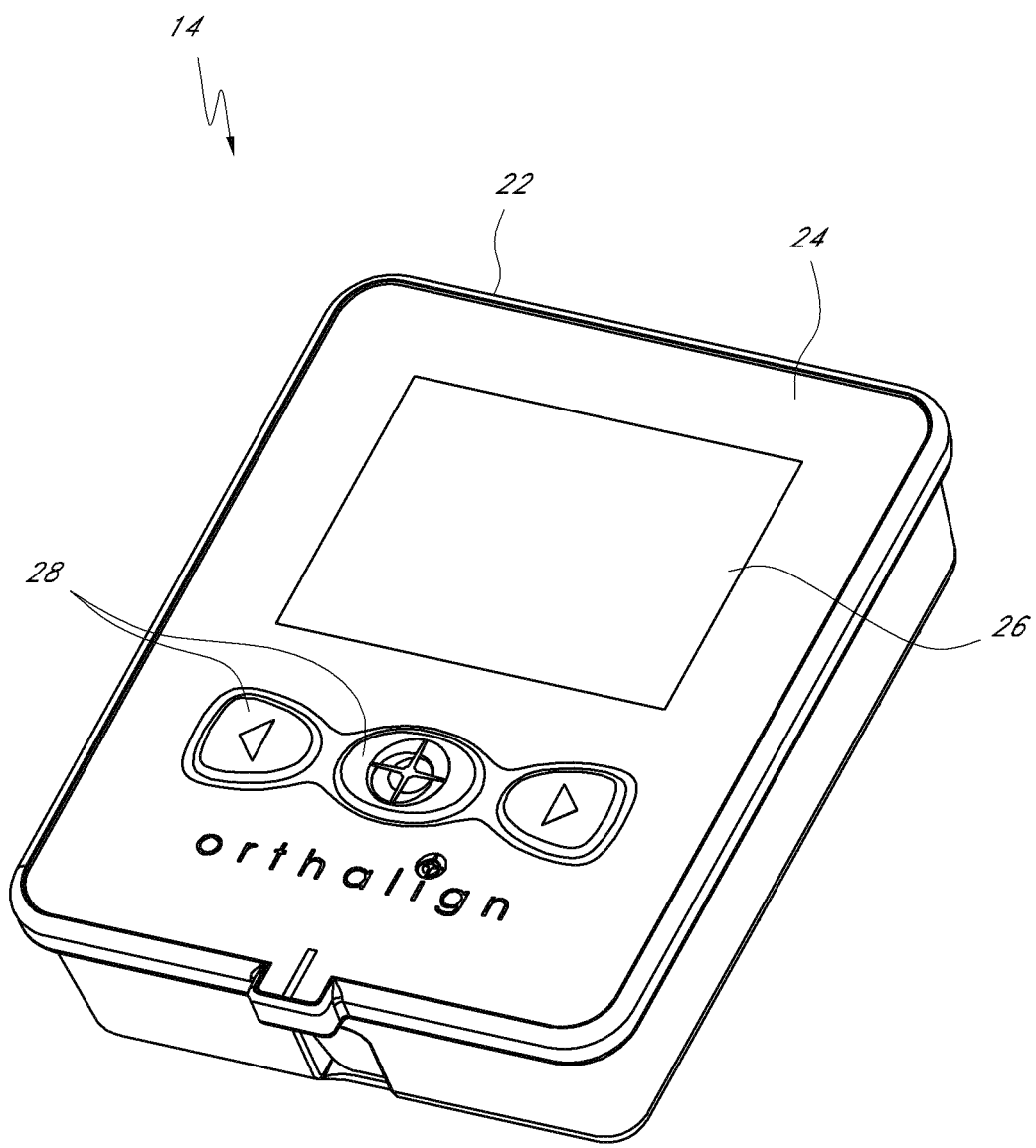
FIG. 3 is a perspective view of a surgical orientation device that can be used with the femoral preparation system of FIGS. 2A and 2B.

Referring to FIG. 3, which shows an embodiment of the surgical orientation device 14, the surgical orientation device 14 can comprise a generally rectangular-shaped, box-like structure having an outer housing 22. The outer housing 22 can be portable. The outer housing 22 can be comprised, at least in part, of plastic including but not limited to ABS, polycarbonate, or other suitable material. The surgical orientation device 14 can be configured for hand-held use.

With continued reference to FIG. 3, a front side 24, or a portion of the front side 24, of the surgical orientation device 14 can comprise a display 26. The display 26 can be a separate component from the outer housing 22 or can be integrated on or within the outer housing 22. The display 26 can comprise an output device. For example, the display 26 can comprise a liquid crystal display ("LCD") or Ferroelectric Liquid Crystal on Silicon ("FLCOS") display screen. The display screen can be sized such that a user can readily read numbers, lettering, and/or symbols displayed on the display screen while performing a medical procedure. In at least one embodiment, the display 26 can comprise a Quarter Video Graphics Array ("QVGA") Thin Film Transistor ("TFT") LCD screen. Other types of display screens can also be used, as can other shapes, sizes, and locations for the display 26 on the surgical orientation device 14.

The surgical orientation device 14 can further comprise at least one user input device 28. The at least one user input device 28 can comprise a plurality of buttons located adjacent the display 26. The buttons can be activated, for example, by a finger, hand, and/or instrument to select a mode or modes of operation of the surgical orientation device 14, as discussed further below. In a preferred arrangement, the at least one user input device 28 can comprise three buttons located underneath the display 26 as illustrated in FIG. 3. In other embodiments, the user input device 28 can be a separate component from the housing 22. For example, the user input device 28 can comprise a remote input device coupled to the surgical orientation device 14 via a wired or wireless connection. In yet other embodiments, the user input device 28 can comprise a microphone operating in conjunction with a speech recognition module configured to receive and process verbal instructions from a user.

As discussed further herein, the surgical orientation device 14 can include a user interface with which a user can interact during a procedure. In one embodiment, the display 26 and at least one user input device 28 can form a user interface. The user interface can allow a surgeon, medical personnel, and/or other user to operate the surgical orientation device 14 with ease, efficiency, and accuracy. Specific examples and illustrations of how the user interface can operate in conjunction with specific methods are disclosed further herein.

Figure 4:
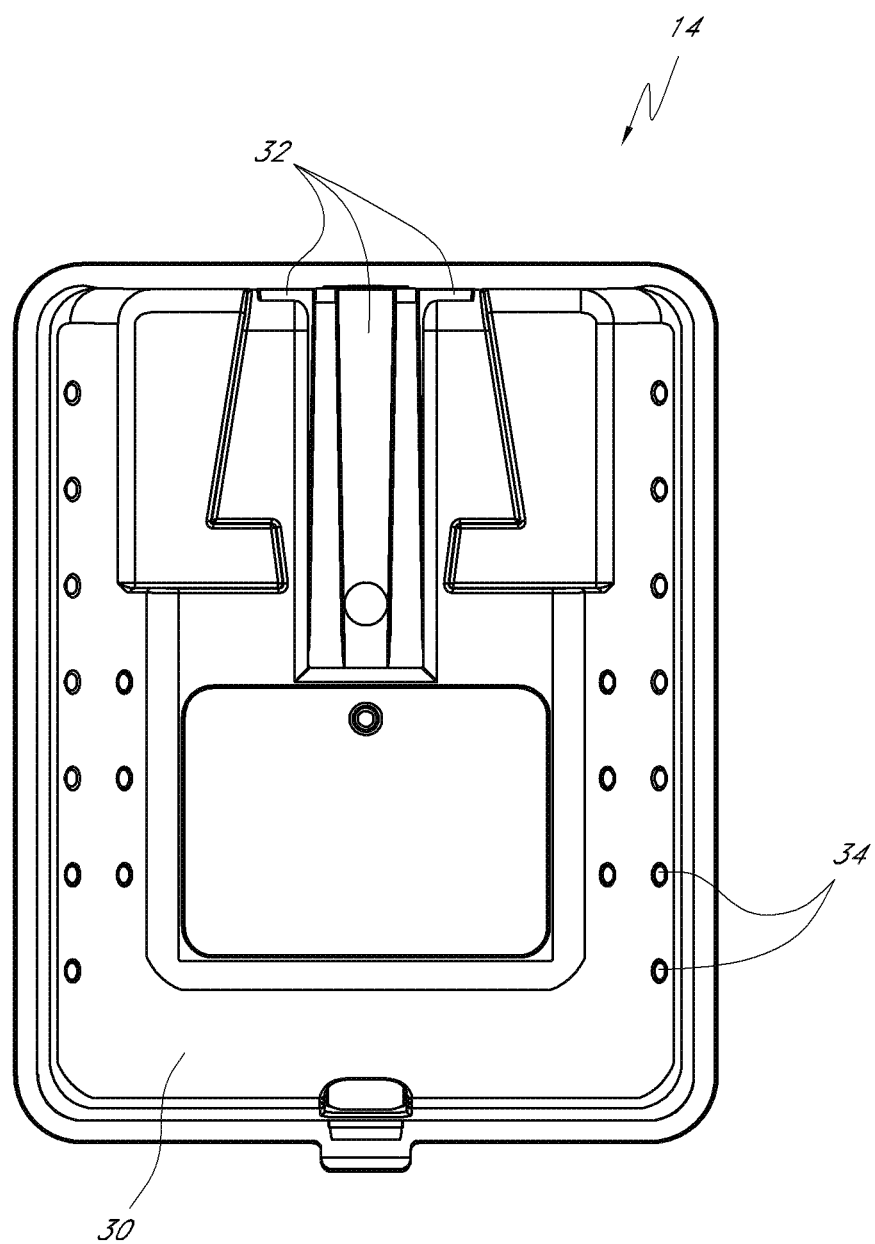
FIG. 4 is a back view of the surgical orientation device of FIG. 3.
Figure 5:
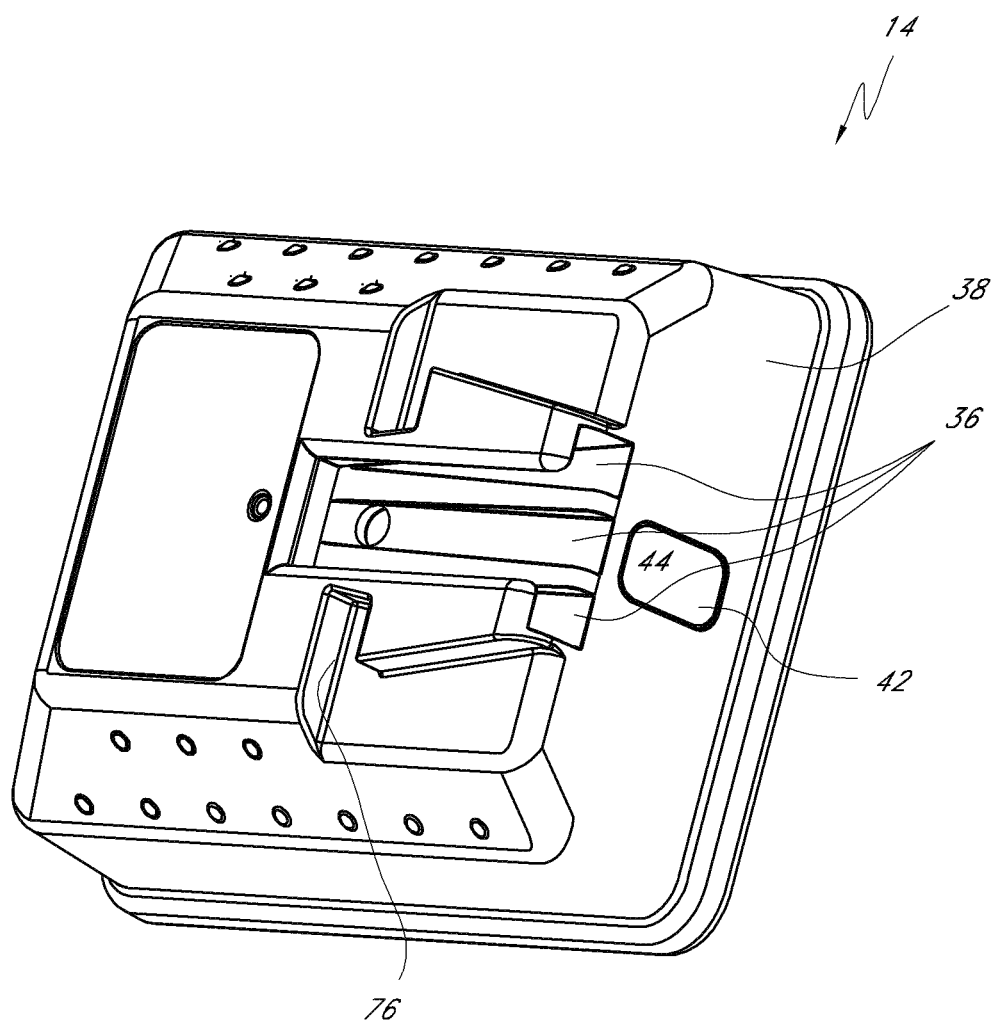
FIG. 5 is a perspective view of the surgical orientation device of FIG. 3.

FIGS. 4 and 5 show a back side 30 of the surgical orientation device 14. The back side 30 can include an attachment structure or structures 32, as well as a gripping feature or features 34 for facilitating handling of the surgical orientation device 14. The attachment structures 32 can facilitate attachment of the surgical orientation device 14 to another device, such as for example the first coupling device 18. In a preferred arrangement, the attachment structures 32 comprise grooves, or channels 36, along a portion of the back side of the surgical orientation device 14.

The attachment structures 32 can be formed, for example, from protruding portions of the back side of the surgical orientation device 14, and can extend partially, or entirely, along the back side of the surgical orientation device 14. The attachment structures 32 can receive corresponding, or mating, structures from the first coupling device 18, so as to couple, or lock, the first coupling device 18 to the surgical orientation device 14.

Figure 6:
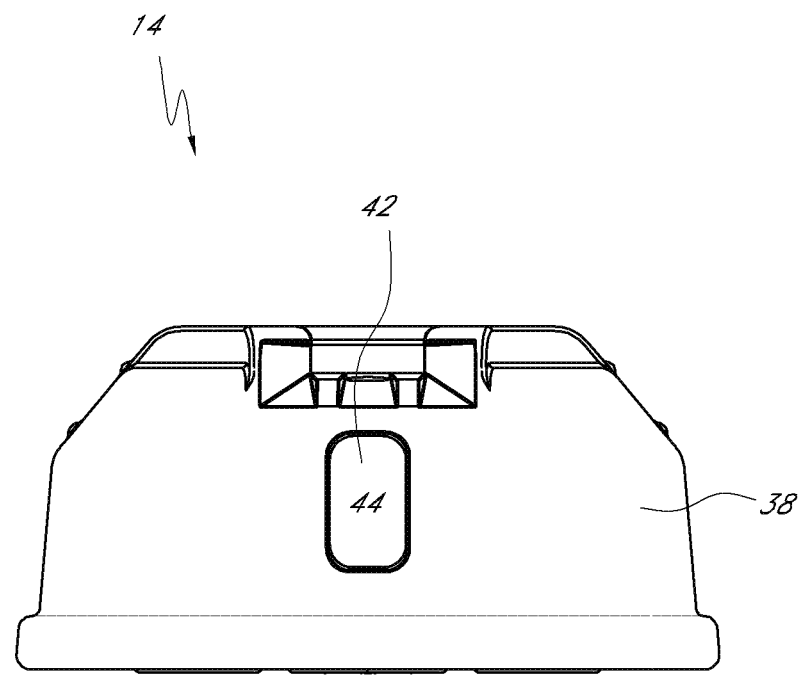
FIG. 6 is a top view of the surgical orientation device of FIG. 3.
Figure 7:
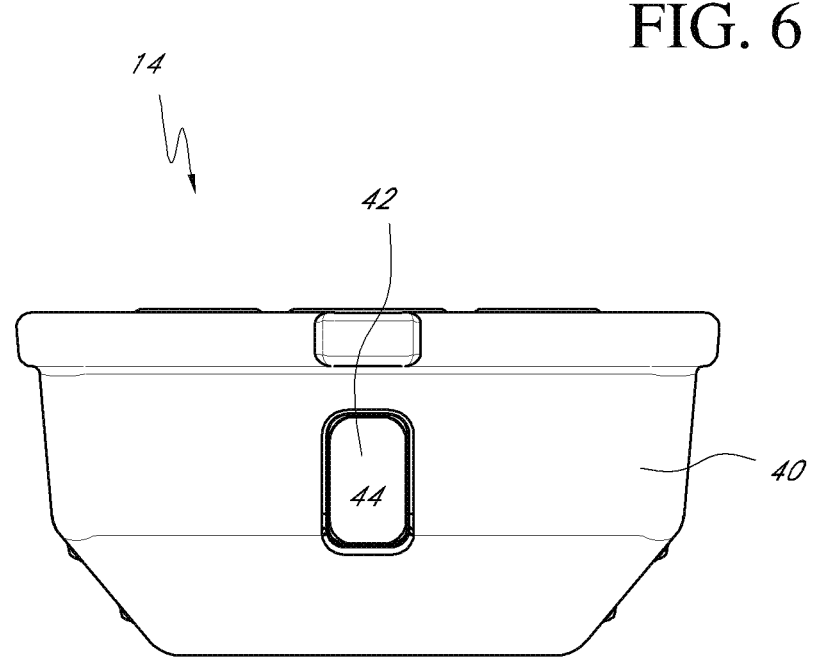
FIG. 7 is a bottom view of the surgical orientation device of FIG. 3.

FIGS. 5-7 show a top side 38 and bottom side 40 of the surgical orientation device 14. In some embodiments the surgical orientation device 14 can include optical components 42 located on the top side 38, the bottom side 40, or both the top and bottom sides 38, 40 of the surgical orientation device 14. The optical components 42 can comprise transparent windows 44 integrated into the surgical orientation device 14. The optical components 42 can be windows that permit visible light (e.g. laser light) to emit from the top side 38, the bottom side 40, or both the top and bottom sides 38, 40 of the surgical orientation device 14. While the embodiment illustrated in FIGS. 6 and 7 shows two windows 44 for transmitting light, other numbers are also possible, including having no windows 44 or optical components 42. Additionally, while the optical components 42 are shown located on the top and bottom of the surgical orientation device 14, in other embodiments the optical components 42 can be located in other positions and/or on other portions of the surgical orientation device 14.

Figure 8:
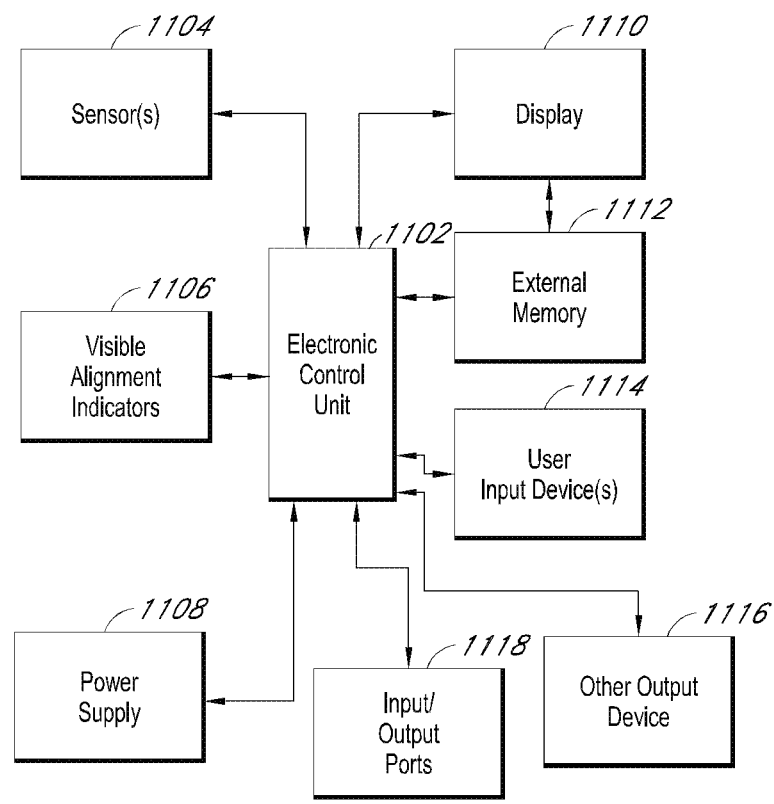
FIG. 8 is a block diagram of an electrical system of the surgical orientation device of FIG. 3.

FIG. 8 illustrates a high-level block diagram of an embodiment of an electrical system 1100 of the surgical orientation device 14. The electrical system 1100 can comprise an electronic control unit 1102 that communicates with one or more sensor(s) 1104, one or more optional visible alignment indicators 1106, a power supply 1108, a display 1110, external memory 1112, one or more user input devices 1114, other output devices 1116, and/or one or more input/output ("I/O") ports 1118.

In general, the electronic control unit 1102 can receive input from the sensor(s) 1104, the external memory 1112, the user input devices 1114 and/or the I/O ports 1118, and can control and/or transmit output to the optional visible alignment indicators 1106, the display 1110, the external memory 1112, the other output devices 1116 and/or the I/O ports 1118. The electronic control unit 1102 can be configured to receive and send electronic data, as well as perform calculations based on received electronic data. In certain embodiments, the electronic control unit 1102 can be configured to convert the electronic data from a machine-readable format to a human readable format for presentation on the display 1110. The electronic control unit 1102 can comprise, by way of example, one or more processors, program logic, or other substrate configurations representing data and instructions, which can operate as described herein. In some embodiments, the electronic control unit 1102 can comprise a controller circuitry, processor circuitry, processors, general purpose single-chip or multi-chip microprocessors, digital signal processors, embedded microprocessors, microcontrollers and/or the like. The electronic control unit 1102 can have conventional address lines, conventional data lines, and one or more conventional control lines. In some embodiments, the electronic control unit 1102 can comprise an application-specific integrated circuit (ASIC) or one or more modules configured to execute on one or more processors. In some embodiments, the electronic control unit 1102 can comprise an AT91SAM7SE microcontroller available from Atmel Corporation.

The electronic control unit 1102 can communicate with internal memory and/or the external memory 1112 to retrieve and/or store data and/or program instructions for software and/or hardware. The internal memory and the external memory 1112 can include random access memory ("RAM"), such as static RAM, for temporary storage of information and/or read only memory ("ROM"), such as flash memory, for more permanent storage of information. In some embodiments, the external memory 1112 can include an AT49BV160D-70TU Flash device available from Atmel Corporation and a CY62136EV30LL-45ZSXI SRAM device available from Cypress Semiconductor Corporation. The electronic control unit 1102 can communicate with the external memory 1112 via an external memory bus.

In general, the sensor(s) 1104 can be configured to provide continuous real-time data to the surgical orientation device 14. The electronic control unit 1102 can be configured to receive the real-time data from the sensor(s) 1104 and to use the sensor data to determine, estimate, and/or calculate an orientation or position of the surgical orientation device 14. The orientation information can be used to provide feedback to a user during the performance of a surgical procedure, such as a total knee joint replacement surgery, as described in more detail herein.

In some arrangements, the one or more sensors 1104 can comprise at least one orientation sensor configured to provide real-time data to the electronic control unit 1102 related to the motion, orientation, and/or position of the surgical orientation device 14. For example, the one ore more sensors 1104 can comprise at least one gyroscopic sensor, accelerometer sensor, tilt sensor, magnetometer and/or other similar device or devices configured to measure, and/or facilitate determination of, an orientation of the surgical orientation device 14. In some embodiments, the sensors 1104 can be configured to provide measurements relative to a reference point(s), line(s), plane(s), and/or gravitational zero. Gravitational zero, as referred to herein, refers generally to an orientation in which an axis of the sensor is perpendicular to the force of gravity, and thereby experiences no angular offset, for example tilt, pitch, roll, or yaw, relative to a gravitational force vector. In some embodiments, the sensor(s) 1104 can be configured to provide measurements for use in dead reckoning or inertial navigation systems.

In some embodiments, the sensor(s) 1104 can comprise one or more accelerometers that measure the static acceleration of the surgical orientation device 14 due to gravity. For example, the accelerometers can be used as tilt sensors to detect rotation of the surgical orientation device 14 about one or more of its axes. The one or more accelerometers can comprise a dual axis accelerometer (which can measure rotation about two axes of rotation) or a three-axis accelerometer (which can measure rotation about three axes of rotation). The changes in orientation about the axes of the accelerometers can be determined relative to gravitational zero and/or to a reference plane registered during a tibial or femoral preparation procedure as described herein. In one embodiment, the sensor(s) 1104 can comprise a three-axis gyroscopic sensor and a three-axis accelerometer sensor.

In some embodiments, a multi-axis accelerometer (such as the ADXL203CE MEMS accelerometer available from Analog Devices, Inc. or the LIS331DLH accelerometer available from ST Microelectronics.) can detect changes in orientation about two axes of rotation. For example, the multi-axis accelerometer can detect changes in angular position from a horizontal plane (e.g., anterior/posterior rotation) of the surgical orientation device 14 and changes in angular position from a vertical plane (e.g., roll rotation) of the surgical orientation device 14. The changes in angular position from the horizontal and vertical planes of the surgical orientation device 14 (as measured by the sensor 1104) can also be used to determine changes in a medial-lateral orientation (e.g., varus/valgus rotation) of the surgical orientation device 14.

In some arrangements, the sensor(s) 1104 comprise at least one single- or multi-axis gyroscope sensor and at least one single- or multi-axis accelerometer sensor. For example, the sensor(s) 1104 can comprise a three-axis gyroscope sensor (or three gyroscope sensors) and a three-axis accelerometer (or three accelerometer sensors) to provide positional and orientational measurements for all six degrees of freedom of the surgical orientation device 14. In some embodiments, the sensor(s) 1104 can provide an inertial navigation or dead reckoning system to continuously calculate the position, orientation, and velocity of the surgical orientation device 14 without the need for external references.

In some embodiments, the sensors 1104 can comprise one or more accelerometers and at least one magnetometer. The magnetometer can be configured to measure a strength and/or direction of one or more magnetic fields in the vicinity of the surgical orientation device 14 and/or the reference sensor. The magnetometer can advantageously be configured to detect changes in angular position about a horizontal plane. In some embodiments, the sensor(s) 1104 can comprise one or more sensors capable of determining distance measurements. For example a sensor located in the surgical orientation device 14 can be in electrical communication (wired or wireless) with an emitter element mounted at the end of a measurement probe. In some embodiments, the electronic control unit 1102 can be configured to determine the distance between the sensor and emitter (for example, an axial length of a measurement probe corresponding to a distance to an anatomical landmark, such as a malleolus).

In some embodiments, the one or more sensors 1104 can comprise a temperature sensor to monitor system temperature of the electrical system 1100. Operation of some of the electrical components can be affected by changes in temperature. The temperature sensor can be configured to transmit signals to the electronic control unit 1102 to take appropriate action. In addition, monitoring the system temperature can be used to prevent overheating. In some embodiments, the temperature sensor can comprise a NCP21WV103J03RA thermistor available from Murata Manufacturing Co. The electrical system 1100 can further include temperature, ultrasonic and/or pressure sensors for measuring properties of biological tissue and other materials used in the practice of medicine or surgery, including determining the hardness, rigidity, and/or density of materials, and/or determining the flow and/or viscosity of substances in the materials, and/or determining the temperature of tissues or substances within materials.

In some embodiments, the sensor(s) 1104 can facilitate determination of an orientation of the surgical orientation device 14 relative to a reference orientation established during a preparation and alignment procedure performed during orthopedic surgery.

The one or more sensor(s) 1104 can form a component of a sensor module that comprises at least one sensor, signal conditioning circuitry, and an analog-to-digital converter ("ADC"). In some embodiments, the components of the sensor module can be mounted on a stand-alone circuit board that is physically separate from, but in electrical communication with, the circuit board(s) containing the other electrical components described herein. In some embodiments, the sensor module can be physically integrated on the circuit board(s) with the other electrical components. The signal conditioning circuitry of the sensor module can comprise one or more circuit components configured to condition, or manipulate, the output signals from the sensor(s) 1104. In some embodiments, the signal conditioning circuitry can comprise filtering circuitry and gain circuitry. The filtering circuitry can comprise one more filters, such as a low pass filter. For example, a 10 Hz single pole low pass filter can be used to remove vibrational noise or other low frequency components of the sensor output signals. The gain circuitry can comprise one or more operational amplifier circuits that can be used to amplify the sensor output signals to increase the resolution potential of the sensor(s) 1104. For example, the operational amplifier circuit can provide gain such that a 0 g output results in a midrange (e.g., 1.65 V signal), a +1 g output results in a full scale (e.g., 3.3 V) signal and a −1 g output results in a minimum (0 V) signal to the ADC input.

In general, the ADC of the sensor module can be configured to convert the analog output voltage signals of the sensor(s) 1104 to digital data samples. In some embodiments, the digital data samples comprise voltage counts. The ADC can be mounted in close proximity to the sensor to enhance signal to noise performance. In some embodiments, the ADC can comprise an AD7921 two channel, 12-bit, 250 Kiloseconds per Sample ADC. In an arrangement having a 12-bit ADC, the 12-bit ADC can generate 4096 voltage counts. The ADC can be configured to interface with the electronic control unit 1102 via a serial peripheral interface port of the electronic control unit 1102. In some embodiments, the electronic control unit 1102 can comprise an on-board ADC that can be used to convert the sensor output signals into digital data counts.

With continued reference to FIG. 8, in some embodiments the optional visible alignment indicators 1106 can comprise one or more lasers, which can be configured to project laser light through the optical component or components 42 described above. For example, the optional visible alignment indicators 1106 can comprise a forward laser and an aft laser. The laser light can be used to project a point, a plane, and/or a cross-hair onto a target or targets, including but not limited to an anatomical feature or landmark, to provide alternative or additional orientation information to a surgeon regarding the orientation of the orientation device 14. For example, laser light can be used to project a plane on a portion of bone to indicate a resection line and a cross-hair laser pattern can be used to ensure alignment along two perpendicular axes. In certain embodiments, the visible alignment indicators 1106 can be used to determine a distance to an anatomical feature or landmark (for example, a laser distance measurement system). For example, the electronic control unit 1102 can project laser light to a target and a sensor 1104 within the surgical orientation device can sense the laser light reflected back from the target and communicate the information to the electronic control unit 1102. The electronic control unit 1102 can then be configured to determine the distance to the target. The lasers can be controlled by the electronic control unit 1102 via pulse width modulation ("PWM") outputs. In some embodiments, the visible alignment indicators 1106 can comprise Class 2M lasers. In other embodiments, the visible alignment indicators 1106 can comprise other types of lasers or light sources.

The power supply 1108 can comprise one or more power sources configured to supply DC power to the electronic system 1100 of the surgical orientation device 14. In certain embodiments, the power supply 1108 can comprise one or more rechargeable or replaceable batteries and/or one or more capacitive storage devices (for example, one or more capacitors or ultracapacitors). In some embodiments, power can be supplied by other wired and/or wireless power sources. In preferred arrangements, the power supply 1108 can comprise two AA alkaline, lithium, or rechargeable NiMH batteries. The surgical orientation device 14 can also include a DC/DC converter to boost the DC power from the power supply to a fixed, constant DC voltage output (e.g., 3.3 volts) to the electronic control unit 1102. In some embodiments, the DC/DC converter comprises a TPS61201DRC synchronous boost converter available from Texas Instruments. The electronic control unit 1106 can be configured to monitor the battery level if a battery is used for the power supply 1108. Monitoring the battery level can advantageously provide advance notice of power loss. In some embodiments, the surgical orientation device 14 can comprise a timer configured to cause the surgical orientation device 14 to temporarily power off after a predetermined period of inactivity and/or to permanently power off after a predetermined time-out period.

As discussed above, the display 1110 (e.g. display 26 seen in FIG. 4) can comprise an LCD or other type screen display. The electronic control unit 1102 can communicate with the display via the external memory bus. In some embodiments, the electronic system 1100 can comprise a display controller and/or an LED driver and one or more LEDs to provide backlighting for the display 1110. For example, the display controller can comprise an LCD controller integrated circuit ("IC") and the LED driver can comprise a FAN5613 LED driver available from Fairchild Semiconductor International, Inc. The electronic control unit 1102 can be configured to control the LED driver via a pulse width modulation port to control the brightness of the LED display. For example, the LED driver can drive four LEDs spaced around the display screen to provide adequate backlighting to enhance visibility. The display can be configured to display one or more on-screen graphics. The on-screen graphics can comprise graphical user interface ("GUI") images or icons. The GUI images can include instructive images, such as illustrated surgical procedure steps, or visual indicators of the orientation information received from the sensor(s) 1104. For example, the display 1110 can be configured to display degrees and either a positive or negative sign to indicate direction of rotation from a reference plane and/or a bubble level indicator to aid a user in maintaining a particular orientation. The display 1110 can also be configured to display alphanumeric text, symbols, and/or arrows. For example, the display 1110 can indicate whether a laser is on or off and/or include an arrow to a user input button with instructions related to the result of pressing a particular button.

With continued reference to FIG. 8, the user input device(s) 1114 (e.g. user input devices 28 seen in FIG. 4) can comprise buttons, switches, a touch screen display, a keyboard, a joystick, a scroll wheel, a trackball, a remote control, a microphone, and the like. The user input devices 1114 can allow the user to enter data, make selections, input instructions or commands to the surgical orientation device 14, verify a position of the surgical orientation device 14, turn the visible alignment indicators 1106 on and off, and/or turn the entire surgical orientation device 14 on and off. The other user output devices 1116 (i.e. other than the display 1110) can comprise an audio output, such as a speaker, a buzzer, an alarm, or the like. For example, the audio output can provide a warning to the user when a particular condition occurs. The output devices 1116 can also comprise a visible output, such as one or more LED status or notification lights (for example, to indicate low battery level, an error condition, etc.). The audio output can comprise different patterns, tones, cadences, durations, and/or frequencies to signify different conditions or events. In some embodiments, output from the electronic control unit 1102 can be sent to external display devices, data storage devices, servers, and/or other computing devices (e.g., via a wireless network communication link).

The I/O ports 1118 of the electronic control unit 1102 can comprise a JTAG port and one or more serial communication ports. The JTAG port can be used to debug software installed on the electronic control unit 1102 during testing and manufacturing phases. The JTAG port can be configured such that it is not externally accessible post-manufacture. The serial communication ports can include a Universal Serial Bus ("USB") port and/or one or more universal asynchronous receiver/transmitters ("UART") ports. At least one of the UART ports can be accessible externally post-manufacture. The external UART port can be an infrared ("IR") serial port in communication with an infrared ("IR") transceiver. The IR serial port can be used to update the software installed on the electronic control unit 1102 post-manufacture and/or to test the operation of the electronic control unit 1102 by outputting data from the electronic control unit 1102 to an external computing device via an external wireless connection. Other types of I/O ports are also possible.

Figure 8A:
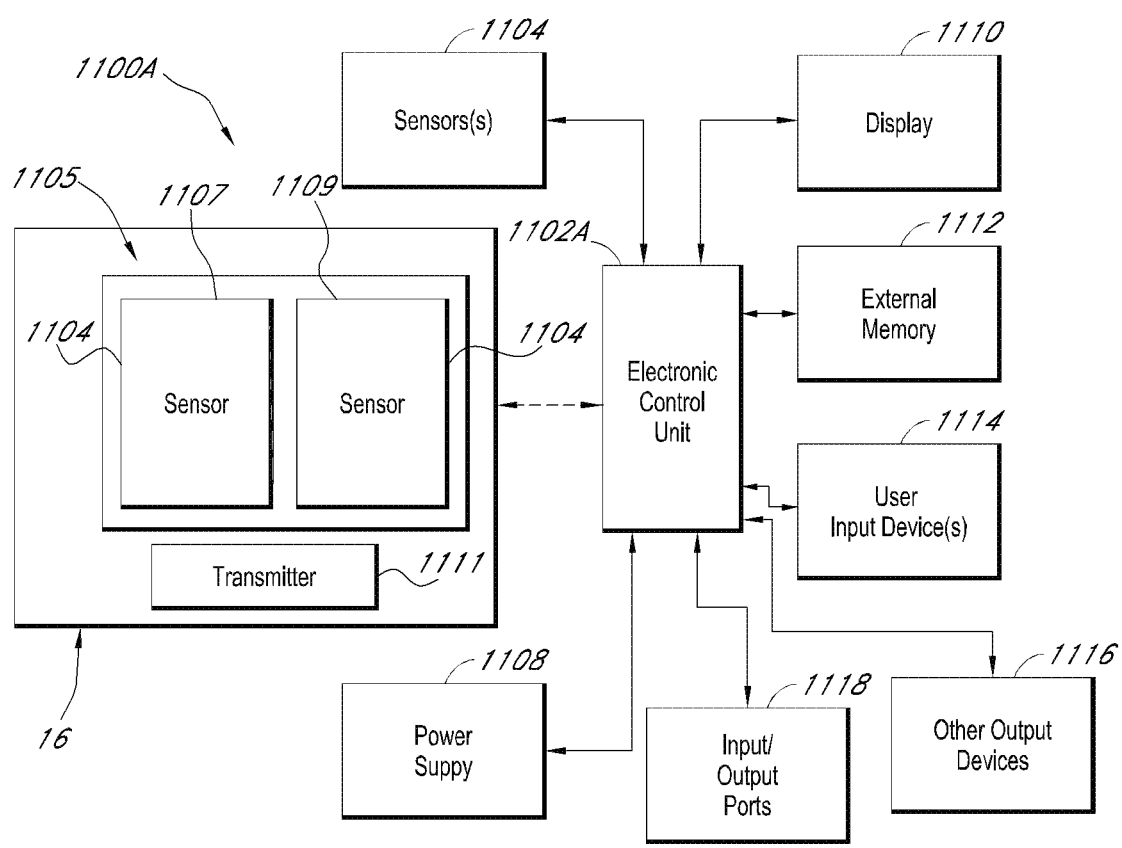
FIG. 8A is a block diagram of an electrical system of an orthopedic preparation system that includes a surgical orientation device and a reference device such as that illustrated in FIGS. 15-16.

FIG. 8A illustrates another high-level block diagram of an embodiment of an electrical system 1100A that can form a part of a surgical orientation system. In one embodiment, the surgical orientation system includes the surgical orientation device 14 and a reference device 16. In one embodiment, the components schematically grouped in the box "16" can be disposed in a first enclosure of the reference sensor 16 while the other components in FIG. 8A can be housed in a second enclosure of the orientation device 14. The electrical system 1100A in FIG. 8A can be similar to the electrical system of FIG. 8. The electrical system 1100A of FIG. 8A can comprise an electronic control unit 1102A that is adapted to communicate with one or more sensor(s) 1104, a power supply 1108, a display 1110, external memory 1112, one or more user input devices 1114, other output devices 1116, and/or one or more input/output ("I/O") ports 1118. As illustrated in FIG. 8A, the input ports 1118 can be configured to receive information from an outside source. For example, the input ports 1118 can be configured to receive radio frequency data (RF) from reference device 16. As illustrated in FIG. 8A, the reference device 16 includes in one embodiment a plurality of sensors that together form an inertial measurement unit 1105 (IMU). In particular, the IMU 1105 includes a first sensor 1107 for determining acceleration and a second sensor 1109 for determining gyroscopic positioning. As discussed herein, the first sensor can be an accelerometer and the second sensor can be a gyroscopic sensor. The reference device 16 also includes a transmitter 1111 for sending data from the sensors to the electrical system 1100A of the surgical orientation device 14. The information received from the reference device 16 can be fed to an input port 1118, or alternatively, the electronic control unit 1102 can itself receive the information (e.g., wirelessly as illustrated by the dashed line). The information from the reference device 16 can correspond, for example, to the position and/or orientation of the reference device 16, and can be used by the surgical orientation device 14 to determine an aggregate, or overall, position and/or orientation of the surgical orientation device 14.

In alternate embodiments, components of the reference device 16 illustrated in FIG. 8A can be incorporated into the surgical orientation device 14. For example, the IMU 1105 can be disposed in the surgical orientation device 14 so that the surgical orientation device can be used to determine the spatial location of an anatomical axis and the reference device can be used for other purposes, such as to track relative position changes of a patient's femur, leg, or other bone or limb.

Figure 9:
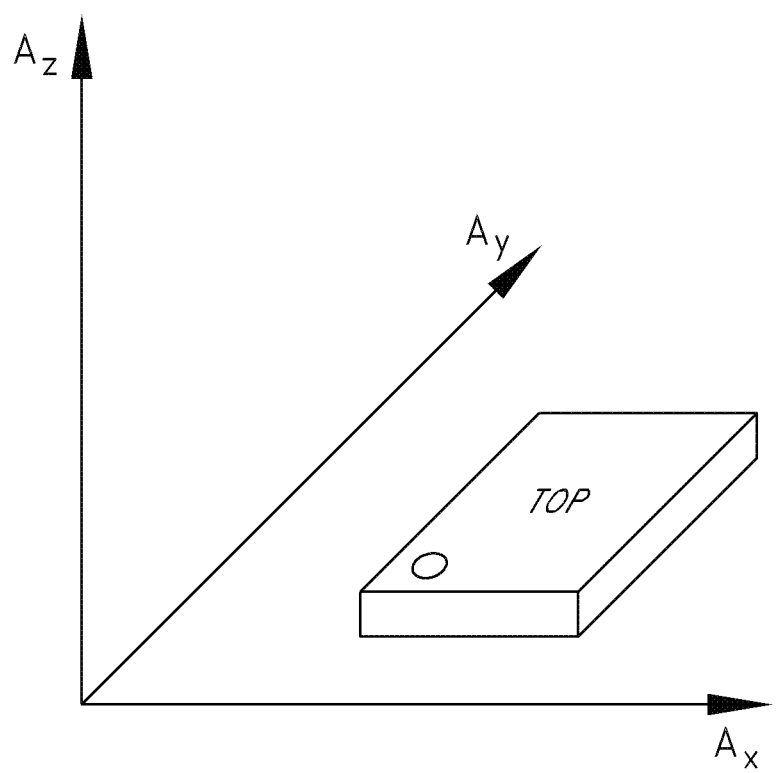
FIGS. 9-11 illustrate operation of accelerometers according to embodiments that can be used as sensors in the electrical system of FIG. 8.
Figure 10:
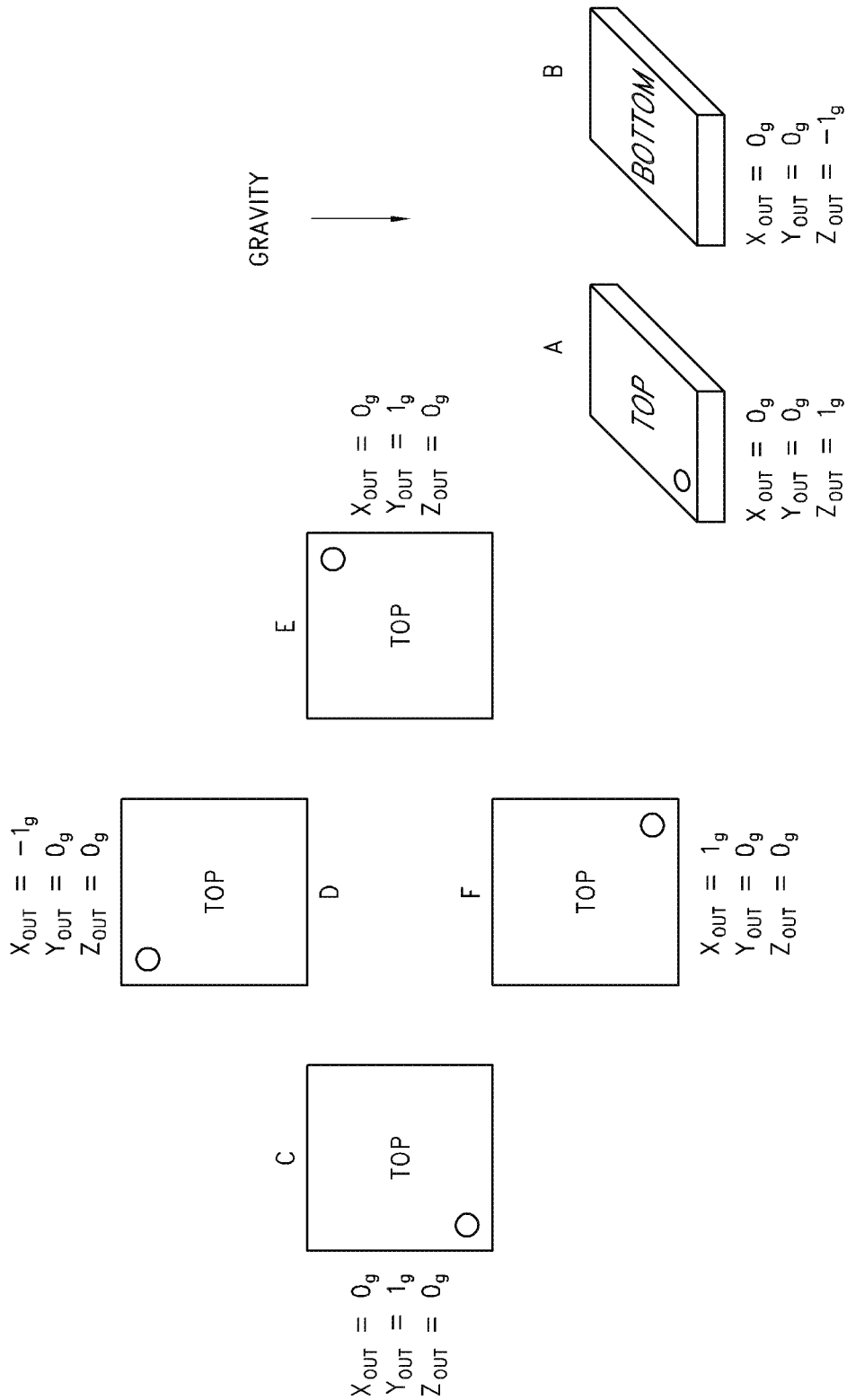

Referring to FIGS. 8-10, the sensor(s) 1104 can comprise one or more accelerometers. Accelerometers can measure the static acceleration of gravity in one or more axes to measure changes in tilt orientation. For example, a three-axis accelerometer can measure the static acceleration due to gravity along three orthogonal axes, as illustrated in FIG. 10. A two-axis accelerometer can measure the static acceleration due to gravity along two orthogonal axes (for example, the x and y axes of FIG. 9). The output signals of an accelerometer can comprise analog voltage signals. The output voltage signals for each axis can fluctuate based on the fluctuation in static acceleration as the accelerometer changes its orientation with respect to the gravitational force vector. In certain embodiments, an accelerometer experiences static acceleration in the range from −1 g to +1 g through 180 degrees of tilt (with −1 g corresponding to a −90 degree tilt, 0 g corresponding to a zero degree tilt, and +1 g corresponding to a +90 degree tilt. The acceleration along each axis can be independent of the acceleration along the other axis or axes.

FIG. 10 illustrates a measured acceleration along each of the three axes of a three-axis accelerometer in six different orientation positions. TOP and BOTTOM labels, as well as a circle indicating Pin 1 of the accelerometer, have been included to aid in determining the various orientations. A gravitational force reference vector is illustrated as pointing straight down toward the Earth's surface. At positions A and B, the x-axis and the y-axis of the accelerometer are perpendicular to the force of gravity and the z-axis of the accelerometer is parallel to the force of gravity; therefore, the x and y acceleration components of static acceleration due to gravity at positions A and B are 0 g and the z component of static acceleration due to gravity at positions A and B is +1 g and −1 g, respectively. At positions C and E, the x-axis and the z-axis of the accelerometer are perpendicular to the force of gravity and the y-axis is parallel to the force of gravity; therefore, the x and z acceleration components of static acceleration due to gravity at positions C and E are 0 g and the y component of static acceleration due to gravity at positions C and E is +1 g and −1 g, respectively. At positions D and F, the y-axis and z-axis are perpendicular to the force of gravity and the x-axis is parallel to the force of gravity; therefore, the y and z acceleration components of static acceleration due to gravity at positions D and F are 0 g and the x component of static acceleration due to gravity at positions D and F is +1 g and −1 g, respectively. A dual-axis accelerometer operates in the same manner but without the z component. In certain arrangements, a three-axis accelerometer can be used as a tiltmeter to measure changes in orientation about two axes.

Figure 11:
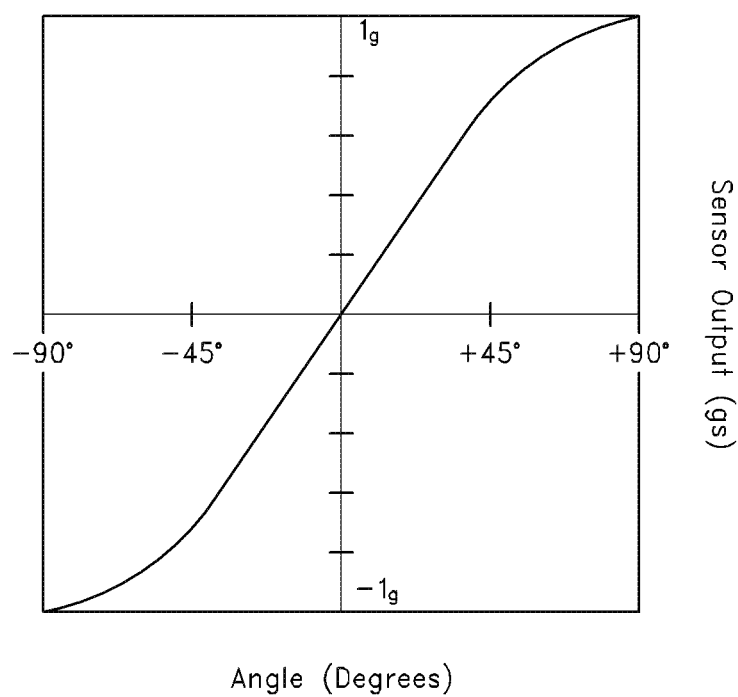

Multi-axis accelerometers can be conceptualized as having a separate accelerometer sensor for each of its axes of measurement, with each sensor responding to changes in static acceleration in one plane. In certain embodiments, each accelerometer sensor is most responsive to changes in tilt (i.e., operates with maximum or optimum accuracy and/or resolution) when its sensitive axis is substantially perpendicular to the force of gravity (i.e., when the longitudinal plane of the accelerometer sensor is parallel to the force of gravity) and least responsive when the sensitive axis is parallel to the force of gravity (i.e., when the longitudinal plane of the accelerometer sensor is perpendicular to the force of gravity). FIG. 11 illustrates the output of the accelerometer in g's as it tilts from −90 degrees to +90 degrees. As shown, the tilt sensitivity diminishes between −90 degrees and −45 degrees and between +45 degrees and +90 degrees (as shown by the decrease in slope). This resolution problem at the outer ranges of tilt motion can make the measurements less accurate for tilt measurements over 45 degrees. In certain embodiments, when the mounting angle of the surgical orientation device 14 is known, the sensor(s) 1104 can be mounted to be offset at an angle such that the accelerometer sensors can operate in their more accurate, steeper slope regions. In other arrangements, the sensor(s) 1104 can be mounted to be offset to account for a predetermined range of motion about other axes of rotation as well. In yet other arrangements, for example, when a multi-axis accelerometer is used, the accelerometer sensor(s) 1104 can be mounted in parallel with the anterior-posterior axis of the surgical orientation device 14. In one multi-axis accelerometer arrangement, a handoff system can be incorporated to ensure that the accelerometer sensor(s) 1104 with the most accurate reading (e.g., <45 degrees) are being used at each orientation position. The handoff system can employ hysteresis to avoid "bouncing" phenomena during the handoffs between the accelerometer sensor(s) 1104. In yet other embodiments, the multi-axis accelerometers can be mounted without any offset angle.

Figure 12:
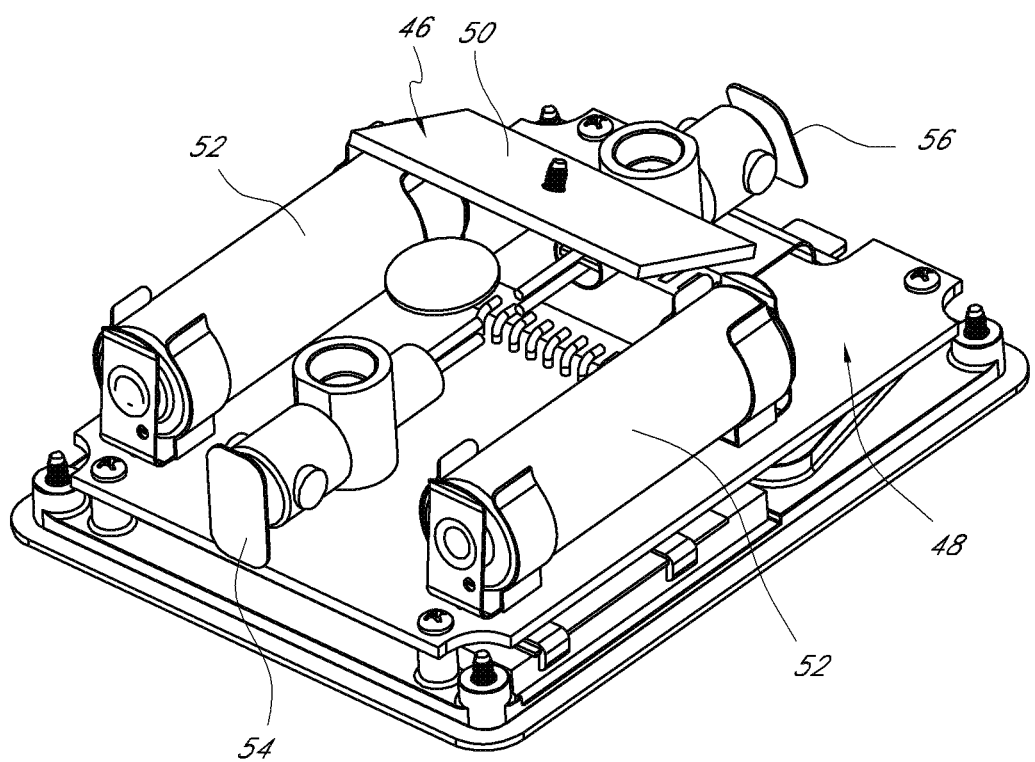
FIG. 12 is a perspective view of interior components of the surgical orientation device of FIG. 3.

FIG. 12 illustrates an embodiment of the inside of the surgical orientation device 14. The surgical orientation device 14 can comprise one or more circuit boards and/or other circuitry capable of installation within the surgical orientation device 14. As illustrated, the surgical orientation device 14 can comprise a sensor board 46 and a main board 48. In some embodiments, the components of the sensor module described above can be mounted on the sensor board 46 and the other components of the electrical system 1100 can be mounted on the main board 48. The sensor board 46 can comprise one or more sensors 50 (e.g., sensor(s) 1104 as described above). In alternative embodiments, the sensor board 46 and the main board 48 can be combined into a single circuit board. The sensor board 46 and the main board 48 can comprise rigid or flexible circuit boards. The sensor board 46 and the main board 48 can be fixedly or releasably attached to the outer housing 22.

As illustrated, the sensor board 46 can be mounted at an approximately 22-degree angle relative to a plane extending longitudinally through the housing 22, which can be parallel to or co-planar with an anterior-posterior axis of the main board 48. In some embodiments, the sensor board 46 can be mounted at an approximately 0 degree angle relative to a plane extending longitudinally through the housing 22, which can be parallel to or correspond to an anterior-posterior axis of the main board 46. As shown in FIG. 12, the surgical orientation device 14 can include two AA, alkaline, lithium, or rechargeable NiMH batteries 52 as the power supply 1110 for providing power to the surgical orientation device 14. In some embodiments, the surgical orientation device 14 also can include lasers 54 and 56 as the optional visible alignment indicators 1106 described above.

In a preferred arrangement, the surgical orientation device 14 described above can advantageously be disposed of after use. Once the surgical orientation device 14 has been used during a total knee replacement procedure or other medical procedure, the surgical orientation device 14 can be discarded, so as to inhibit and/or prevent contamination during subsequent procedures and reduce the need for sterilization.

Figure 13:
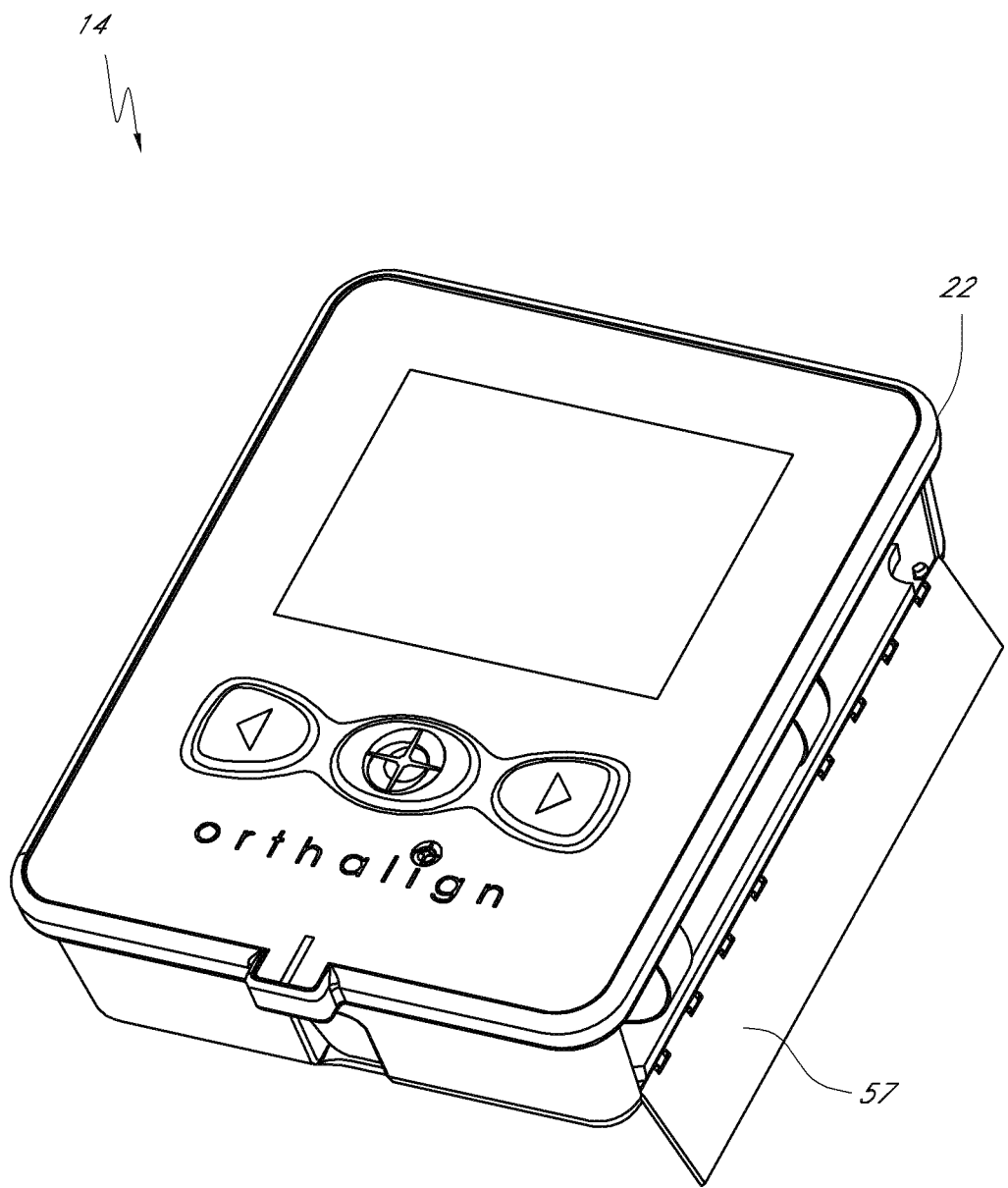
FIG. 13 is a perspective view of another embodiment of the surgical orientation device that can be used with the femoral preparation system of FIGS. 2A and 2B.

In other embodiments, the surgical orientation device 14 can alternatively have a disposable outer housing 22, such that the internal components of the surgical orientation device (e.g. sensors 50, batteries 52, etc.) can be reused, while the outer housing 22 is discarded. For example, with reference to FIG. 13 in some embodiments the outer housing can comprise a flap 57 that releases to allow removal of the internal components of the surgical orientation device 14.

Further description of embodiments of a surgical orientation device 14 and its sensor(s) can be found in U.S. Patent Application Publication No. 2010/0063508, the contents of which are incorporated herein by reference in their entirety.

B. Device for Coupling the Surgical Orientation Device to Another Orthopedic Fixture Referring to FIG. 14, the first coupling device 18 can be used to attach the surgical orientation device 14 to another orthopedic fixture. "Orthopedic fixture" is a broad term and is to be given its ordinary and customary meaning to a person of ordinary skill in the art (i.e. it is not to be limited to a special or customized meaning) and includes, without limitation, jigs or other mechanical and/or electrical structures that can be used in an orthopedic procedure. For example, the first coupling device 18 can be used to attach the surgical orientation device 14 to the femoral jig assembly 12. The first coupling device 18 can advantageously enable the surgical orientation device 14 to be quickly coupled and decoupled with the femoral jig assembly 12 during a surgical procedure. This enables the surgical orientation device 14 to be used in a modular fashion, with a variety of orthopedic fixtures at one or more stages of a procedure.

The first coupling device 18 can include an orientation device interface 58 attached to an interface support member 60. The orientation device interface 58 can be designed to connect with the attachment structures 32 of the surgical orientation device 14 described above, thereby facilitating a secure but releasable attachment between the surgical orientation device 14 and the femoral jig assembly 12. In one embodiment, the orientation device interface 58 can be inserted into the grooves or channels 36 along the back portion of the surgical orientation device 14 described above.

Figure 14:
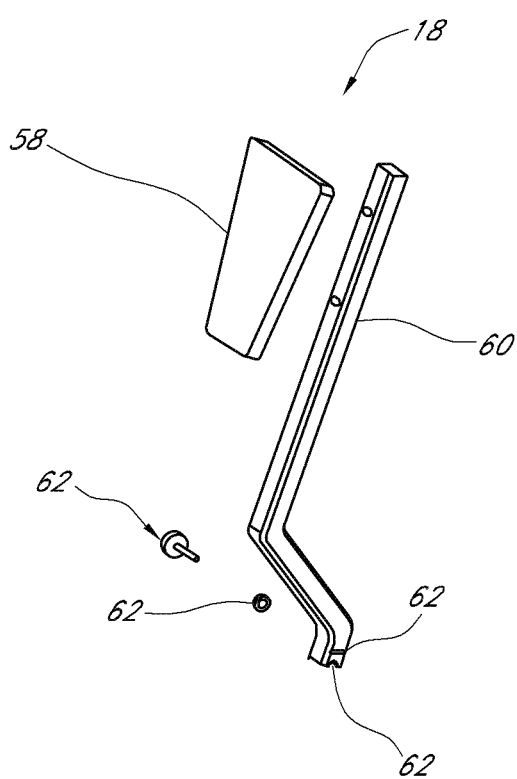
FIG. 14 is an exploded view of the first coupling device of the femoral preparation system of FIGS. 2A and 2B.

With continued reference to FIG. 14, the interface support member 60 can include jig attachment features 62. The jig attachment features 62 can be used to mate the first coupling device 18 to a microblock assembly of the femoral jig assembly 12 (see, e.g. the microblock assembly 90 illustrated in FIGS. 17 and 19). (The term "microblock" is a general term, and is not intended to be limited only to assemblies that are small in nature. Thus, the term "microblock" can refer to an assembly of any size.) Mating the jig attachment features 62 with corresponding attachment features of a microblock assembly allows the interface support member 60 to be attached to the microblock assembly in a secure but releasable fashion. The jig attachment features 62 and the attachment features of the microblock assembly can be any suitable attachment structures that provide a secure but releasable attachment, including but not limited to (i) friction or pressure fit features; and (ii) openings, apertures, bores and holes (non-threaded, threaded, partially extended through a structure or entirely through a structure) and corresponding pins or screws (collectively referred hereinafter as "attachment structures").

While the first coupling device 18 described above can be used to attach and/or couple the surgical orientation device 14 with the femoral jig assembly 12, other methods and devices for attaching and/or coupling the components of the femoral preparation system 10 are also possible.

Additionally, in a preferred arrangement, the femoral jig assembly 12 and the first coupling device 18 of the femoral system 10 can be biocompatible for short term exposure to the inner anatomy of the knee or other body joint, and can be sterilized by autoclave and/or gas ("autoclavable components"). Other components of the femoral system 10 including but not limited to the reference device 16 described below may optionally have autoclavable components as well. The autoclavable components can operate without lubricants. Materials for the autoclavable components can be selected and treated to prevent galling and provide smooth operation consistent with expectations for a high quality surgical instrument. In general, the autoclavable components can be made robust to withstand normal and abusive use, especially rough handling during cleaning and/or sterilization.

The components of the femoral system 10 can optionally be etched with part numbers, revisions levels, and company name and logo. Other markings can also be added to provide clarity.

C. Reference Sensor Device

Figure 15:
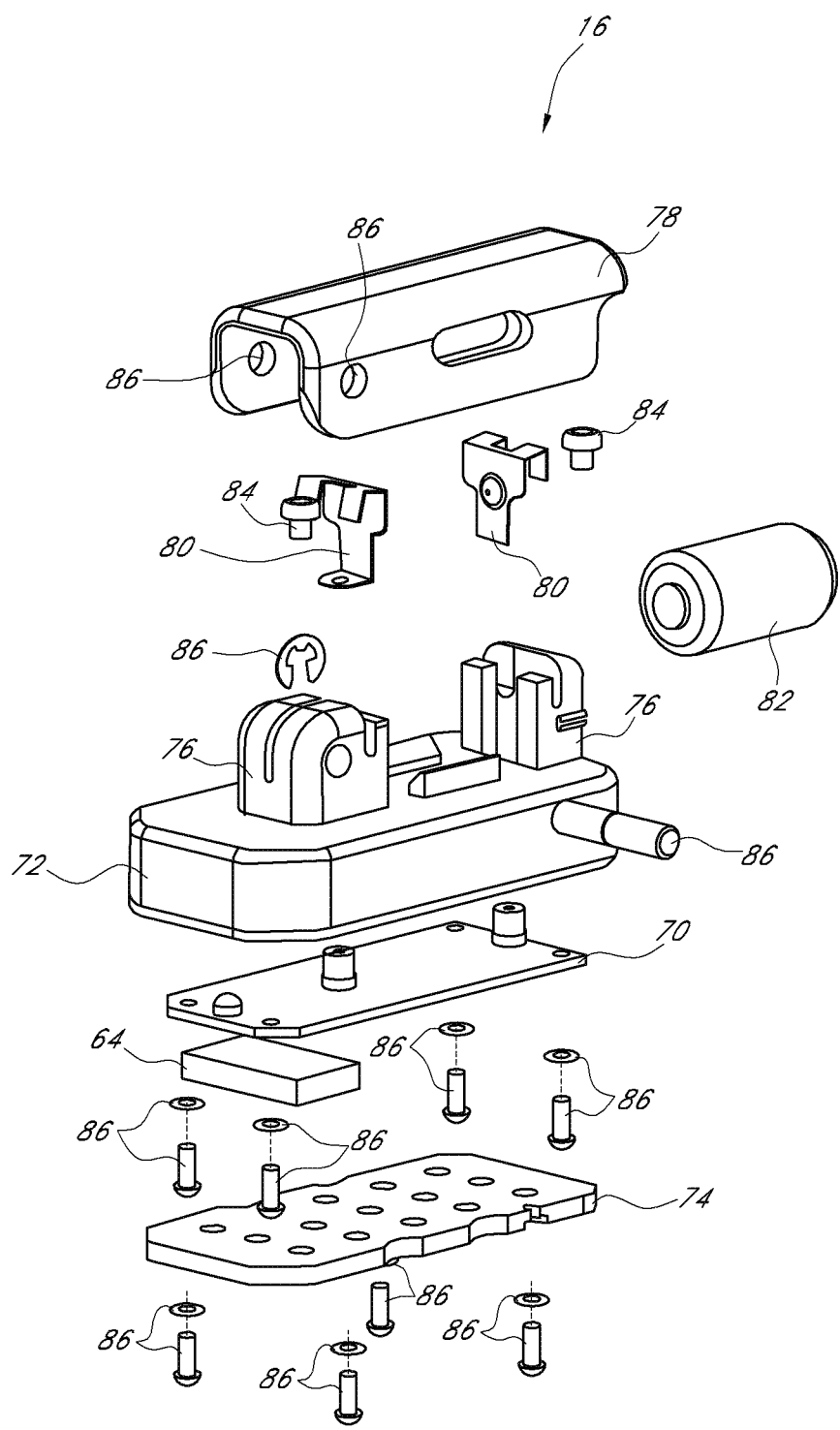
FIG. 15 is a first exploded view of an embodiment of the reference device of the femoral preparation system of FIGS. 2A and 2B.

Referring to FIG. 15, the reference sensor device 16 can be used to measure and record the location of anatomical landmarks used in a total knee procedure, such as the location of the mechanical axis of a leg (and femur). "Reference sensor device" is a broad term and is to be given its ordinary and customary meaning to a person of ordinary skill in the art (i.e. it is not to be limited to a special or customized meaning) and includes, without limitation, any device that can be used to reference another device, and/or to provide orientation information or perform calculations identically or similar to the surgical orientation device 14 described above. In some embodiments, the reference sensor device 16 can comprise the same or similar components as the surgical orientation device 14 described above. Further description of a reference sensor can be found, for example and without limitation, in paragraphs [0176]-[0178] of U.S. patent application Ser. No. 12/509,388, which is incorporated by reference herein.

In a preferred arrangement, the reference sensor device 16 can be configured for portable hand-held use. With reference to FIG. 15, in one embodiment the internal components of the reference sensor device 16 can comprise a sensor 64 inside of a reference sensor housing 66 (not shown). The reference sensor 64 can include a microcontroller and/or communication device such as infrared, RF, Bluetooth or other wireless technology which can relay information from the reference sensor 64 to the electronic control unit 1102 of the surgical orientation device 14. The reference sensor 64 can be, for example, any one of the sensors described for use as sensor 1104 (e.g. sensor 50) described above. The reference sensor device 16 can include a circuit board 70 upon which the components of the reference sensor 64 are mounted thereon. During a knee replacement procedure, the reference sensor 64 can detect changes in movement of a femur in a varus/valgus, flexion/extension, and/or other directions.

The electronic control unit 1102 of the surgical orientation device 14 can be configured to receive information from the reference sensor 64 (e.g., a receiver of infrared, RF, Bluetooth™, or other wireless technology) and to combine that information with information from the sensor(s) 50 located within the surgical orientation device 14 to calculate an overall, or aggregate, movement and orientation of the reference sensor 64 relative to an axial line or plane, for example as illustrated in FIG. 8A. The electronic control unit 1102 in the surgical orientation device 14 can correct for changes in position of this axis or plane, and the display 26 can indicate to the user an appropriate varus/valgus and/or flexion/extension angle for resection, based on the actual location of the mechanical axis or plane.

Referring to FIG. 15, the reference sensor device 16 can include a circuit board enclosure 72 and a cover 74. The enclosure 72 can be an open box of rectangular shape. The reference sensor device 16 can further include a battery enclosure 76 and a battery cover 78. The battery enclosure 76 can include electric features 80 for electric communication between a replaceable battery 82 and the reference sensor 64. The electric features 80 can be attached to the battery enclosure 76 using various methods (e.g., the screws 84 shown in FIG. 15). The battery enclosure 76 and the battery cover 78 can be attached in a secure but releasable fashion using any suitable attachment structures 86. For example and referring to FIG. 15, the battery enclosure 76 and the battery cover 78 can be attached in a secure but releasable fashion using one or more of the following attachment structures 86: a pin, through holes, and a locking clip. The circuit board enclosure 72, the cover 74 and the circuit board 70 can all be attached together in a secure but releasable fashion using attachment structures 86 such as the screws and washers shown in FIG. 15.

Figure 16:
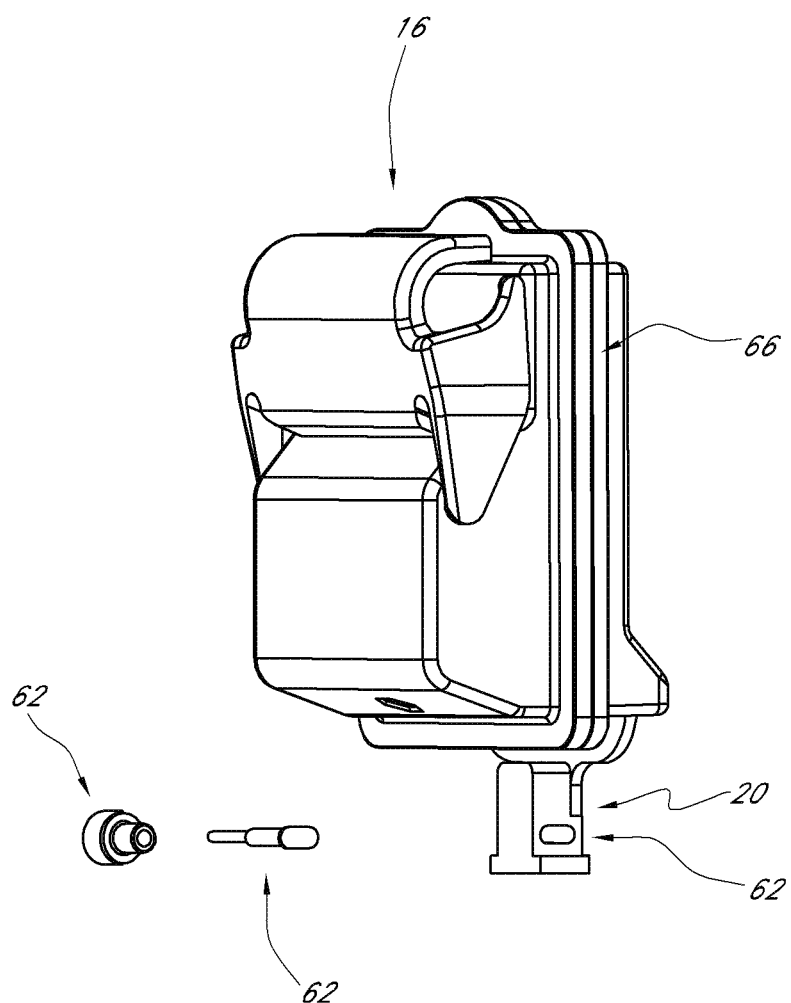
FIG. 16 is a second exploded view of an embodiment of the reference device of the femoral preparation system of FIGS. 2A and 2B.

D. Device for Coupling the Reference Sensor Device to Another Orthopedic Fixture Referring to FIG. 16, the reference sensor device 16 can be used in a variety of orthopedic procedures (e.g., femoral and tibial preparation methods). Accordingly, the housing 66 can optionally include various structural features for attachment with a variety of orthopedic fixtures.

For example, the femoral jig assembly 12 can comprise a second coupling device 20. The second coupling device 20 can be attached to the reference sensor housing 66. In one embodiment, the second coupling device 20 can be securely but releasably attached to the sensor housing 66 by common attachment structures. In another embodiment the second coupling device 20 can be formed as a structural part of the sensor housing 66. The second coupling device 20 can include the same or similar type of jig attachment features 62 that are on the first coupling device 18. The jig attachment features 62 can mate with corresponding attachment features of a microblock assembly to form a secure but releasable attachment with the femoral jig assembly 12 (see, e.g. the microblock assembly 90 illustrated in FIGS. 17 and 19).

While the second coupling device 20 described above can be used to attach and/or couple the reference sensor device 16 with the femoral jig assembly 12, other methods and devices for attaching and/or coupling the components of the femoral preparation system 10 are also possible.

E. Orthopedic Assembly for Femoral Preparation

Figure 17:
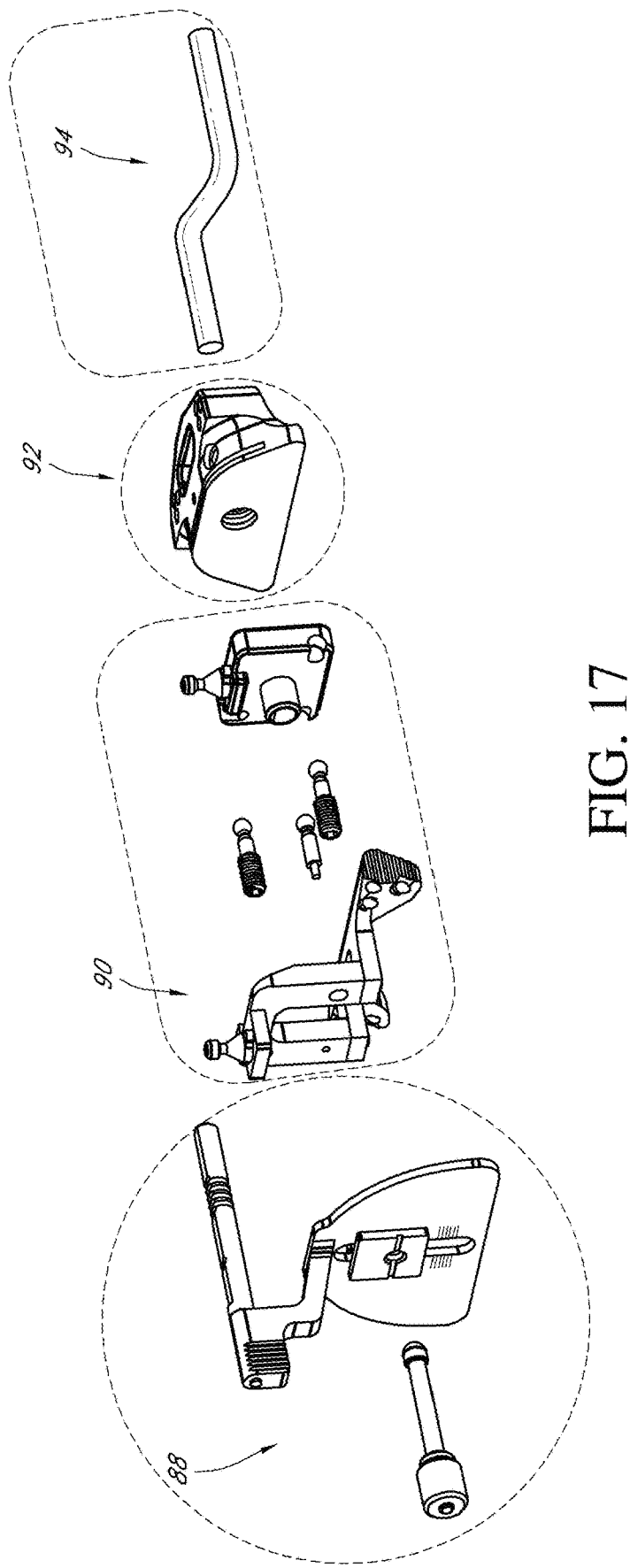
FIG. 17 is an exploded view of the femoral jig assembly of the femoral preparation system of FIGS. 2A and 2B.

Referring to FIG. 17, the femoral jig assembly 12 can comprise an orthopedic assembly for femoral preparation during a total knee replacement procedure. In a preferred arrangement, the femoral jig assembly 12 can comprise a distal guide assembly 88, a microblock assembly 90, a cutting block 92 and an optional anterior probe 94.

Figure 18:
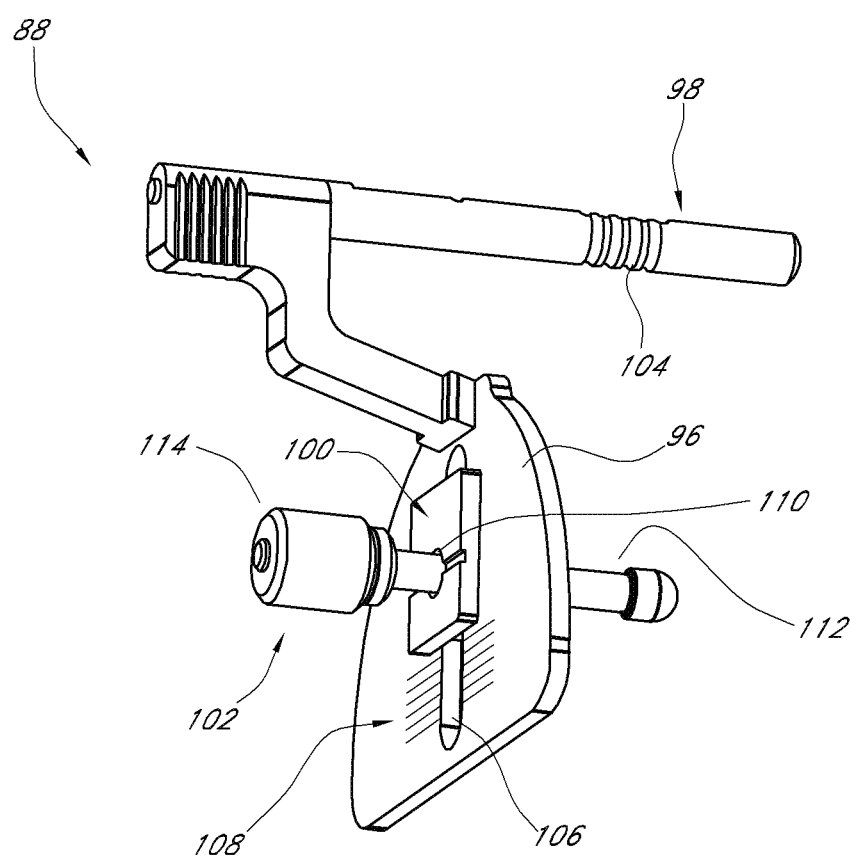
FIG. 18 is a perspective view of the distal guide assembly of the femoral jig assembly shown in FIG. 17.

Referring to FIG. 18, the distal guide assembly 88 can comprise a modular paddle 96, an articulating arm 98, a midline guide 100, and a midline pin 102. The articulating arm 98 can be configured to attach to the microblock assembly 90 and either the cutting block 92 or the anterior probe 94 in a secure but releasable fashion using, for example, the types of attachment structures described above. The arm 98 may be considered to articulate at least by being moveably coupled with other structures, such as the microblock assembly 90. In some embodiments, the articulating arm 98 includes a simple rod, arm, or elongate rigid member that can swing about an axis between a plurality of positions, as discussed below. In one embodiment, the articulating arm 98 can include position adjustment features 104 such as notches spaced in a scale of desired increment distances (e.g. 1 mm or 2 mm). These notches can facilitate the adjustment of the position of a cutting block 92 when the articulating arm 98 is attached to the cutting block 92, resulting in adjustment of the femoral resection depth.

Referring to FIG. 18, the modular paddle 96 can include a channel 106 that is adapted to accept the midline guide 100. The channel 106 can allow the midline guide 100 to move or slide up and down the channel 106. Adjacent the channel 106, the modular paddle 96 can include reference markings 108. The reference markings 108 can be provided in a scale of desired increment distances (e.g., 1 mm or 2 mm increments or the like). The midline guide 100 can include a midline pin receiving feature 110 that allows an insert portion 112 of the midline pin 102 to pass through the midline guide 100. The midline pin 102 can include both the insert portion 112 and a knob portion 114. The knob portion 114 can be designed for interaction with a user allowing the user to move the midline pin 102 up and down the modular paddle 96 (e.g., in a flexion/extension direction upon attachment to a distal end portion of a femur during femoral preparation methods). The insert portion 112 can be designed to have a suitable length that allows the midline pin 102 to enter and pass through the midline guide 100 and into a desired depth of a distal end portion of a femur.

Figure 19:
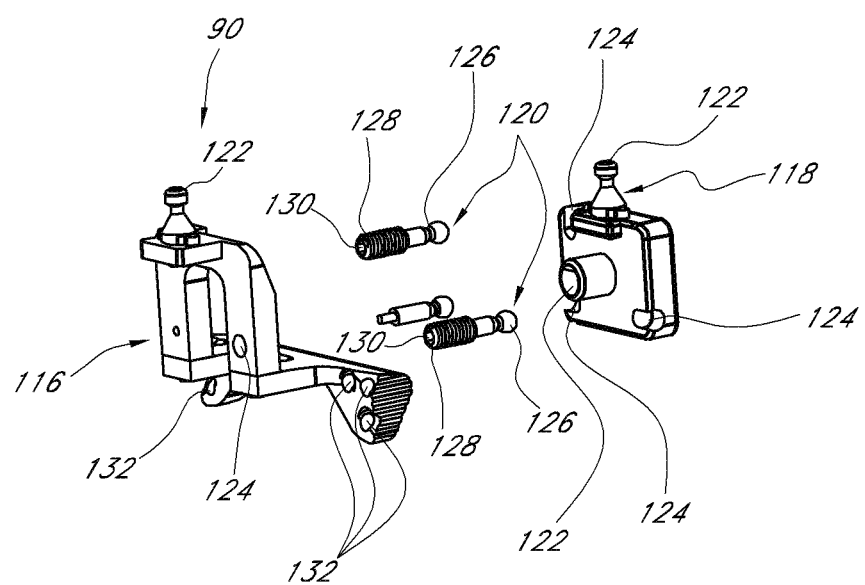
FIG. 19 is an exploded view of the microblock assembly of the femoral jig assembly shown in FIG. 17.

Referring to FIG. 19, the microblock assembly 90 can include a microblock member 116, a translating member 118, and a translation structure or structures 120. The microblock member 116 and the translating member 118 can both include an attachment feature or features 122 for secure but releasable attachment with each other, the articulating arm 98, the cutting block 92, the anterior probe 94, the first coupling device 18, and/or the second coupling device 20.

Both the microblock member 116 and the translating member 118 can include translation receiving features 124. The translation receiving features 124 can allow both the microblock member 116 and the translating member 118 to receive the translation structures 120, with first ends 126 of the translation structures 120 attached to the translating member 118 and second ends 128 of the translation structures 120 attached to the microblock member 116. The second ends 128 of the translation structures 120 can include a translation adjustment feature 130 (e.g. slot or socket for receiving a tool such as a screwdriver) that can be used to move the first ends 126 of the corresponding translation structure 120 to cause a desired directional movement of translating member 118 (e.g., in a varus/valgus direction or in a flexion/extension direction when the microblock assembly 90 is attached to the distal end portion of a femur). At least one of the translation receiving features 124 of the translating member 118 can be adapted to allow movement of the translating member 118 in a varus/valgus direction when the microblock assembly 90 is attached to the distal end portion of a femur. Additionally, at least another one of the translation receiving features 124 of the translating member 118 can be adapted to allow movement of the translating member 118 in a flexion/extension direction when the microblock assembly 90 is attached to the distal end portion of a femur. The design described above can allow the translation structure(s) 120 to move at least a portion of the microblock assembly 90 (and any other components attached to the microblock assembly 90) in a varus/valgus direction and/or in a flexion/extension direction. The translation structure's ability to move at least a portion of the microblock assembly 90 can be controlled by the translation adjustment features 130.

In one embodiment and referring to FIG. 19, the translation structures 120 are ball screws, the translation adjustment features 130 are features for receiving a hex driver (not shown) or the like, and the translation receiving features 124 are channels contained within the translating member 118. At least one of the channels can run in a varus/valgus direction and at least another can run in a flexion/extension direction. To move the translating member 118 of the microblock assembly 90 (and any other components attached to the translating member 118) in a varus/valgus direction and/or in a flexion/extension direction using the translation structures 120, the translation adjustment features 130 can each be turned by a hex driver in either a clockwise or a counter-clockwise direction.

Referring to FIG. 19, the microblock member 116 can also include multiple microblock pin receiving features 132 such as through holes or the like which allow microblock pins (not shown) to attach the microblock assembly 90 (and other components of the femoral preparation system 10) to the distal end portion of a femur. In some embodiments, the microblock pin receiving features 132 can be angled inward and posteriorly.

Figure 20:
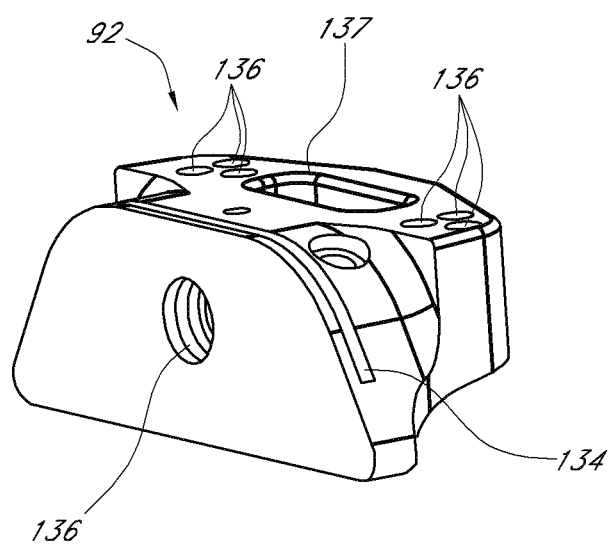
FIG. 20 is a perspective view of the cutting block of the femoral jig assembly shown in FIG. 17.
Figure 21:
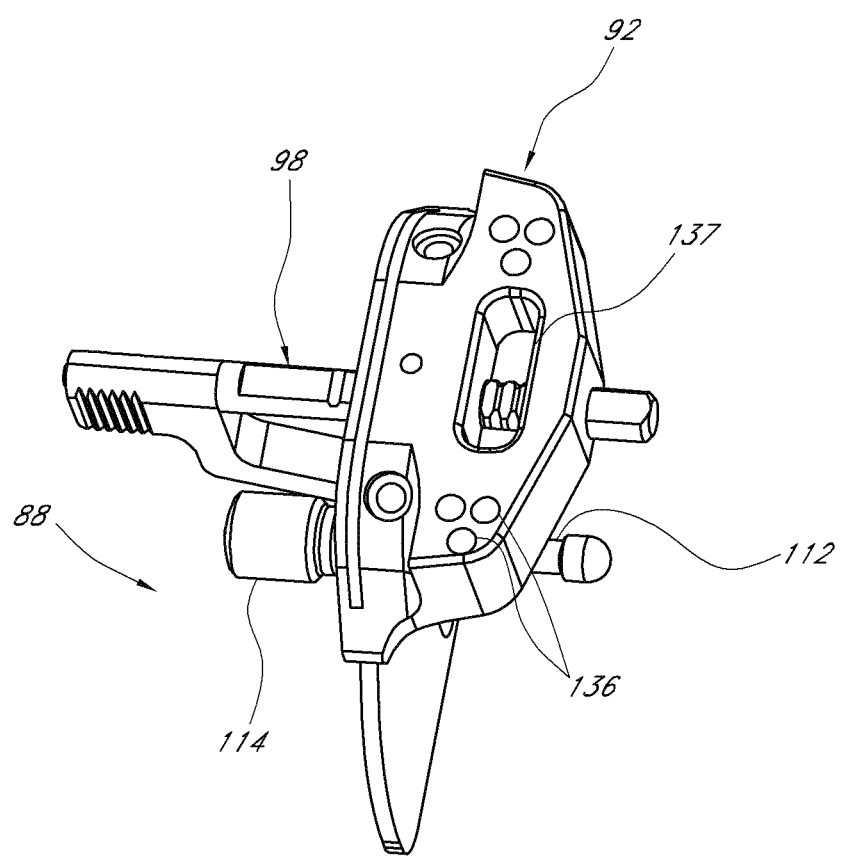
FIG. 21 is a top perspective view of the distal guide assembly and the cutting block of the femoral jig assembly shown in FIG. 17.

Referring to FIGS. 20 and 21, the cutting block 92 can include at least one opening 134 configured to receive a cutting tool such as for example a cutting saw and/or other referencing tool. The cutting block 92 can further include receiving features 136 for receiving, for example (i) corresponding attachment features 122 from the microblock assembly 90; (ii) the articulating arm 98 from the distal guide assembly 88; and (iii) positional pins (not shown) for a secure but releasable attachment to the microblock assembly 90, the distal guide assembly 88, and/or the distal portion of a femur. In one embodiment, the receiving features 136 for receiving the articulating arm 98 of the distal guide assembly 88 can include one or more through holes and/or other features along which the cutting block 92 can be moved. The movement of the cutting block 92 can be controlled and adjusted based upon the position adjustment features 104 of the articulating arm 98 as shown in FIG. 18. For example, the cutting block 92 can comprise a window or opening 137 through which the position adjustment features 104 of the articulating arm 98 can be seen as the cutting block 92 is moved along the articulating arm 98.

Referring to FIGS. 19, 20, 21, and 28, the cutting block 92 can be used for distal femoral resection during a femoral preparation method. The cutting block 92 can be oriented and translated in a varus/valgus direction and a flexion/extension direction by other components of the femoral preparation system 10 during the femoral preparation method, providing at least two degrees of freedom. During the femoral preparation method, the cutting block's attachment to the articulating arm 98 can provide an initial placement of the cutting block 92 adjacent to the distal end portion of a femur 82. Thereafter, the microblock assembly 90 can be used to physically adjust the orientation of the cutting block 92 when the cutting block 92 is attached to the microblock assembly 90 and the microblock assembly 90 is attached to the distal end portion of the femur.

Figure 28:
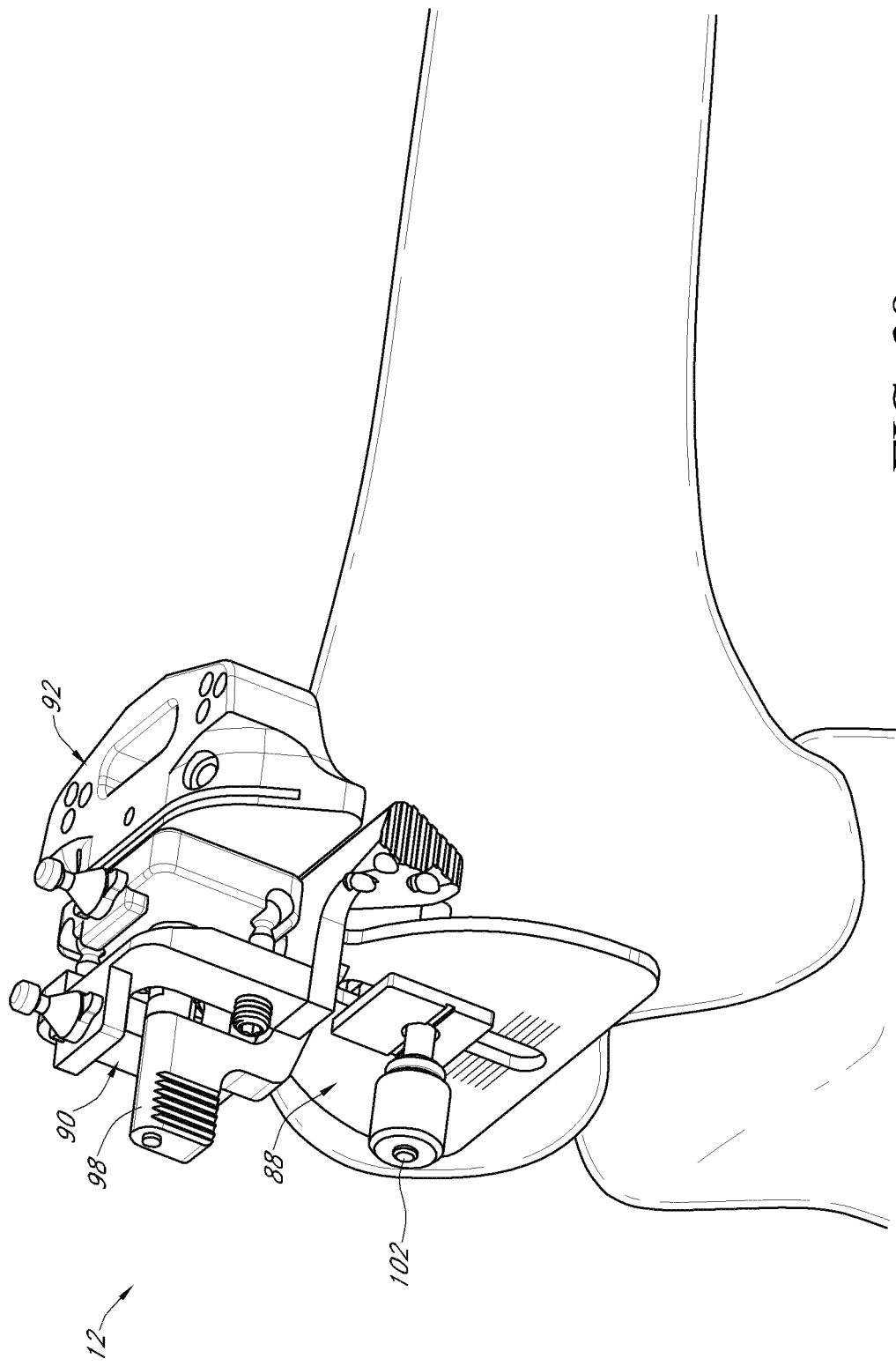
FIG. 28 is a perspective view of the femoral preparation system of FIGS. 2A and 2B being used during another stage of the femoral preparation method.

Referring to FIGS. 19, 20, and 28, the physical adjustment of the orientation of the cutting block 92 can be achieved by adjusting the translation adjustment features 130 of the translation structures 120 as discussed above. For example and referring to FIG. 19, the translation structure 120 can comprise two ball screws, and the translation adjustment feature 130 of each of the translation structures 120 can comprise a feature for receiving a hex driver. Turning the translation adjustment feature 130 of one of the ball screws in a clockwise direction or counter clockwise direction can change the cutting angle of the cutting block 92 in a flexion-extension direction. Turning the translation adjustment feature 130 of the other one of the ball screws can change the cutting angle of the cutting block 92 in a varus-valgus direction. In some embodiments, the translation structures 120 can facilitate pivoting of the cutting block 92 within a range of approximately twenty degrees (e.g. +−ten degrees on either side of a predetermined angle). Other ranges are also possible.

Figure 23:
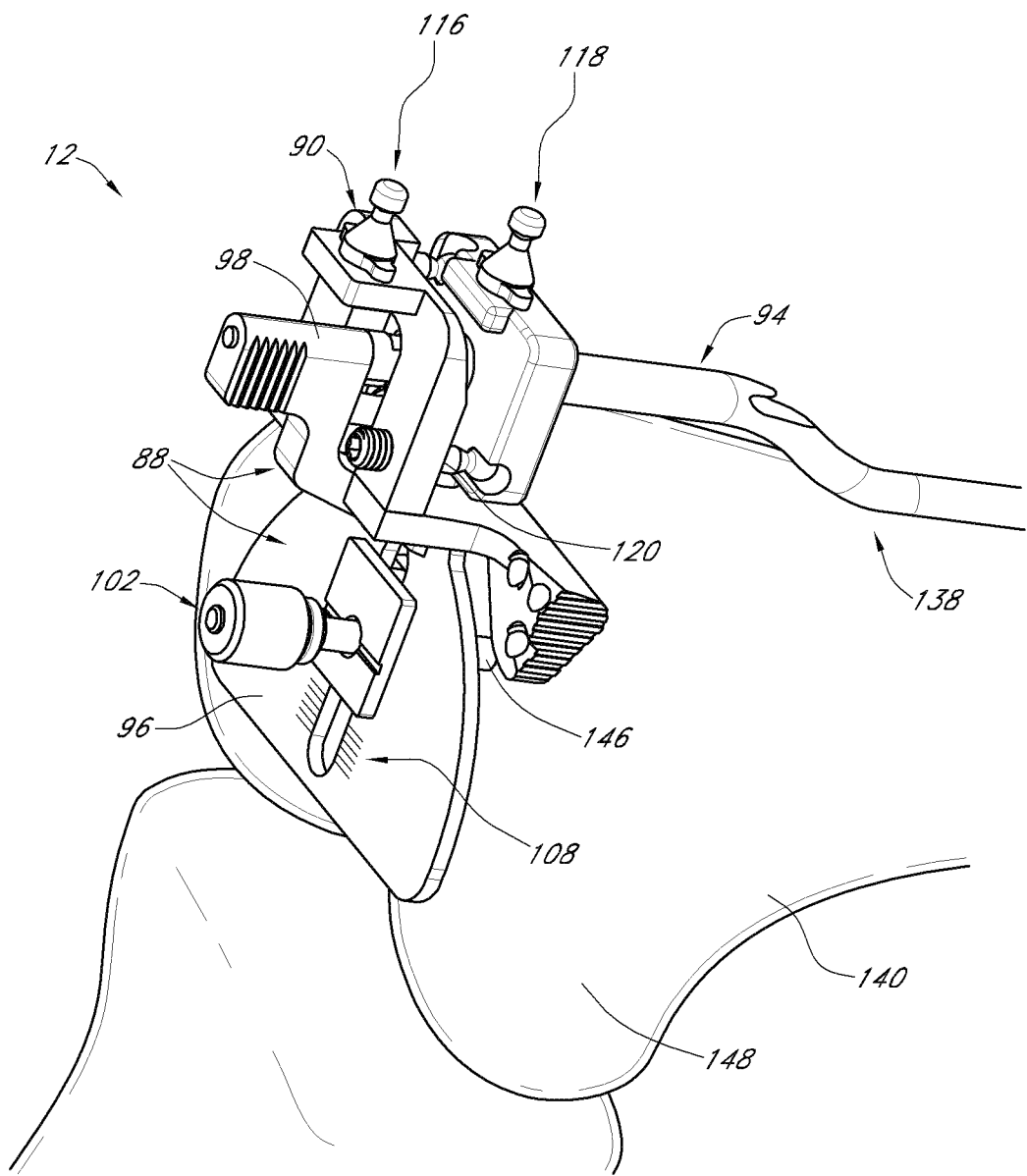
FIG. 23 is a perspective view of the femoral jig assembly shown in FIG. 17 in an assembled fashion attached to a distal end portion of a femur.
Figure 24:
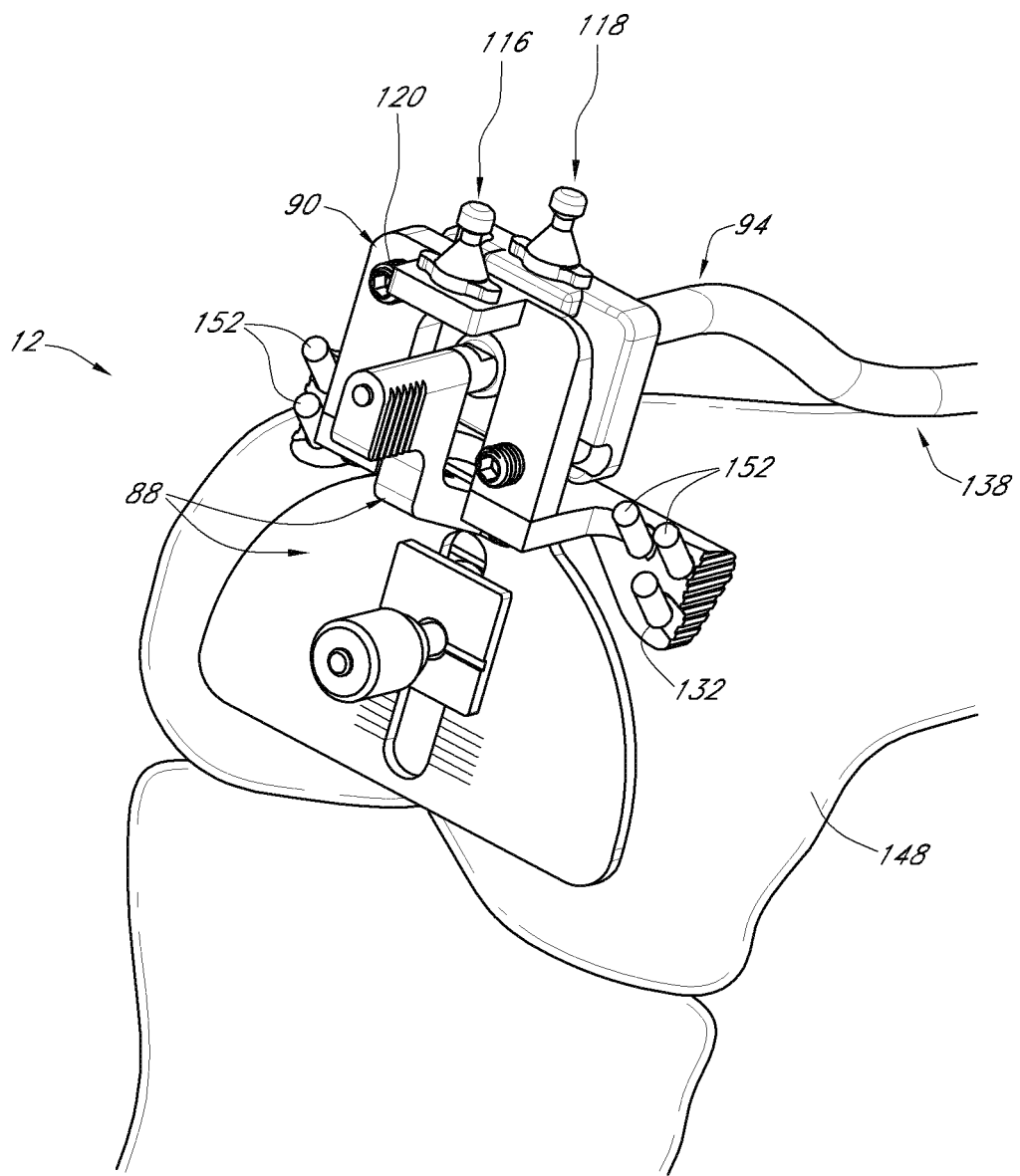
FIG. 24 is a perspective view of the femoral jig assembly shown in FIG. 17 in an assembled fashion including at least one pin.

Referring to FIGS. 23 and 24, the anterior probe 94 can be a member adapted to be attached in a secure but releasable fashion to, for example, (i) the articulating arm 98 of the distal guide assembly 88; or (ii) the microblock assembly 90. During a femoral preparation method, the anterior probe 94 can extend from the microblock assembly 90 to an anterior cortex 138 of a femur 140. The anterior probe 94 can be adjustable via push button, screw, or other mechanism to assist in referencing the anterior cortex 138. The anterior probe 138 can allow the femoral jig assembly 12 to be stabilized in an approximate desired flexion angle during a femoral preparation method.

III. Femoral Preparation Methods

Referring to FIGS. 22-31, the femoral preparation system 10 described above can be used to prepare the femur for a total knee replacement.

A. Attaching an Orthopedic Assembly on a Femur

Figure 22:
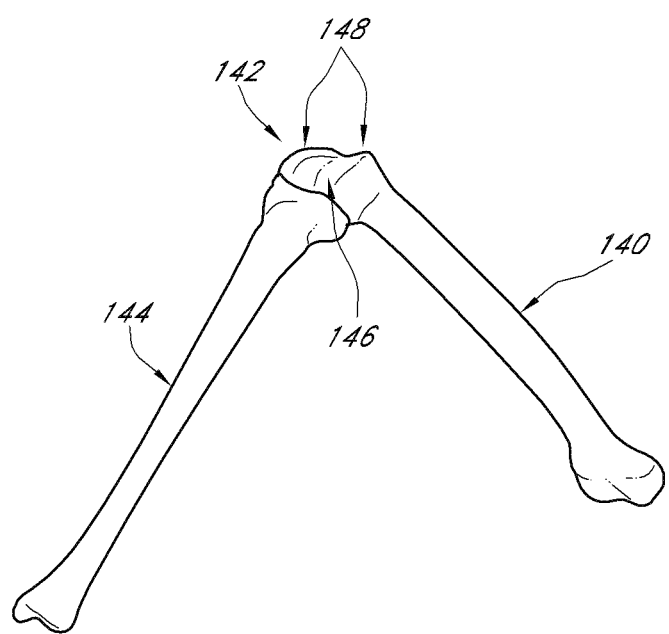
FIG. 22 is a femur and a tibia of a leg shown in a flexion position with a small hole drilled in the intercondylar notch of the femur.

Referring to FIG. 22, in preparation for the distal femoral resection, the method can begin with locating a distal point that is intersected by the mechanical axis of the femur.

In one technique for locating a distal point of the mechanical axis of the femur 140, a distal end portion 142 of the femur is exposed using any conventional surgical technique. The tibia 144 and the femur 140 can then be placed in approximately 90 degrees of flexion as shown in FIG. 22. It is possible to place the leg in other degrees of flexion.

A small hole 146 for receiving a portion of the midline pin 102 can then be drilled using any conventional surgical technique at an appropriate anatomical location within the distal end portion 142. The anatomical location can be the center of the intercondylar notch, a location near the insertion of the anterior cruciate ligament ("ACL"), an entry point to the intramedullary canal, or other suitable anatomical landmark or combination of landmarks within the distal end portion 142. In one embodiment, the small hole 146 can be drilled at the approximate center of the intercondylar notch as shown in FIG. 22.

The method can further comprise installing the femoral jig assembly 12 onto the distal end portion 142 by inserting the midline pin 102 into the small hole 146 as shown in FIGS. 22 and 23. Placement of the midline pin 102 in the approximate center of the intercondylar notch places the femoral jig assembly 12 in an approximate center position of the distal end portion 142 and the modular paddle 96 on distal condyles 148 of the femur 140. The modular paddle 96 can then be fitted to a distal apex of the distal condyles 148 thereby allowing the femoral jig assembly 12 to be placed in an approximate neutral varus/valgus direction as shown in FIG. 23.

The method can further include an optional step of adjusting the anterior probe 94 by placing the anterior probe 94 on the anterior cortex 138 of the femur 140. The anterior probe 94 can be adjusted via push button, screw, or other mechanism to assist in referencing the anterior cortex 138 as shown in FIG. 23. Placement of the anterior probe 94 on the anterior cortex 138 can allow the femoral jig assembly 12 to be stabilized in the approximate desired flexion angle. In some embodiments the femoral jig assembly 12 does not need to be precisely set in a flexion/extension direction. Rather, the initial placement can serve as a visual tool to avoid hyper-flexion or hyper-extension.

Once the femoral jig assembly 12 is placed by the midline pin 102 in an approximate neutral varus/valgus orientation or angle and by the anterior probe 94 in the approximate desired flexion angle, the method can further include verifying the rotational positioning of the femoral jig assembly 12 in an effort to ensure that the femoral jig assembly 12 is in the desired position. In one embodiment, the desired position may be less than about 15 degrees rotation relative to a Whitesides line or epicondylar axis. In another embodiment, the desired position may range from about 0 degrees to about 30 degrees relative to a Whitesides line or epicondylar axis. This verification process can be completed by obtaining the information provided by the reference markings 108 of the modular paddle 96. The reference markings 108 can inform the user of an offset distance 150 (see, eg., FIG. 2B) of the reference sensor device 16 in a frontal plane or a flexion/extension direction (e.g. an "AP Offset Data"). The AP Offset Data can generally be the offset distance 150 measured from a reference point on the reference device 16, such as the center of the sensor 64 in the reference device 16, to a reference point on the femoral jig assembly 12, such as the center of the midline pin 102 as shown in FIG. 2B. Upon completion of this verification process, the method can include inserting microblock pins 152 into the appropriate microblock pin receiving features 132, allowing the microblock assembly 90 to be attached to the distal femoral condyles 148 in an approximate desired position as shown in FIG. 24.

Once the microblock assembly 90 is attached to the distal femoral condyles 148, the method can include noting the indicia of distance provided by the reference markings 108 and the location of the midline pin 102 in relation to the reference markings 108 in order to establish the AP Offset Data discussed above. The AP Offset Data can then be entered into the surgical orientation device 14. In some embodiments, this process of obtaining and entering AP Offset Data into the surgical orientation device 14 can be avoided if a fixed offset distance is provided by the configuration of the femoral preparation system 10.

Figure 25:
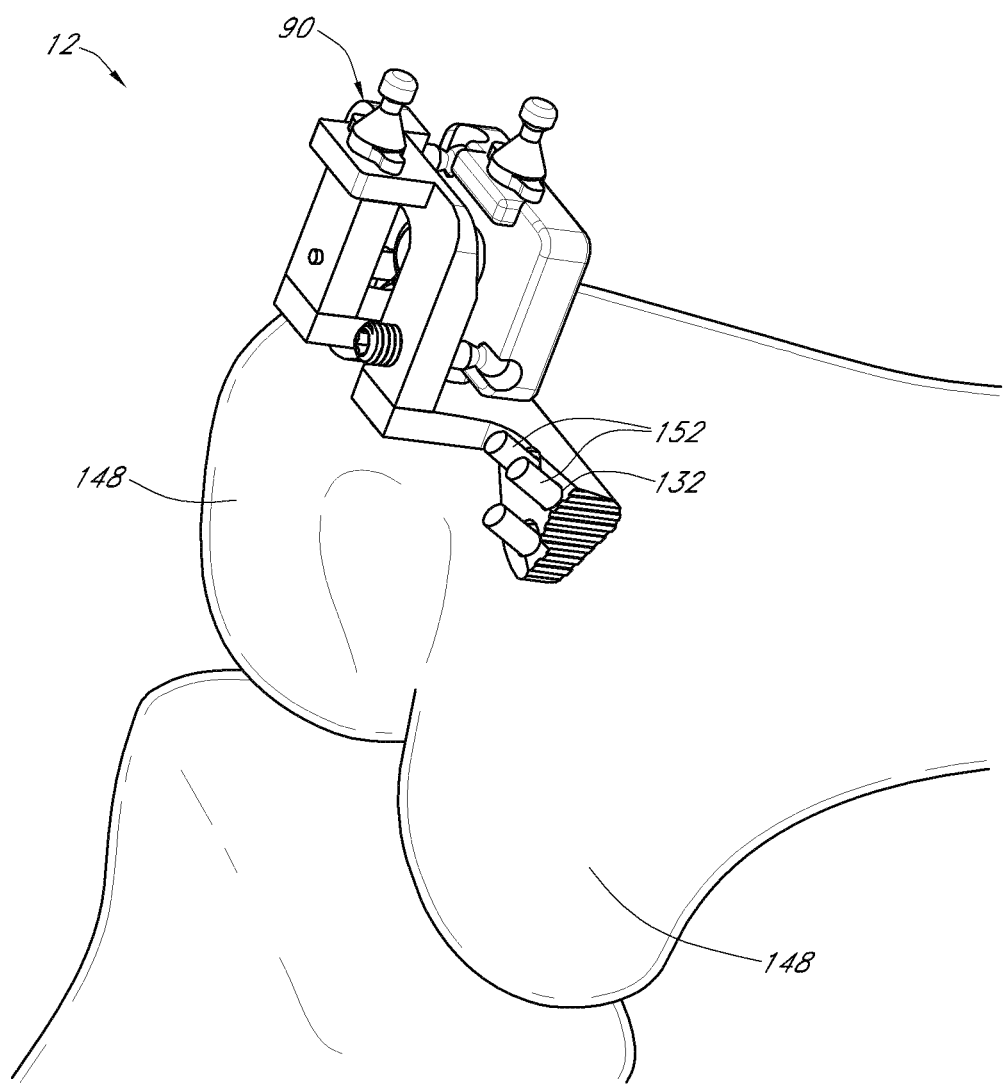
FIG. 25 is a perspective view of the femoral preparation system of FIGS. 2A and 2B being used during a stage of a femoral preparation method according to one embodiment of the present invention.

Referring to FIG. 25, the method can further include removing the distal guide assembly 88 and the anterior probe 94 from the femoral jig assembly 12, leaving only the microblock assembly 90 present and attached to the distal condyles 148.

Figure 26:
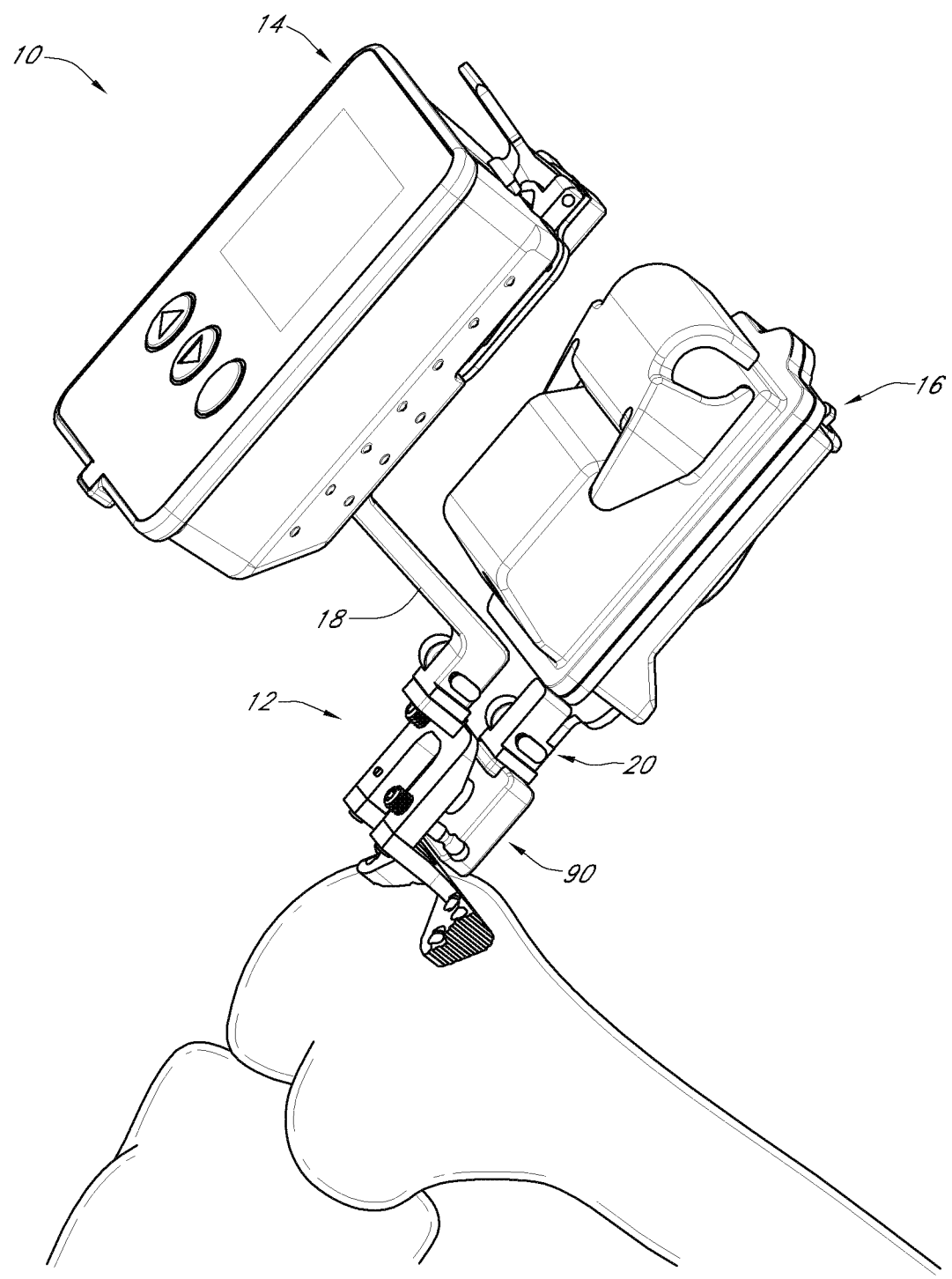
FIG. 26 is a perspective view of the femoral preparation system of FIGS. 2A and 2B being used during another stage of a femoral preparation method according to one embodiment of the present invention.

Referring to FIG. 26, the method can further include attaching the surgical orientation device 14 and the reference sensor device 16 to the microblock assembly 90 using the first coupling device 18 and second coupling device 20 and their respective components for attachment as discussed above. Once the surgical orientation device 14 and the reference sensor device 16 are attached to the microblock assembly 90, the method can further include placing the leg in extension as shown in FIG. 27.

In the method thus far, a distal point corresponding to the mechanical axis of the femur can be approximated by using a portion of the femoral jig 12 to locate the center of the femur. In addition to the above anatomy that can approximate this location, a clinician can employ a method that considers the most distal point of the sulcus of the trochlea to correspond to the distal portion of the mechanical axis. In some embodiments, the IMU is offset a certain distance from the center of the distal femur. This offset can be accounted for by using the AP Offset Data, as discussed above. This offset can be communicated to the surgical orientation device 14 so that the system can factor it in its calculation of the mechanical axis. For example, in certain embodiments, the reference sensor 16 encloses the IMU 1105 and is spaced a variable distance anterior to the center of the distal femur. This distance can be entered into the surgical orientation device 14 to eliminate a bias error that would be created by this offset. In other embodiments, instrumentation can be provided that eliminates the variability of this distance, such that the distance between the IMU (e.g., incorporated into the reference sensor 16) and the center of the femur is constant. In that case, the surgical orientation device 14 or a system employing the surgical orientation device 14 can be configured to automatically eliminate this bias error.

B. Calculating the Location of the Mechanical Axis Using an Orientation Device

Figure 27:
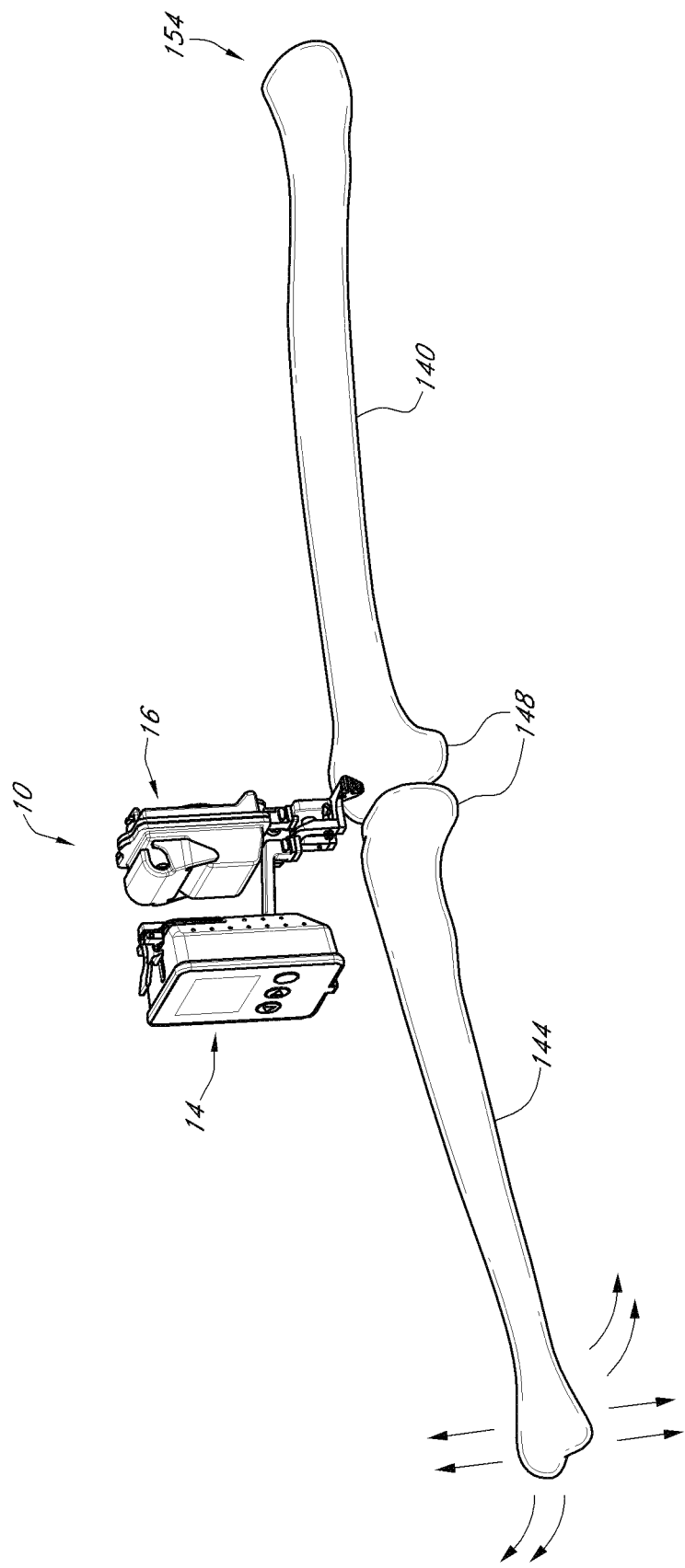
FIG. 27 is a perspective view of the femoral preparation system of FIGS. 2A and 2B being used during yet another stage of the femoral preparation method.

Referring to FIG. 27, in a preferred embodiment, an orientation device can be used to calculate the location of the mechanical axis in the femur. For example, the reference sensor device 16 and/or orientation device 14 can be used to determine the relative coordinates of a center pivot point on the femur. By determining the coordinates of the pivot point of the femoral head 154, the reference sensor device 16 and/or surgical orientation device 14 can calculate the location and/or orientation of the mechanical axis that extends through the femur.

In order to determine the coordinates of the pivot point of the femoral head 154 (i.e. the pivot point of the mechanical axis), the leg can be moved (e.g. swung). For example, the leg can be moved in several different directions and/or planes (see arrows in FIG. 27), with the reference sensor device 16 and/or surgical orientation device 14 attached. Readings such as angular rate and acceleration ("surgical orientation device 14 and/or reference sensor device 16 data") of the femur 140 can be obtained by the reference sensor device 16 and/or surgical orientation device 14 until the location and/or orientation of the mechanical axis of the leg and the femur 140 ("femoral mechanical axis") is found. In one embodiment, where one or more multi-axis (e.g., two-axis) accelerometers and gyroscopes are used, surgical orientation device 14 and/or reference sensor device 16 data for each movement of the femur 140 can be numerically integrated over time to obtain a trajectory of position and velocity points (one point for each IMU data). The IMU data can be integrated without imposing any plane trajectory constraints on movements of the femur 140.

The acceleration and angular rate sensed by the reference sensor device 16 and/or surgical orientation device 14 during the leg movement can be processed while the leg is moved about its pivot point. The reference sensor device 16 and/or surgical orientation device 14 can provide an output vector representing the center of the rotation with respect to the inertial sensor axes of the reference sensor device 16 and/or surgical orientation device 14.

The IMU data can be input to a microprocessor in the reference sensor device 16 and/or surgical orientation device 14. In a preferred embodiment, the microprocessor can be located on the reference sensor device 16, and output from the microprocessor of the reference sensor device 16 can be transmitted via an RF wireless link to the surgical orientation device 14. The leg can be moved about its pivot point while inertial data is being processed by the microprocessor. An algorithm implemented on the microprocessor can process the inertial data in real time and determine if the leg is static or dynamically moving. Data from both states can be used by the algorithm to determine the pivot point.

The method of calculating the location and/or orientation of the mechanical axis described herein, and for calculating in general the location and/or orientation of any axis based on a pivot point, can provide accurate determination of pivot point location and radius of curvature without the burdensome and sometimes near impossible restraints of external measurements encountered in medical procedures. For example, the method can permit calculation of pivot points in blind situations where the end joint is typically hidden or unobservable, such as for the case of the head of a femur.

Examples of three possible leg movement trajectories for calculating the IMU data are: (i) a horizontal swing from the leg's position of origin to the surgeon's right and then back again; (ii) a horizontal swing from the origin to the surgeon's left and then back again; and (iii) a vertical swing upward and then back again. In some protocols, at least one horizontal movement and at least one vertical movement are included to provide IMU data. During each swing trajectory the IMU data can be stored for future processing.

In some embodiments, the mechanical axis can be detected by moving and/or swinging the leg when it is attached to the surgical orientation device 14 and the reference sensor device 16 on a horizontal plane (e.g. a plane along the operating table), starting from a known fixed position and orientation ("home position", which can be close to the surface of the horizontal plane) and obtaining IMU data. The arrows shown in FIG. 27 illustrate at least one example of how the direction or directions the leg 100 can be moved. In one embodiment, the leg can be placed in full extension and subjected to the following movements: (i) abducting the leg about 30 degrees and returning the leg substantially to a home position; and (ii) raising the leg about 30 degrees and returning the leg substantially to a home position. The abduction can occur before the raising movement or vice versa. During the placement and movements discussed above, the leg can stay extended and the microblock assembly 90 (including the microblock pins 152 attaching the microblock assembly 90 to the distal condyles 148) can clear the tibia 144 through a full range of motion. In some embodiments, the leg can be abducted about 20 degrees and returned to the home position, and raised about 20 degrees and returned to the home position. In yet other embodiments, the leg can be abducted between about 10 degrees and returned to the home position, and raised between about 10 degrees and returned to the home position. In yet other embodiments, the leg can be abducted between about 5 degrees and returned to the home position, and raised between about 5 degrees and returned to the home position. Other ranges and degrees of movement are also possible. In some embodiments, the leg can be swung in one generally looping motion from a home position back to the home position, the looping motion causing both an abduction and raising of the leg.

The reference sensor device 16 and/or surgical orientation device 14, which can be coupled to the leg during such movements, can have axes angled with respect to an axis of the sensor(s) disposed in the reference device 16 and/or in the surgical orientation device 14. For example, as illustrated in FIG. 12, the sensor board 46 can be mounted at an acute angle to a plane extending longitudinally through the housing 22. In other embodiments, the reference sensor device 16 and/or surgical orientation device 14 have axes that are not angled, e.g., parallel to or co-planar with, an axis of the reference sensor device and/or surgical orientation device 14.

As the leg is swung, the sensors inside the reference sensor device 16 and/or surgical orientation device 14 can detect movement of the reference sensor device 16 and/or surgical orientation device 14, collect IMU data on this movement, and transmit the IMU data to, for example, the surgical orientation device 14. From receiving all of the IMU data transmitted from the sensors inside both the surgical orientation device 14 and reference sensor device 16, the reference sensor device 16 and/or surgical orientation device 14 can then calculate, and in some cases display, the location of the center of rotation of the femur 140, the center of the femoral head 154, and/or the femoral mechanical axis.

In a preferred arrangement, where the surgical orientation device 14 is disposable and the reference sensor device 16 is reusable, the reference sensor 16 can be configured to take measurements as the femur is moved to calculate the center of femoral rotation, while the surgical orientation device 14 can be configured to receive information from the reference sensor device 16 and/or to display information on display 26. In such an arrangement, the surgical orientation device 14 can comprise a multi-axis accelerometer, and the reference sensor device can comprise both a multi-axis accelerometer and a multi-axis gyroscope. In this manner, the more expensive components necessary to make such calculations can be incorporated into the re-usable reference sensor device 16. However, in other embodiments the surgical orientation device 14, rather than the reference sensor device 16, can include the additional components and/or sensors necessary to calculate the center of femoral rotation.

Various formulae, which can be derived from basic centripetal acceleration physics coupled with optimal estimation or Kalman filtering techniques, can be used during the process described above to perform the calculations in the reference sensor device 16 or surgical orientation device 14.

C. Error Correction Technique to Remove Biases

In some embodiments, prior to determining the location and/or orientation of the center of rotation of the mechanical axis, an error correction technique can be used to remove biases in the surgical orientation device 14 and/or reference sensor device 16. For example, an error correction technique can include assessing 1) static bias; 2) gyroscopic bias; and 3) accelerometer bias in the surgical reference sensor device 16 and/or surgical orientation device 14.

1. Static Bias Determination

In a preferred embodiment, static bias determination can comprise acquiring data from the IMU of the reference sensor device 16 and/or surgical orientation device 14 in a static condition. This static condition can provide a baseline for the reference sensor device 16 and/or surgical orientation device 14 and can permit determination of biases for internal sensor(s).

For example, once a user is ready to commence the method of determining the center point of rotation of the mechanical axis as described above, the user can press a user input 28 on the surgical orientation device 14. Once the user input 28 is pressed, the surgical orientation device 14 can indicate that the user should hold the surgical orientation device 14 motionless. The user can be required to hold the surgical orientation device 14 motionless for a given period of time. In a preferred embodiment, the user can be required to hold the surgical orientation device 14 motionless for approximately three seconds, though other times or ranges or times are also possible. For example, in some embodiments the user can be required to hold the surgical orientation device motionless for at least one but no more than three seconds. By holding the surgical orientation device motionless, any static biases can be determined, and can subsequently be removed (e.g. subtracted) during data acquisition.

In some embodiments, if the user does not hold the surgical orientation device 14 still for a long enough period, a fail condition can be displayed on the surgical orientation device 14, and the user can be required to start over again by pressing the user input 28.

Inclusion of a gravitation vector can be used for more accurate final results. For example, initial orientation of the reference sensor device 16 and/or surgical orientation device 14 during static bias determination can be used to create an initial gravity vector transformation matrix relating the orientation of the IMU to the inertial gravity vector. Angular rate data can be used to propagate the attitude of the reference sensor device 16 and/or surgical orientation device 14 and update the inertial gravity vector transformation matrix during subsequent motion.

2. Gyroscope and Accelerometer Bias Determination

Removing gyroscope and accelerometer biases can help to correct for errors that may arise from starting and stopping in a rotated orientation. A gyroscope bias determination can comprise, for example, propagating a direction cosine matrix (DCM) using rate sensors in the surgical orientation device 14 and/or reference sensor device 16. An accelerometer bias determination can comprise, for example, propagating a direction cosine matrix from the gyro bias to remove a gravity component of the accelerometers.

In order to determine gyroscope and accelerometer bias in the surgical orientation device 14 and/or reference sensor device 16, the leg (with surgical orientation device 14 and/or reference sensor device 16 attached) can be moved by an operator or other means in such a way that sufficient rate and acceleration data is achieved for all axes. In a preferred arrangement, during this data acquisition phase, and/or any other phase for error correction or data collection during an orthopedic method, the reference sensor device 16 and/or surgical orientation device 14 can determine, without user intervention, what phase of data collection it is in, static or dynamic. In contrast, in some embodiments the user can press a user input 28, for example, to tell the reference sensor device 16 and/or surgical orientation device 14 that it is in a static or dynamic state.

During gyroscope and accelerometer bias determination, the leg can be moved (e.g. swung through at least different two planes), and an average angular rate of leg movement of at least 30 degrees per second can be provided to acquire data, though other rates are also possible. For example, in some embodiments an average angular rate of at least 20 degrees can suffice. In yet other embodiments an average angular rate of at least 10 degrees can suffice.

In a preferred arrangement, the leg can be moved in more than one plane, or for example in a loop configuration, and a beginning and ending attitude of the leg after leg movement is complete can be within 15 degrees on any axis, though other beginning and ending attitudes are also possible. In a preferred arrangement, the leg can be swung and returned back to its home position within approximately 2 cm in the abduction plane, though other ranges and values are also possible.

In a preferred embodiment, the surgical orientation device 14 and/or reference sensor device 16 can advantageously detect when motion (e.g. swinging) of the leg has stopped, and can detect if the leg has returned to its home (i.e. starting) position. For example, the surgical orientation device 14 and/or reference sensor device 16 can include a 1 Hz filter to prevent false stopping detection. The surgical orientation device 14 and/or reference sensor device 16 can average the rate of motion over half a second to determine whether the movement of the leg, and consequently the movement of the surgical orientation device 14 and/or reference sensor device 16, has come to a stop.

By moving (e.g. swinging) the leg in the manner described above and returning it to a home position, gyroscope and accelerometer biases can be accounted for in the surgical orientation device 14 and/or reference sensor device 16. With these biases accounted for, the method of determining the center of rotation of the mechanical axis can be made more accurate.

D. Additional Detail for Determining the Mechanical Axis

Provided below is additional detail that describes the methodology behind the surgical orientation device 14 and/ or reference device 16 and how it is used to make certain calculations:

At least one purpose of the surgical orientation device 14 and/or reference device 16 and systems described herein is to provide guidance to the surgeon as to how to position a cutting block on the bone in order to achieve a cutting plane that is perpendicular to the load bearing axis of the bone (or some number of degrees off of that perpendicular plane if desired). A jig, such as that described above, can be fixed to the bone to be cut and the reference sensor device 16 and surgical orientation device 14 can be attached to that jig (one device is attached to a fixed portion of the jig to act as a reference to the bone's orientation and the other device is attached to an articulating arm of the jig to provide the surgeon a means to find and set the desired cutting plane). The articulating arm of the jig can be constrained to only be moved in two dimensions—pitch and yaw (not rotation). These two axes form a plane that can be adjusted to guide the placement of the cutting block which guides the saw to cut the bone on that plane.

Embodiments of a general approach can include determining the yaw (or varus/valgus (V/V)) and pitch (extension/flexion) angles required to bring the surgical orientation device 14 and/or reference device 16 from its initial orientation (provided by the other device, i.e. surgical orientation device 14 and/or reference device 16) to its present orientation.

In some embodiments, both sensors can begin aligned generally to the same gravity vector (so that small angle assumptions apply). The present orientation of the fixed sensor in the surgical orientation device 14 and/or reference device 16 can be considered the initial orientation of the navigation sensor. The sensor in the surgical orientation device 14 and/or reference device 16 can be free to move in pitch and yaw from the initial orientation, but roll is considered fixed X, Y, and Z coordinate axes for both sensors can be generally aligned. Both sensors can be calibrated with offset and gain and corrected for misalignment.

The surgical orientation device 14 and/or reference sensor device 16 can both be 3 axis accelerometers and either one can play the role of a fixed sensor. They can report the X, Y and Z components of the local gravity vector within the sensors coordinate system. For example, the fixed sensor can be the reference sensor device 16 and reports X1, Y1, Z1. The navigation sensor can be the surgical orientation device 14 Unit and reports X2, Y2, Z2.

At least one purpose of the system described herein is to provide an apparatus and method to determine the relative coordinates of a center pivot point on a rigid linkage that overcomes the requirement for direct physical measurement. The acceleration and angular rate sensed by the surgical orientation device 14 and/or reference device 16 can be processed while the link is moved by some means about its pivot point. The apparatus can provide an output vector representing the center of the linkage rotation with respect to the inertial sensor axes.

A method can start with the step of attaching the surgical orientation device 14 and/or reference device 16 to the linkage in a rigid manner. The data required from the surgical orientation device 14 and/or reference device 16 can be acceleration and angular rate. The data is input to a microprocessor. In a preferred embodiment, the microprocessor is located on the link and output from the processor is transmitted via RF wireless link, though this collocation is not a necessary condition. The link can be moved about its pivot point while inertial data is being processed by the microprocessor. The algorithm implemented on the microprocessor can process the inertial data in real time and determines if the link is static or dynamically moving. Data from both states is used by the algorithm to determine the center of the link rotation. This result is output by the microprocessor to the user.

The method and apparatus can provide accurate determination of pivot point location and radius of curvature without requiring any external measurements. This allows determination of effective link pivot point in blind situations where the end joint is hidden or unobservable. An example of this is determination of the pivot point location a human femur. Below are formulae which are derived from basic centripetal acceleration physics coupled with optimal estimation or Kalman filtering techniques to determine pivot point location.

The instantaneous translational velocity of a point on a rigid body is related to the link length and angular rate by $$\dot{\bar{R}}_w = \bar{\omega} = \bar{R}$$

Further, the translational velocity can be computed by integrating acceleration over the same time interval as shown here $$\dot{\bar{R}}_a = \int_{t1}^{t2} \ddot{R} + \dot{R}_0$$

Both of these can be further integrated into a position vector, R, which represents the mechanical axis of the system, or the radial arm to the center of rotation. The unknown vector R is the key desired output from the apparatus. The vector R is found thru optimal estimation of the system. One cost function that can be used for estimation is $$J = \tfrac{1}{2} e^T W e$$

where e is the residual value computed from the difference between the measured value and the expected values. For this method and apparatus, the measured value is the translational velocity and/or position determined by integration of the accelerometer. The expected value is the translational velocity and/or position determined by multiplying the estimated link vector by the measured angular rate data and the time interval across which that rate data is obtained in some cases. W is a matrix of weighting values that is typically all evenly weighted at unity.

One method is to vary an estimated vector, R, in such a way that the cost function is minimized.

There are many types of optimal estimator formulation. One can use a Gauss-Newton in this description. Other methodology can also be used. Kalman filter estimators and other optimal (or even sub-optimal) methods are valid also.

Prior to the final estimation, noise and error removal and reduction from the raw sensor data can be performed. This includes rate sensor bias, bias stability, angle random walk, scale factor errors and mechanical misalignments. Also included are accelerometer bias, bias stability, velocity random walk, scale factor errors and mechanical misalignments. Possible errors introduced by inaccurate removal of gravitational influence are reduced. The amount of noise and error removal is proportional to the inherent capabilities of the sensors. As sensor technology gets better, certain portions of the algorithm may no longer be needed to achieve the same accuracy.

There can be two modes to the operation of the system, data acquisition and optimal estimation. During the data acquisition phase, data is acquired from the surgical orientation device 14 and/or reference device 16 in a static condition, i.e. motionless. This static condition provides a baseline for the sensor and allows determination of biases for all internal sensors. The surgical orientation device 14 and/or reference device 16 is then moved by an operator or other means in such a way that sufficient rate and acceleration data is achieved for all axes. Lack of sufficient motion in any axes can reduce the effectiveness of the final output. During the data acquisition phase, the apparatus can determine without user intervention what phase of data collection it is in, static or dynamic.

Correct inclusion of gravitation vector in the method can be important for accurate final results. Initial orientation of the surgical orientation device 14 and/or reference device 16 during the static phase of data acquisition is used to create an initial gravity vector transformation matrix relating the orientation of the surgical orientation device 14 and/or reference device 16 to the inertial gravity vector. Angular rate data can be used to propagate the attitude of the unit and update the inertial gravity vector transformation matrix during subsequent motion.

Once the data acquisition phase is determined to be complete, the second phase, optimal estimation, is entered. This phase is further broken down into three sub phases. These include gyro bias estimation, accelerometer bias estimation, and finally pivot point link vector estimation.

Some representative criteria for operation are now described that provide the most accurate pivot point estimation. During the static data collection, at least 1 second, but no more than 3 seconds of data can necessary in some embodiments. Longer periods of static data do not adversely affect the output. During the dynamic motion of the link, average angular rate in excess of 30 degrees per second are desired Beginning and ending attitude of the link after dynamic motion is complete should be within 15 degrees on any axis in some embodiments.

The output pivot point center location, computed in an X,Y,Z vector format, can be transformed into relative 2 dimensional angles (e.g. pitch and yaw) representing the angular misalignment of the surgical orientation device 14 and/or reference device 16 sensor axis with respect to the mechanical line of action for the rigid link.

There can be 4 major phases to the overall method:

Data Acquisition and Pre-Scaling

Static biases are removed from the data and the average body frame gravity vector is put back in the data Optimal Estimation of Delta Theta (Rate Sensor) Bias A bias is added to the rate sensor data in order to counter noise and other effects that result in the final orientation of the device being misaligned from the starting alignment, despite the fact that the user is required to return the unit back to the starting orientation.

Optimal Estimation of Delta Velocity (Accelerometer) Bias

A bias can be added to the accelerometer data in order to counter noise and other effects that result in the final velocity of the device being non-zero.

Optimal Estimation of Femur Vector and Resolution into Angles

Below are mathematical bases for each section.

Data Acquisition and Pre-Scaling

The acquisition and pre-scaling required can be dependent on the sensors selected for the device. One example of is described in the steps below.

Surgical orientation device 14 and/or reference device 16 raw data can be acquired from a combination of accelerometers and rate sensors.

Data can be scaled into delta theta (radians) and delta velocity (cm/s) using the data sample rate. There are alternate formulations that may work with the surgical orientation device 14 and/or reference device 16 data natively, but this makes integration and other repeated functions using this data less computationally intense when implemented on a microprocessor.

In some embodiments, the average of the raw data per each sensor and axis during static conditions can be determined.

In some embodiments, the Direction Cosine Matrix required for level to current orientation can be computed.

In some embodiments, the estimated average starting gravity vector in IMU body frame can be computed.

In some embodiments, the biases from all channels (rate and acceleration) can be removed.

In some embodiments, the body gravity vector can be added to the accelerometer channels.

Optimal Estimation of Delta Theta Bias

The purpose of this step can be to determine the optimum rate sensor corrections (in the form of a single constant bias for each sensor axis) that "force" the final attitude of the unit at the end of the maneuvers to be identical to the starting attitude.

Let the matrix $C_i^p$ be the direction cosine matrix that represents the rotation from the initial attitude (i) to the propagated attitude (p) at a given instant in time, t. $C_i^p$ includes the term $\Delta\theta_{axis,i}$, which is the rate sensor data from the IMU at each time step and $\Delta\theta_{axis,b}$ a constant correction term. This final correction is determined in the following steps to augment the data in an optimal fashion to ensure that the calculated final attitude matches the initial attitude despite noises and other errors that alter the propagation from the correct solution.

Let $\bar{\rho}$ be the equivalent set of Euler angles that represent the single rotation from the initial attitude to the current attitude represented by $C_i^p$.

The surgeon can move the surgical orientation device 14 and/or reference device 16 in a prescribed set of motions and return the unit back to the starting attitude. The assumption is that sensor noises will result in an incorrect attitude at the end of the motions. Using Gauss-Newton or any variety of similar optimal estimation algorithm, the $\Delta\bar{\theta}_{axis,b}$ terms will be determined that minimize the attitude error cost function.

For determination of $\Delta\bar{\theta}_{axis,b}$ terms, we define the cost function as:

$$J = \bar{\rho}_{initial} - \bar{\rho}_{final}$$

This cost function can be minimized by altering the $\Delta\bar{\theta}_{axis,b}$ terms according to an optimal estimation algorithm. We present a Gauss-Newton approach here, though other equivalent approaches are also appropriate.

Given a loss function, $\bar{J}$, evaluated at a local point $\bar{x}_i$, we want to modify $\bar{x}_i$ by $\Delta\bar{x}_i$ as: $\bar{x}_{i+1} = \bar{x}_i + \Delta\bar{x}_i$, so that $\bar{J}$ is decreased. Standard texts and references show methods to solve this problem.

Using a Gauss Newton algorithm to solve this problem, we substitute $\bar{J} = \bar{\rho}_{initial} - \bar{\rho}_{final}$ for the loss function with $\bar{\rho}_{initial} = 0$ by definition, and $\bar{x}_i = \Delta\bar{\theta}_{axis,b}$.

Figure 50:
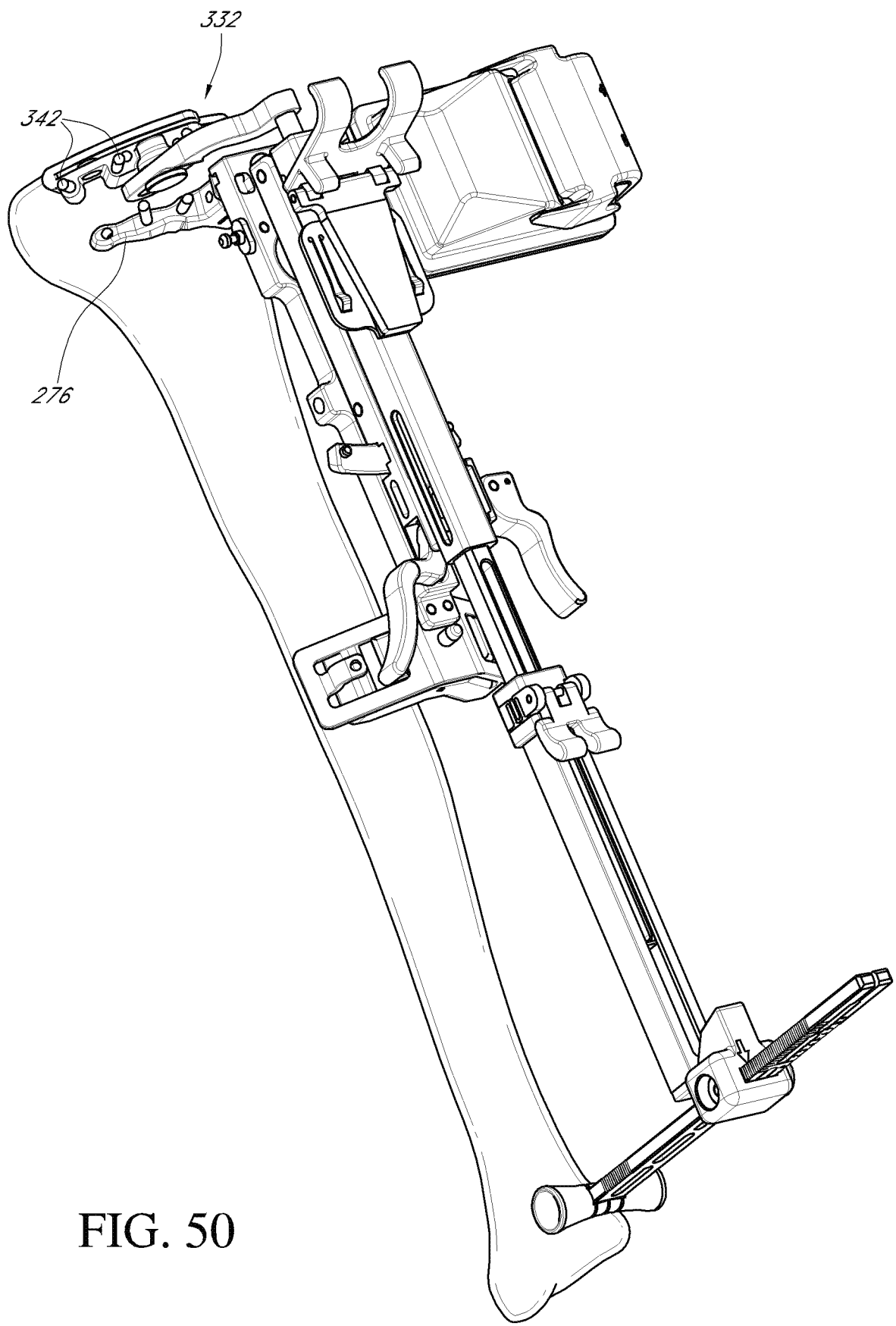
FIG. 50 is a perspective view of the tibial preparation system of FIG. 33 being used during another stage of a tibial preparation method according to one embodiment of the present invention.
Figure 50A:
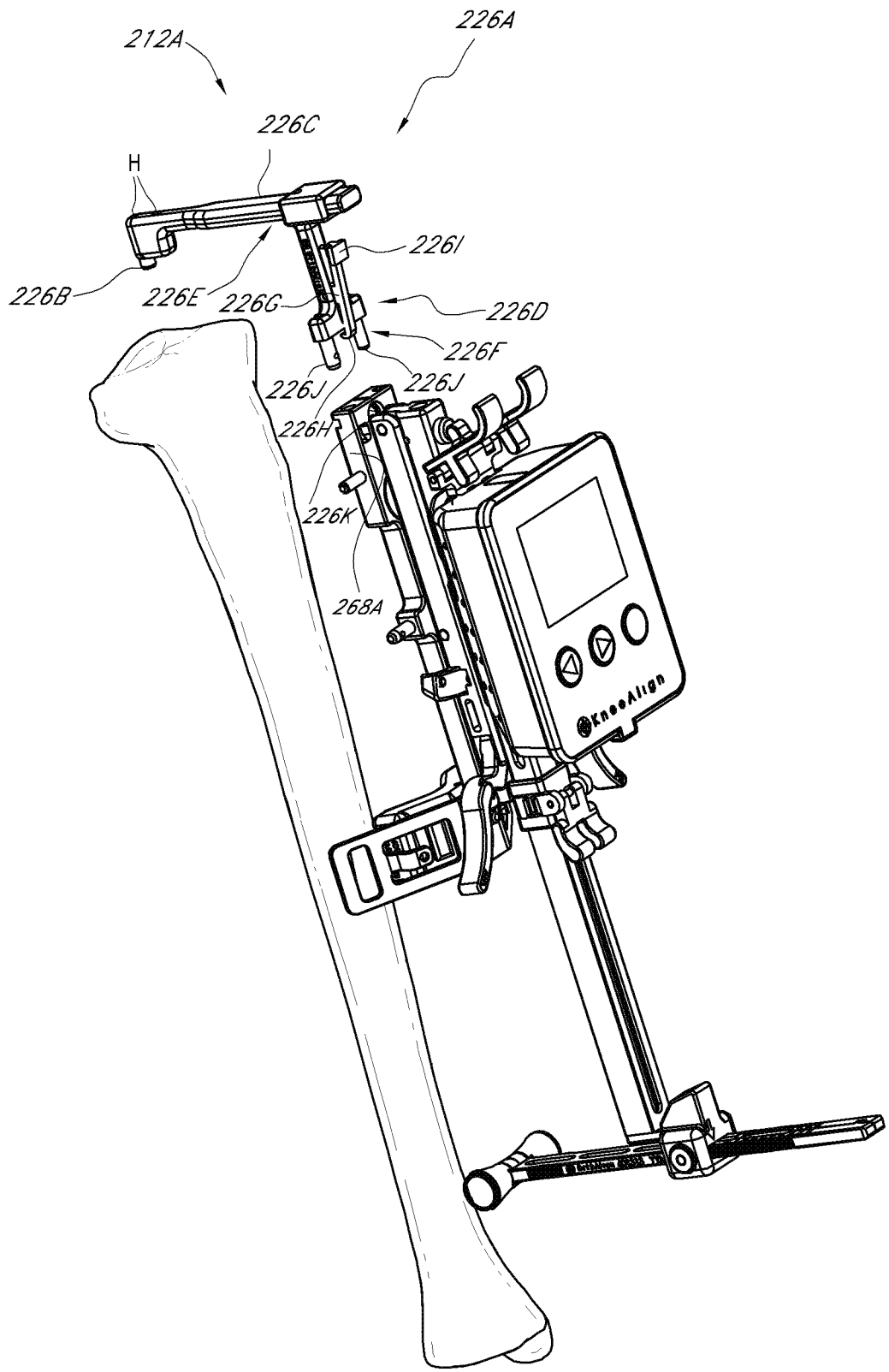
FIGS. 50A-B are perspective views of a variation of the tibial preparation system of FIG. 33 that couples a proximal portion thereof with a tibial plateau.
Figure 50B:
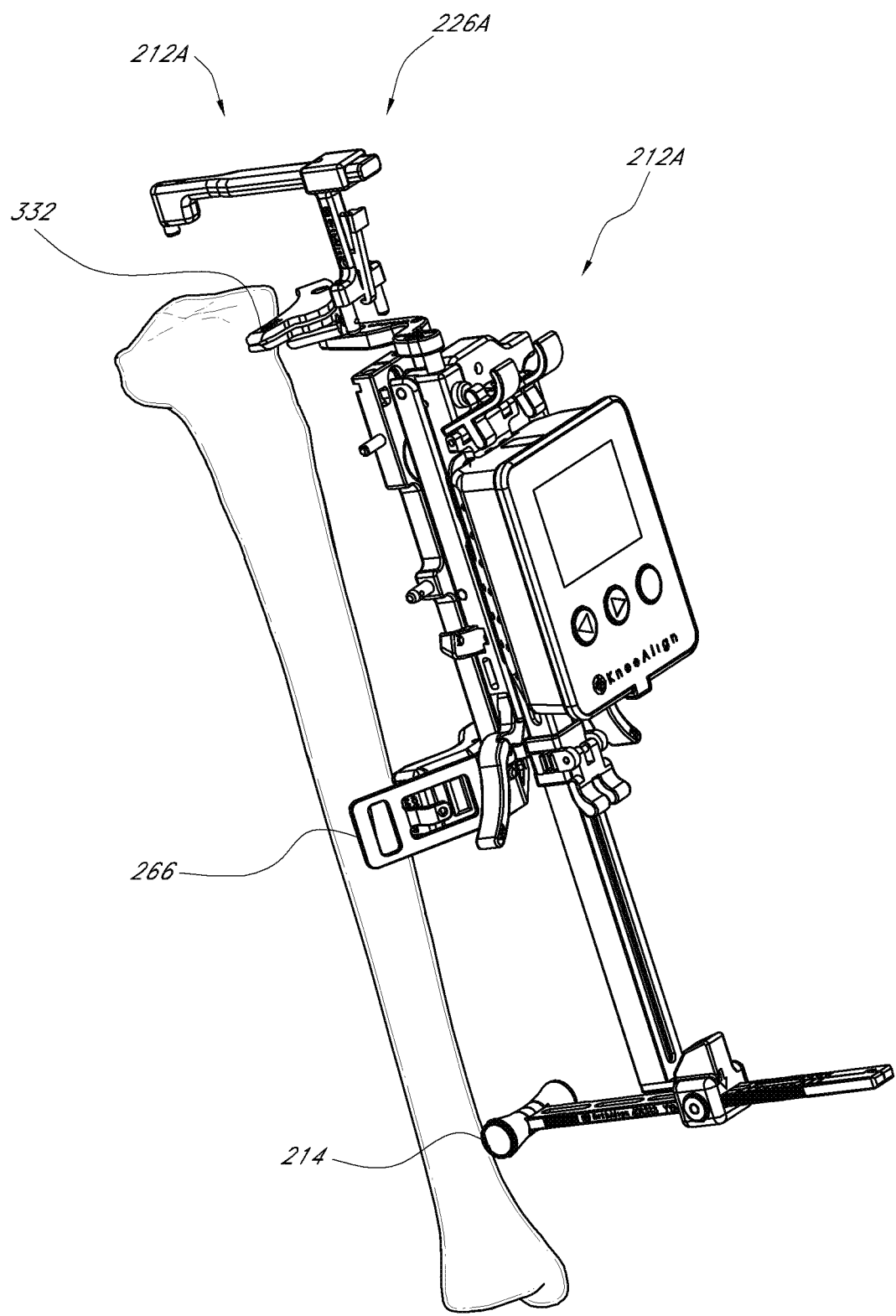
Figure 50C:
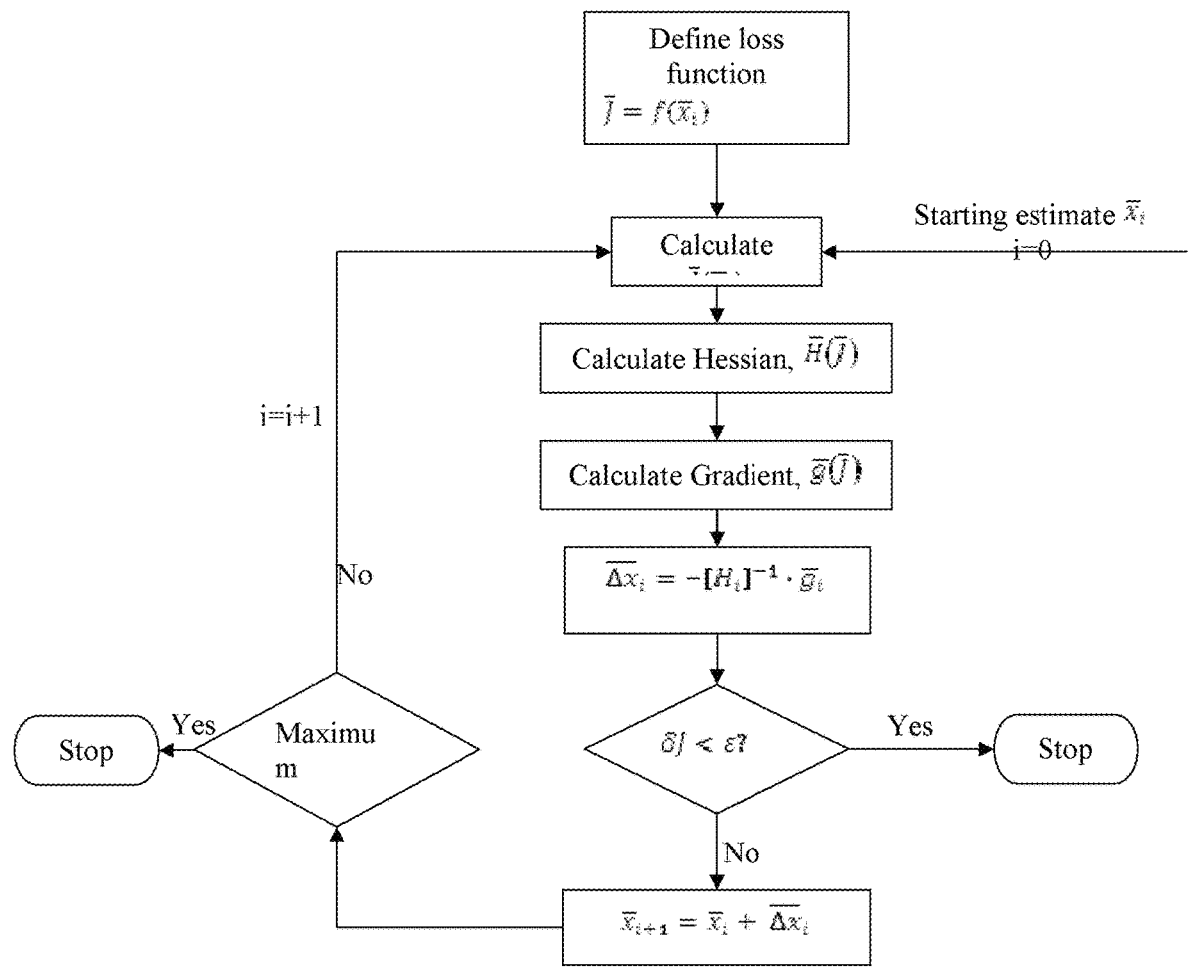
FIG. 50C is a schematic illustration showing calculations and operations for an embodiment of a method.

FIG. 50C is a flow chart for calculations and operations shows the procedure that is used to iteratively solve for the optimal value of $\Delta\bar{\theta}_{axis,b}$.

The output result is a set of data that represents the change in angular rotation based on corrected rate sensor data.

Optimal Estimation of Delta Velocity Bias

The purpose of this step is to determine the optimum accelerometer sensor corrections (in the form of a single constant bias for each sensor axis) that "force" the final velocity of the unit at the end of the maneuvers to be identical to the starting velocity based on integrated acceleration data.

This approach can be augmented to include an additional constraint that the starting and stopping positions must be identical as well.

Let the matrix $C_i^p$ be the direction cosine matrix that represents the rotation from the initial position (i) to the propagated position (p) at a given instant in time. This has been presented previously.

This rotation matrix is applied to the accelerometer data and a correction term ($\overline{\Delta V}_{axis,b}$) to transform it into the inertial reference frame.

The surgeon can move the unit in a prescribed set of motions and return the unit back to the starting position. The assumption is that sensor noises will result in an incorrect velocity at the end of the motions. Using Gauss-Newton or similar optimal estimation algorithm, the $\overline{\Delta V}_{axis,b}$ terms will be determined that minimize a representative velocity error cost function.

For determination of $\overline{\Delta V}_{axis,b}$ terms, we define the cost function as:

$$J = \bar{V}_{initial} - \bar{V}_{final}$$

This cost function can be minimized by altering the $\overline{\Delta V}_{axis,b}$ terms according to an optimal estimation algorithm.

We do not repeat the procedure here, but the prior Gauss-Newton flow chart is applicable to this estimator.

The output result is a set of data that represents the change in position in the inertial frame of the IMU based on the accelerometer data.

Optimal Estimation of Femur Vector

The purpose of this step is to determine the optimum vector from the surgical orientation device 14 and/or reference device 16 frame to its rigid body center of rotation. The accelerometer sensor data provides a linear acceleration estimate of velocity and motion. In a similar manner, the rate sensors on the surgical orientation device 14 and/or reference device 16 will provide estimates of position and motion if the rigid vector to the unit is known.

The accelerometer data provides a position vector at each time step $\bar{R}_a(t)$. The creation of this data set has been detailed.

The rate sensor data can provide a position vector at each time step per the equation:

$$\bar{R}_g(t) = \Delta\theta_c(t) \times \bar{R}_{est}$$

For determination of $\bar{R}_{est}$ terms, we define the cost function as:

$$J = \bar{R}_a - \bar{R}_g$$

This cost function can be minimized by altering the $\bar{R}_{est}$ terms according to an optimal estimation algorithm.

We do not repeat the procedure here, but the prior Gauss-Newton flow chart is applicable to this estimator.

To use the previous method, we substitute $J = \bar{R}_a - \bar{R}_g$ for the loss function with $\bar{R}_a$ an unchanging dataset created previously and $\bar{R}_g$ created thru the cross product of the $\overline{\Delta\theta}_c$ data set and the current estimated vector.

The output result is an optimal estimation of the vector from the IMU to the center of the rotation, $\bar{R}_{est}$.

This vector is located in the body frame of the IMU.

Angles in pitch and yaw to the center of the joint can be computed based on this vector.

E. Adjusting an Angle of Resection

Once biases have been removed, and the reference sensor device 16 and/or surgical orientation device 14 has calculated the pivot point of the mechanical axis as described above and located the mechanical axis, the user can begin adjusting and orienting the cutting block 92 relative to the location of the mechanical axis. For example, the surgical orientation device 14 can display the varus/valgus and flexion/extension angle adjustments needed for the surgical orientation device 14 (and the femoral jig assembly 12) to reach neutral alignment with the mechanical axis that passes through the femoral head 154.

Advantageously, in some embodiments the reference sensor device 16 can enable the procedure to proceed without fixation of the leg being operated upon because the reference sensor device 16 can track the relative positions of the leg.

For example, at least one of the reference sensor device 16 and the surgical orientation device 14 can communicate with the other, such that any relative movement of one of the devices can be tracked by the other, and the resulting overall orientation of the reference sensor device 16 and/or surgical orientation device 14 can be displayed on display 26 of the surgical orientation device 14. In some embodiments, the reference sensor device 16 can track movement of the leg (i.e. femur or tibia), such that if the leg moves during a procedure, the overall orientation of the surgical orientation device 14 can remain accurate.

With continued reference to FIGS. 22-31, a femoral preparation method can comprise placing the leg back into a flexion position (similar to the position shown in FIG. 22) and using varus/valgus and flexion/extension angle adjustment information provided by the surgical orientation device 14 in order to adjust an intended angle(s) of resection. The varus/valgus and flexion/extension angle adjustments of the femoral jig assembly 12 can be made by the translation structures 120 discussed above (e.g., by turning each of the translation adjustment features 130 in a clockwise or counter-clockwise position, and reading the resulting change in orientation on the display 26 of the surgical orientation device 14).

Any varus/valgus and flexion/extension angle adjustments of the femoral jig assembly 12 made by the adjusting the translation adjustment features 130 as discussed above can be reflected and displayed in approximately real time by the surgical orientation device 14. The varus/valgus and flexion/extension angle adjustments of the femoral jig assembly 12 can be made until the user is satisfied with the varus/valgus and flexion/extension angles of the femoral jig assembly 12 being reflected and displayed by the surgical orientation device 14. In some embodiments, when the surgical orientation device 14 and the femoral jig assembly 12 are aligned with the mechanical axis, the surgical orientation device 14 can provide a signal, such as for example a flashing green light on its display 26.

Furthermore, the surgical orientation device 14 can provide an indication of degrees of movement. For example, the surgical orientation device 14 can inform the user how many degrees (e.g. in half degree increments) the surgical orientation device 14 and the femoral jig assembly 12 are rotated past the mechanical axis of the leg in one or more planes. The surgical orientation device 14 can display this information in its display 26, and/or provide audio indications to the user.

After the femoral jig assembly 12 is aligned with the femoral mechanical axis and/or the cutting angles are selected, the method can include attaching the cutting block 92 and the distal guide assembly 88 to the microblock assembly 90 of the femoral jig assembly 12 as shown in FIG. 28. The cutting block 92, distal guide assembly 88, and microblock assembly 90 can be coupled, e.g., attached to each other or coupled independently to the femur. In most cases, the distal guide assembly 88 will have moved from the original position illustrated in FIG. 22, so the pin 102 would not necessarily line up with the hole created as discussed in connection with FIG. 22. In these cases, cutting block 92, distal guide assembly 88, and microblock assembly 90 can be coupled by connecting the articulating arm 98 with the microblock assembly 90 and the cutting block 92 via the attachment features 122 and the receiving features 136. If at this point of the procedure the distal guide assembly 88 is in the original position, the pin 102 also can be inserted back into the hole 146 to aid in coupling the cutting block 92, distal guide assembly 88, and microblock assembly 90.

As discussed above, the distal femoral resection depth can be set by moving the articulating arm 98 in a desired position in relation to the cutting block 92 by adjusting the position adjustment features 104.

Figure 29:
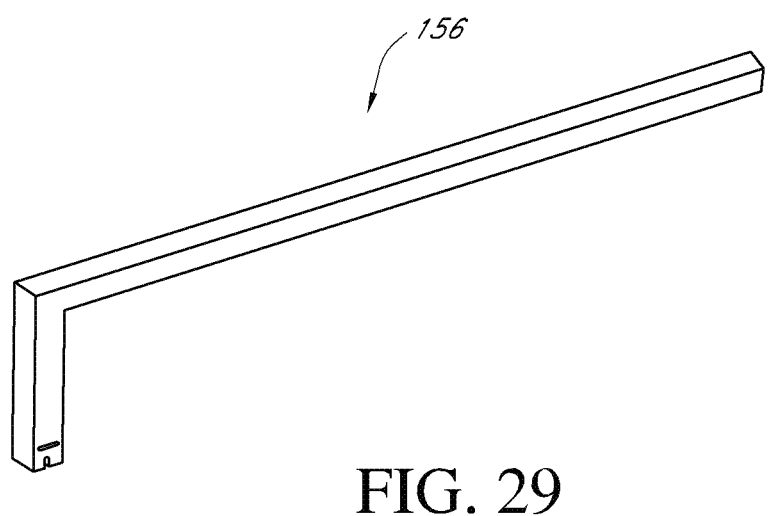
FIG. 29 is a perspective view of one embodiment of an optional alignment rod of the femoral preparation system of FIGS. 2A and 2B.
Figure 30:
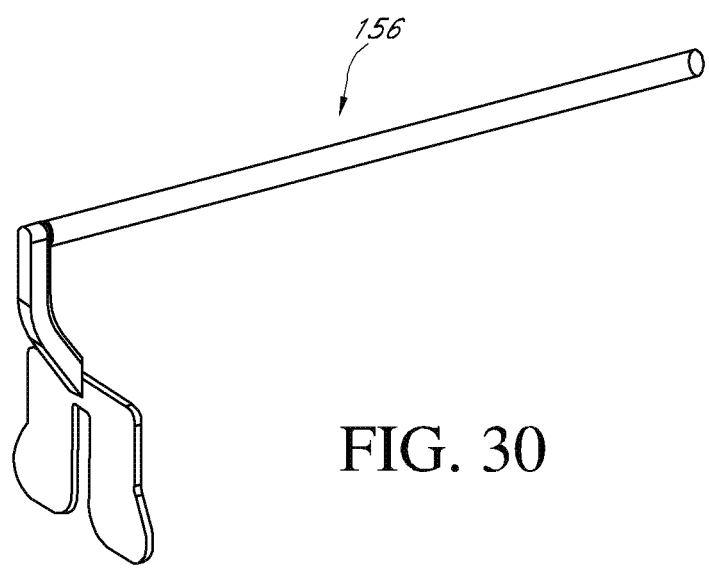
FIG. 30 is a perspective view of another embodiment of an optional alignment rod of the femoral preparation system of FIGS. 2A and 2B.

Referring to FIGS. 29 and 30, the femoral jig assembly 12 optionally can include an alignment rod 156 if the user desires to confirm alignment by referencing the anterior superior iliac spine visually. The optional alignment rod 154 can be attached to different parts of the femoral jig assembly 12 such as to one of the attachment features 122 of the microblock assembly 90 or one of the receiving features 136 or opening in the cutting block 92. Two exemplary embodiments of the optional alignment rod 156 are shown in FIGS. 29 and 30.

Figure 31:
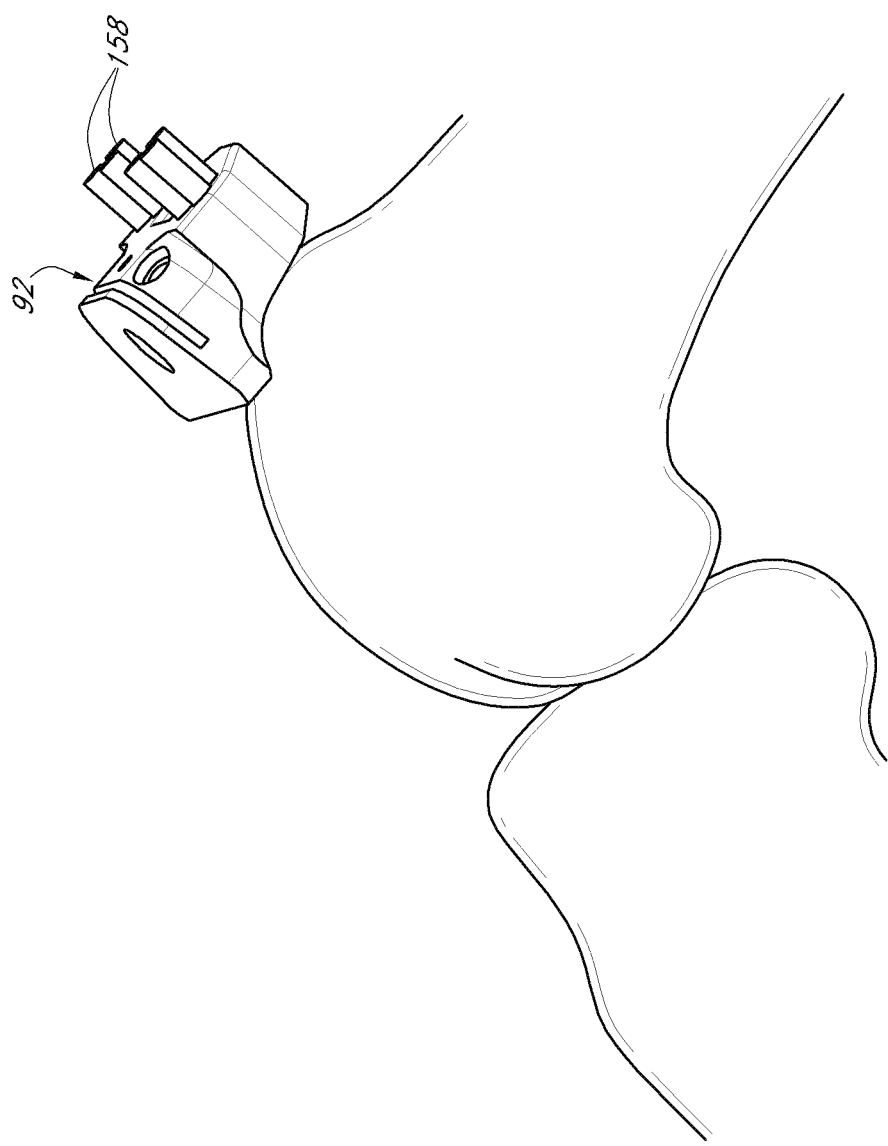
FIG. 31 is a perspective view of the femoral preparation system of FIGS. 2A and 2B being used during yet another stage of the femoral preparation method.

Referring to FIG. 31, the femoral preparation method can include immobilizing the cutting block 92 at the femoral resection location by inserting positional pins 158 into the appropriate receiving features 136. Any number of positional pins 158 (e.g., 2 or more) can be inserted into the appropriate receiving features 136. Except for the cutting block 92 immobilized at the femoral resection location by the positional pins 158, all other components of the femoral preparation system 10 such as the surgical orientation device 14, the reference sensor device 16, the first coupling device 18, the second coupling device 20, the distal guide assembly 88 and the microblock assembly 90 can all be disconnected and removed during this stage of the method as shown in FIG. 31.

The method can further include using the cutting block 92 to perform the desired distal femoral resection using standard methods. For example, a cutting tool or tools can be moved through the at least one opening 134 of the cutting block 58, so as to prepare the distal femur for receiving a knee joint prosthetic. After a distal femoral resection is completed in accordance with the method described above, the proximal (i.e. upper) tibia can then be resected.

IV. Alternative Embodiments of Femoral Jig Assembly/Method

Figure 31A:
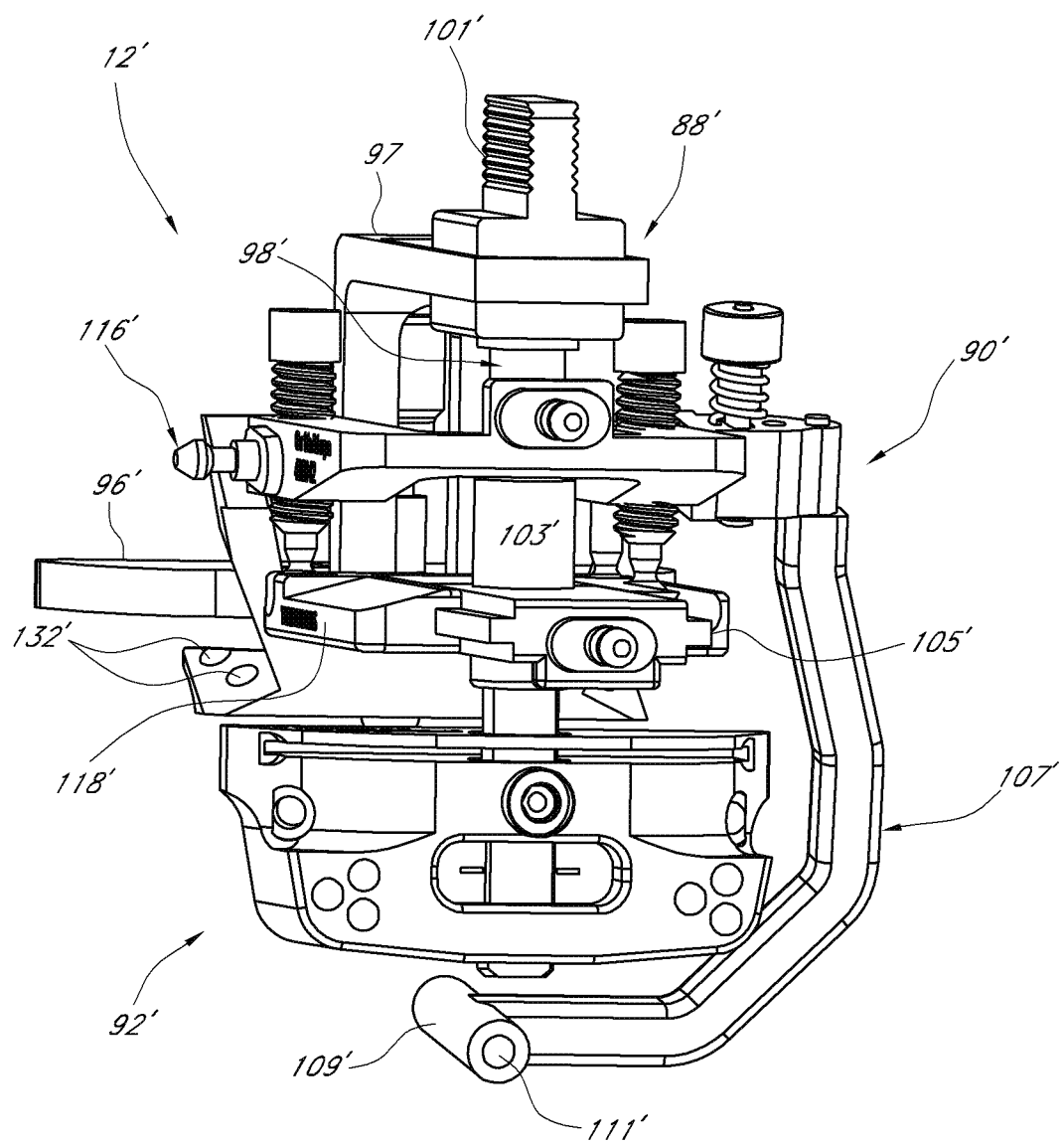
FIGS. 31A-C are perspective views of an alternative embodiment of a femoral preparation system.
Figures 31B, 31C:
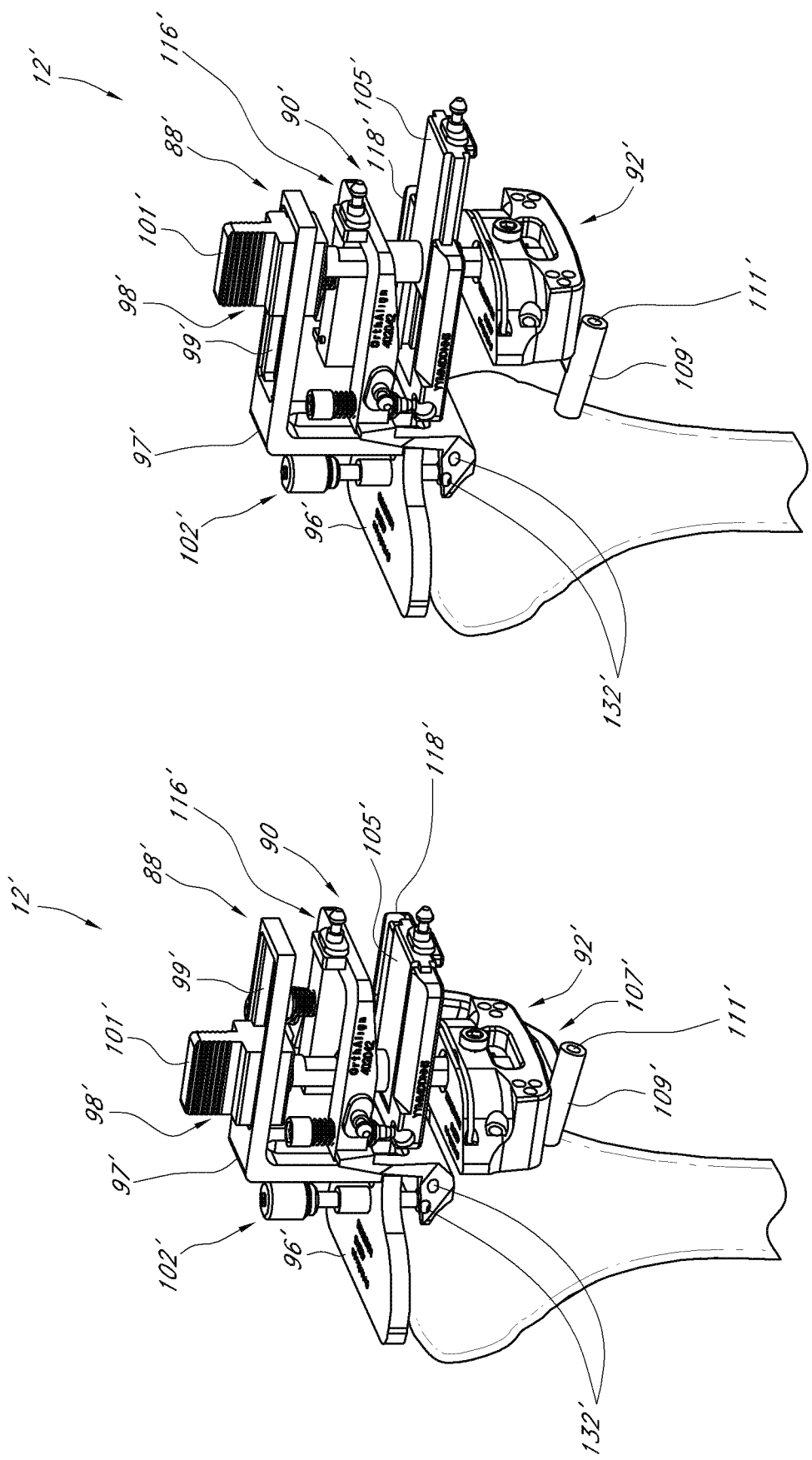

Referring to FIGS. 31A-C, an alternative embodiment of a femoral jig assembly 12' can comprise an orthopedic assembly for femoral preparation during a total knee replacement procedure. The jig assembly 12' provides three point connection to a bone to enhance stability. Although the jig 12 allows as many as six microblock pins 152 to be inserted into the femur and thus provide a stable configuration, an arrangement that provides a pin location that is spaced away from the location of the pins 152 can provide a triangular pin arrangement, which is much more stable and less prone to rocking.

The femoral jig assembly 12' can be similar to the femoral jig assembly 12 described above, and have similar components. For example, the femoral jig assembly 12' can comprise a distal guide assembly 88', a microblock assembly 90', and a cutting block 92'.

The distal guide assembly 88' can comprise a modular paddle 96', an articulating arm 98', and a midline pin 102'. The modular paddle 96' can comprise an extension 97'. As used in this specification, the term "modular paddle" or more generally "modular" includes structures that can form part of a kit, for example, of selectable parts. Various other kits, including any combination of the components described herein, can also be used or implemented in accordance with the methods described herein. The extension 97' can comprise, for example, a generally L-shaped structure having a slot 99' for receiving or for facilitating movement of the articulating arm 98'. The extension 97' can comprise a marking or markings (not shown), similar to the markings 108 on the paddle 96 described above, for indicating an AP offset. For example, a series of lines can be provided along the slot 99' such as on one or more of the distal, lateral, or medial surfaces of the extension 97'. These lines can be used to collect AP Offset Data, as discussed above to enable one or more orientation or reference devices coupled with the femoral jig assembly 12' to account for the offset from the midline pin 102' and the orientation or reference device.

The articulating arm 98' can comprise or be coupled with a gripping structure 101' located on an end of the articulating arm 98' that extends through the slot 99'. The gripping structure 101' can be configured to be gripped by a user's hand or fingers and moved, along with the rest of articulating arm 98', in an anterior/posterior direction (see, e.g. FIGS. 31B and 31C showing a change in position of the articulating arm 98' from posterior to anterior). The articulating arm 98' can extend through the slot 99', and through, for example, a sleeve 103' located within the microblock assembly 90'. As illustrated in FIGS. 31B and 31C, the sleeve 103' can form part of a sliding member 105' that sits within the microblock assembly 90' (e.g. within grooves of a member 118'). Thus, when the gripping structure 101' is held and moved in an anterior/posterior direction, the articulating arm 98', sleeve 103', and 105' move as well. The cutting block 92' can rest on or be attached to the articulating arm 98', such that movement of the gripping structure 101' additionally causes anterior/posterior movement of the cutting block 92', moving the cutting block 92' closer to the condyles of the femur when ready for resection. This advantageously allows the cutting block 92' to be moved close to the femur, making it easier to insert pins and secure the cutting block when needed.

The microblock assembly 90' can comprise a microblock member 116' that includes a stabilizing bar 107'. The stabilizing bar 107' can be formed integrally with or attached to the microblock member 116'. In other embodiments, the stabilizing bar 107' can be integrally formed with or attached to the distal guide assembly 88'. The stabilizing bar 107' can be used to help anchor and/or secure the jig assembly 12' to the femur by providing a third anchoring location. For example, the microblock member 116' can comprise openings 132' on either side of the microblock member 116' (e.g. medial and lateral) for receiving pins. The stabilizing bar 107' enhances stability of the microblock member 116' provided by the two openings 132' to further reduce rotational movement of the jig assembly 12' about an axis extending between the two openings 132' on either side of the microblock member 116'. The stabilizing bar 107' can be used to provide a third anchoring point, completing a triangular array of anchoring points (e.g., medial and lateral of an anterior-posterior mid-plane, adjacent to the condyles and proximal of the condyles) along the femur that add stability to the jig assembly 12'. In the illustrated embodiment, two anchor locations can be disposed distally of the cutting block 92' and one can be positioned proximally thereof. For example, the stabilizing bar 107' can extend around one side of the microblock assembly 90' (i.e. depending on how the knee anatomy is structured and/or moved during a procedure). In some embodiments, the stabilizing bar 107' can project posteriorly to attach to the distal femur (e.g. to the back side of the femur, or to a ledge, condyle, plateau or side of the femur). In one technique, during the procedure the patella is displaced to a lateral side of the knee joint and the stabilizing bar 107' is coupled with and extends from a portion of the microblock assembly 90' that will be disposed on a medial side of the knee joint during the procedure. The stabilizing bar 107' can comprise a pin tube 109' with an opening 111' for receiving a pin (not shown) that extends through the femur and helps to anchor the jig assembly 12' in place.

As discussed elsewhere herein, a variation on the femoral jig assembly 12' enables procedures that do not require collecting AP offset data. For example, the arm 98' can be configured not to be moveable, e.g., to be in a fixed anterior-posterior location relates to the midline pin 102' during at least one phase of the procedure. In the embodiment of FIGS. 31A-31C, positioning of the cutting block 92' is facilitated by the movement of the arm 98'. If the arm 98' is fixed, the block 92' can be mounted on a separate mechanism that is moveable in the anterior-posterior direction to facilitate positioning the block 92' away from the femur at one point of a procedure and up adjacent to the femur in another phase.

Figure 31D:
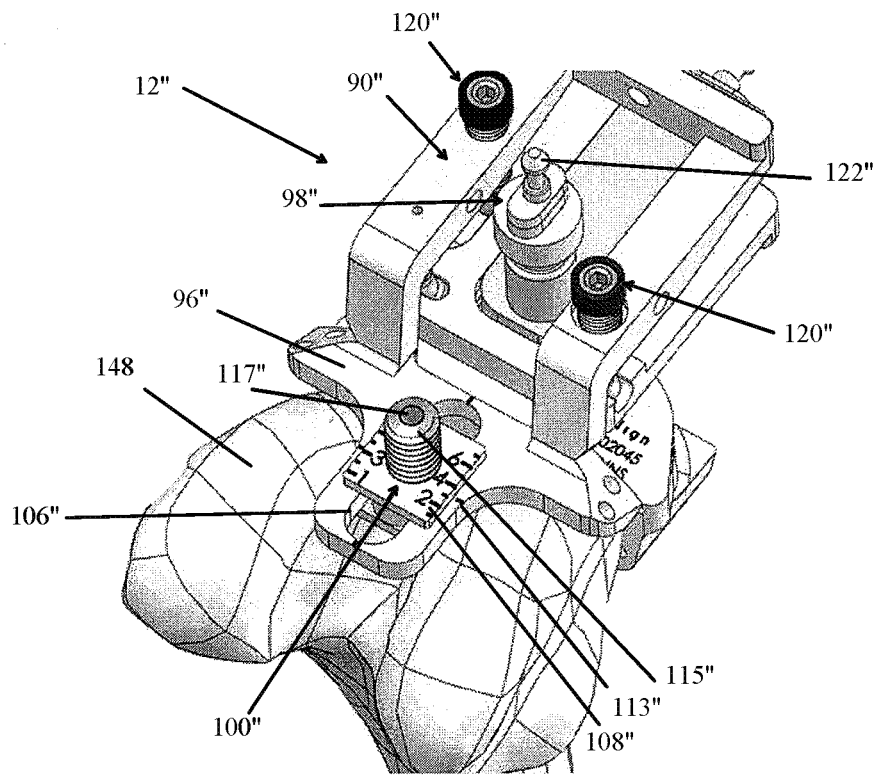
FIGS. 31D-F are perspective views of another alternative embodiment of a femoral preparation system.
Figure 31E:
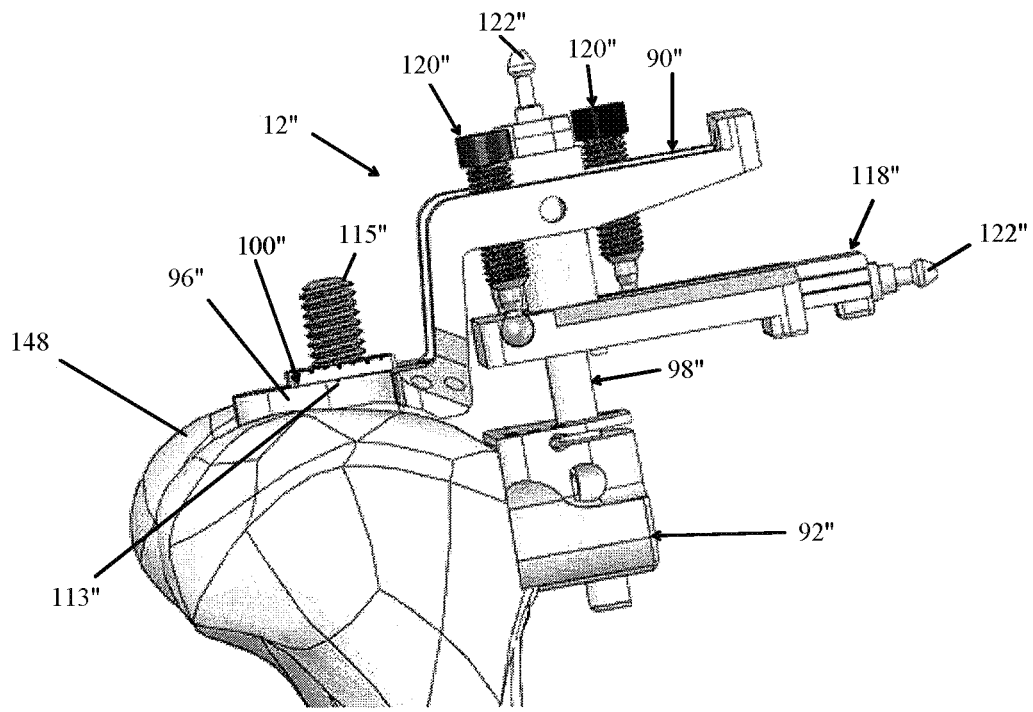
Figure 31F:
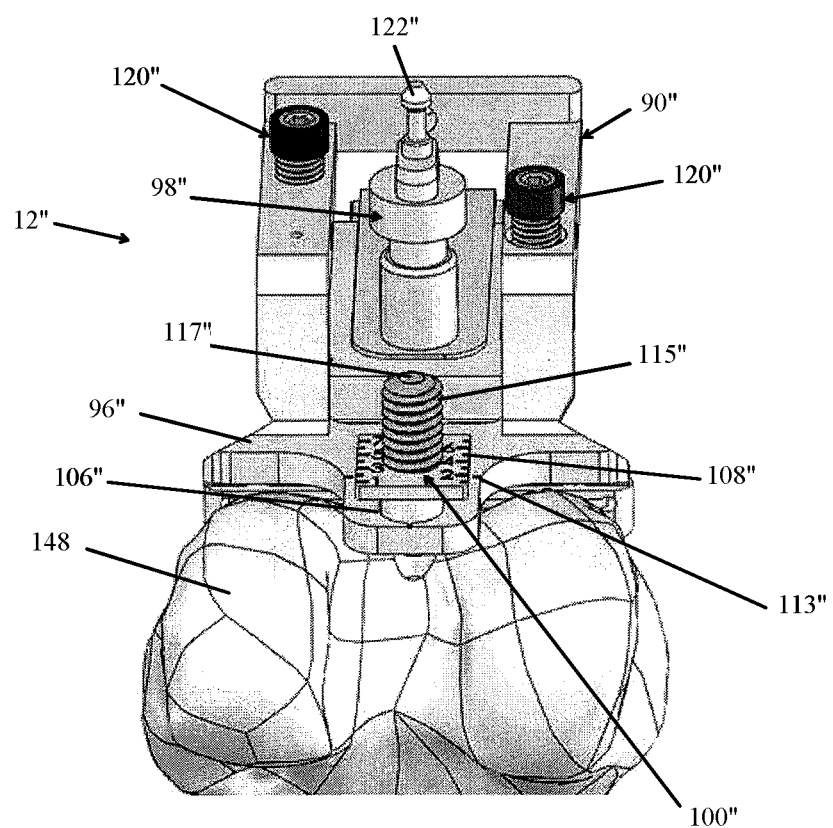

Referring to FIGS. 31D-F, another alternative embodiment of a femoral jig assembly 12" can comprise an orthopedic assembly for femoral preparation during a total knee replacement procedure. The jig assembly 12" can include similar components to those described above. For example, the jig assembly 12" can include a microblock assembly 90", cutting block 92", translating member 118", translation structures 120", and attachment features 122". In some embodiments, a surgical orientation device 14 and/or reference sensor device 16 can be attached to attachment features 122" of femoral jig assembly 12".

With continued reference to FIGS. 31D-F, in some embodiments the femoral jig assembly 12" can include a microblock assembly 90" that includes an integrated distal guide 96", which provides a function similar to that of the paddle 96 described above. The distal guide 96" can be configured to extend over and press against one or more of the distal condyles 148 of a knee bone, such as a femur. The distal guide 96" can be integrally formed with the microblock assembly 90". The distal guide 96" provides advantages over the paddle 96 by integrating the functions of a separate distal guide component with a microblock assembly that is already rigidly attached to the distal femur. Fewer separate components can be used, thus making the overall jig assembly 12" and method of using the jig 12" more efficient. In some embodiments, a separate articulating arm 98" can extend through the microblock assembly 90", as well as through the cutting block 92".

The jig assembly 12" can also include a midline guide 100". The midline guide 100" can be similar to midline guide 100 shown in FIG. 18. For example, the midline guide 100" can be moved relative to the distal guide 96" within a channel 106". The midline guide 100" can include one or more guide markings 108", and the distal guide 96" can include one or more distal guide markings 113". The midline guide markings 108" and distal guide markings 113" can be used to determine a relative offset of the microblock assembly 90", and/or cutting block 92", relative to a fixed location. For example, the midline guide markings 108" and paddle markings 113" can be used to determine an anterior/posterior offset of the cutting block 92", surgical orientation device 14, or reference sensor device 16 relative to a mechanical axis extending through the femur. Such an offset can be entered, for example, into the surgical orientation device 14 or reference sensor device 16.

With continued reference to FIGS. 31D-F, the midline guide 100" can include at least one pin mounting structure 115". In some embodiments, the pin mounting structure 115" can comprise a threaded structure. The pin mounting structure 115" can be configured to receive at least one pin or other mounting feature. For example, the pin mounting structure 115" can include an opening 117". The opening 117" can be configured to receive a mounting pin. The mounting pin can be inserted into and can extend through the opening 117", and into the distal end of a femur. Once the pin is inserted into a distal end of the femur, the midline guide 100" can be fixed in place, and the microblock assembly 90" can be moved relative the midline guide 100", for example in an anterior/posterior direction, to adjust a position of the cutting block 92".

Yet even further embodiments of femoral jig assemblies and methods for their use, as well as methods for determining a center of rotation of a head of the femur, can be found in, for example without limitation, paragraphs [305]-[333] and FIGS. 5 and 40-43 of U.S. patent application Ser. No. 12/509,388, which is incorporated by reference herein.

V. Testing of the Embodiments of the Invention

Embodiments of the invention similar to those described herein have recently been tested. In a comparison with a commercially available, FDA-cleared optical-based computer-assisted surgery system currently used in the United States operating rooms, 20 mechanical tibial mechanical axis registrations were conducted on 4 cadaver legs and 30 femoral mechanical axis registrations were conducted on 5 cadaver legs using each of an embodiment of the invention and the standard optical-based computer-assisted surgery system. (See tables below; registrations labeled N/A were not taken into account because they did not meet test criteria) The average difference between the distal femoral cutting block mechanical axis orientation calculated by the embodiment of the invention and that calculated by the optical-based computer assisted surgery system was no more than 1 degree for both varus/valgus and flexion/extension angles. Similarly, the average difference between the tibial cutting block mechanical axis orientation calculated by the embodiment of the invention and that calculated by the commercially-available optical-based computer assisted surgery system was no more than 1 degree for both varus/valgus and posterior slope angles. These results provide acceptable performance in a very compact and simple to use system. Also, these excellent results are produced by much less costly devices.

TABLE 1

FEMORAL

| | | KneeAlign 2 | | Computer Assisted System | | Deviation | |
|---|---|---|---|---|---|---|---|
| Femur | Registration | Varus (+)/ Valgus (−) | Flex (+)/ Exten (−) | Varus (+)/ Valgus (−) | Flex (+)/ Exten (−) | Varus (+)/ Valgus (−) | Flex (+)/ Exten (−) |
| 1 | 1 | N/A | N/A | N/A | N/A | N/A | N/A |
|   | 2 | N/A | N/A | N/A | N/A | N/A | N/A |
|   | 3 | N/A | N/A | N/A | N/A | N/A | N/A |
|   | 4 | N/A | N/A | N/A | N/A | N/A | N/A |
|   | 5 | 0 | 0 | 1.0 | −1.0 | −1.0 | 1.0 |
|   | 6 | 0 | 0 | 0.5 | −1.0 | −0.5 | 1.0 |
|   | 7 | 0 | 0 | 0.5 | −1.0 | −0.5 | 1.0 |
|   | 8 | 0 | 0 | 0.5 | 0.0 | −0.5 | 0.0 |
|   | 9 | 0 | 0 | −0.5 | 0.0 | 0.5 | 0.0 |
| 2 | 1 | −2 | 3 | −3.5 | 3.5 | 1.5 | −0.5 |
|   | 2 | −2 | 3 | −3.5 | 2.5 | 1.5 | 0.5 |
|   | 3 | −2 | 3 | −3.5 | 3 | 1.5 | 0 |
|   | 4 | −2 | 3 | −2 | 3 | 0 | 0 |
|   | 5 | −2 | 3 | −3 | 2.5 | 1 | 0.5 |
| 3 | 1 | 2 | 3 | 0.5 | 3 | 1.5 | 0 |
|   | 2 | 2 | 3 | 1 | 1.5 | 1 | 1.5 |
|   | 3 | 2 | 3 | 0.5 | 0.5 | 1.5 | 2.5 |
|   | 4 | 2 | 3 | 3 | 3 | −1 | 0 |
|   | 5 | 2 | 3 | 1 | 0.5 | 1 | 2.5 |
|   | 6 | 2 | 3 | 2 | 1 | 0 | 2 |
|   | 7 | 2 | 3 | 0.5 | 0.5 | 1.5 | 2.5 |
| 4 | 1 | N/A | N/A | N/A | N/A | N/A | N/A |
|   | 2 | N/A | N/A | N/A | N/A | N/A | N/A |
|   | 3 | 0 | 5 | −1.5 | 3.5 | 1.5 | 1.5 |
|   | 4 | 0 | 5 | 0.5 | 3.5 | −0.5 | 1.5 |
|   | 5 | 0 | 3 | 2 | 6 | −2 | −3 |
|   | 6 | 0 | 0 | 1.5 | 0.5 | −1.5 | −0.5 |
|   | 7 | 0 | 0 | 1.5 | 0 | −1.5 | 0 |
|   | 8 | 0 | 0 | 0 | 0 | 0 | 0 |
|   | 9 | 0 | 0 | 0 | 0.5 | 0 | −0.5 |
|   | 10 | 0 | 0 | 1 | 1 | −1 | −1 |

TABLE 1-continued

FEMORAL

| Femur | Registration | KneeAlign 2 Varus (+)/ Valgus (−) | KneeAlign 2 Flex (+)/ Exten (−) | Computer Assisted System Varus (+)/ Valgus (−) | Computer Assisted System Flex (+)/ Exten (−) | Deviation Varus (+)/ Valgus (−) | Deviation Flex (+)/ Exten (−) |
|---|---|---|---|---|---|---|---|
| 5 | 1 | 0 | 5 | 0 | 3 | 0 | 2 |
|   | 2 | 0 | 5 | 0.5 | 3.5 | −0.5 | 1.5 |
|   | 3 | 0 | 5 | 0 | 4.5 | 0 | 0.5 |
|   | 4 | 0 | 5 | 0 | 4.5 | 0 | 0.5 |
|   | 5 | 0 | 5 | 0 | 4 | 0 | 1 |
|   |   |   |   |   | Mean | 0.0 | 0.6 |
|   |   |   |   |   | Stdev | 1.09 | 1.17 |
|   |   |   |   |   | Max | 2.00 | 3.00 |

TABLE 2

TIBIAL

| Tibia | Registration | KneeAlign 2 Varus (+)/ Valgus (−) | KneeAlign 2 Flex (+)/ Exten (−) | Computer Assisted System Varus (+)/ Valgus (−) | Computer Assisted System Flex (+)/ Exten (−) | Deviation Varus (+)/ Valgus (−) | Deviation Flex (+)/ Exten (−) |
|---|---|---|---|---|---|---|---|
| 2 | 1 | 0 | 3 | 1.0 | 3.5 | −1.0 | −0.5 |
|   | 2 | 0 | 3 | 0.0 | 3.5 | 0.0 | −0.5 |
|   | 3 | 0 | 3 | −0.5 | 2.5 | 0.5 | 0.5 |
|   | 4 | 0 | 3 | 0.0 | 3.5 | 0.0 | −0.5 |
|   | 5 | 0 | 3 | 0.0 | 3.0 | 0.0 | 0.0 |
| 3 | 1 | 2 | 5 | 0 | 6.5 | 2.0 | −1.5 |
|   | 2 | 2 | 5 | 0.5 | 6.5 | 1.5 | −1.5 |
|   | 3 | 2 | 5 | 1 | 7 | 1.0 | −2.0 |
|   | 4 | 2 | 5 | 2 | 5 | 0.0 | 0.0 |
|   | 5 | 2 | 5 | 1 | 6.5 | 1.0 | −1.5 |
| 4 | 1 | 0 | 7 | −1 | 9 | 1.0 | −2.0 |
|   | 2 | 0 | 7 | −1 | 9 | 1.0 | −2.0 |
|   | 3 | 0 | 7 | −0.5 | 8 | 0.5 | −1.0 |
|   | 4 | 0 | 7 | 0 | 8 | 0.0 | −1.0 |
|   | 5 | 0 | 7 | −0.5 | 7.5 | 0.5 | −0.5 |
| 5 | 1 | 0 | 7 | 0 | 8 | 0.0 | −1.0 |
|   | 2 | 0.5 | 7 | 2.5 | 7.5 | −2.0 | −0.5 |
|   | 3 | 0 | 7 | 1.5 | 9.5 | −1.5 | −2.5 |
|   | 4 | 0 | 7 | 1 | 6 | −1.0 | 1.0 |
|   | 5 | 0 | 7 | 0.5 | 9 | −0.5 | −2.0 |
|   |   |   |   |   | Mean | 0.2 | −1.0 |
|   |   |   |   |   | Stdev | 1.00 | 0.93 |
|   |   |   |   |   | Max | 2.00 | 2.5 |

VI. User Interfaces for Femoral Preparation Methods

As discussed above, various components such as the electronic control unit 1102, the user input 26 and the display 26 of the surgical orientation device 14 can form an interactive user interface. The interactive user interface can include a graphical user interface having an interactive window displaying on-screen graphics on the surgical orientation device 14. The interactive user interface can provide the user with a plurality of screen displays illustrating steps to be performed in a surgical procedure and can guide the user through the performance of the steps. Each screen display can comprise one or more on-screen graphics. The on-screen graphics can comprise one or more visual cues or indicators to prompt the user as to what step or steps to take next during one of the procedural methods described above.

The visual cues referenced herein can comprise instructive images, diagrams, pictorial representations, icons, animations, visual cues, charts, numerical readings, measurements, textual instructions, warnings (visual and/or audible), or other data. The interactive user interface can be configured to alter attributes (e.g., color) of the on-screen graphics according to one or more data protocols. The interactive user interface can provide visual feedback to the user during performance of one or more surgical procedures. The interactive user interface can be configured to generate GUI images to be displayed to the user. As described above, the user can interact with the surgical orientation device 14 via one or more user input devices 1114 (e.g., buttons, switches, touch screen displays, scroll wheel, track ball, keyboard, remote controls, a microphone in conjunction with speech recognition software). The interactive user interface can further allow a user to confirm that a step has been completed (for example, by pressing a user input button). The interactive user interface can allow the user to enter data (e.g., a numerical value, such as a distance, an angle, and/or the like), verify a position of the surgical orientation device 14, turn an optional visible alignment indication system on and off, and/or turn the entire surgical orientation device 14 on and off.

In certain embodiments, the interactive user interface can provide one or more drop-down lists or menus from which a user can make selections. For example, the user can make selections from a drop-down list using a scroll wheel, trackball, and/or a series of button presses. In some embodiments, the user interface provides a drop-down list of predicates that dynamically updates based on user input.

In at least one embodiment, a module for creating an interactive user interface can comprise a computer readable medium having computer readable program code embodied therein. The computer readable program code can include computer readable program code configured to display one or more of a plurality of GUI images on the user interface of the surgical orientation device 14, the GUI images comprising instructive images related to the performance of a surgical procedure. The computer readable program code can be configured to receive instructions from a user identifying the surgical procedure to be performed. The computer readable program code can be configured to show the user steps to be performed in the identified process for the identified surgical procedure. The computer readable program code can be configured to guide the user in performance of the steps. For example, the computer readable program code can be configured to receive from the user an instruction to continue to the next step in the procedure, to receive orientation data from a sensor mounted within the surgical orientation device, and to display the orientation data on the user interface of the surgical orientation device.

In at least one embodiment, the surgical orientation device 14 can include a display module configured to display information and at least one sensor module configured to monitor the position and orientation of the surgical orientation device 14 and the reference sensor device 16 in a three-dimensional coordinate reference system, and to generate orientation data corresponding to the monitored positions and orientations of the surgical orientation device 14 and the reference sensor device 16.

The surgical orientation device 14 can further comprise a control module configured to receive orientation data from the at least one sensor module and convert it to objective signals for presentation on a display module. The control module can be configured to display a set of GUI images or other on-screen graphics on the display module, the GUI images or on-screen graphics representing the orientation data received from the sensor module and also representing instructive images related to the performance of the joint replacement surgery.

In at least one embodiment, the surgical orientation device 14 can receive orientation data from a sensor module, receive input commands from a user input module to store orientation data from a user input module, convert the orientation data to a human readable format for presentation on a display device, and display on the display device on-screen graphics or GUI images for communicating information to a user based on the input commands and the orientation data, the information comprising instructive images for performing a joint replacement surgery and one or more visual indicators of a current orientation of the display device with respect to a fiducial, or reference, orientation.

FIGS. 32A-J display exemplary screen shots that can be displayed by the interactive user interface of the surgical orientation device 14 (e.g. displayed on an LCD screen on the front of the surgical orientation device 14) during the various steps of an orthopedic procedure.

Figure 32A:
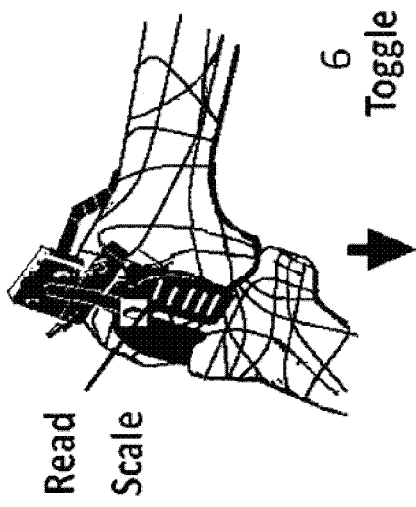
FIGS. 32A-J show screen displays for a femoral preparation method generated by one embodiment of the interactive user interface of the surgical orientation device of FIG. 3.

For example, FIG. 32A displays a screen shot that provides a visual cue informing the user that the knee being operated on is to be placed in a flexion position and that the femoral jig assembly 12 should be attached to the distal end portion of the knee.

Figure 32B:
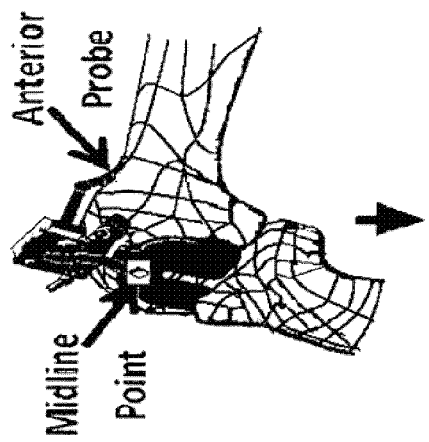

FIG. 32B displays a screen shot that provides a visual cue informing the user to enter an AP Offset Data. The image in FIG. 32B can be displayed in response to pressing a user input button 28 specified by the surgical orientation device 14 in FIG. 32A. In another embodiment, and as described above, the process of obtaining and entering AP Offset Data into the surgical orientation device 14 can be avoided if a fixed offset distance is provided by the configuration of the femoral preparation system 10.

Figure 32C:
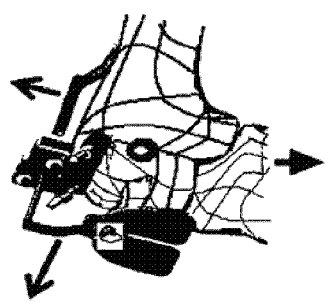

FIG. 32C displays a screen shot that provides a visual cue informing the user to perform a removal step of the method described above. The image in FIG. 32C can be displayed in response to pressing a user input 28 button specified by the surgical orientation device 14 in FIG. 32B.

Figure 32D:
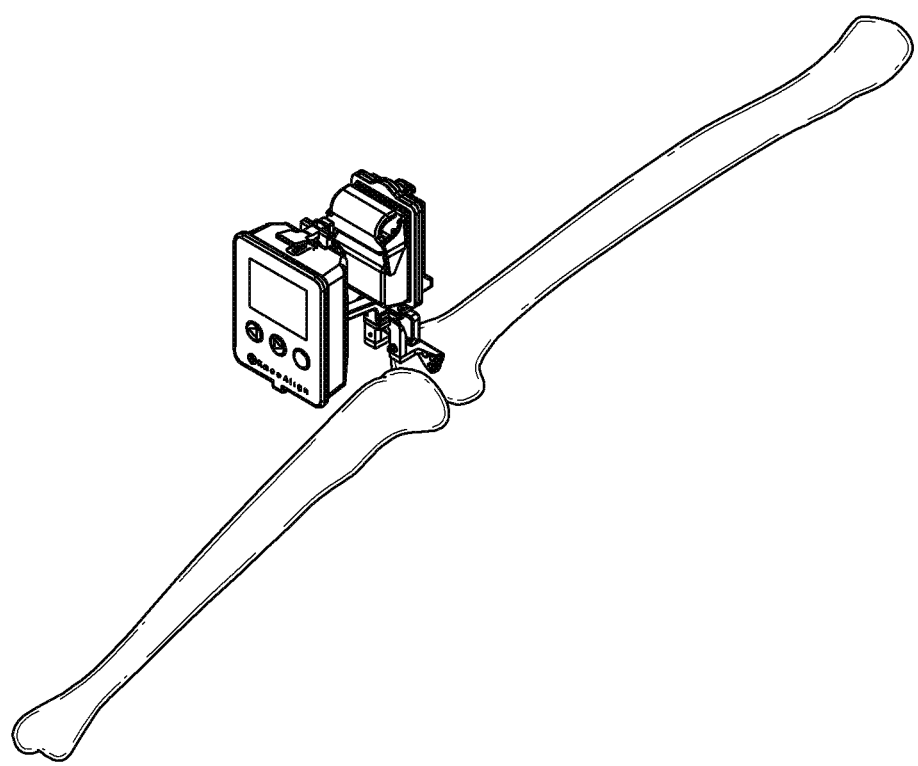

FIG. 32D displays a screen shot that provides a visual cue informing the user to perform installation and leg extension placement steps of the method described above. The image in FIG. 32D can be displayed in response to pressing a user input button 28 specified by the surgical orientation device 14 in FIG. 32C.

Figure 32E:
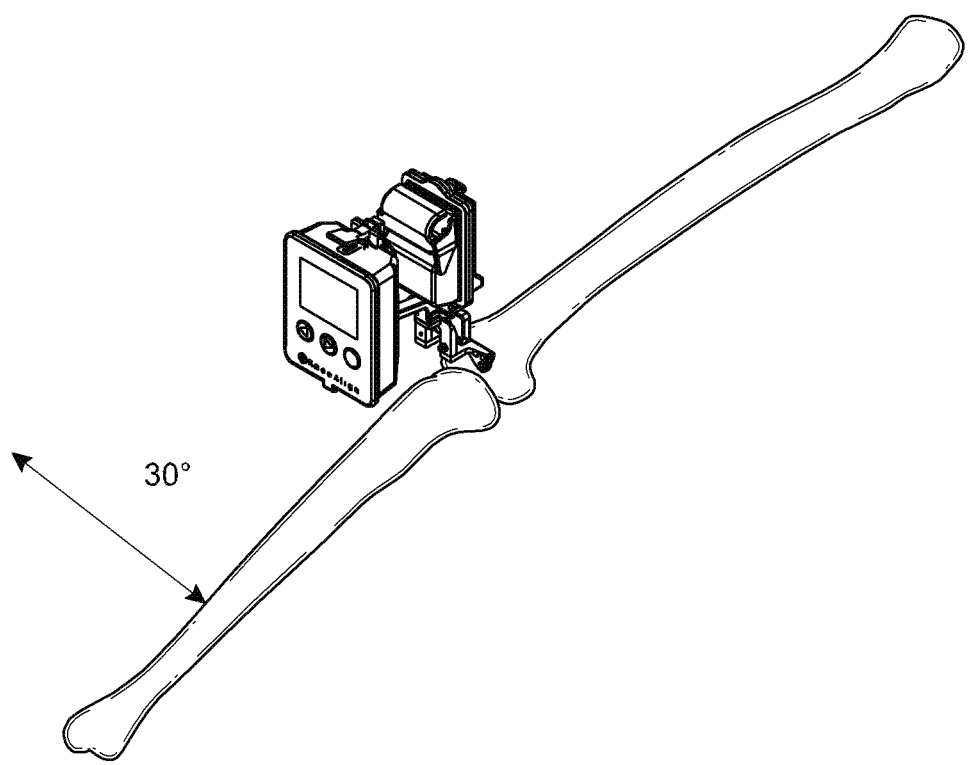

FIG. 32E displays a screen shot that provides a visual cue informing the user to perform a 30 degree abduction step. The image in FIG. 32E can be displayed in response to pressing a user input button 28 specified by the surgical orientation device shown in FIG. 32D.

Figure 32F:
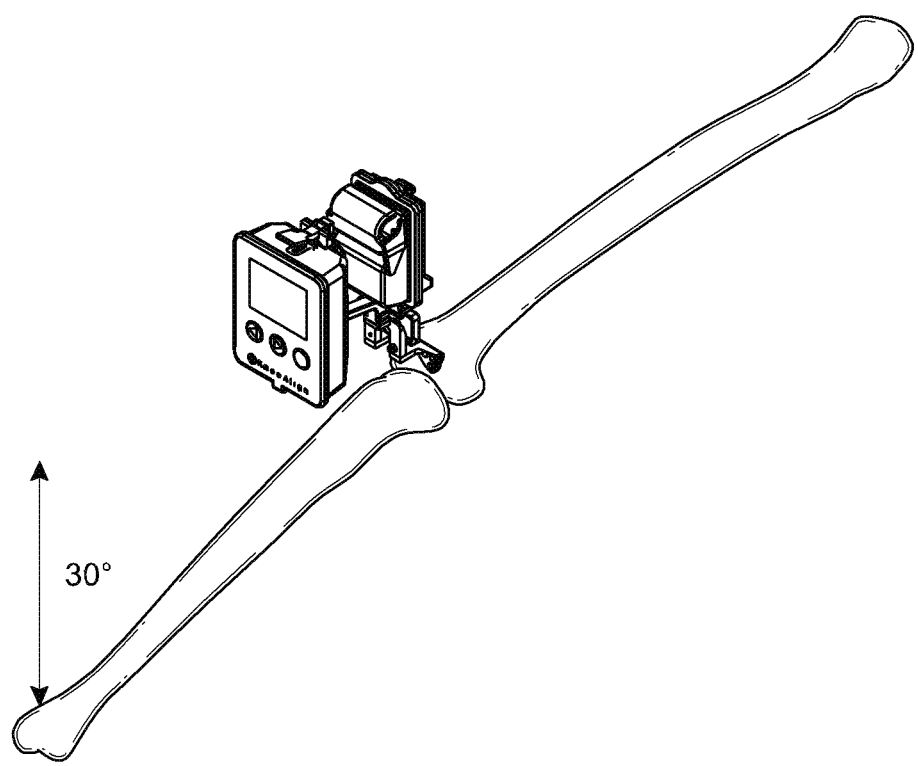

FIG. 32F displays a screen shot that provides a visual cue informing the user to perform a 30 degree raising leg step. The image in FIG. 32F can be displayed in response to pressing a user input button 28 specified by the surgical orientation device 14 in FIG. 32E. Alternatively, it is possible to change the sequence so that FIG. 32F is displayed in response to pressing the user input button 28 specified by the surgical orientation device 14 in FIG. 32D and FIG. 32E is displayed in response to pressing the user input button 28 specified by the surgical orientation device in FIG. 32F.

Figure 32G:
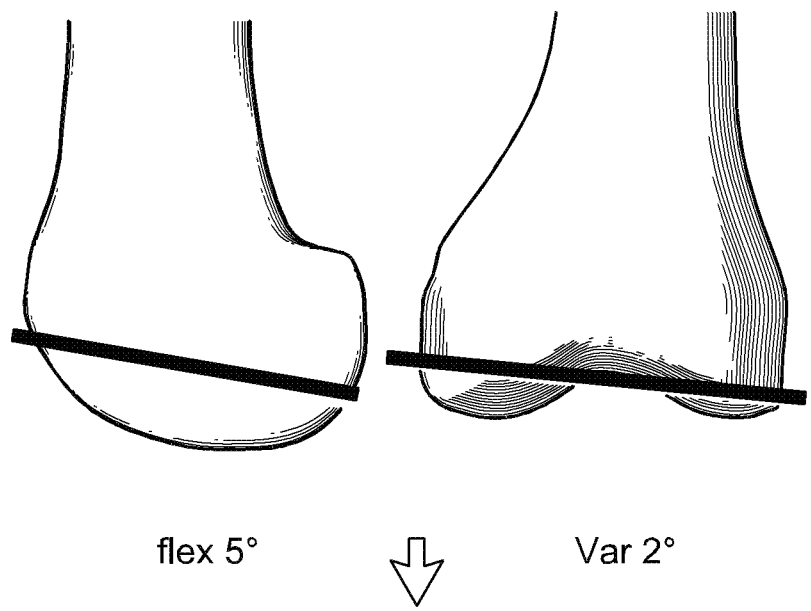

FIG. 32G is a screen shot that provides a visual cue informing the user of angle adjustments (e.g. varus/valgus and flexion/extension angle adjustments) needed for the surgical orientation device 12 and the femoral jig assembly 12 to reach neutral alignment with the mechanical axis. The image in FIG. 32G can be displayed in response to pressing a user input button 28 specified by the surgical orientation device 14 in FIG. 32F.

Figure 32H:
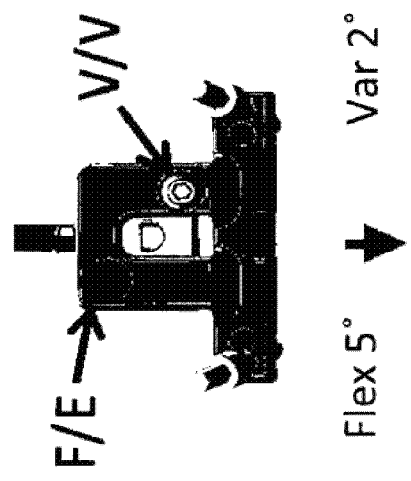

FIG. 32H displays a screen shot that provides a visual cue informing the user how to perform angle adjustments (e.g. varus/valgus and flexion/extension angle adjustments) of the translating member 118 by using the translation structures 120. FIG. 32H can be displayed in response to pressing a user input button 28 specified by the surgical orientation device 14 in FIG. 32G.

Figures 32I, 32J:
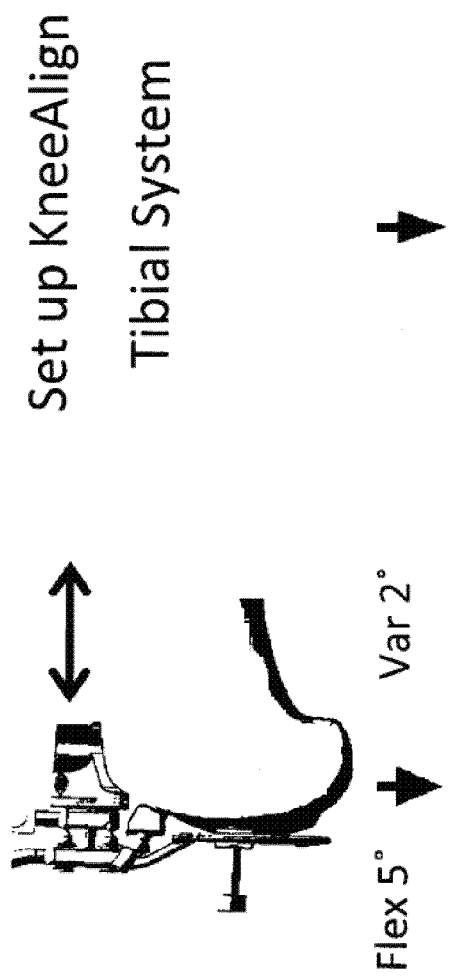

FIG. 32I displays a screen shot that provides a visual cue informing the user to perform a femoral resection depth adjustment step. The image in FIG. 32I can be displayed in response to pressing a user input button 28 specified by the surgical orientation device 14 shown in FIG. 32H. At this step, the cutting block 92, which can be attached to the microblock assembly 90, can be at a desired location aligned with the mechanical axis for distal femoral resection.

FIG. 32J displays a screen shot that provides a visual cue informing the user to perform a tibial preparation method. The image in FIG. 32J can be displayed in response to pressing a user input button 28 specified by the surgical orientation device 14 shown in FIG. 32H. In some embodiments, the display 26 of the interactive user interface can be configured to automatically shut off after the femoral procedure is completed, rather than moving directly to the tibial preparation.

Further embodiments of user interfaces, for use for example in an orthopedic method, can be found in paragraphs [0377]-[430] and FIGS. 58A-61K of U.S. patent application Ser. No. 12/509,388, which is incorporated by reference herein.

VII. Tibial Preparation Systems

Referring to FIG. 33, a tibial preparation system 210 can be used for modifying a natural tibia with a proximal tibial resection to enable a prosthetic component to be securely mounted upon the proximal end of the tibia. The tibial preparation system 210 can comprise, for example, a tibial jig assembly 212, a landmark acquisition assembly 214, a surgical orientation device 14 (e.g. the surgical orientation device described above), and a reference sensor device 16 (e.g. the reference sensor device described above).

A. Orthopedic Assembly for Angular Adjustment

The tibial jig assembly 212 can comprise an orthopedic assembly for use in preparing a tibia for a prosthetic component, and in particular for making angular adjustments relative to an anatomical feature. Referring to FIGS. 34-38, the tibial jig assembly 212 can comprise for example one or more of a posterior slope assembly 216, a varus-valgus assembly 218, and a mounting bar assembly 220. The tibial jig assembly 212 can be configured to be coupled with one or more additional components. For example, the tibial jig assembly 212 can be coupled with a stylus resection guide 222, a tibial cutting block assembly 224, and/or a midline probe assembly 226, as illustrated in FIGS. 43, 44A-B, and 45A-C, respectively.

Figure 34:
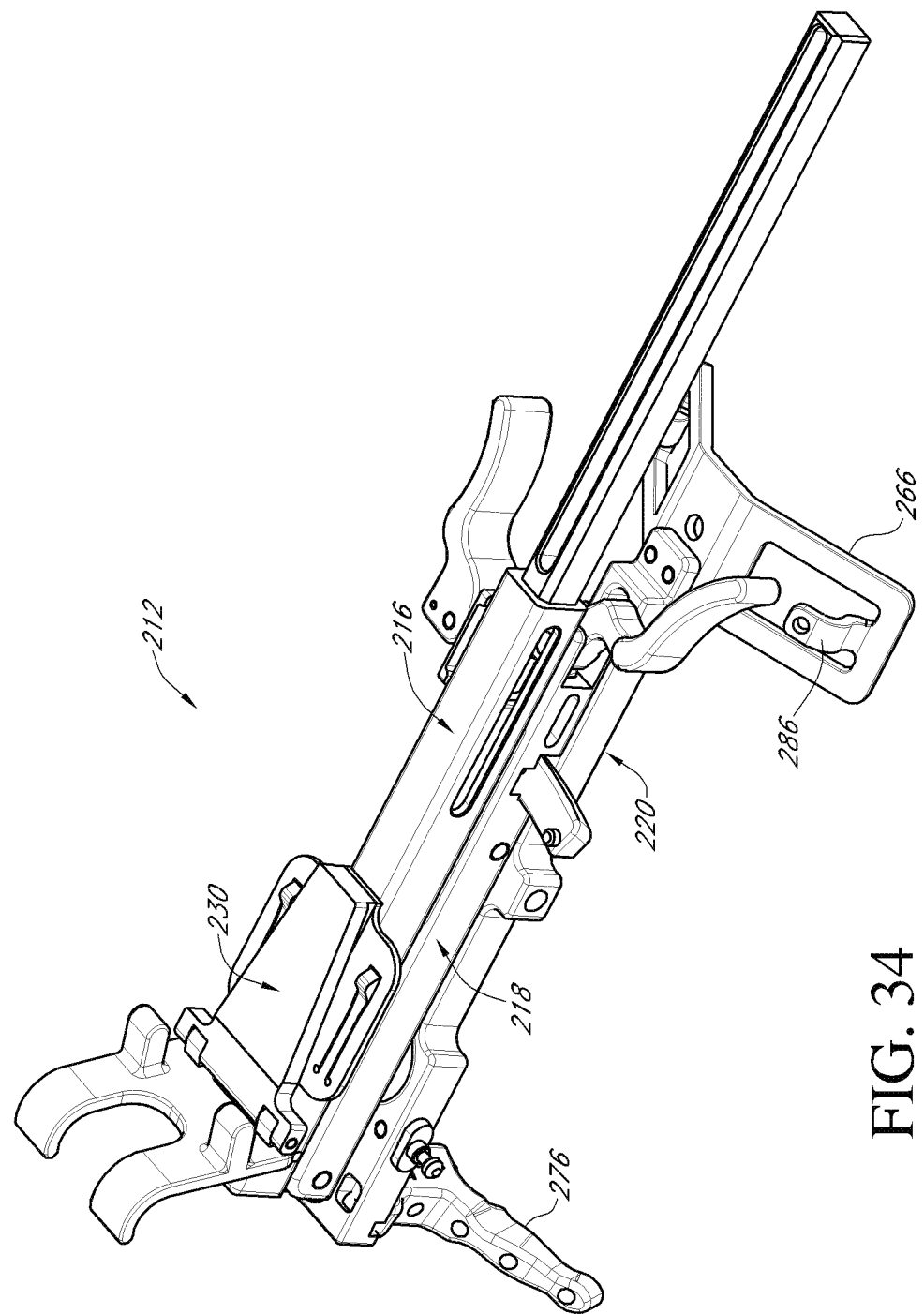
FIGS. 34-38 are assembled and exploded views of the tibial jig assembly of the tibial preparation system of FIG. 33.
Figure 38:
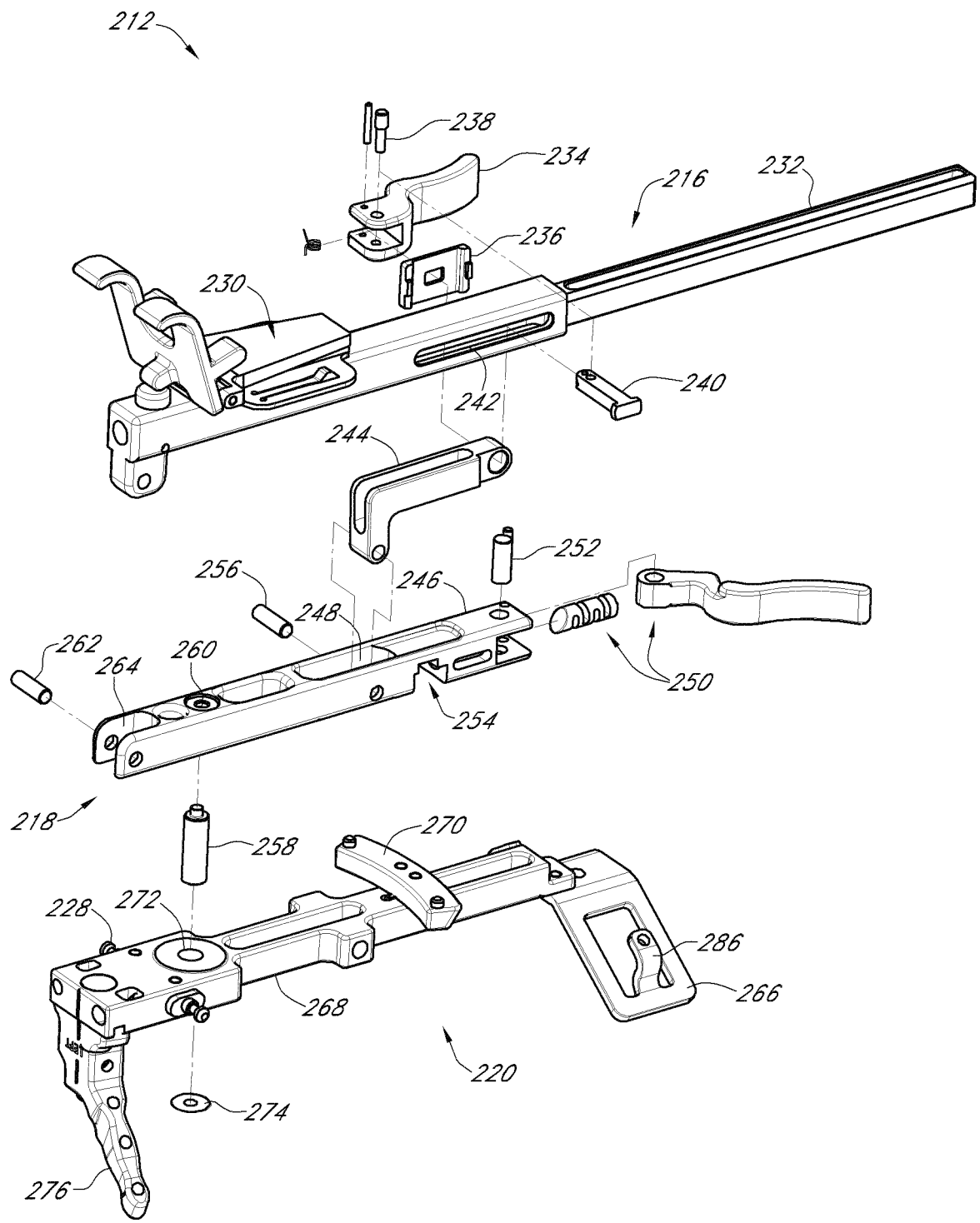

Referring to FIGS. 34 and 38, the tibial jig assembly 212 can include a reference sensor device interface 228 by which the reference sensor device 16 can be coupled to the tibial jig assembly 212, and a surgical orientation device interface 230 by which the surgical orientation device 14 can be coupled to the tibial jig assembly 212. The reference sensor device 16 can preferably be coupled with the tibial jig assembly 212 such that during a total knee replacement procedure, the reference sensor device 16 follows the movement of the tibia, and generally does not move independently with respect to the tibia. In some embodiments, reference sensor device interface 228 can comprise a plurality of posts disposed on a side surface of the mounting bar assembly 220 for connecting with the reference sensor device 16. The configuration of the reference sensor device interface 228 can enable low profile mounting of the reference sensor device 16 beneath other components of the tibial jig assembly 212, such that the reference sensor device 16 can be located between at least one moving component of the tibial jig assembly 212 and the tibia of the patient.

In a preferred arrangement, the orientation device interface 230 and the reference sensor device interface 228 can be coupled with portions of the tibial jig assembly 212 that are capable of moving relative to each other. For example, the orientation device interface 230 can be disposed on a movable portion of the tibial jig assembly 212, such as the posterior slope assembly 216, whereas the reference sensor device interface 228 can be disposed on a generally stationary portion of the tibial jig assembly 212, such as the mounting bar assembly 220.

1. Device for Adjusting a Posterior/Anterior Slope of a Cutting Block

In a preferred arrangement, the tibial jig assembly 212 can comprise a component for adjusting a posterior/anterior slope of the surgical orientation device 14 and/or a cutting block. For example, as seen in FIGS. 34-38, and 40A-B, the tibial jig assembly 212 can comprise a posterior slope assembly 216 that is adjustable in a posterior and anterior direction relative to the mounting bar assembly 220. With reference to FIG. 38, the posterior slope assembly 216 can comprise an elongate posterior slope arm 232, a posterior slope cam 234, a washer 236, a first posterior slope cam pin 238, a second posterior slope cam pin 240, a posterior slope opening (e.g. slot) 242, and a posterior slope pivot arm 244.

2. Device for Adjusting a Varus/Valgus Slope of a Cutting Block

In a preferred arrangement, the tibial jig assembly 212 can also comprise a component for adjusting the varus/valgus slope of a cutting block. For example, as seen in FIGS. 34-38, the tibial jig assembly 212 can comprise a varus/valgus assembly 218 that is adjustable in a varus and valgus direction. With reference to FIG. 38, the varus-valgus assembly 218 can comprise an elongate varus-valgus arm 246, an opening 248 to receive the posterior slope pivot arm 244, a varus-valgus cam assembly 250, a varus-valgus cam pin 252, a varus-valgus slide opening 254, a posterior pivot pin 256, a varus-valgus pivot pin 258, an opening 260 to receive the varus-valgus pivot pin 258, a posterior pivot pin 262, and an opening 264 to receive at least a portion of the elongate arm 232 described above.

3. Device for Securing an Orthopedic Fixture Against the Tibia

Figure 39A:
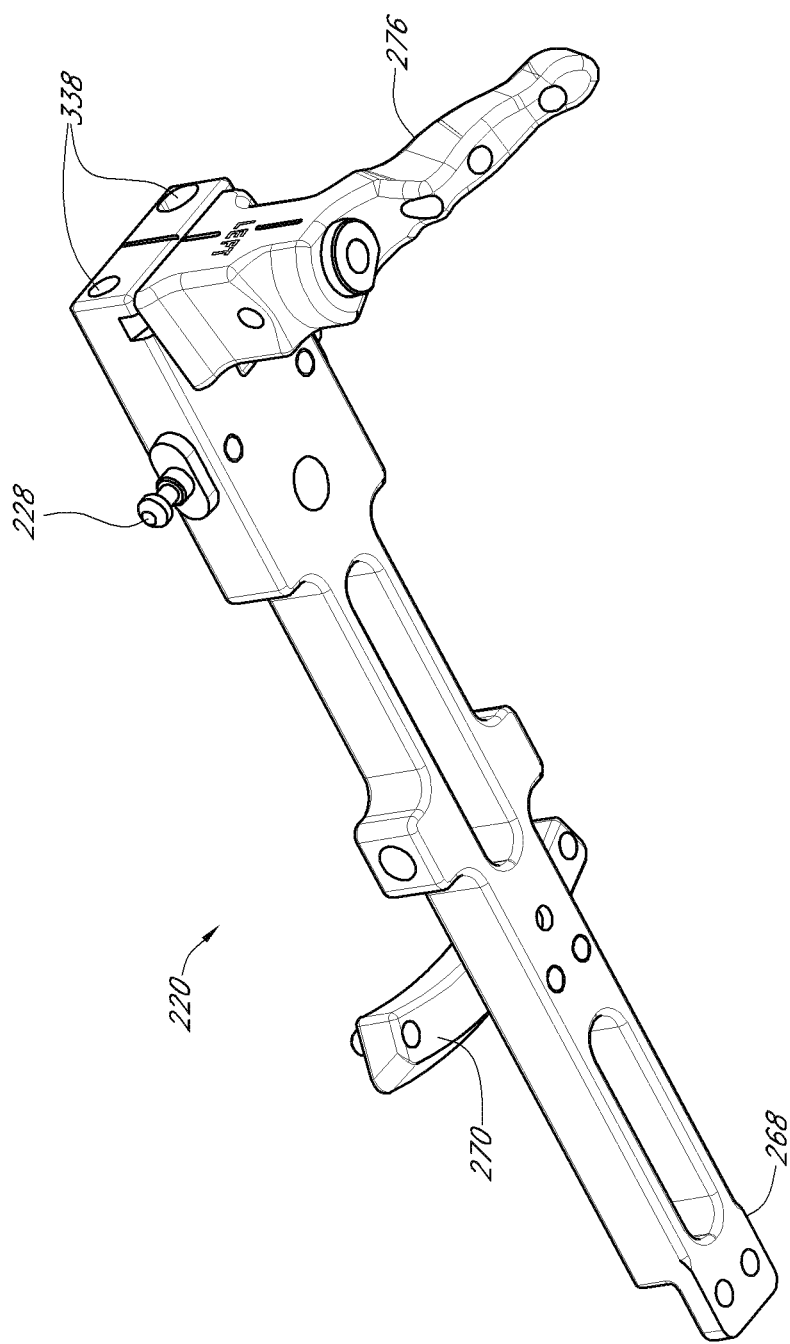
FIGS. 39A-B are perspective and exploded views of the mounting bar assembly of the tibial jig assembly of FIG. 34.
Figure 39B:
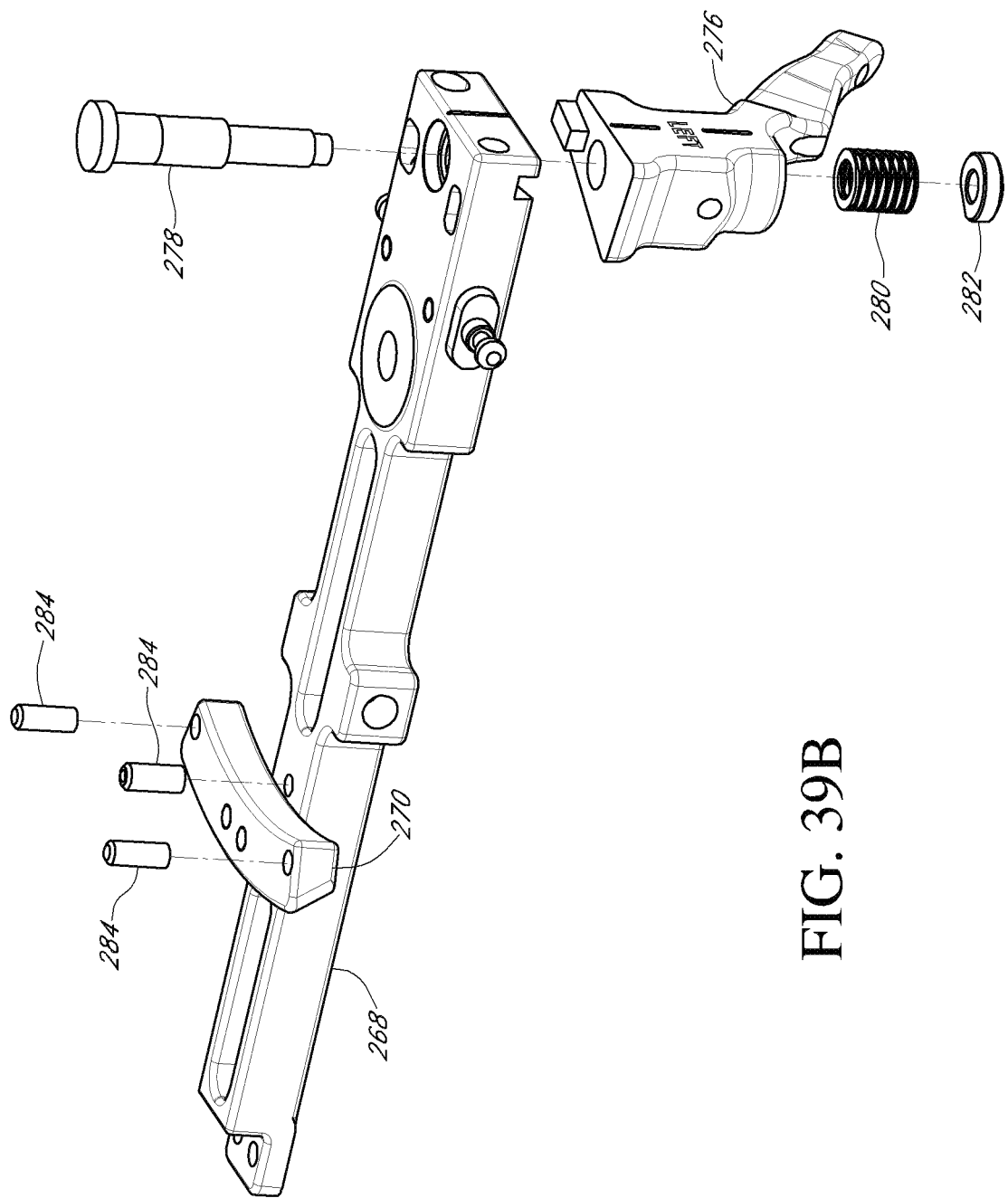
Figure 40A:
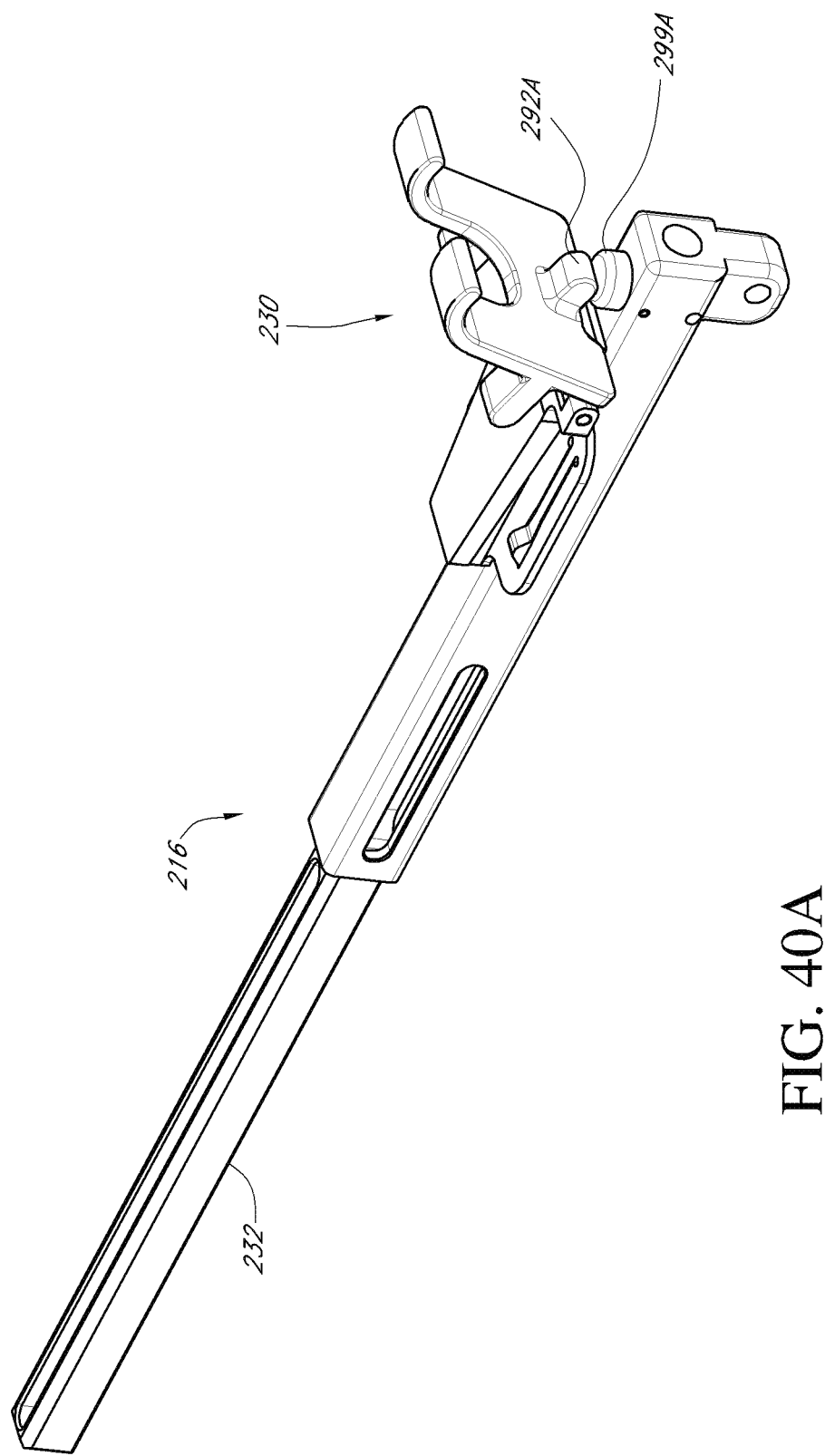
FIGS. 40A-B are perspective and exploded views of the posterior slope assembly of the tibial jig assembly of FIG. 34.
Figure 40B:
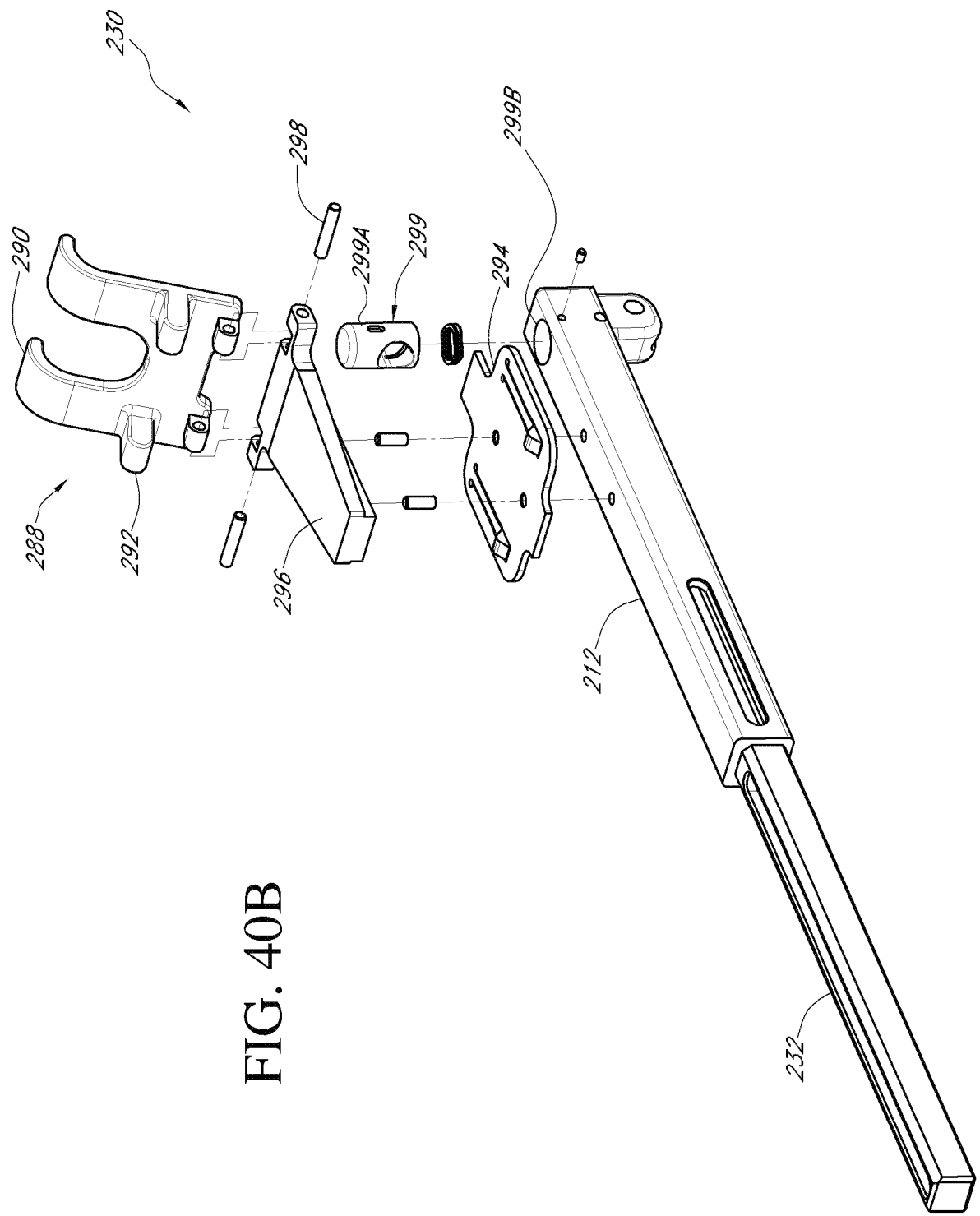

In a preferred arrangement, the tibial jig assembly 212 can also comprise a device for securing an orthopedic fixture against the tibia. For example, as seen in FIGS. 34-39B, in some embodiments the tibial jig assembly 212 can comprise a mounting bar assembly 220 that is configured to be secured (e.g. anchored) to a tibia. The mounting bar assembly 220 can comprise a mounting bar 266 configured to rest against the lower leg or tibia. The mounting bar 266 can have a generally v-shaped formation, or any other formation that facilitates alignment and/or placement against a lower leg. The mounting bar assembly 220 can further comprise an elongate mounting bar arm 268, a pivot guide member 270 configured to extend within the varus-valgus slide opening 254 described above, an opening 272 configured to receive the varus-valgus pivot pin 258 described above, a rotation pin washer 274, and a bone rest 276. As illustrated in FIG. 39B, the bone rest 276 can comprise a rotation pin 278, anchor spring 280, and rotation pin washer 282 that permits the bone rest 276 to be rotated 180 degrees (e.g. to be used on a left leg as opposed to a right leg and vice versa). As illustrated in FIG. 39B, the pivot guide member 270 can further comprise at least one varus-valgus stop pin 284 to limit the rotational movement of the tibial jig assembly 212 described above. The bone rest 276 can be optional. For example, FIGS. 50A-50B show a variation of the tibial preparation system that couples a proximal portion thereof with a tibial plateau instead of with an anterior face of the tibia. The embodiment of FIGS. 50A-50B is advantageous at least in that it eliminates the need for drilling holes in the anterior face of the tibia for mounting the bone rest 276.

Secure engagement of the mount bar assembly 220 with the lower leg of the patient can be enhanced by providing a spring (not shown) that, in use, wraps around the posterior side of the leg and couples to medial and lateral sides of the mounting bar 266. The spring can be secured to tabs 286 of the mounting bar 266 seen in FIG. 38. The spring can also be a tension member or another form of biasing member.

Figure 35:
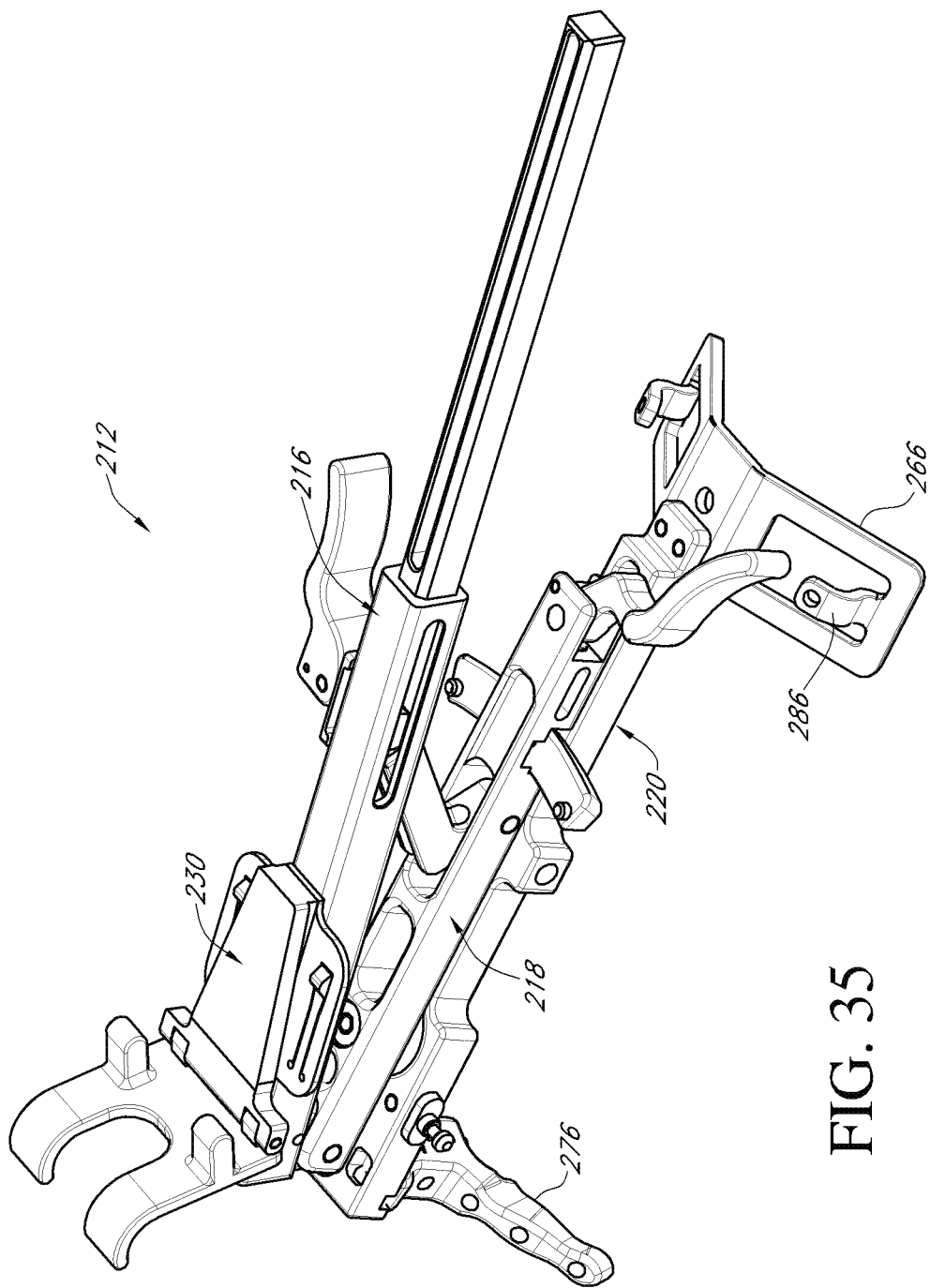
Figure 36:
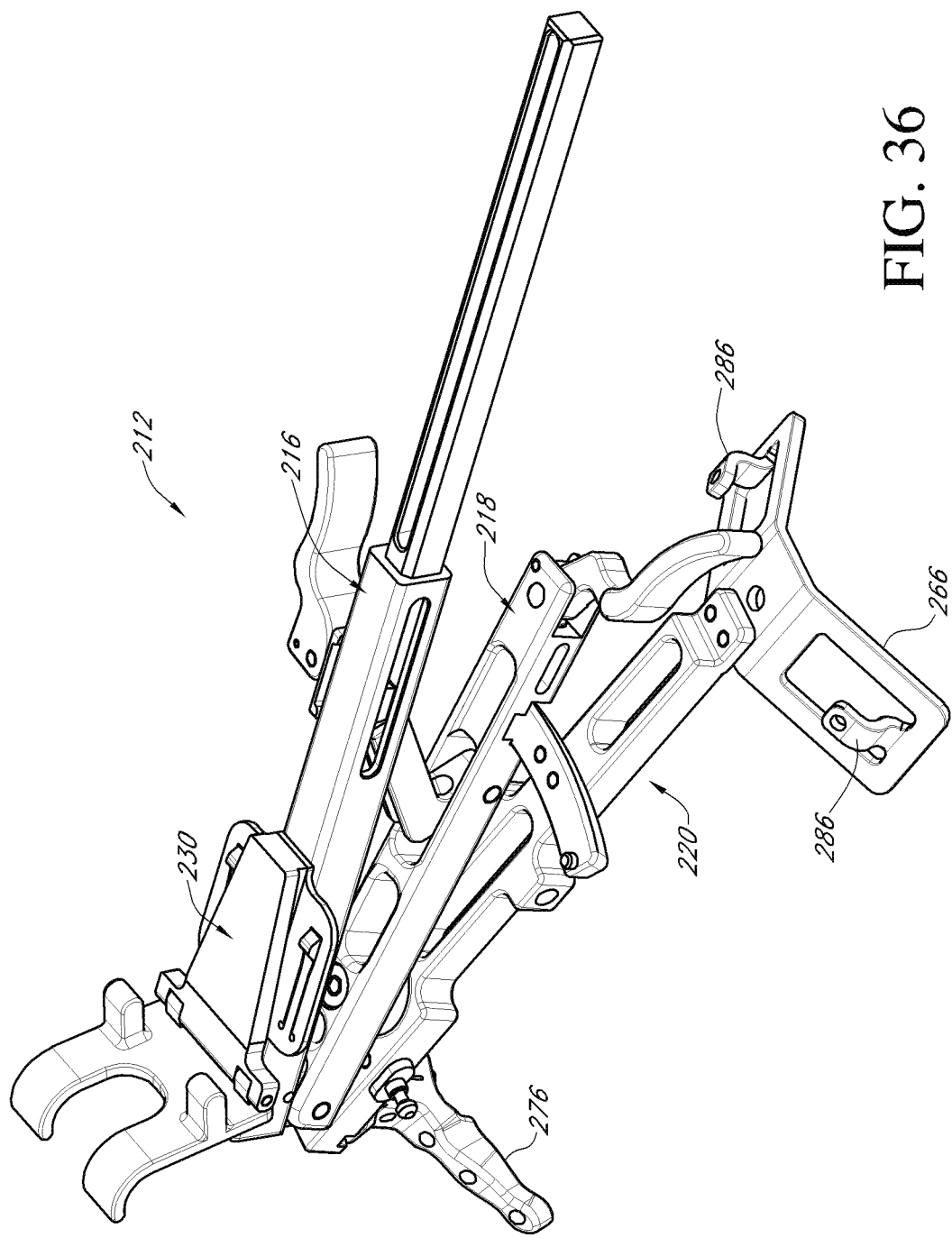
Figure 37A:
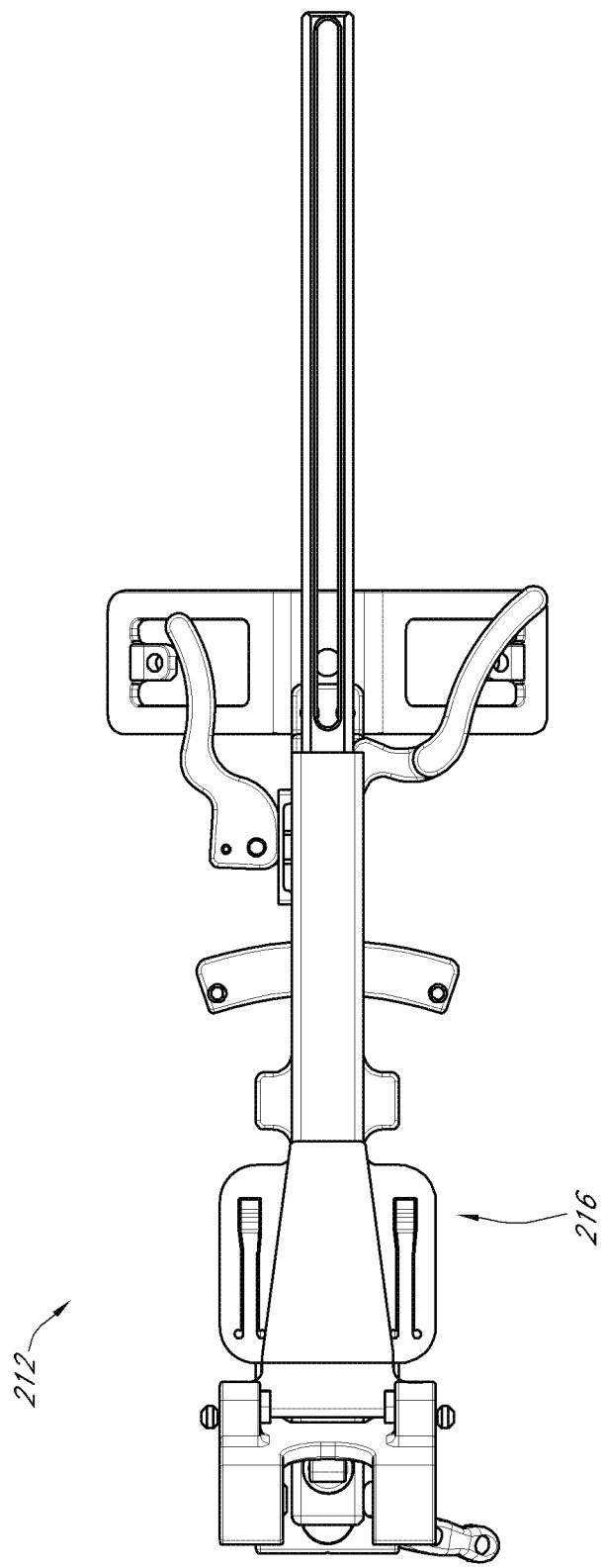
Figure 37B:
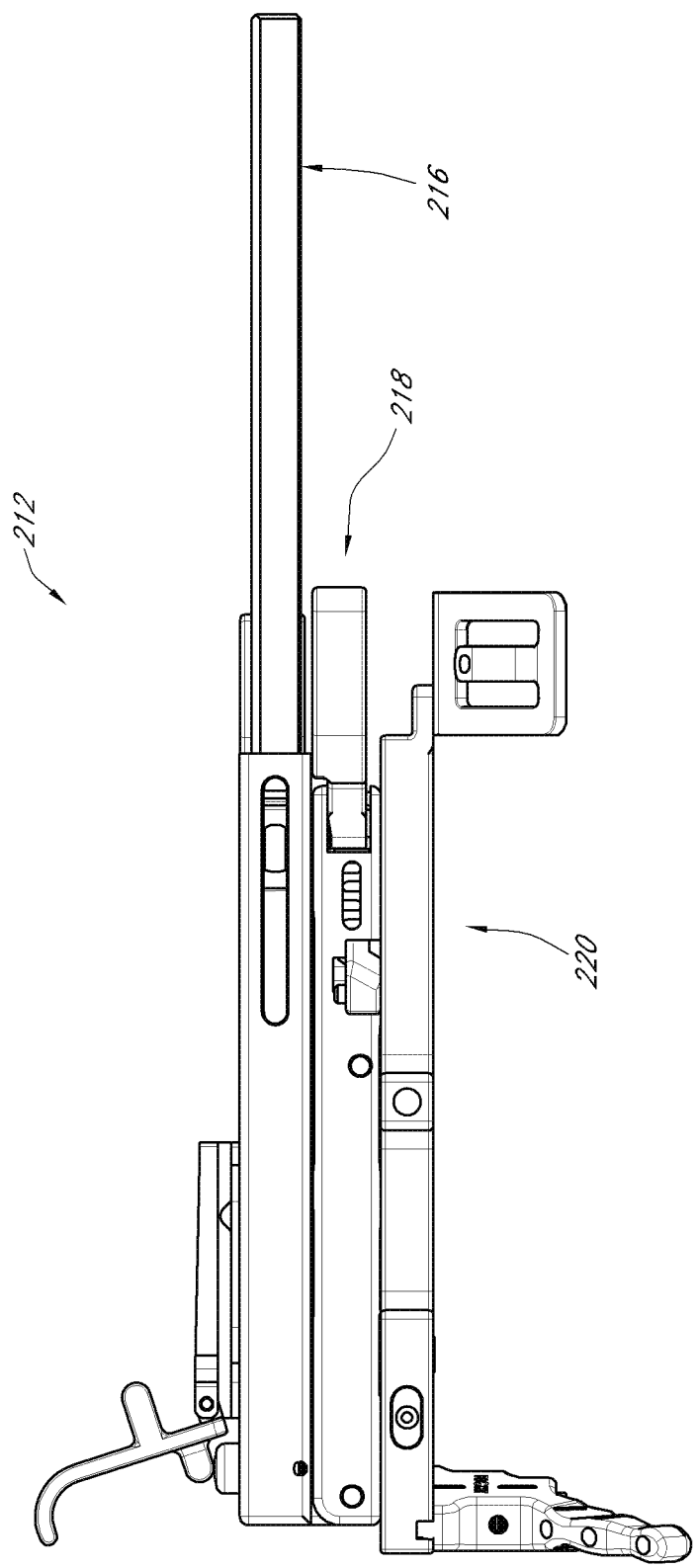
Figure 37C:
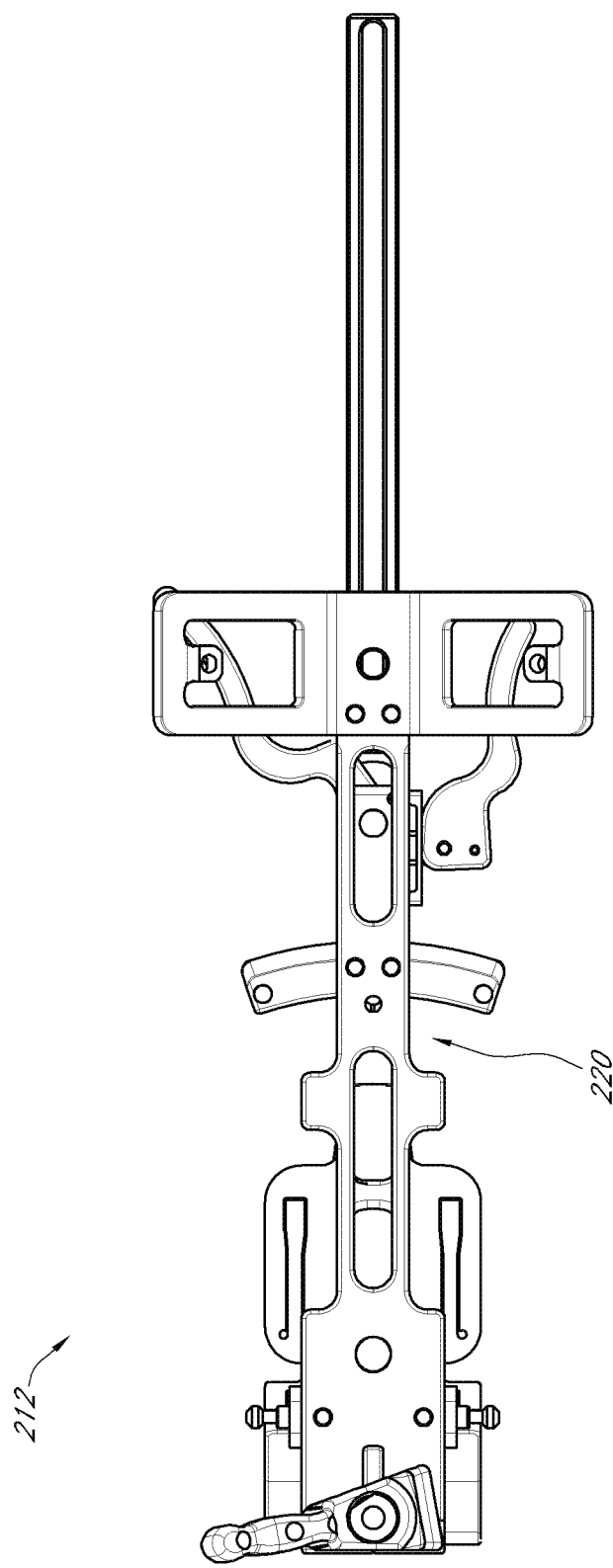
Figure 37D:
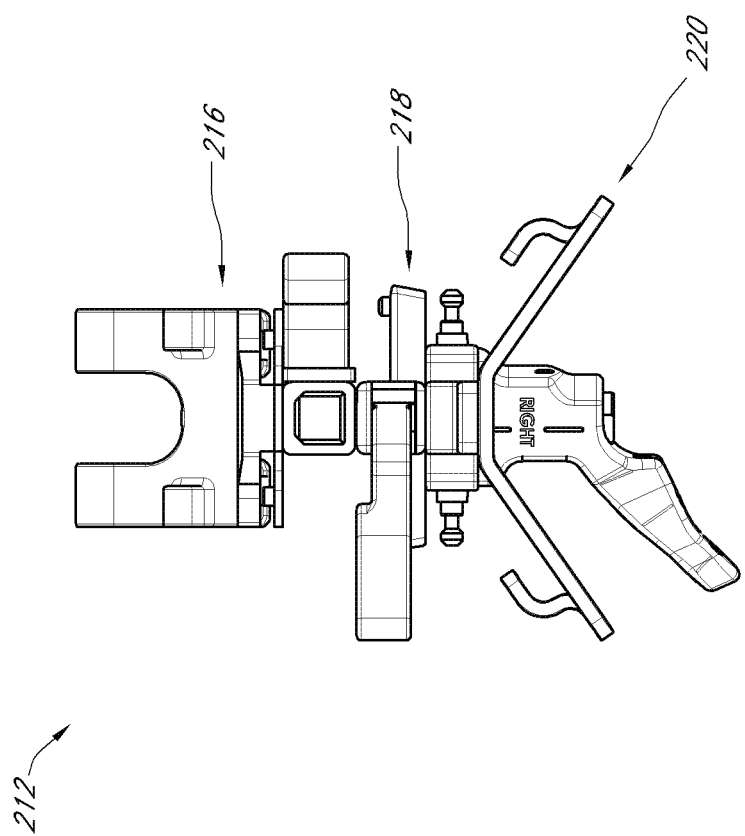

As illustrated in FIGS. 34-36, the components of the tibial jig assembly 212 can be adjusted and moved relative to one another. For example, FIG. 34 is a perspective view of the tibial jig assembly 212 with the posterior slope assembly 216 at a generally neutral position. In FIG. 34, the varus-valgus assembly 218 is also in a neutral position. As used herein the "neutral position" is a broad term that includes any position in which a selected portion of the tibial jig assembly 212 or components associated therewith is parallel to or in a common plane with a mechanical axis or other relevant axis of the knee joint.

FIG. 35 is a perspective view of the tibial jig assembly 212 of FIG. 34, with the posterior slope assembly 216 out of the neutral position providing an anterior to posterior slope adjacent a proximal end of the tibial jig assembly 212. Such a slope can correspond to an anterior to posterior slope for a cutting block.

FIG. 36 is a perspective view of the tibial jig assembly 212 of FIG. 34, with both the posterior slope assembly 216 and the varus-valgus assembly 218 out of their neutral positions. For example, in FIG. 36, the varus-valgus assembly 218 is oriented to provide a lateral to medial slope if applied to a patient's left knee.

The movement of the posterior slope assembly 216 and the varus-valgus assembly 218 can be controlled by suitable mechanisms, such as for example those illustrated in FIG. 38 and described above. The tibial jig assembly 212 can also be locked in any of a range of varus-valgus and/or posterior/anterior positions, such as for example by the cam-locking devices illustrated in FIG. 38.

As described above, the surgical orientation device 14 and reference sensor device 16 can be attached to the tibial jig assembly 212. Preferably, the surgical orientation device 14 can be locked in place relative the tibial jig assembly 212. For example, referring to FIG. 40B, the orientation device interface 230 can include a release device 288 for releasably holding the orientation device 14 on the tibial jig assembly 212. The release device 288 can include an actuating member 290, and a device 292 for applying a force to the surgical orientation device 14 (e.g. a clamp). The release device 288 can further comprise a mounting bracket 294, a saddle 296, and saddle pins 298. In one arrangement, at least one of the surgical orientation device 14 and the reference sensor device 16 can be releasably attached to the tibial jig assembly 212.

In one arrangement, the release device 288 can also be used to actuate a locking device 299 disposed at a proximal end of the tibial assembly 212. The locking device 299 includes a push button 299A that is slideably received in a channel 299B extending posteriorly from an anterior surface of the posterior slope assembly 216. See FIG. 40A. The push button 299A can be coupled with a gripping device disposed inside the posterior slope assembly 216 that can be biased into gripping engagement with a portion of the cutting block assembly 224 (or other removable component) inserted into the posterior slope assembly 216. By depressing the push button 299A, the grip can be released from the portion of the cutting block assembly 224 inserted into the posterior slope assembly 216. In one arrangement, the release device 288 has a proximally extending projection 292A for actuating the push button 299A. These features are discussed below in greater detail in connection with FIGS. 44A-B and 47-48.

FIGS. 50A-50B show a tibial jig assembly 212A that includes a tibial plateau mounting arrangement. The assembly 212A is similar to the tibial jig assembly 212 except as discussed below. The assembly 212A includes a mounting bar 268A and a tibial plateau anchor 226A that is adapted to engage with the tibial plateau in a manner that secures the proximal end of the jig assembly 212A to the tibia. This arrangement eliminates the need to secure the bone rest 276 to the tibia and can facilitate eliminating the bone rest completely. Also, this arrangement permits greater adjustability in the proximal-distal directions compared to the embodiment illustrated in FIG. 50, which shows the bone rest 276 disposed distally of the position of the cutting block 332. The degree of distal adjustment of the cutting block 332 is limited in that the bottom surface of the cutting block 332 would eventually contact the top surface of the bone rest 276 is sufficient distal adjustment is made. In the embodiment of FIGS. 50A-50B, the bone rest 276 is not present and thus does not limit the proximal-distal adjustment.

The tibial plateau anchor 226A includes an anchor pin 226B, an arm 226C that can extend anteriorly of the anchor pin 226B, and a locking device 226D that can be releasably secured to the proximal end of the mounting bar 268A. The anchor pin 226B can take any suitable configuration but preferably includes a rigid pin that extends in a distal-proximal direction when the jig assembly 212A is in use. The free (distal) end of the anchor pin 226B can include teeth that engage with the tibial plateau. In one technique the distal end of the anchor pin 226B is embedded in the tibial plateau by an amount sufficient to stabilize the tibial jig assembly 212A. In another embodiment, the arm 226C is secured to the tibial plateau by two screws (not shown) that are drive through through-holes H that extend proximal to distal through posterior end of the arm 226C. Preferably the through-holes H include at least two through-holes H that are angled relative to each other so that the arm 226C cannot slide proximally off of the screws.

An end of the arm 226C opposite the through-holes H extends anteriorly to an anterior location that would correspond to the position of the mounting bar 268A, i.e., just in front of the anterior face of the tibia in use. The arm 226C can be slidably coupled with the locking device 226D at a joint 226E. The joint 226E can be a ring having an inner perimeter matching the outer perimeter of the arm 226C. The arm 226C can have other features that facilitate mounting to the tibia, such as those described in connection with the midline probe assembly 226.

The locking device 226D can take any suitable configuration, but preferably is adapted to connect to the mounting bar 268A by a release device 226F. The release device 226F includes a finger actuatable lever 226G that has a hook 226H at a distal end and a toggle 226I at a proximal end. The hook 226H is adapted to be received in a recess formed in the proximal end of the mounting bar 268A. The locking device 226D can also include a plurality of pins 226J that can be received in corresponding recesses 226K in the proximal end of the mounting bar 268A.

FIG. 50B shows that in use, the jig assembly 212A can be secured to the tibia with screws, as discussed above, or by contacting or embedding the pin 226B in the tibial plateau and resting the mounting bar 266 and the landmark acquisition device 214 on an anterior face of the leg. Thereafter the cutting block 332 (discussed below in connection with FIGS. 44A-B, can be positioned against the tibial section to be resected. As discussed above, with the bone rest not present, the degree of proximal-distal adjustment of the cutting block 332 is enhanced. Prior to resecting the proximal tibia, the screws placed through the through-holes H could be removed if the resection plane is to be proximal of the distal end of the screws.

B. Orthopedic Assembly for Landmark Acquisition

Figure 41:
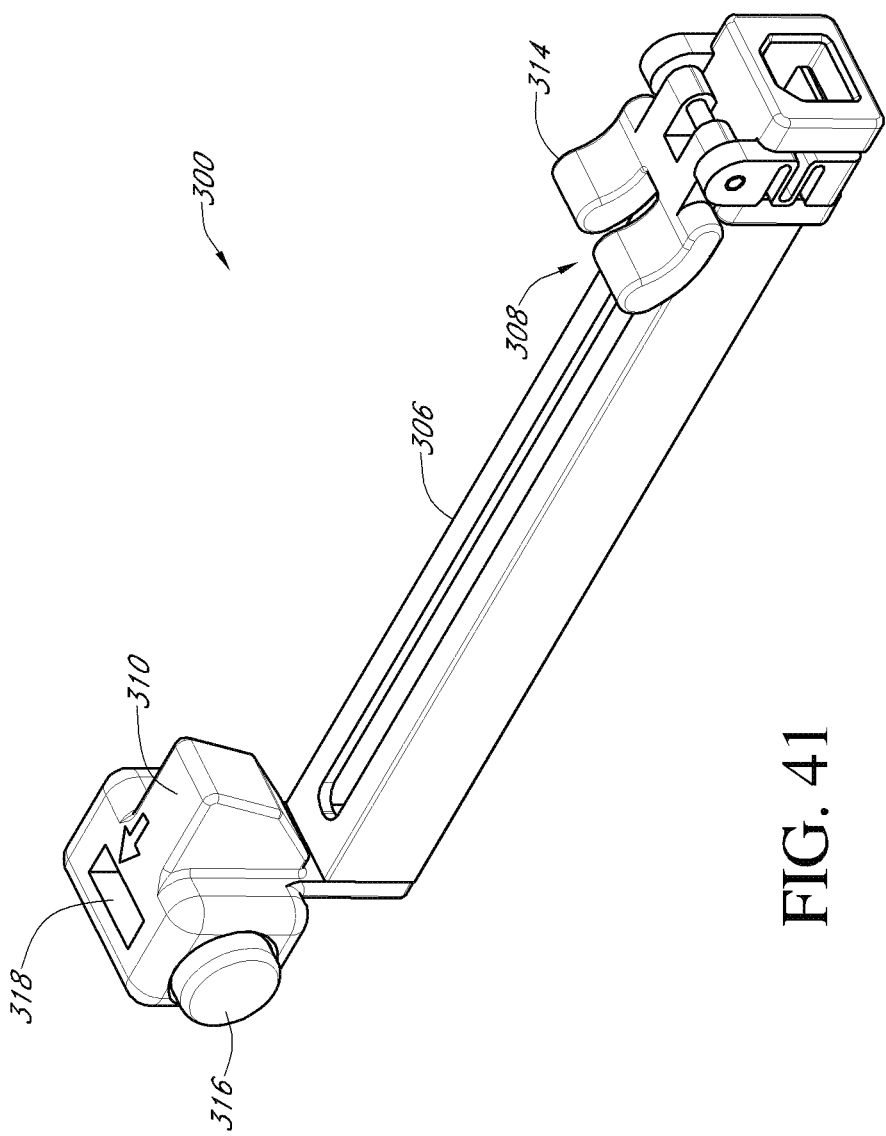
FIG. 41 is a perspective view of the distal tube assembly of the tibial preparation system of FIG. 33.
Figure 42:
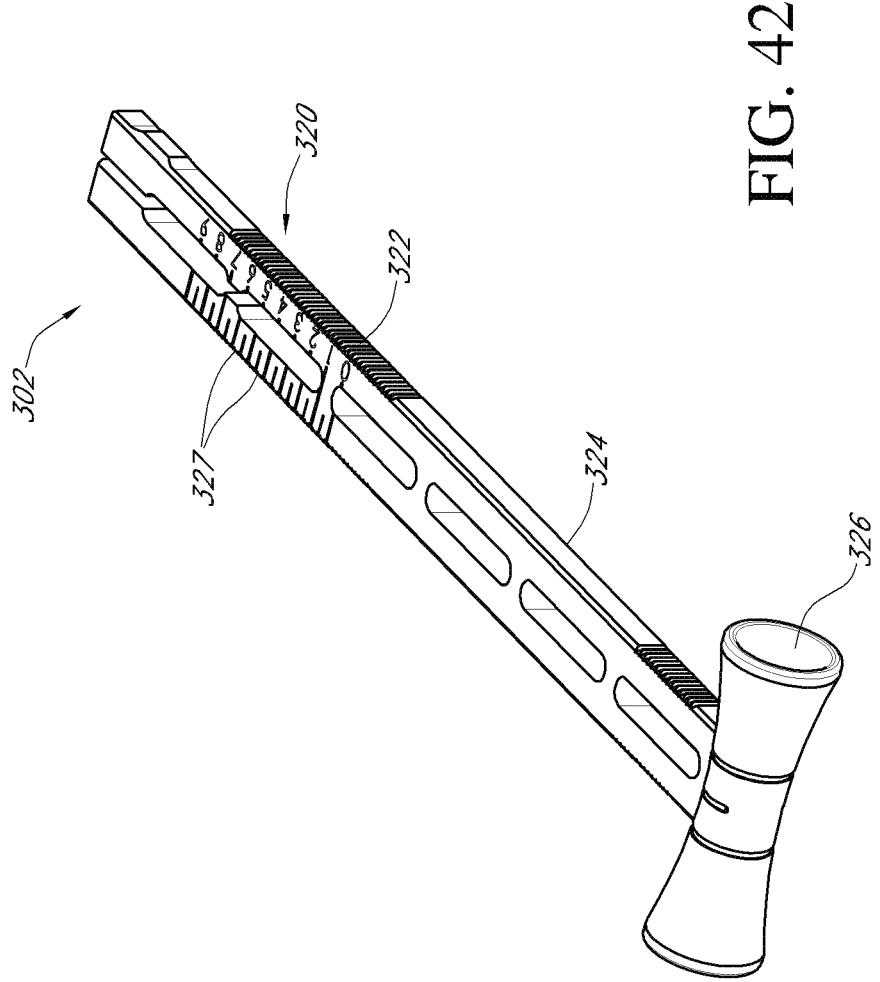
FIG. 42 is a perspective view of the probe assembly of the tibial preparation system of FIG. 33.

FIGS. 41 and 42 illustrate various features of the landmark acquisition assembly 214. The landmark acquisition assembly 214 can comprise a structure that is configured to contact and/or obtain information about anatomical landmarks on the human body. The landmark acquisition assembly 214 can be attached to or form part of the tibial jig assembly 212. For example, the landmark acquisition assembly 214 can be releasably attached to the posterior slope assembly 216. The landmark acquisition assembly 214 can comprise a distal tube assembly 300, as well as a probe assembly 302.

The distal tube assembly 300 can comprise an elongate member 306, a first clamping device 308 disposed at a proximal end of the elongate member 306, and a second clamping device 310 located at the distal end of the elongate member 306. The first clamping device 308 can include a cam member 314, and can be used to releasably fasten the distal tube assembly 300 to the posterior slope assembly 216. The second clamping device 310 can include a knob 316 and slot 318. The knob 316 can be used to tighten and/or adjust a position of a probe assembly positioned within the slot 318.

Referring to FIG. 42, the probe assembly 302 can include an elongate member 320. The elongate member 320 can have a first portion 322 and a second portion 324. In some embodiments, the first and second portions 322, 324 are an angled relative to each other. In other embodiments, the elongate member 320 can generally be straight. The probe assembly 302 can comprise a probe member 326 that is located on at least one end of the elongate member 320. The probe member 326 can be configured to contact an anatomical landmark, such as for example a malleolus on a patient's ankle. The elongate member 320 can further comprise a series of markings 327, indicating distance and/or length. The markings can be used to measure, for example, an AP offset of the probe member 326.

C. Resection Guide for Resecting an Anatomical Feature

Figure 43:
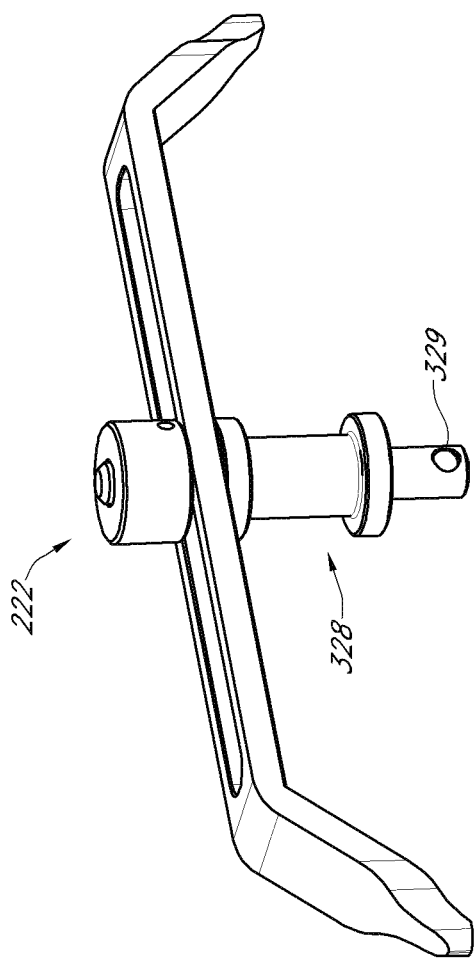
FIG. 43 is a perspective view of the stylus resection guide of the tibial preparation system of FIG. 33.

FIG. 43 illustrates various features of a stylus resection guide 222 for resecting an anatomical feature. The resection guide 222 can comprise a post 328 that can be received in a mount recess on a proximal aspect of the tibial jig assembly 212 (not shown). The stylus resection guide 222 can further include a locking device 329, such as a detent mechanism component, disposed thereon. The detent mechanism can be configured to engage a corresponding feature in the tibial jig assembly 212 to selectively mount the stylus resection guide 222 to the tibial jig assembly 212.

D. Cutting Block Assembly for Resecting an Anatomical Structure

Figure 44A:
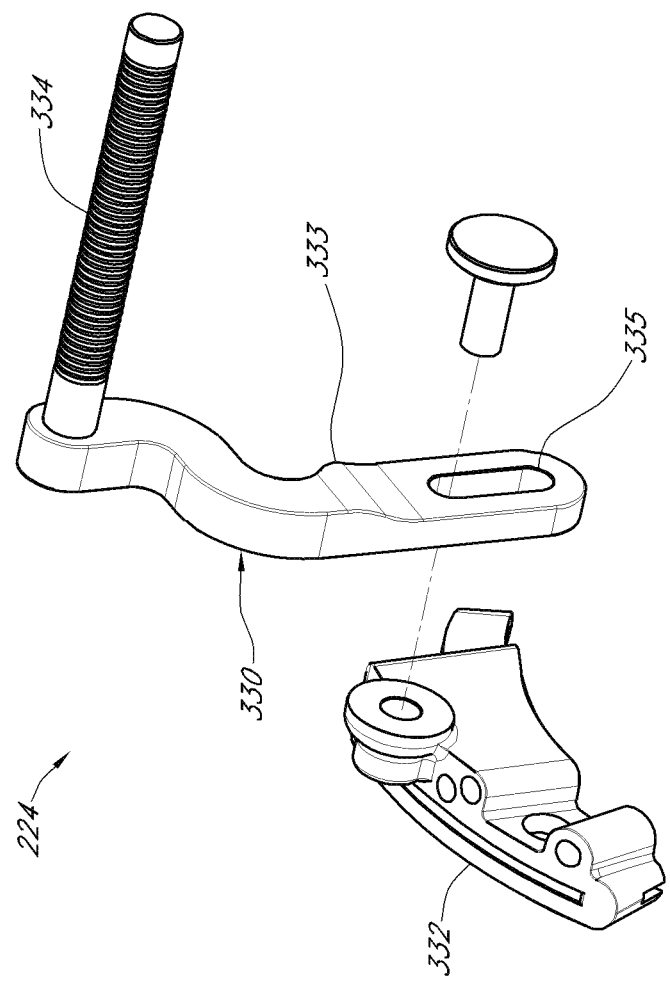
FIGS. 44A-B are exploded and perspective view of the tibial cutting block assembly of the tibial preparation system of FIG. 33.
Figure 44B:
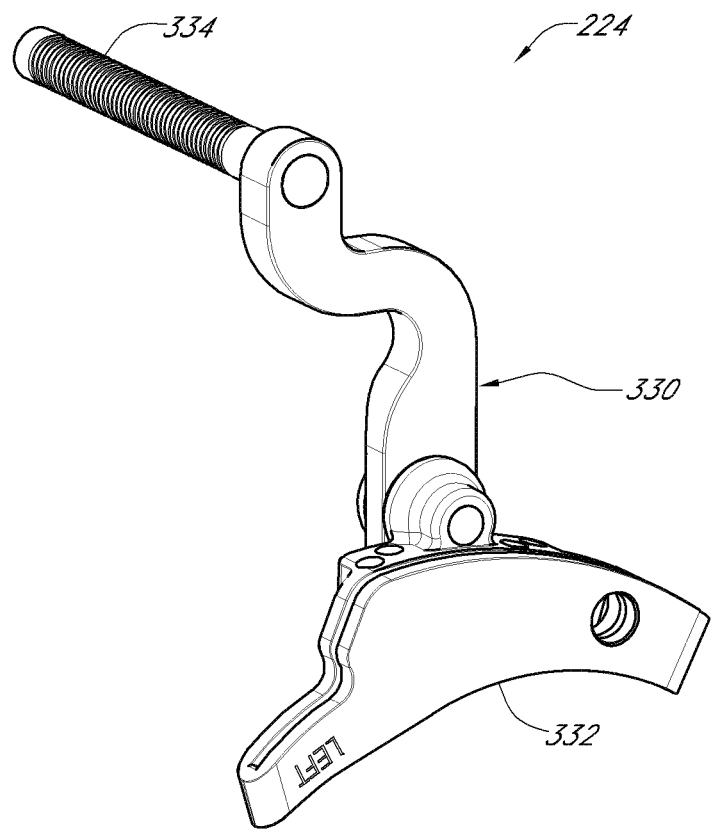
Figure 48:
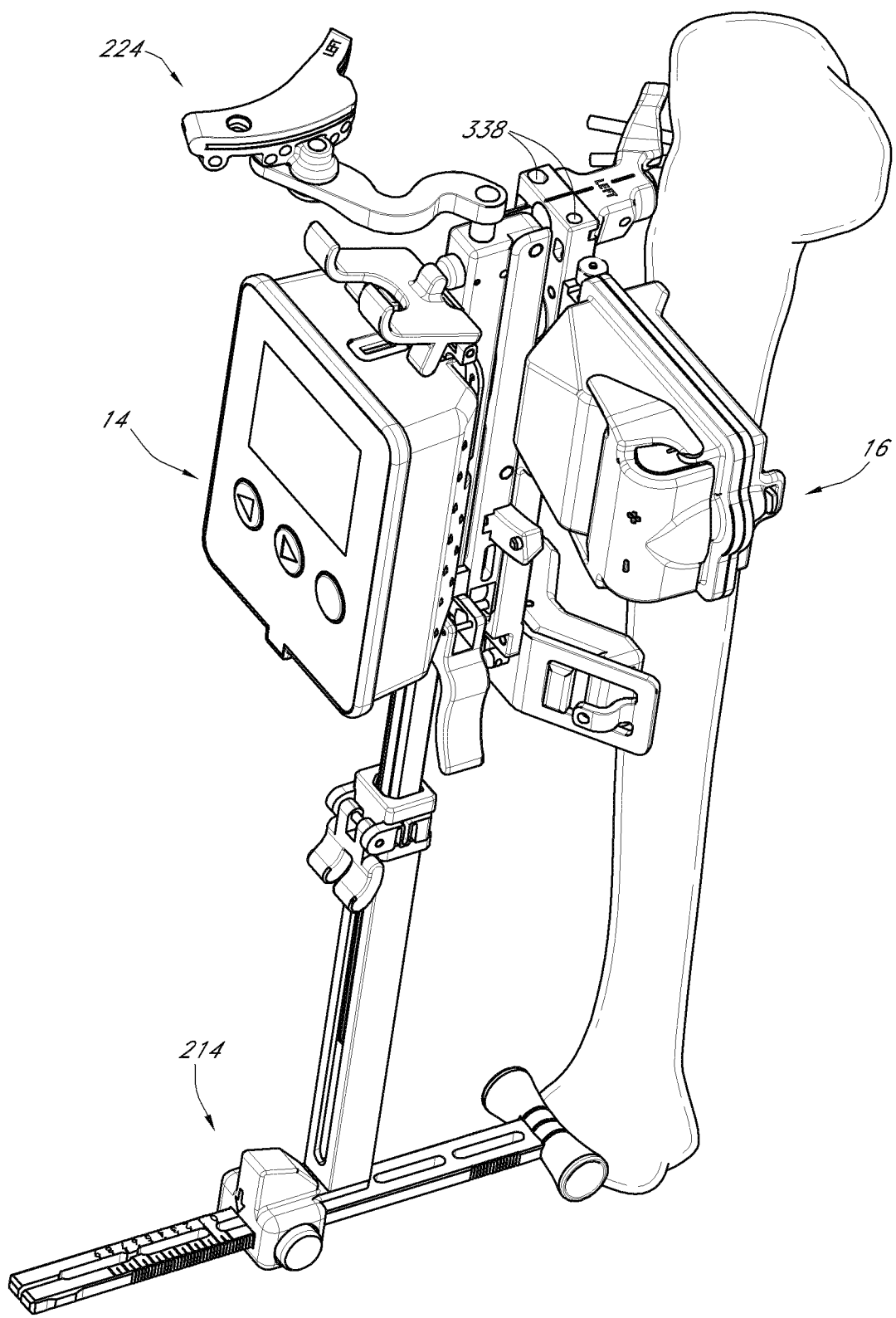
FIG. 48 is a perspective view of the tibial preparation system of FIG. 33 being used during another stage of a tibial preparation method according to one embodiment of the present invention.
Figure 49:
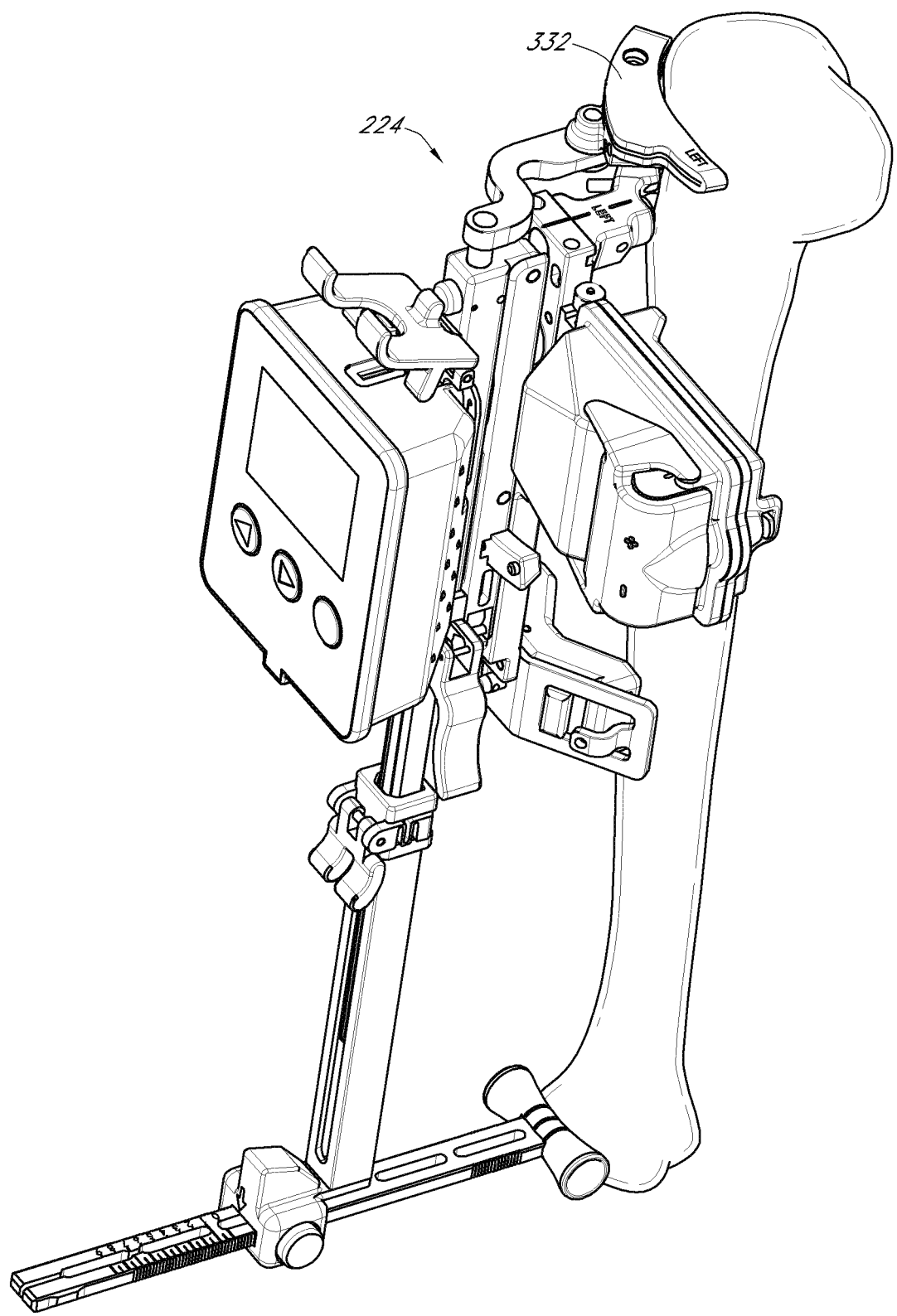
FIG. 49 is a perspective view of the tibial preparation system of FIG. 33 being used during another stage of a tibial preparation method according to one embodiment of the present invention.

FIGS. 44A and 44B illustrate various features of a cutting block assembly 224 for resecting an anatomical structure. The cutting block assembly 224 illustrated in FIGS. 44A and 44B is a left cutting block assembly 224. The cutting block assembly 224 can be optimized, for example, for resecting the proximal tibia of the left leg of the patient. The cutting block assembly 224 preferably can be configured to be moveable from a first position spaced away from an anterior surface of the tibia to a second position up against the tibia (e.g. as seen in FIGS. 48 and 49). A right cutting block assembly 224 can be formed as a mirror image of the left cutting block assembly 224.

The cutting block assembly 224 can comprise an adjustment mechanism 330 for distal-proximal adjustment of a cutting block 332. For example, the adjustment mechanism 330 can include a fastening device 334. The fastening device 334 can comprise, for example, a threaded rod or other type member that permits rotational movement of the adjustment mechanism 330. The fastening device 334 can be inserted into a recess 299C (see FIG. 46) that extends distally from a proximal surface of the tibial assembly 212. Thereafter, a gripping device coupled with the push button 299A can be urged into frictional or teeth-to-teeth engagement within the recess 299C. The proximal-distal position of the cutting block 332 can be adjusted by raising the actuating member 290 to cause the projection 292A to depress the button 299A to release the gripping device from the threaded rod or other fastening device 334. Once the desired proximal-distal position is achieved, the actuating member 290 can be released to permit the push button 299A to move anteriorly, which permits the gripping device to once again grip the threaded rod (see FIGS. 48, 49).

In some embodiments, the fastening device 334 can be secured by a spring loaded locking member that is actuated by the actuating member 290 as discussed above.

In one embodiment, the cutting block assembly 224 can include a cutting block 332 and a positioning device coupled with the cutting block 332. The positioning device can comprise a coupling member for connecting the cutting block assembly 224 to another portion of the tibial jig assembly 212, a cantilevered member 333 and a fine adjustment device. The coupling member can be an elongate member such as a rod. In one embodiment, cylindrical grooves can be formed along the length of the coupling member for engagement with a locking member. In one embodiment, the fine adjustment device can include a slot 335 formed in the cantilevered member along which the cutting block 332 can be moved. Preferably the cutting block 332 can also be attached to the cantilevered member in a way that permits the cutting block 332 to rotate about an axis extending perpendicular to the cantilevered member (e.g., about a vertical axis). See FIG. 44A.

The cantilevered member can be shaped to facilitate positioning the cutting block 332 around other features of a jig. For example, the locking device 226D of the tibial jig assembly 212A can be positioned directly between the location where the rod of the fastening device 334 is received in the posterior slope assembly 216 and the location where the cutting block 332 is desired to be positioned. The cantilever member of the adjustment mechanism 330 can be curved to extend laterally or medially around the locking device 226. See FIG. 50B. This enables the center of rotation to be positioned anterior of the locking device 226D.

E. Midline Probe Assembly

Figure 45A:
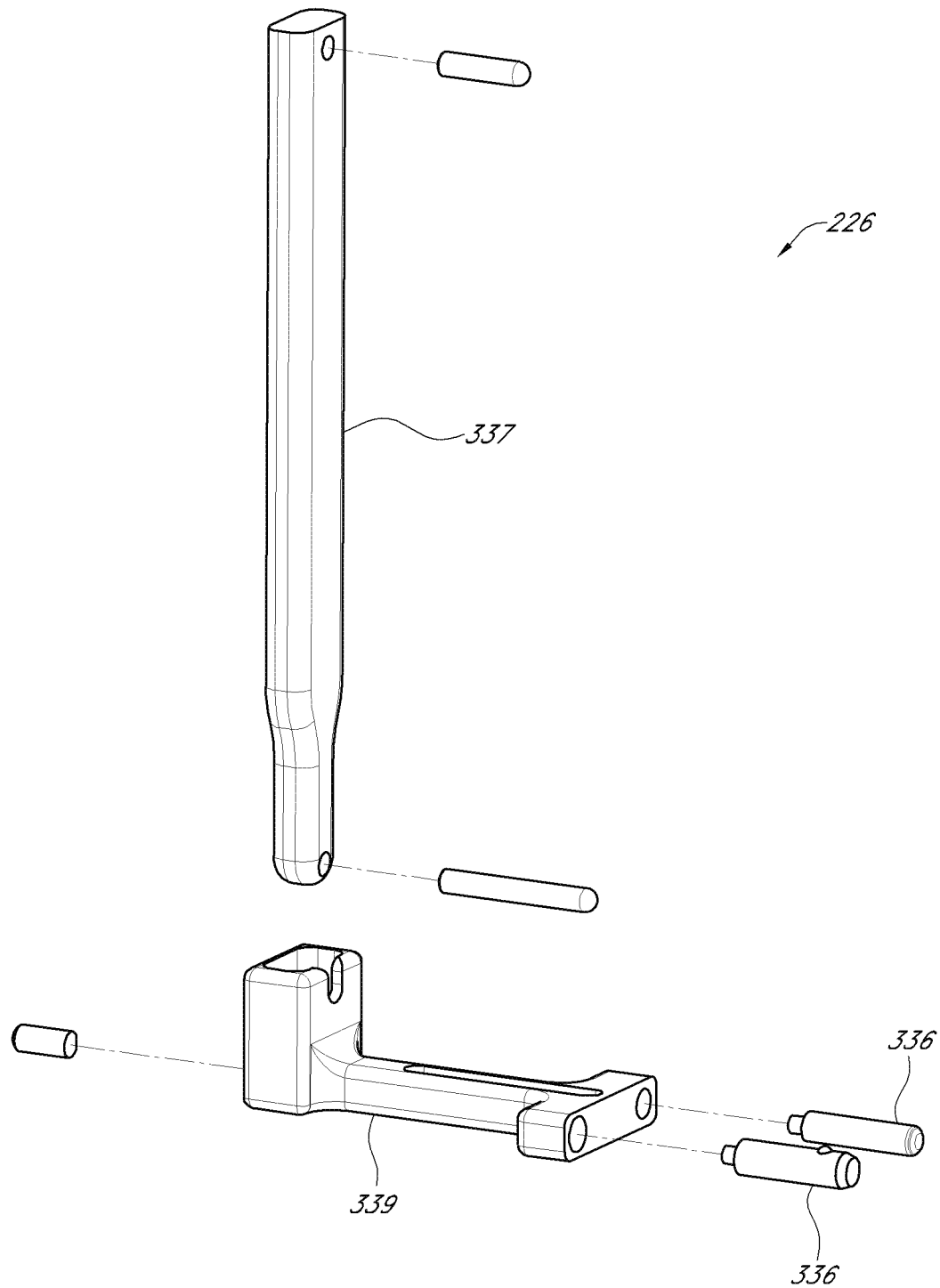
FIGS. 45A-C are exploded and perspective views of a midline probe assembly of the tibial preparation system of FIG. 33.
Figure 45B:
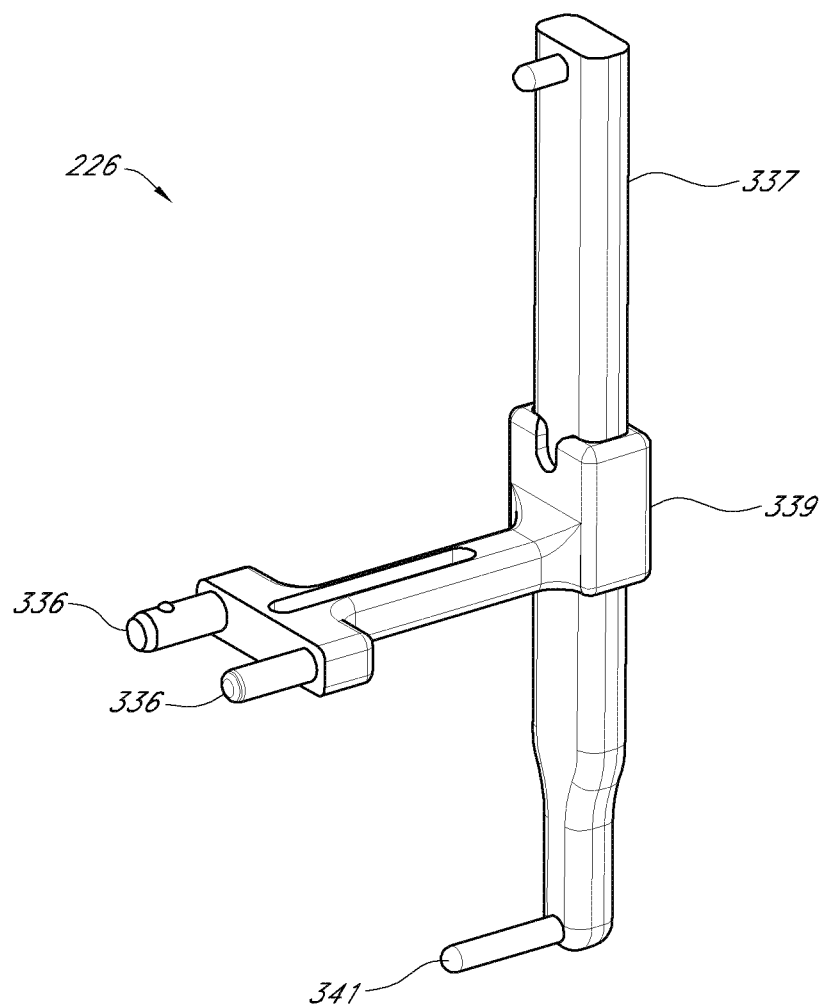
Figure 45C:
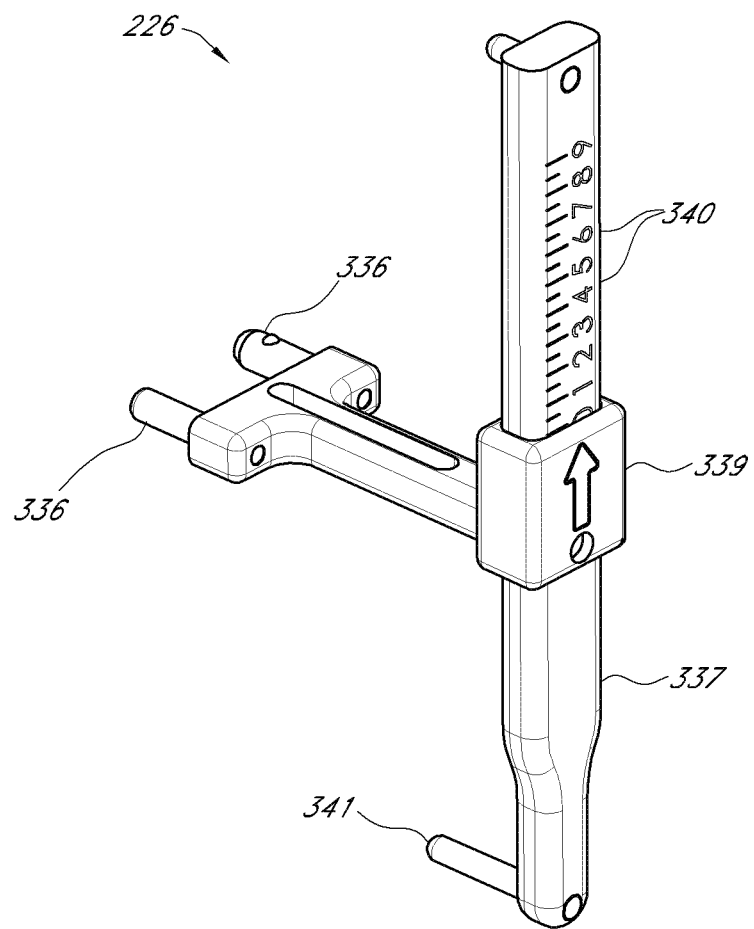

FIGS. 45A-C illustrate various features of the midline probe assembly 226. The midline probe assembly 226 can be used for determining a resection depth and/or an A/P offset of the tibial assembly 212. The midline probe assembly 226 can comprise, for example, mounting pins 336 that can be received in corresponding recesses 338 (see FIG. 48) in a proximal aspect of the tibial jig assembly 212, for example on a proximal surface of the mount bar assembly 220. The midline probe assembly can further comprise a set of markings 340 for helping to identify an A/P offset, along with an adjustable probe bar 337 and guide bar 339, the guide bar 339 having an opening for receiving the probe bar 337.

VIII. Tibial Preparation Methods

Referring to FIGS. 46-50, the tibial preparation system 210 described above can be used to prepare the tibia for a total knee replacement.

Figure 46:
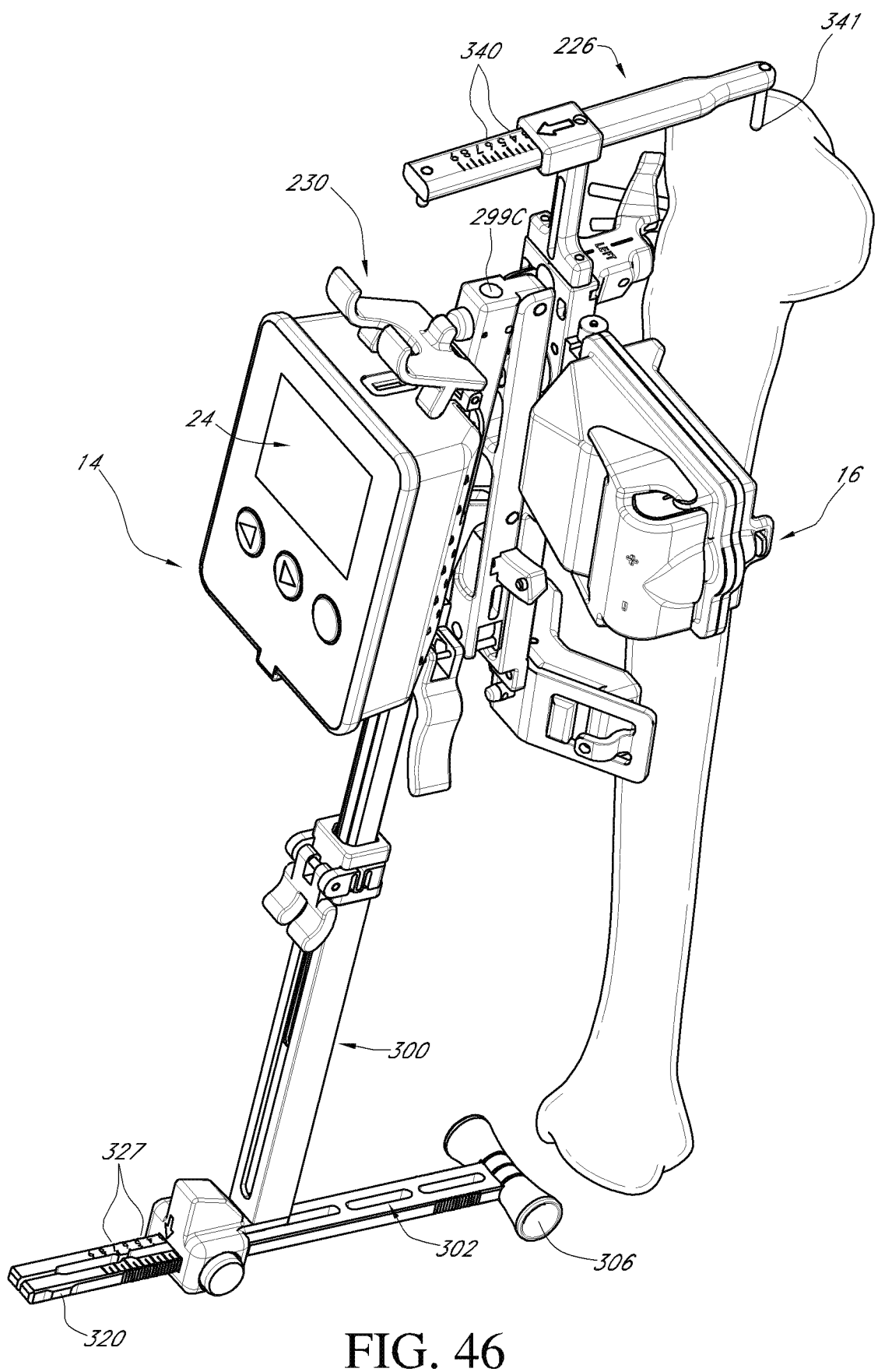
FIG. 46 is a perspective view of the tibial preparation system of FIG. 33 being used during a stage of a tibial preparation method according to one embodiment of the present invention.

FIG. 46 illustrates the tibial jig assembly 212 fully assembled with a reference sensor device 16 coupled to the reference sensor device interface 228 and with a surgical orientation device 14 coupled with the orientation device interface 230. Advantageously, and as described above, the reference sensor device 16 can enable the procedure to proceed without fixation of the leg being operated upon because the reference sensor device 16 can track the relative positions of the tibia and the surgical orientation device 14.

The midline reference probe assembly 226 can be coupled with a proximal face of the mounting bar assembly 220 and can be positioned at an appropriate anatomical location at the proximal tibia, for example at a point just posterior to the insertion of the anterior cruciate ligament (ACL), or at another suitable anatomical landmark. For example, a tip 341 of the midline reference probe assembly 226 can be resting over the insertion point of the anterior cruciate ligament in the knee, and/or a soft point on the top of the tibia commonly referred to as the A/P point of the mechanical axis. This point is generally located along a tibial spine on top of the tibia, and marks the location of a point along the mechanical axis of the leg. Indicia of distance on an upper surface of the midline reference probe assembly 226 (e.g. via markings 340) can be noted and a corresponding A/P offset position can be set in the landmark acquisition assembly 214 (e.g. via markings 327 described above) See FIG. 46.

Figure 47:
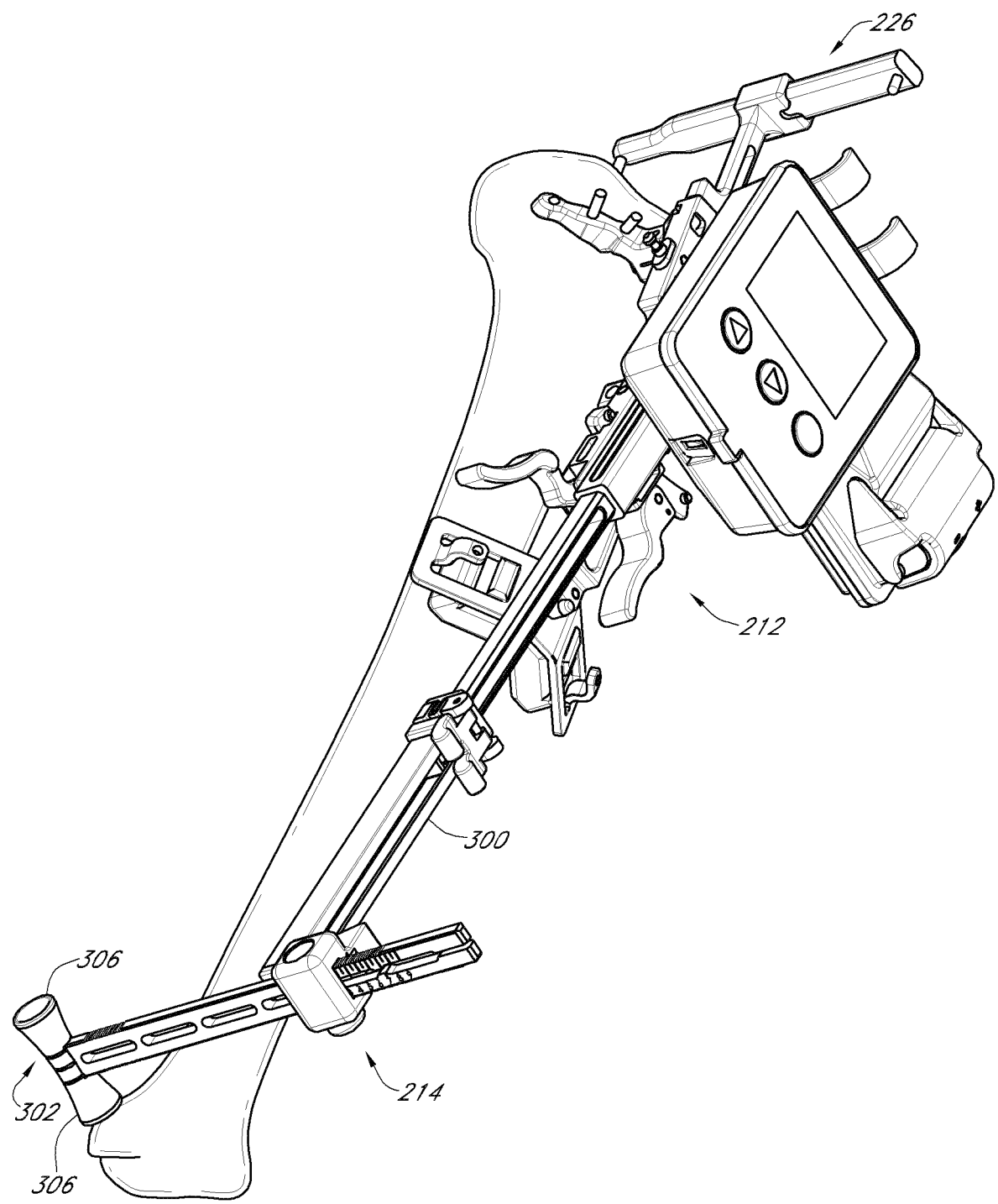
FIG. 47 is a perspective view of the tibial preparation system of FIG. 33 being used during another stage of a tibial preparation method according to one embodiment.

Referring to FIG. 47, the method can further comprise acquiring landmarks to determine the location of the mechanical axis passing through the tibia. For example, landmarks can be acquired by engaging the probe member 306 of probe assembly 302 first with a medial malleolus, and then with the lateral malleolus (or vice versa). FIG. 47 illustrates acquisition of one malleolus. Acquisition of the other malleolus can similarly be accomplished by swinging the distal tube assembly 300 and a portion or portions of the tibial jig assembly 212 such that the probe member 306 contacts the other side of the leg. Thereafter, the surgical orientation device 14 can determine the location of the mechanical axis, e.g., by locating sagittal and coronal planes extending through the mechanical axis. In some embodiments, the surgical orientation device can calculate the location of the mechanical axis by assuming that the mechanical axis extends from the point of contact of the midline reference probe assembly 226 with the proximal tibia through a point that is halfway between the two malleolus points contacted by the probe member 306 on either side of the leg, or any other appropriate point.

In some embodiments, the user can activate the surgical orientation device 14, such as by pressing one of the user inputs 28 on the surgical orientation device 14, during each landmark acquisition. Once activated, the, surgical orientation device 14 can register (e.g. record) the orientation of the surgical orientation device 14 as a reference position (e.g. a first reference position). For example, the surgical orientation device 14 can register and/or calculate the current orientation of the surgical orientation device 14 based on data collected from the sensor(s) inside the surgical orientation device 14. The orientation of the surgical orientation device 14 in a first reference position can be used to identify and register the orientation of a coronal plane which contains the mechanical axis of the leg, as well as to determine a first reference point for identifying the location and/or orientation of a sagittal plane containing this same mechanical axis.

The user can then swing the probe member 306 over to the other (e.g. medial) side of the leg, such that the reference probe 306 is located adjacent the other malleolus. During each landmark acquisition, the user can palpate the ankle. Once the location of the other (e.g. medial) malleolus is identified, the user can press one of the user inputs 28 on the surgical orientation device 14 to cause the surgical orientation device 14 to determine the orientation of the surgical orientation device 14 in a second reference position. For example, the surgical orientation device 14 can register and/or calculate the current orientation of the surgical orientation device 14 based on data collected from the sensor(s) inside the surgical orientation device 14.

The orientation of the surgical orientation device 14 in the second reference position can again be used to identify the orientation of a coronal plane extending through the tibia that contains the mechanical axis of the leg, and/or can be used to locate a second reference point for identifying the location and/or orientation of a sagittal plane containing the same mechanical axis.

When using the surgical orientation device 14 to determine the first and second reference positions, output of the sensor(s) in the surgical orientation device 14 can be monitored in a manner that minimizes error in the reading. For example, a transient phase can be eliminated in the output of the sensors to arrive at an accurate estimation of the given anatomical landmark.

Once information about both the first and second reference positions has been acquired and registered in the surgical orientation device 14, the surgical orientation device 14 can determine (e.g. calculate) the location of a desired plane between the lateral malleolus and the medial malleolus. The desired plane can correspond to the sagittal plane containing the mechanical axis. The desired plane can vary, depending on factors such as the patient's specific anatomy and the surgeon's training and experience. For example, the desired plane can be located midway between the lateral malleolus and medial malleolus, or 55% toward the medial malleolus from the lateral malleolus, or at some other predetermined location.

The user can use one or more user inputs 28 to direct the surgical orientation device 14 to calculate the location of and/or orientation of the sagittal plane. Once the surgical orientation device 14 has calculated where the sagittal plane is, the surgical orientation device 14 can provide location feedback to the user, for example in the form of a visual signal or signals on the display 26, indicating that the location of the sagittal plane has been calculated.

In some embodiments a laser can be provided on the surgical orientation device 14 to confirm the position. The tibial assembly 212 can be configured to interact with the laser to provide a confirmation of alignment. In one embodiment, the laser can emit a cross-hair laser pattern in which a first component is directed through slots and a second component impinges on indicia on the probe member 306 distally and/or on the midline reference probe assembly 226 proximally as a confirmation of appropriate positioning of the midline reference probe assembly 226. Embodiments of laser use are described, for example, in U.S. Patent Publication No. 2010/0063508, the contents of which are incorporated by reference in their entirety.

Referring to FIG. 48, once the mechanical axis has been identified, the midline reference probe assembly 226 can be removed and replaced with the tibial cutting block assembly 224. The cutting block assembly 224 can be positioned such that the cutting block 332 is spaced away from anterior surface of the tibia. The surgical orientation device 14, and tibial assembly 212, can be used to adjust the cutting block 332 in order to obtain a desired orientation for resection of the top of the tibia.

For example, the posterior slope assembly 216 and varus/valgus assembly 218 can each be independently adjusted to change the angle of the cutting block 332, and subsequently, the angle of the intended resection. During this adjustment, the surgical orientation device 14 can provide a reading or readings on its display 26 indicating whether the surgical orientation device 14 (and likewise the cutting block 332) is aligned with the sagittal plane and/or coronal plane containing the mechanical axis.

Referring to FIG. 49, the method can further comprise rotating the cutting block 332 such that the cutting block 332 is positioned up against an anterior surface of the proximal tibia once the desired angle has been set.

Referring to FIG. 50, once the cutting block is in position, the cutting block 332 can be mounted to an anterior surface of a proximal portion of the tibia by a plurality of pins 342. The surgical orientation device 14 can be removed, as can the tibial assembly 212. After the cutting block 332 has been mounted to the tibia, a proximal portion of the tibia can be resected.

IX. User Interfaces for Tibial Preparation Methods

As discussed above, in at least one embodiment, the surgical orientation device 14 can display on-screen graphics or GUI images for communicating information to a user based on input commands and orientation data. The images can be instructive for performing a joint replacement surgery.

FIGS. 51A-51L display exemplary screen shots that can be displayed by the interactive user interface of the surgical orientation device 14 (e.g. displayed on an LCD screen on the front of the surgical orientation device 14) during the various steps of an orthopedic method.

Figure 51B:
FIGS. 51A-L show screen displays for a tibial method generated by one embodiment of the interactive user interface of the surgical orientation device of FIG. 3.
Figure 51A:
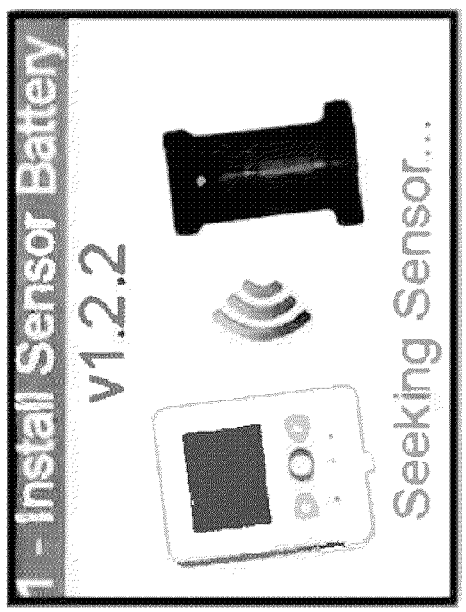

For example, FIG. 51A displays a screen shot that provides a visual cue informing the user to check the surgical orientation device 14 and reference sensor device 16 to see if batteries are installed, and to check to make sure the surgical orientation device 14 is detecting the reference sensor device 16.

FIG. 51B displays a screen shot that provides a visual cue informing the user to confirm whether a green LED light is lit on the reference sensor device. If there is a green light, the surgical orientation device 14 has detected the reference sensor device 16. The image in FIG. 51B can be displayed in response to pressing a user input button 28 specified by the surgical orientation device 14 in FIG. 51A.

Figure 51D:
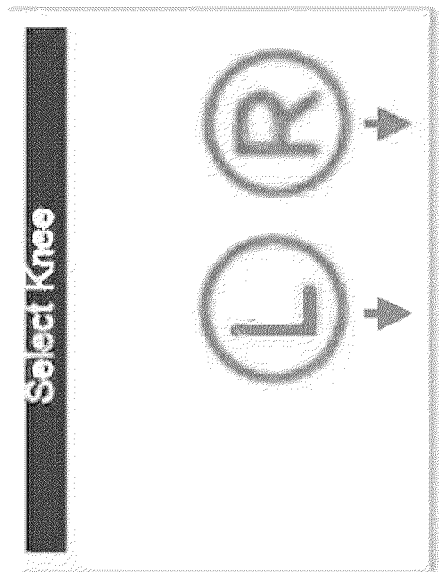
Figure 51C:
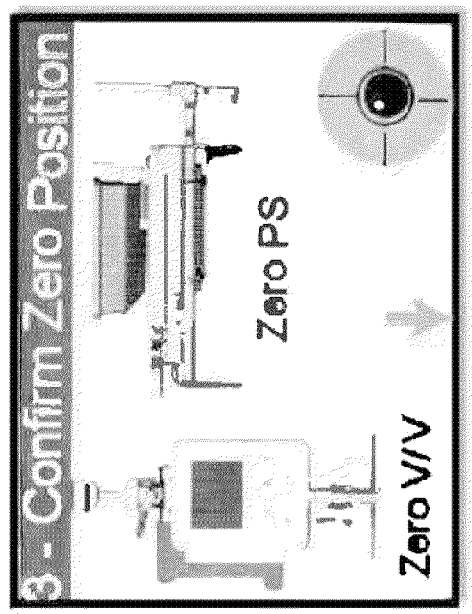

FIG. 51C displays a screen shot that provides a visual cue informing the user to acquire and confirm a neutral position of the surgical orientation device 14. For example, the user can place the surgical orientation device 14 on a level surface with its display screen 26 facing up, and the user can confirm whether there is a 0 degree reading for both varus/valgus and posterior slope. The image in FIG. 51C can be displayed in response to pressing a user input 28 button specified by the surgical orientation device 14 in FIG. 51B.

FIG. 51D displays a screen shot that provides a visual cue informing the user to select the right or left knee. The image in FIG. 51D can be displayed in response to pressing a user input 28 button specified by the surgical orientation device 14 in FIG. 51C.

Figure 51F:
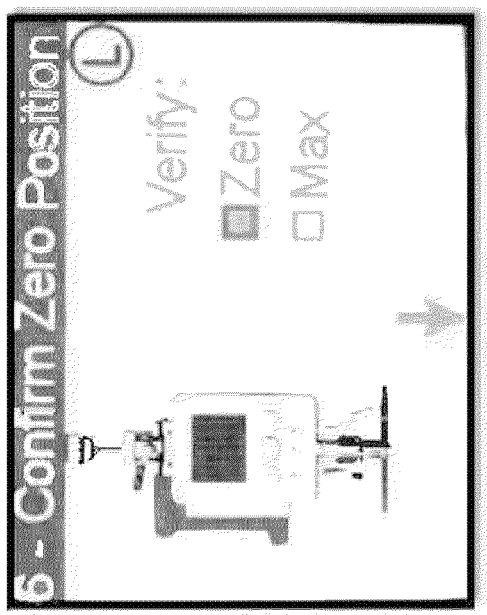
Figure 51E:
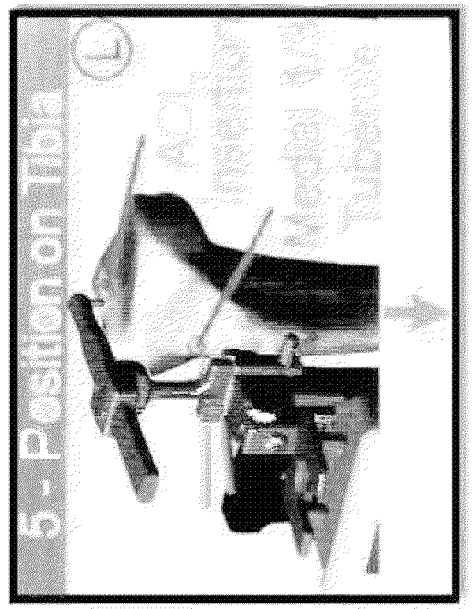

FIG. 51E displays a screen shot that provides a visual cue informing the user to place the tibial assembly 212 against the tibia, to secure the reference sensor device 16 to the tibial assembly 212, and to secure the mounting bar assembly 220 to the tibia, for example with pins. The image in FIG. 51E can be displayed in response to pressing a user input 28 button specified by the surgical orientation device 14 in FIG. 51D.

FIG. 51F displays a screen shot that provides a visual cue informing the user to confirm that the tibial assembly 212 is in a neutral position. The image in FIG. 51F can be displayed in response to pressing a user input 28 button specified by the surgical orientation device 14 in FIG. 51E.

Figure 51H:
Figure 51G:
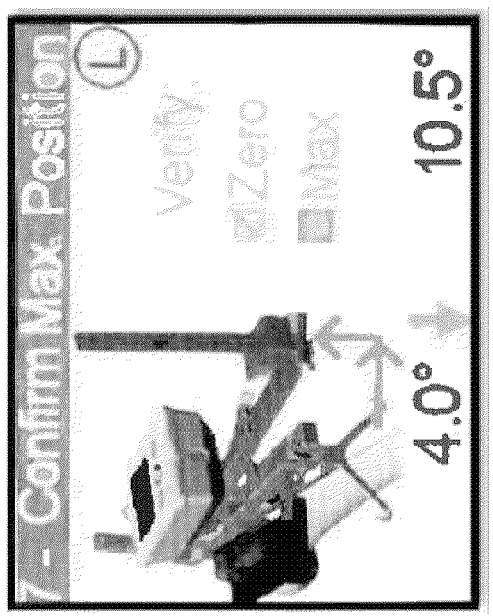

FIG. 51G displays a screen shot that provides a visual cue informing the user to confirm movement capabilities of the swing arms (e.g. movement of posterior slope assembly 216 and varus/valgus assembly 218). In some embodiments, the user can confirm maximum ranges of angular adjustment. The image in FIG. 51G can be displayed in response to pressing a user input 28 button specified by the surgical orientation device 14 in FIG. 51F.

FIG. 51H displays a screen shot that provides a visual cue informing the user to confirm an A/P offset based on markings on the midline probe assembly 226 and landmark acquisition assembly 214. The image in FIG. 51H can be displayed in response to pressing a user input 28 button specified by the surgical orientation device 14 in FIG. 51G.

Figure 51J:
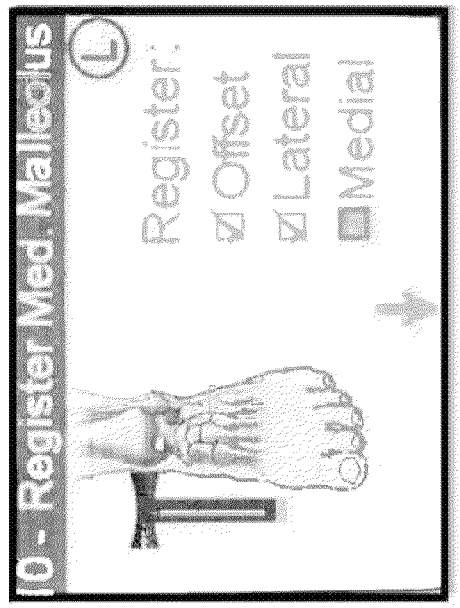
Figure 51I:
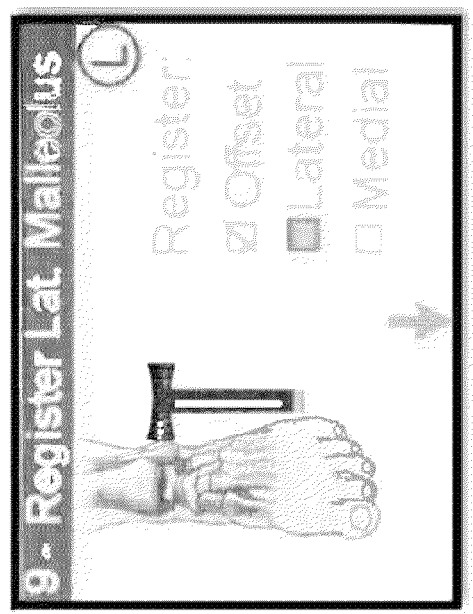

FIG. 51I displays a screen shot that provides a visual cue informing the user to register a first landmark (e.g. malleolus). The image in FIG. 51I can be displayed in response to pressing a user input 28 button specified by the surgical orientation device 14 in FIG. 51H.

FIG. 51J displays a screen shot that provides a visual cue informing the user to register a second landmark. The image in FIG. 51J can be displayed in response to pressing a user input 28 button specified by the surgical orientation device 14 in FIG. 51I.

Figure 51L:
Figure 51K:
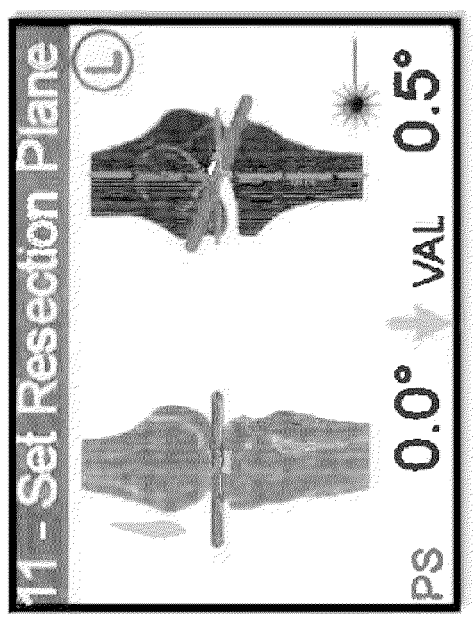

FIG. 51K displays a screen shot that provides a visual cue informing the user to determine a desired anterior/posterior slope angle and varus/valgus slope angle for resection. The image in FIG. 51K can be displayed in response to pressing a user input 28 button specified by the surgical orientation device 14 in FIG. 51J.

FIG. 51L displays a screen shot that provides a visual cue informing the user to remove the midline probe assembly 212 and to set a resection depth using the stylus 222. The image in FIG. 51L can be displayed in response to pressing a user input 28 button specified by the surgical orientation device 14 in FIG. 51K.

FIGS. 52-55 display additional exemplary screen shots that can be displayed by the interactive user interface of the surgical orientation device 14 (e.g. displayed on an LCD screen on the front of the surgical orientation device 14) during the various steps of an orthopedic procedure.

Figure 52:
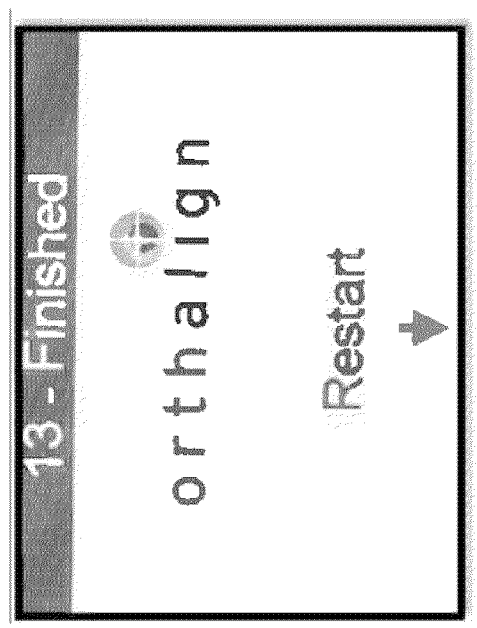

For example, FIG. 52 displays a screen shot that provides a visual cue informing the user that a procedure is finished.

Figure 53:
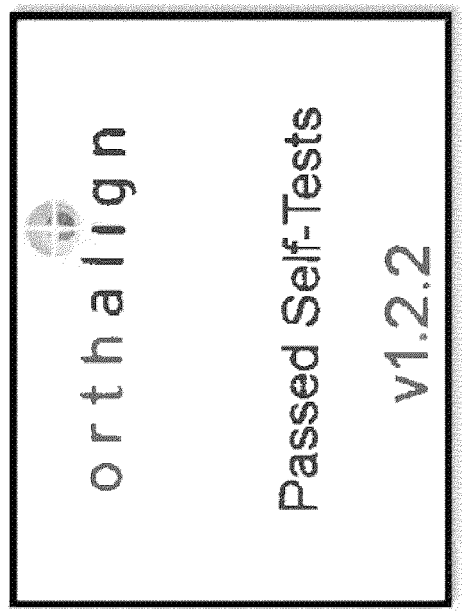
FIGS. 52-55 show additional screen displays generated by one embodiment of the interactive user interface of the surgical orientation device of FIG. 3.

FIG. 53 displays a screen shot that provides a visual cue informing the user that the surgical orientation device 14 has completed and passed one or more self-tests.

Figure 54:
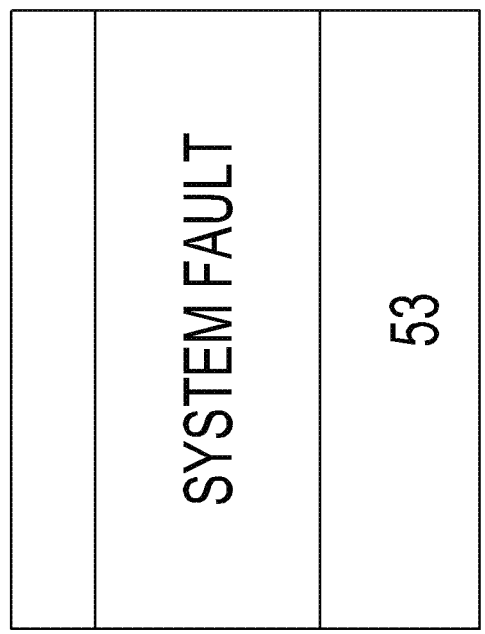

FIG. 54 displays a screen shot that provides a visual cue informing the user that the surgical orientation device 14 is experiencing a system fault.

Figure 55:
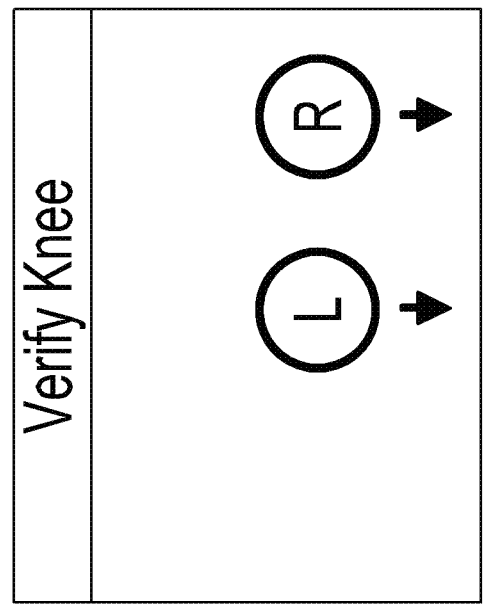

FIG. 55 displays a screen shot that provides a visual cue informing the user to confirm again whether the left or right leg is being prepared. This visual cue can appear, for example, if the user is registering the lateral malleolus and the tibial assembly 212 continues to move in a lateral direction, as opposed to a medial direction.

Further embodiments of user interfaces, for use for example in an orthopedic method, can be found in paragraphs [0377]-[430] and FIGS. 58A-61K of U.S. patent application Ser. No. 12/509,388, which is incorporated by reference herein.

X. Attachment of Prosthetic Components

Once all of the tibial and/or femoral cuts are made with the systems and/or methods described above, a knee joint prosthetic or prosthetics can be attached to the distal femur and/or proximal tibia. The knee joint prosthetic devices can comprise a replacement knee joint. The replacement knee joint can be evaluated by the user to verify that alignment of the prosthetic components in the replacement knee joint does not create any undesired wear, interference, and/or damage to the patient's anatomy, or to the prosthetic components themselves.

While the systems and methods presented herein are described in the context of a knee joint replacement procedure, the systems and/or their components and methods can similarly be used in other types of medical procedures, including but not limited to shoulder and hip replacement procedures.

Additionally, while the systems and methods presented herein are described in the context of individual components and assemblies, in some embodiments one or more of the assemblies can be provided in the form of a kit for use by a surgeon. For example, in some embodiments a kit can comprise each of the components of the femoral preparation system 10 and the tibial preparation system 210 described above. In some embodiments, a kit may comprise only the surgical orientation device 14 and reference sensor device 16. In some embodiments a kit may comprise only the femoral preparation system 10, or only the tibial preparation system 210. Various other combinations and kits are also possible.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments can be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A method of orthopedic surgery, comprising:
    coupling an orthopedic fixture to a bone of a patient, wherein the orthopedic fixture comprise a first interface and a second interface,
    coupling a first orientation device to the first interface, wherein the first orientation device is configured to sense changes in motion, orientation, and/or position of the bone;
    coupling a second orientation device to the second interface, wherein the second orientation device is configured to sense changes in motion, orientation, and/or position of the second orientation device; and
    wherein at least one of the first orientation device and the second orientation device is configured to send information about motion, orientation, and/or position of the at least one of the first orientation device and the second orientation device to the other of the first orientation device and the second orientation device.

2. The method of claim 1, wherein the second orientation device comprises a display.

3. The method of claim 1, further comprising locating a mechanical axis.

4. The method of claim 1, further comprising acquiring at least one landmark to determine a point on a mechanical axis passing through the bone.

5. The method of claim 1, further comprising acquiring a center of rotation.

6. The method of claim 1, further comprising acquiring at least two landmark to determine a point on a mechanical axis passing through the bone.

7. The method of claim 1, further comprising performing a tibial resection.

8. The method of claim 1, further comprising performing a femoral resection.

9. A method of orthopedic surgery, comprising:
    coupling a first orientation device to a fixed portion of an orthopedic fixture coupled to a bone of a patient, wherein the first orientation device is configured to sense changes in motion, orientation, and/or position of the first orientation device;
    coupling a second orientation device to a movable portion of the orthopedic fixture, wherein the second orientation device is configured to sense changes in motion, orientation, and/or position of the second orientation device; and
    wherein at least one of the first orientation device and the second orientation device is configured to send information about a motion, orientation, and/or position of the at least one of the first orientation device and the second orientation device to the other of the first orientation device and the second orientation device.

10. The method of claim 9, wherein the second orientation device comprises a display.

11. The method of claim 9, further comprising locating a mechanical axis.

12. The method of claim 9, further comprising performing a tibial resection.

13. The method of claim 9, further comprising performing a femoral resection.

14. The method of claim 9, further comprising coupling the second orientation device to a resection guide.

15. The method of claim 9, wherein the second orientation device provides information indicating whether the second orientation device is aligned with a mechanical axis.

16. The method of claim 9, wherein the second orientation device provides information indicating whether the second orientation device is aligned with a plane containing a mechanical axis of the bone.

17. The method of claim 9, wherein the second orientation device provides information indicating whether the second orientation device is aligned with an pre-determined angle.

18. A method of orthopedic surgery, comprising:
    positioning a first orientation device within a surgical field, wherein the first orientation device is configured to sense changes in motion, orientation, and/or position of the first orientation device;
    positioning a second orientation device within the surgical field, wherein the second orientation device is configured to sense changes in motion, orientation, and/or position of the second orientation device; and
    wherein at least one of the first orientation device and the second orientation device is configured to send information about an motion, orientation, and/or position of the at least one of the first orientation device and the second orientation device to the other of the first orientation device and the second orientation device.

19. The method of claim 18, performing a resection based on information provided by at least one orientation device, wherein the resection is a tibial resection.

20. The method of claim 18, performing a resection based on information provided by at least one orientation device, wherein the resection is a femoral resection.

* * * * *